(12) United States Patent
Ciulli et al.

(10) Patent No.: US 11,925,690 B2
(45) Date of Patent: Mar. 12, 2024

(54) BIFUNCTIONAL MOLECULES FOR TARGETING RPN11

(71) Applicant: AMPHISTA THERAPEUTICS LTD, England (GB)

(72) Inventors: Alessio Ciulli, Dundee (GB); Andrea Testa, Dundee (GB); Scott Hughes, Dundee (GB); Steven Peter Butcher, Dundee (GB)

(73) Assignee: AMPHISTA THERAPEUTICS LIMITED, London (GB)

( * ) Notice: Subject to any disclaimer, the term of this patent is extended or adjusted under 35 U.S.C. 154(b) by 0 days.

(21) Appl. No.: 17/251,615

(22) PCT Filed: Jun. 13, 2019

(86) PCT No.: PCT/EP2019/065481
§ 371 (c)(1),
(2) Date: Dec. 11, 2020

(87) PCT Pub. No.: WO2019/238817
PCT Pub. Date: Dec. 19, 2019

(65) Prior Publication Data
US 2021/0260200 A1 Aug. 26, 2021

Related U.S. Application Data

(60) Provisional application No. 62/835,953, filed on Apr. 18, 2019, provisional application No. 62/684,265, filed on Jun. 13, 2018.

(51) Int. Cl.
| | | |
|---|---|---|
| A61K 47/60 | (2017.01) | |
| A61K 31/277 | (2006.01) | |
| A61K 31/351 | (2006.01) | |
| A61K 31/404 | (2006.01) | |
| A61K 31/407 | (2006.01) | |
| A61K 31/4184 | (2006.01) | |
| A61K 31/423 | (2006.01) | |
| A61K 31/428 | (2006.01) | |
| A61K 31/4375 | (2006.01) | |
| A61K 31/44 | (2006.01) | |
| A61K 31/47 | (2006.01) | |
| A61K 31/4709 | (2006.01) | |
| A61K 31/496 | (2006.01) | |
| A61K 31/506 | (2006.01) | |
| A61K 31/519 | (2006.01) | |
| A61K 31/5355 | (2006.01) | |
| A61K 31/551 | (2006.01) | |
| A61K 47/55 | (2017.01) | |
| C07D 417/14 | (2006.01) | |
| C07D 495/14 | (2006.01) | |

(52) U.S. Cl.
CPC ............ *A61K 47/60* (2017.08); *A61K 31/277* (2013.01); *A61K 31/351* (2013.01); *A61K 31/404* (2013.01); *A61K 31/407* (2013.01); *A61K 31/4184* (2013.01); *A61K 31/423* (2013.01); *A61K 31/428* (2013.01); *A61K 31/4375* (2013.01); *A61K 31/44* (2013.01); *A61K 31/47* (2013.01); *A61K 31/4709* (2013.01); *A61K 31/496* (2013.01); *A61K 31/506* (2013.01); *A61K 31/519* (2013.01); *A61K 31/5355* (2013.01); *A61K 31/551* (2013.01); *A61K 47/55* (2017.08); *C07D 417/14* (2013.01); *C07D 495/14* (2013.01)

(58) Field of Classification Search
CPC .................................................... A61K 47/60
See application file for complete search history.

(56) References Cited

U.S. PATENT DOCUMENTS

| | | | |
|---|---|---|---|
| 4,522,811 A | 6/1985 | Eppstein et al. | |
| 5,521,184 A | 5/1996 | Juerg | |
| 6,468,798 B1 | 10/2002 | Debs et al. | |
| 7,041,298 B2* | 5/2006 | Deshaies | G01N 33/5008 424/193.1 |
| 7,208,157 B2 | 4/2007 | Dashaies et al. | |
| 9,670,482 B2 | 6/2017 | Winter et al. | |
| 10,005,735 B2* | 6/2018 | Deshaies | C07D 413/12 |
| 10,500,198 B2 | 12/2019 | Boden et al. | |
| 10,781,205 B2* | 9/2020 | Casillas | C07D 519/00 |
| 2010/0137254 A1 | 6/2010 | Matteucci et al. | |
| 2010/0183742 A1 | 7/2010 | Ammons et al. | |
| 2014/0235548 A1 | 8/2014 | Zhou et al. | |
| 2016/0176916 A1 | 6/2016 | Bradner et al. | |
| 2017/0050931 A1 | 2/2017 | Deshaies et al. | |
| 2020/0000927 A1 | 1/2020 | Miyamoto et al. | |

FOREIGN PATENT DOCUMENTS

| | | |
|---|---|---|
| EP | 2199283 A1 | 6/2010 |
| EP | 3312273 | 4/2018 |
| WO | WO 1993/020094 A1 | 10/1993 |
| WO | WO 2000/062778 A1 | 10/2000 |
| WO | WO 2002/022577 | 3/2002 |
| WO | WO 2012/078559 | 6/2012 |
| WO | WO 2013/106643 | 7/2013 |
| WO | WO 2015/160845 | 10/2015 |

(Continued)

OTHER PUBLICATIONS

Tinworth, Med. Chem. Commun., 2016, 7, 2206.*
Perez, J. Med. Chem. 2017, 60, 1343-1361 (Feb. 13, 2017).*

(Continued)

*Primary Examiner* — Nizal S Chandrakumar
(74) *Attorney, Agent, or Firm* — Casimir Jones SC; Lisa Mueller

(57) ABSTRACT

The invention provides for bifunctional molecules comprising an Rpn11 binding partner and a target protein binding partner. A bifunctional molecule according to the invention binds to Rpn11 and to the target protein, thereby facilitating degradation of the target protein bound to the target protein binding partner. The invention also provides for use of a bifunctional molecule for preventing or treating disease.

2 Claims, 11 Drawing Sheets

Specification includes a Sequence Listing.

(56) References Cited

FOREIGN PATENT DOCUMENTS

| WO | WO 2016/146985 | | 9/2016 | |
| --- | --- | --- | --- | --- |
| WO | WO 2016146985 | * | 9/2016 | ........... C07D 417/12 |
| WO | WO 2016/197032 | | 12/2016 | |
| WO | WO 2016/204197 | | 12/2016 | |
| WO | WO 2017/024317 | | 2/2017 | |
| WO | WO 2017/024318 | | 2/2017 | |
| WO | WO 2017/024319 | | 2/2017 | |
| WO | WO 2017/031255 A1 | | 2/2017 | |
| WO | WO 2017/046036 A1 | | 3/2017 | |
| WO | WO 2017/182418 A1 | | 10/2017 | |
| WO | WO 2019/152440 | | 8/2019 | |
| WO | WO 2019/165216 | | 8/2019 | |
| WO | WO 2019/165229 | | 8/2019 | |
| WO | WO 2019/199816 | | 10/2019 | |
| WO | WO 2020/141213 A1 | | 7/2020 | |
| WO | WO 2020/146561 | | 7/2020 | |

OTHER PUBLICATIONS

Collins, Biochemical Journal (2017) 474 1127-1147.*
Aguilera, J. Med. Chem. 2022, 65, 1047-1131.*
Venkatesh,, J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784).*
Berndsen et al., New insights into ubiquitin E3 ligase mechanism, Nat.Struct. Mol. Biol., (2014), vol. 21, pp. 301-307.
Boitano et al., Aryl Hydrocarbon Receptor Antagonists Promote the Expansion of Human Hematopoietic Stem Cells, Science, (2010), vol. 329, No. 5997, pp. 1345-1348.
Brough, 4,5-Diarylisoxazole Hsp90 Chaperone Inhibitors: Potential Therapeutic Agents for the Treatment of Cancer, Med.Chem., (2008), vol. 51, p. 196.
Bulatov et al., Targeting Cullin—RING E3 ubiquitin ligases for drug discovery: structure, assembly and small-molecule modulation, Biochem J., (2015), vol. 467, pp. 365-386.
Chang et al., Structural basis for G9a-like protein lysine methyltransferase inhibition by BIX-01294, Nat. Struct. Biol., (2009), vol. 16, No. 3, p. 312.
Chen et al. Metal-based proteasomal deubiquitinase inhibitors as potential anticancer agents, Cancer Metastasis Rev. (2017) 36(4), 655-668x.
Chung et al., Discovery and Characterization of Small Molecule Inhibitors of the BET Family Bromodomains, J. Med. Chem. 2011, 54, 11, 3827-3838.
Dawson et al., Inhibition of BET recruitment to chromatin as an effective treatment for MLL-fusion leukaemia, Nature (2011) 478, 529-533.
Deshaies et al., RING Domain E3 Ubiquitin Ligases, Ann. Rev. Biochem., (2009), vol. 78, pp. 399-434.
Finnin, M. S. et al., Structures of a histone deacetylase homologue bound to the TSA and SAHA inhibitors, Nature, (1999), vol. 40, pp. 188-193.
Hewings et al., 3,5-Dimethylisoxazoles Act As Acetyl-lysine-mimetic Bromodomain Ligands, J. Med. Chem., (2011), vol. 54, pp. 6761-6770.
Jones et al., Small-Molecule Kinase Downregulators, Cell Chem. Biol., (2017), vol. 25, pp. 30-35.
Lauinger et al., Thiolutin is a zinc chelator that inhibits the Rpn11 and other JAMM metalloproteases, Nat. Chem. Biol., (2017) 13, 7, 709-714.
Lee et al., Facilitated Tau Degradation by USP14 Aptamers via Enhanced Proteasome Activity, Sci. Rep. (2015), 5, 10757.
Lee et al., Targeted Degradation of the Aryl Hydrocarbon Receptor by the PROTAC Approach: A Useful Chemical Genetic Tool, ChemBioChem, (2007), vol. 8, No. 17, pp. 2058-2062.
Li et al., Capzimin is a potent and specific inhibitor of proteasome isopeptidase Rpn11, Nat. Chem. Biol. (2017) 13, 486-493.
Li et al., Genome-Wide and Functional Annotation of Human E3 Ubiquitin Ligases Identifies MULAN, a Mitochondrial E3that Regulates the Organelle's Dynamics and Signaling, PLOS One, (2008), vol. 3, p. 1487.
Liu, F. et al., Discovery of a 2,4-Diamino-7-aminoalkoxyquinazoline as a Potent and Selective Inhibitor of Histone Lysine Methyltransferase G9a, J. Med. Chem., (2009), vol. 52, No. 24, p. 7950.
Llinas-Brunet et al., Discovery of a Potent and Selective Noncovalent Linear Inhibitor of the Hepatitis C Virus NS3 Protease (BI 201335), J. Med. Chem., (2010), vol. 53, pp. 6466-6476.
Lountos et al., Structural Characterization of Inhibitor Complexes with Checkpoint Kinase 2 (Chk2), a Drug Target for Cancer Therapy, J. Struct.. Biol., (2011), vol. 176, p. 292.
McCafferty et al., Phage antibodies: filamentous phage displaying antibody variable domains, Nature, (1990), vol. 348, pp. 552-554.
Mehellou and De Clercq, Twenty-Six Years of Anti-HIV Drug Discovery: Where Do We Stand and Where Do We Go?, J. Med. Chem, (2010), vol. 53, pp. 521-538.
Millan, J. Design and Synthesis of Inhaled p38 Inhibitors for the Treatment of Chronic Obstructive Pulmonary Disease, Med, Chem., (2011), vol. 54, p. 7797.
Nicodeme et al. Suppression of inflammation by a synthetic histone mimic, Nature (2010) 468, 1119-1123.
O' Connor et al., Design, synthesis and evaluation of molecularly targeted hypoxia-activated prodrugs, Nat Protoc., (2016), vol. 11, No. 4, pp. 781-794.
Ottis, P and Crews, C. M., Proteolysis-Targeting Chimeras: Induced Protein Degradation as a Therapeutic Strategy, ACS Chem Biol, (2017), vol. 12, pp. 892-898 (Need Article 17).
Perez et al., Discovery of an Inhibitor of the Proteasome Subunit Rpn11, J. Med. Chem., (2017), vol. 60, pp. 1343-1361.
Rodriguez-Gonzalez et al., Targeting steroid hormone receptors for ubiquitination and degradation in breast and prostate cancer, Oncogene, (2008), vol. 27, pp. 7201-7211.
Romero, F.A. et al., Disrupting Acetyl-Lysine Recognition: Progress in the Development of Bromodomain Inhibitors, J. Med. Chem., (2016), vol. 59, No. 4, pp. 1271-1298.
Rusch et al., Identification of Acyl Protein Thioesterases 1 and 2 as the Cellular Targets of the Ras-Signaling Modulators Palmostatin B and M, Angew. Chem. Int. Ed., (2011), vol. 50, pp. 9838-9842.
Sakamoto et al., Development of Protacs to Target Cancer-promoting Proteins for Ubiquitination and Degradation, Mol. Cell Proteomics, (2003), vol. 2, No. 12, pp. 1350-1358.
Sakamoto et al., Protacs: Chimeric molecules that target proteins to the Skp1-Cullin-F box complex for ubiquitination and degradation, Proc. Natl. Acad. Sci. USA, (2001), vol. 98, No. 15, pp. 8554-8559.
Schenkel et al., Discovery of Potent and Highly Selective Thienopyridine Janus Kinase 2 Inhibitors, J. Med. Chem. (2011) 54(24), 8440-8450.
Schneekloth et al., Targeted intracellular protein degradation induced by a small molecule: En route to chemical proteomics, Biorg. Med. Chem. Lett., (2008), vol. 18, pp. 5904-5908.
Schneekloth, Chemical Genetic Control of Protein Levels: Selective in Vivo Targeted Degradation, J. Am. Chem. Soc., (2004), vol. 126, pp. 3748-3754.
Spratt et al., RBR E3 ubiquitin ligases: new structures, new insights, new questions, Biochem., (2014), vol. 458, pp. 421-437.
Sun et al., Cargo-Free Nanomedicine with pH Sensitivity for Codelivery of DOX Conjugated Prodrug with SN38 To Synergistically Eradicate Breast Cancer Stem Cells, Mol. Pharmaceutics, (2018), vol. 15, pp. 3343-3355.
Sun et al., Selective Tumor Hypoxia Targeting by Hypoxia-Activated Prodrug TH-302 Inhibits Tumor Growth in Preclinical Models of Cancer, Clin Cancer Res., (2012), vol. 18, No. 3, pp. 758-770.
Tsuchikama et al., Antibody-drug conjugates: recent advances in conjugation and linker chemistries, Protein Cell, (2018), vol. 9, No. 1, pp. 33-46.
Vallee et al., Tricyclic Series of Heat Shock Protein 90 (Hsp90) Inhibitors Part I: Discovery of Tricyclic Imidazo [4,5-c]pyridines as Potent Inhibitors of the Hsp90 Molecular Chaperone, J.Med.Chem., (2011), vol. 54, p. 7206.

(56) References Cited

OTHER PUBLICATIONS

Van Eis, 2,6-Naphthyridines as potent and selective inhibitors of the novel protein kinase C isozymes, Biorg. Med. Chem. Lett., (2011), vol. 21, No. 24, pp. 7367-7372.
Vassilev et al., In Vivo Activation of the p53 Pathway by Small-Molecule Antagonists of MDM2, Science, (2004), pp. 303844-303848.
Wang et al., Automated Modular Synthesis of Aptamer-Drug Conjugates for Targeted Drug Delivery, J. Am. Chem. Soc., (2014), vol. 136, pp. 2731-2734.
Wang et al., Roles of F-box proteins in cancer, Nat. Rev. Cancer., (2014), vol. 14, pp. 233-347.
Worden et al., Structure of the Rpn11-Rpn8 dimer reveals mechanisms of substrate deubiquitination during proteasomal degradation, Nat. Struct. Mol. Biol. (2014), 21, 220-227.
Wright, Structure-Activity Relationships in Purine-Based Inhibitor Binding to HSP90 Isoforms, Chem Biol., (2004), vol. 11, No. 6, pp. 775-785.
Zhang et al., pH-sensitive prodrug conjugated polydopamine for NIR-triggered synergistic chemo-photothermal therapy, European Journal of Pharmaceutics and Biopharmaceutics, (2018), vol. 128, pp. 260-271.
Zhu, Rui, et al., 4-Nitrobenzyloxycarbonyl Derivatives of O6-Benzylguanine as Hypoxia-Activated Prodrug Inhibitors of O6-Alkylguanine-DNA Alkyltransferase (AGT), Which Produces Resistance to Agents Targeting the O-6 Position of DNA Guanine, J. Med. Chem., (2011), vol. 54, No. 24, pp. 7720-7728.
International Preliminary Report on Patentability for International Patent Application Serial No. PCT/EP2019/065481, dated Dec. 15, 2020.
International Search Report and Written Opinion for International Patent Application Serial No. PCT/EP2019/065481, dated Sep. 26, 2019.
Bondeson, Daniel P., et al., Catalytic in vivo protein knockdown by small-molecule PROTACs, Nature Chemical Biology, vol. 11, No. 8, pp. 611-617, Jan. 1, 2015.
Filippakopoulos, Panagis, et al., Selective inhibition of BET bromodomains, Nature, vol. 468, No. 7327, pp. 1067-1073, Dec. 23, 2010.

* cited by examiner

BIFUNCTIONAL MOLECULES FOR TARGETING RPN11

RELATED APPLICATIONS

The present disclosure is a U.S. National Stage of International Patent Application No. PCT/EP2019/065481, filed: 13 Jun. 2019, titled: BIFUNCTIONAL MOLECULES FOR TARGETING RPN11, published as International Patent Application No. WO 2019/238817 A1, which claims the benefit and priority to U.S. Provisional Patent Application Ser. No. 62/835,953, filed on 18 Apr. 2019; and U.S. Provisional Patent Application Ser. No. 62/684,265, filed on 13 Jun. 2018, all of which are incorporated by reference in their entirety for all purposes.

INCORPORATION BY REFERENCE

In compliance with 37 C.F.R. § 1.52(e)(5), the sequence information contained in electronic file name: MCZ0001_US_Sequence_Listing_ST25.txt; size 4.30 KB; created on: 13 Jun. 2019 using Patent-In 3.5 is hereby incorporated herein by reference in its entirety.

TECHNICAL FIELD

The invention is directed to bifunctional molecules for selected degradation of a protein in a cell.

BACKGROUND OF THE INVENTION

Protein degradation is a highly regulated and essential process that maintains cellular homeostasis. The selective identification and removal of damaged, misfolded, or excess proteins is achieved in part via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis, and viral infection. Covalent attachment of multiple ubiquitin molecules by an E3 ubiquitin ligase typically to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer, among others.

There are over 600 E3 ubiquitin ligases which facilitate the ubiquitination of different proteins in vivo. E3 ligases can be divided into four families: HECT-domain E3s, U-box E3s, monomeric RING E3s and multi-subunit Cullin-RING E3s. See Bulatov et al. (*Biochem* 1, 2015, 467: 365-386), Li et al. (*PLOS One*, 2008, 3, 1487), Berndsen et al. (*Nat. Struct. Mol. Biol.*, 2014, 21, 301-307), Deshaies et al. (*Ann. Rev. Biochem.*, 2009, 78, 399-434), Spratt et al. (*Biochem.* 2014, 458, 421-437), and Wang et al. (*Nat. Rev. Cancer.*, 2014, 14, 233-347).

Proteolysis targeting chimeric (PROTAC) compounds are composed of two ligands joined by a linker—one ligand to engage a target protein and another ligand to recruit an E3 ubiquitin ligase. As such, the target protein is brought to an E3 ligase, is ubiquitinated and then degraded. (See Ottis, P. & Crews, C. M. Proteolysis-Targeting Chimeras: Induced Protein Degradation as a Therapeutic Strategy. *ACS Chem Biol* 12, 892-898 (2017).)

PCT/US2015/025813 (Arvinas), WO 2016/146985 (University of Dundee) and WO 2013/106643 (Yale University et al.) relate to imide-based and hydroxyproline-based PROTAC bifunctional compounds which are intended to recruit endogenous proteins to an E3 Ubiquitin Ligase for degradation. US 2016/0176916, WO 2017/024318, WO 2017/024317, and WO 2017/024319 (all Dana-Farber Cancer Institute) also pertain to target protein degradation using known E3 ligase ligands to ubiquitinate the target protein and direct it to be degraded.

The 26S proteasome is a large multi subunit complex involved in degrading both cytoplasmic and nuclear proteins. It is composed of at least 32 different subunits. The central core cylindrical particle, which contains the proteolytic active sites, is capped by a 19S regulatory particle at one or both ends. The degradation chamber can be reached through a channel that runs along the center of the core particle. The proteasome inhibitor Velcade R is an FDA approved drug for the treatment of multiple myeloma which targets the central catalytic cavity within the 20S. The entrance to the channel is narrow, therefore folded proteins must be at least partially unfolded before they can be threaded into the 20S core particle, cleaved and ultimately degraded. The 19S regulatory particle is composed of at least 19 subunits arranged into two sub-complexes—one called "the lid" and another called "the base". The regulatory particle contains ATPase subunits, which catalyze ATP hydrolysis in order to energetically support its functions. These include gating the entrance to the degradation channel, mediating substrate recognition, proteolytic cleavage of ubiquitin chains (so that ubiquitin is recycled after recognition of the ubiquitinated protein), unfolding, and ultimately translocation into the 20S core particle.

SUMMARY OF THE INVENTION

The invention provides bifunctional molecules which facilitate degradation of a selected target protein in a cell.

In one embodiment, the invention includes a bifunctional molecule comprising an Rpn11 binding partner linked to a target protein binding partner.

Preferably, the Rpn11 binding partner binds to Rpn11 with an affinity of at least 10 nM. Preferably, the Rpn11 binding partner binds to Rpn11 with a Kd of less than 1 µM. A Rpn11 binding partner may be selected from the group of Rpn11 binding molecules provided in Table 1. Preferably, a target protein binding partner may be selected from the group consisting of: kinase inhibitors, phosphatase inhibitors, compounds targeting BET bromodomain-containing proteins, HDM2/MDM2 inhibitors, heat shock protein 90 inhibitors, HDAC inhibitors, human lysine methyltransferase inhibitors and antibodies. In other preferred embodiments, a linker may be a polyethylene glycol (PEG) linker, a hydrocarbon linker, an akyl-ether linker, or a combined PEG, alkyl linker. Preferably the bifunctional molecule, wherein the Rpn11 binding partner is denoted by the formula I

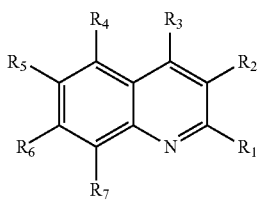

R1 and R6 are preferentially —H, but also —Me, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO . . .

R$_2$, R$_3$, R$_4$ and R$_5$ is selected from a group consisting of —CO—Z, OCH$_3$, —CF$_3$, —COOH, —CH$_2$NH$_2$, —CH$_3$, —H, —Me, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO . . . ; Z is selected from a group consisting of —NH$_2$, —NHY, —OH, and —OY; Y is selected from a group consisting of —CH$_3$, —CH$_2$—COO—,

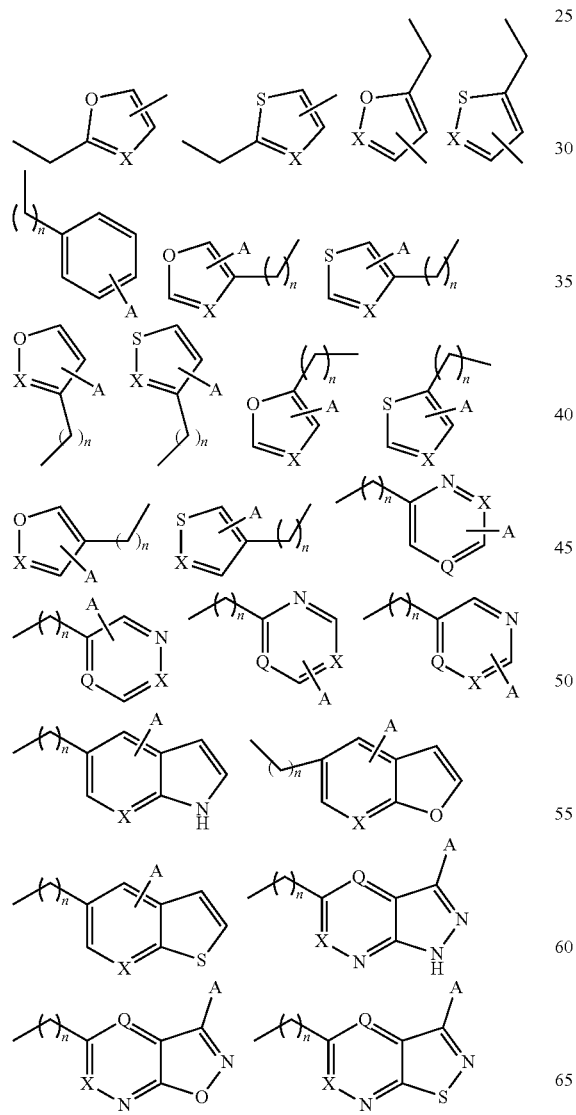

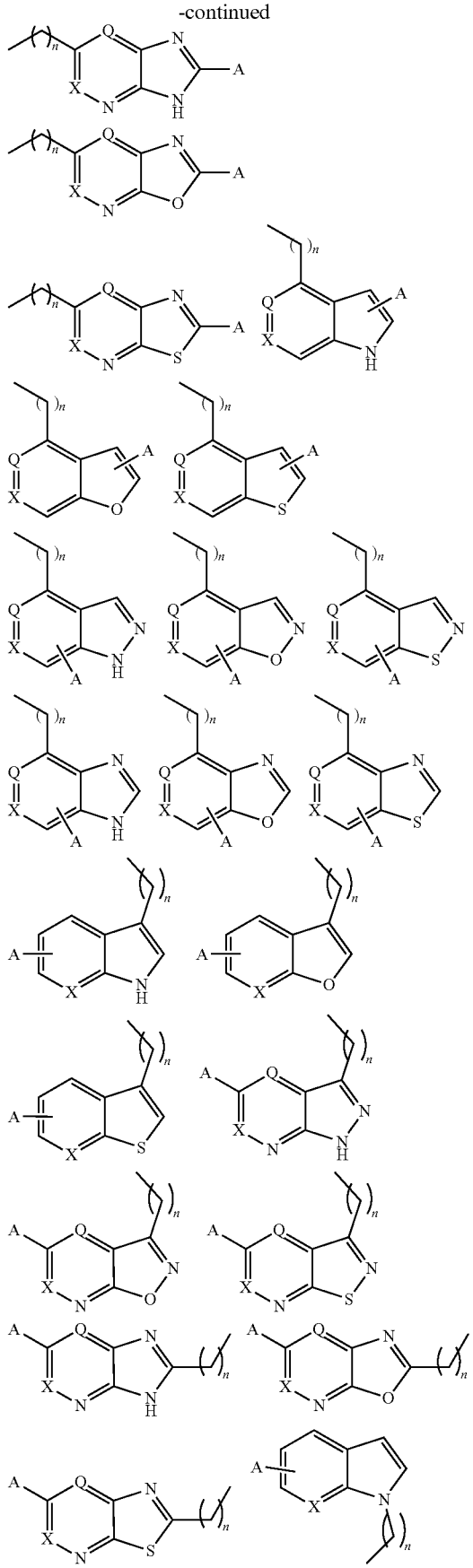

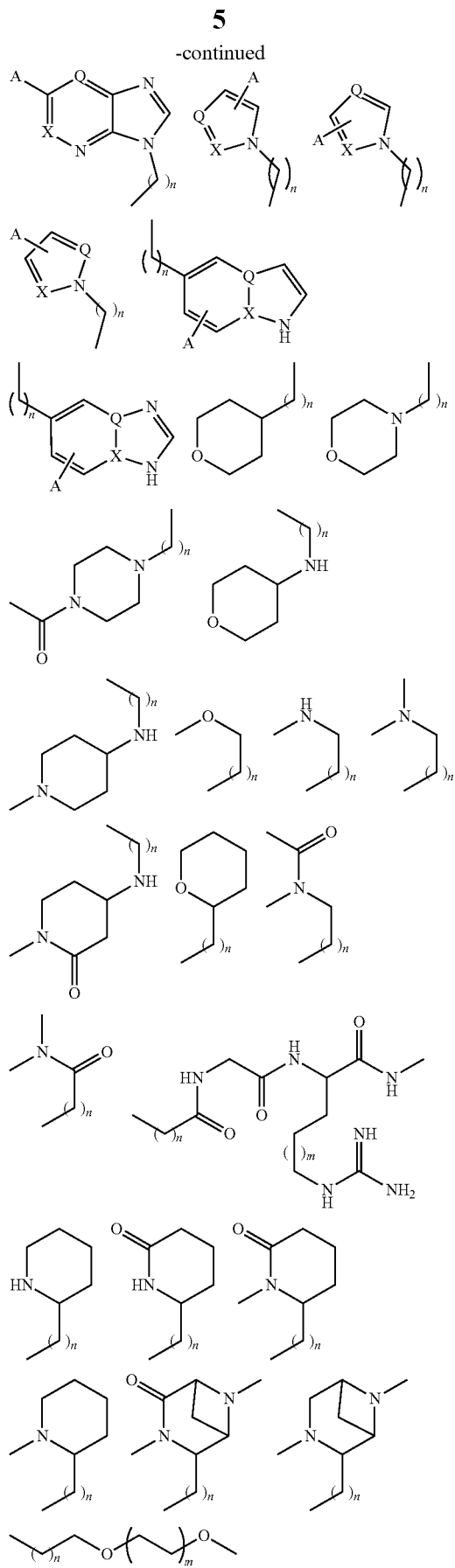
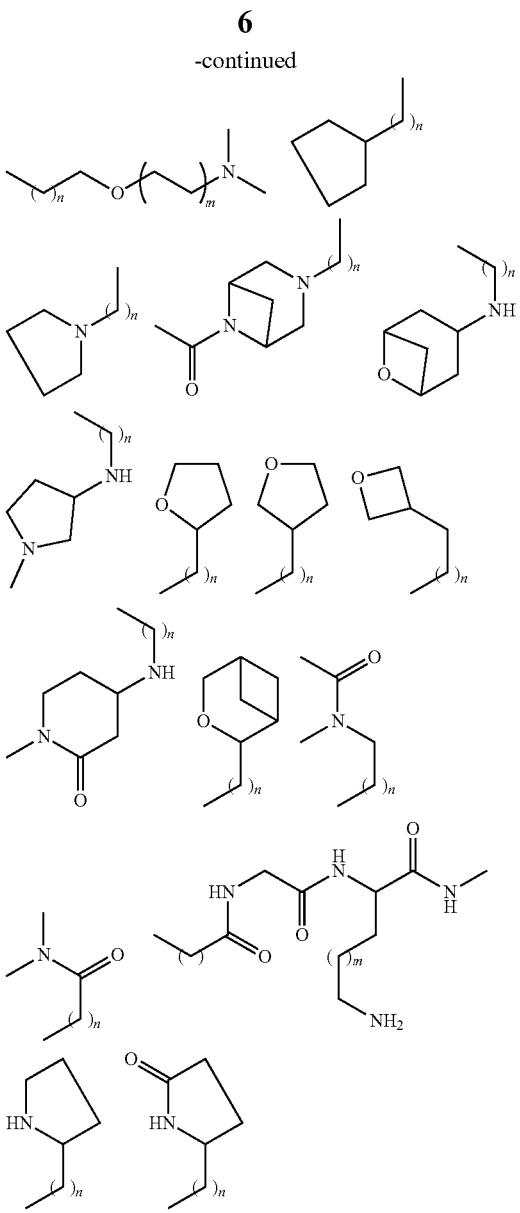

Where:

A is —H, —Me, —F, —Cl, —Br, —I, —$CF_3$, —$CHF_2$, —$CH_2F$, —CN, —OH, —OMe, —SMe, —SOMe, —$SO_2Me$, —$NH_2$, —NHMe, —$NO_2$, —CHO, —$COCH_3$, —$CO_2CH_3$, —$OCF_3$, —$OCHF_2$, —$OCH_2F$, —$SCF_3$, —$SCHF_2$, —$SCH_2F$, —$CONH_2$, —$CONHCH_3$, —$CON(CH_3)_2$, —$CSNH_2$, —$SONH_2$, —$SO_2NH_2$, —$SONHNH_2$ . . .

—X and Q are N or CH.

n=0, 1, 2, 3 or 4; m=0, 1, 2, 3 or 4

$R_2$, $R_3$, $R_4$ and $R_5$ is a CONH—, O-, CH2—, HN—, CC— S-linker connected to a protein binder;

$R_7$ is selected from a group consisting of —SH, —$NH_2$, —OH, SSY, SCOY, OCOY where Y is described above.

In other preferred embodiments, a Rpn11 binding partner is partner is denoted by the formula II

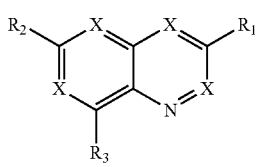
X=CH or N
R$_1$, and R$_2$ is selected from a group consisting of —CO—Z, OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$—COO—,
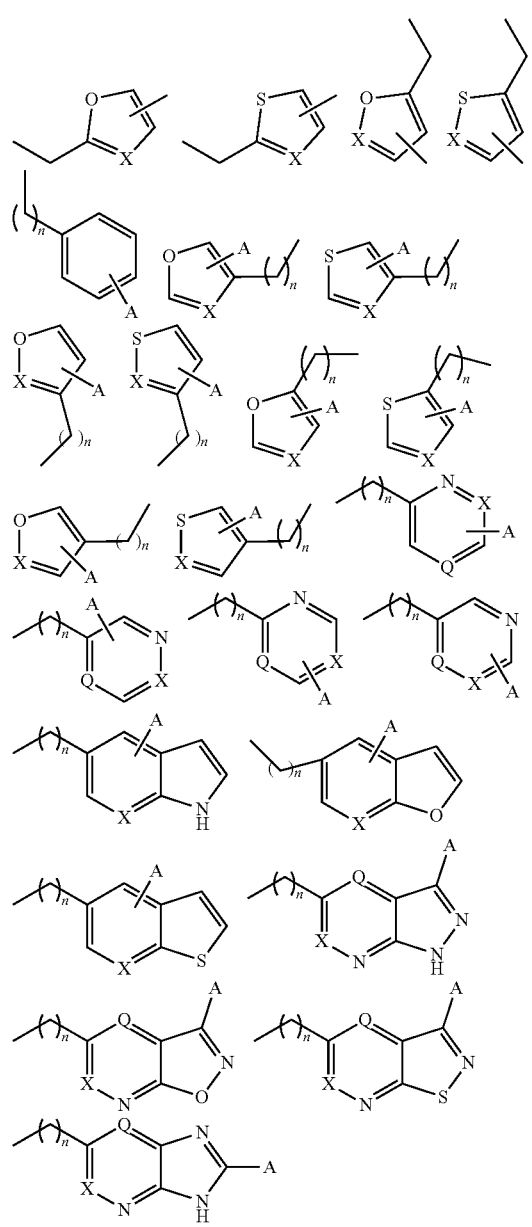
-continued
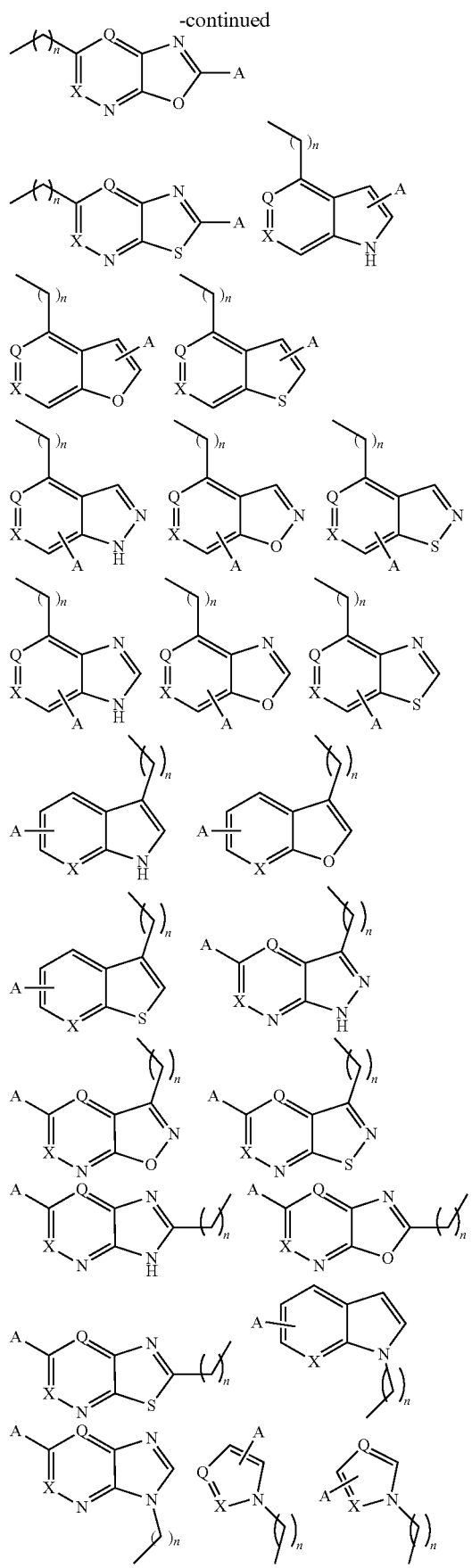

-continued

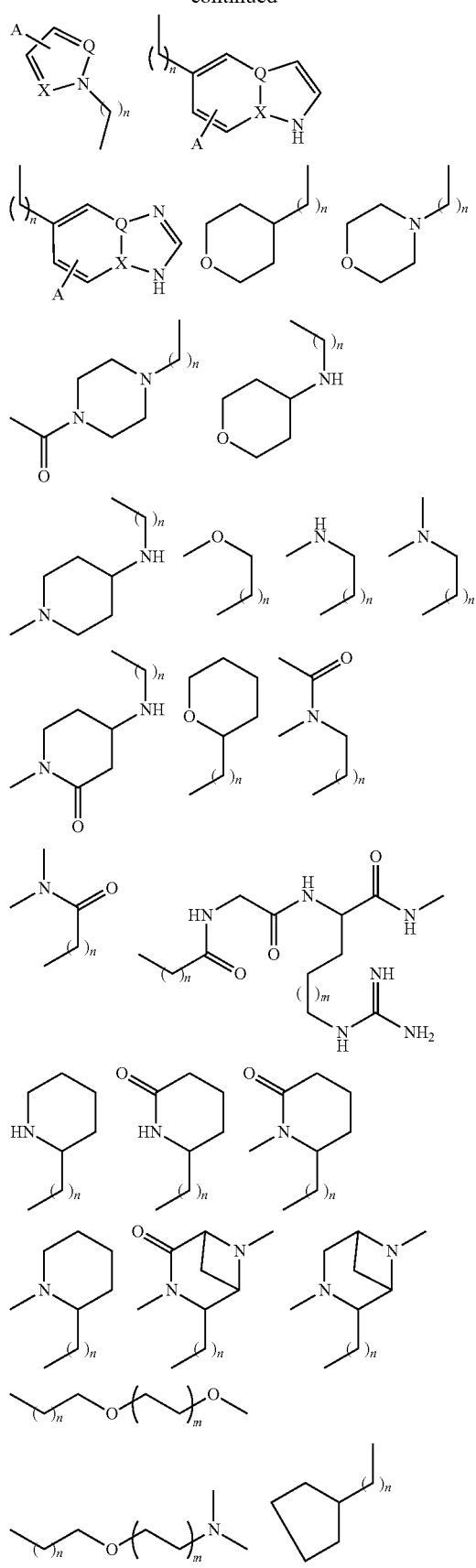

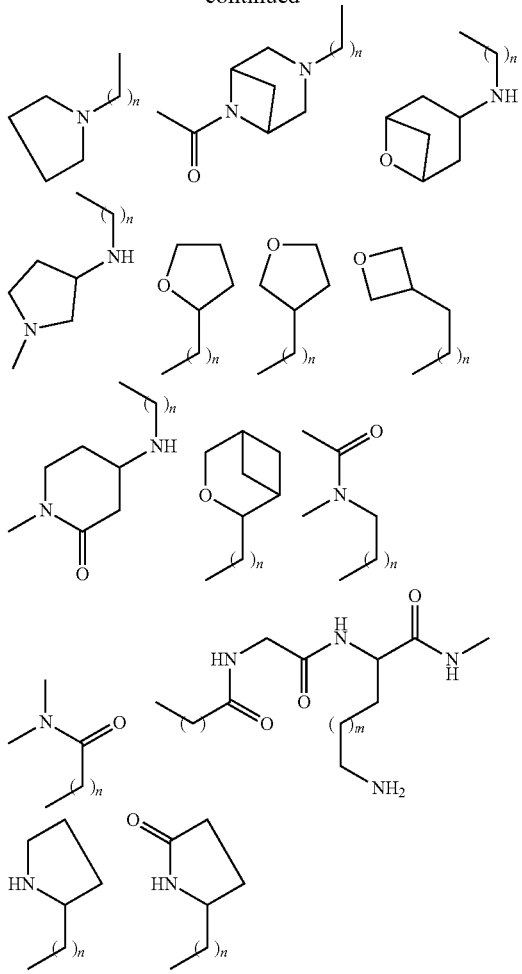

Where:
—A is —H, —Me, —Cl, —F, —Br, —I, —CF$_3$, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
—X and Q are N or CH.
n=0, 1, 2, 3 or 4; m=0, 1, 2, 3 or 4.
R$_1$, and R2 is a CONH—, O-, CH2—, HN—, CC— S-linker connected to a protein binder;
R3 is selected from a group consisting of —SH, —NH$_2$, —OH, —SSY, —SCOY, —OCOY where Y is described above.

In other preferred embodiments, a Rpn11 binding partner is partner is denoted by the formula III

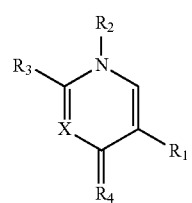

R1 is selected from a group consisting of —SH, —NH$_2$, —OH, —SSY, —SCOY, —OCOY where Y is described above.
R2 and R3 is selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CN, —OH, —OMe, —SMe, —SOMe, —SO$_2$Me, —NH$_2$, —NHMe, NO$_2$, CHO; Z is selected from a group consisting of —NH$_2$, —NHY, —OH, and —OY; Y is selected from a group consisting of —CH$_3$, —CH$_2$—COO—,
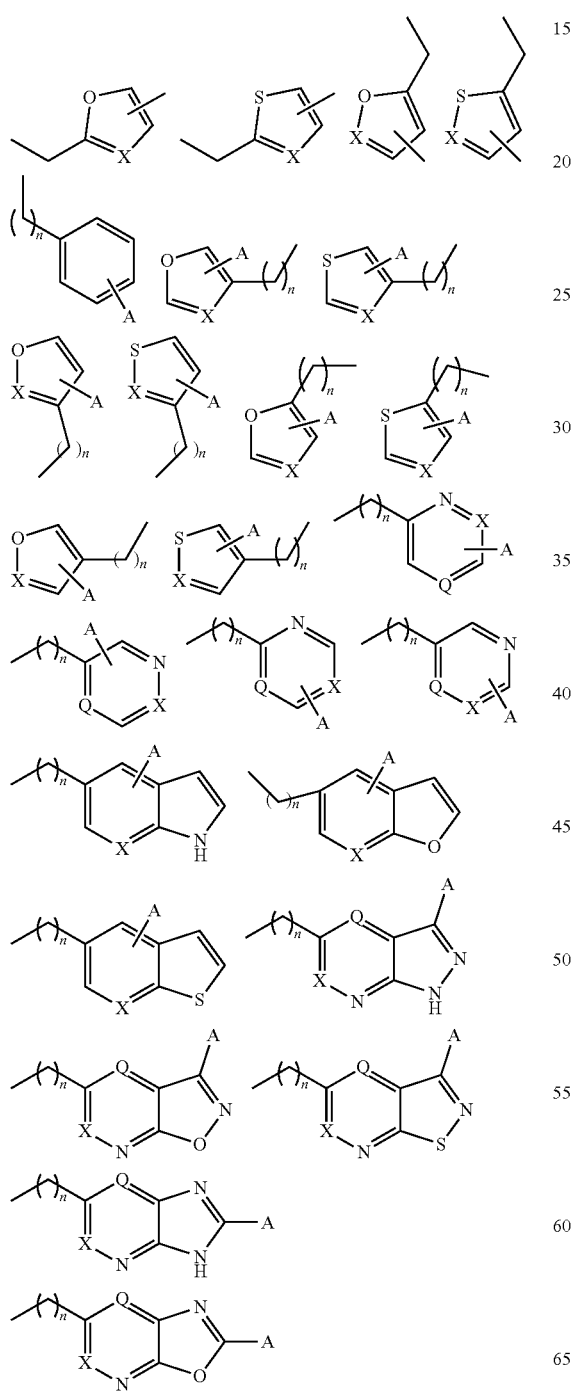
-continued
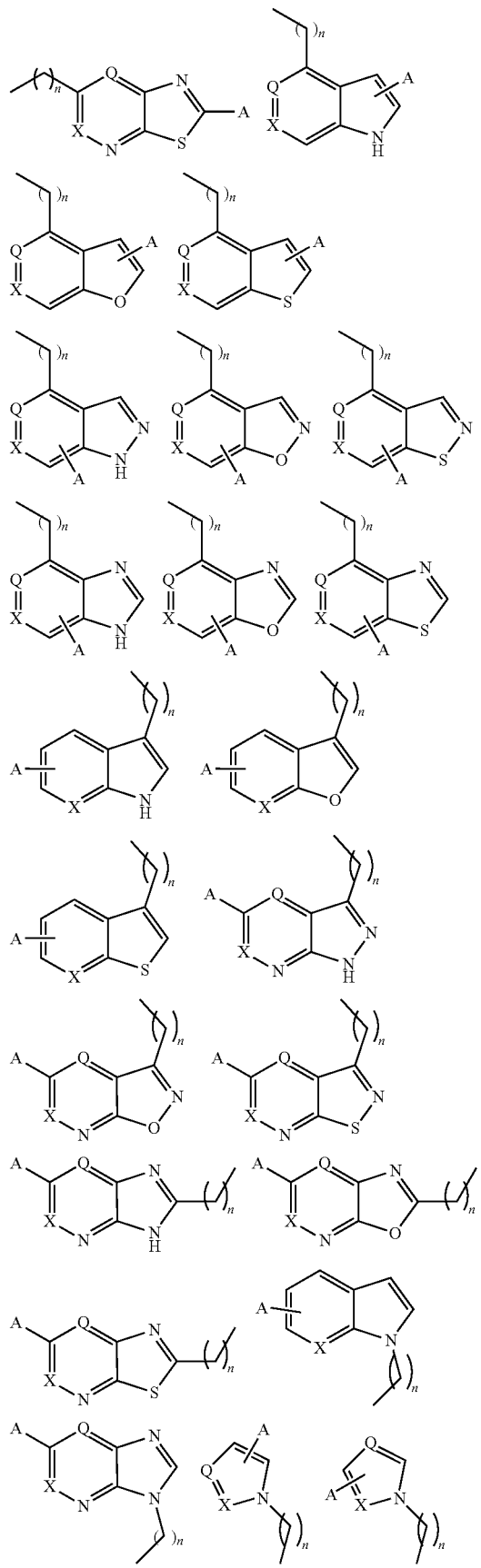

-continued

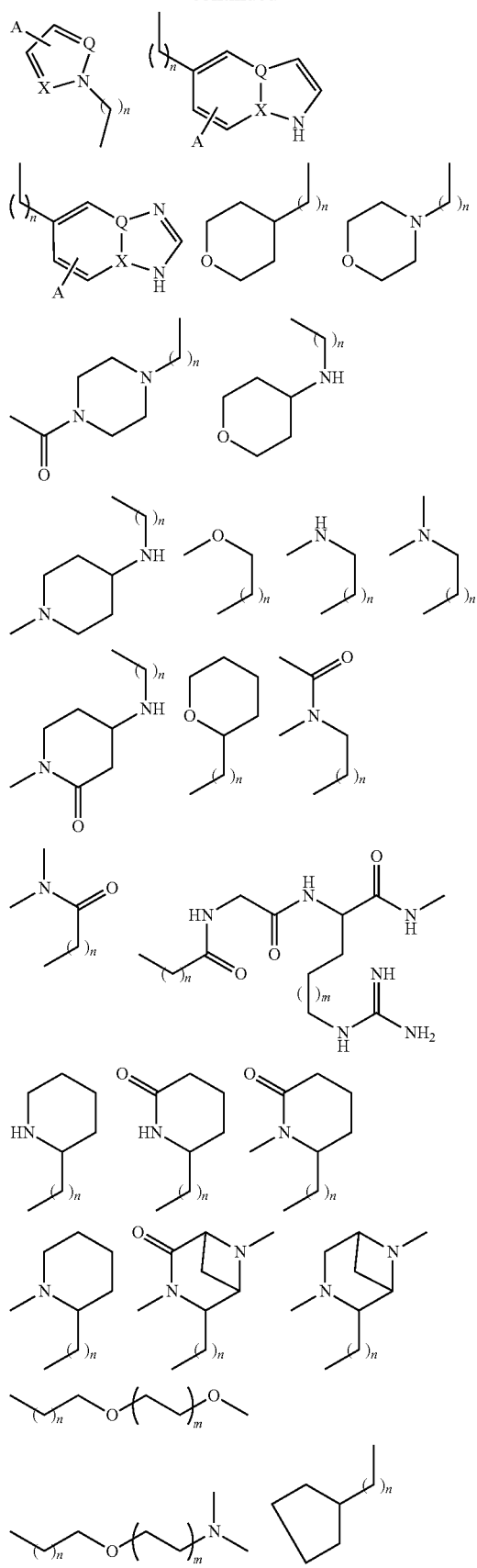

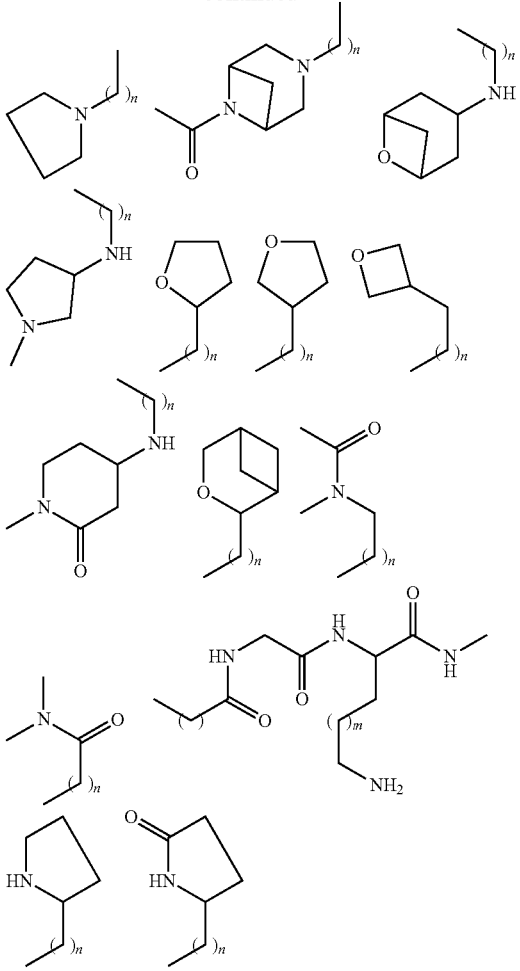

Where:
—A is —H, —Me, —Cl, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
—X and Q are N or CH.
n=0, 1, 2, 3 or 4; m=0, 1, 2, 3 or 4
R$_2$, and R3 is a CONH—, O—, CH2—, HN—, CC— S-linker connected to a protein binder;
R$_4$ is O, S, NH.
In other preferred embodiments, a Rpn11 binding partner is partner is denoted by the formula IV

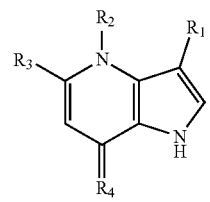

R$_1$, R$_2$ and R$_3$ are selected from a group consisting of —CO—Z, —OCH$_3$, —CF$_3$, —COOH, —CH$_2$NH$_2$, —CH₃, —H, —F, —Cl, —Br, —CF₃, —CHF₂, —CH₂F, —CN, —OH, —OMe, —SMe, —SOMe, —SO₂Me, —NH₂, —NHMe, NO₂, CHO; Z is selected from a group consisting of —NH₂, —NHY, —OH, and —OY; Y is selected from a group consisting of —CH₃, —CH₂—COO—,
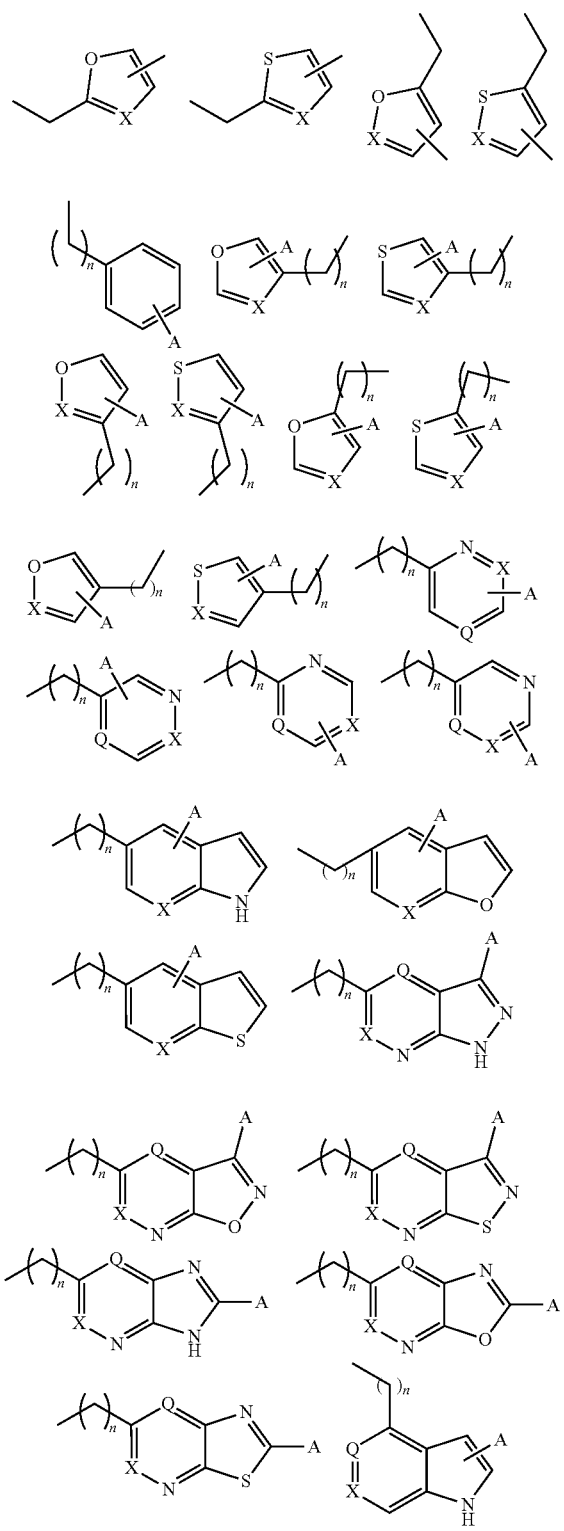
-continued
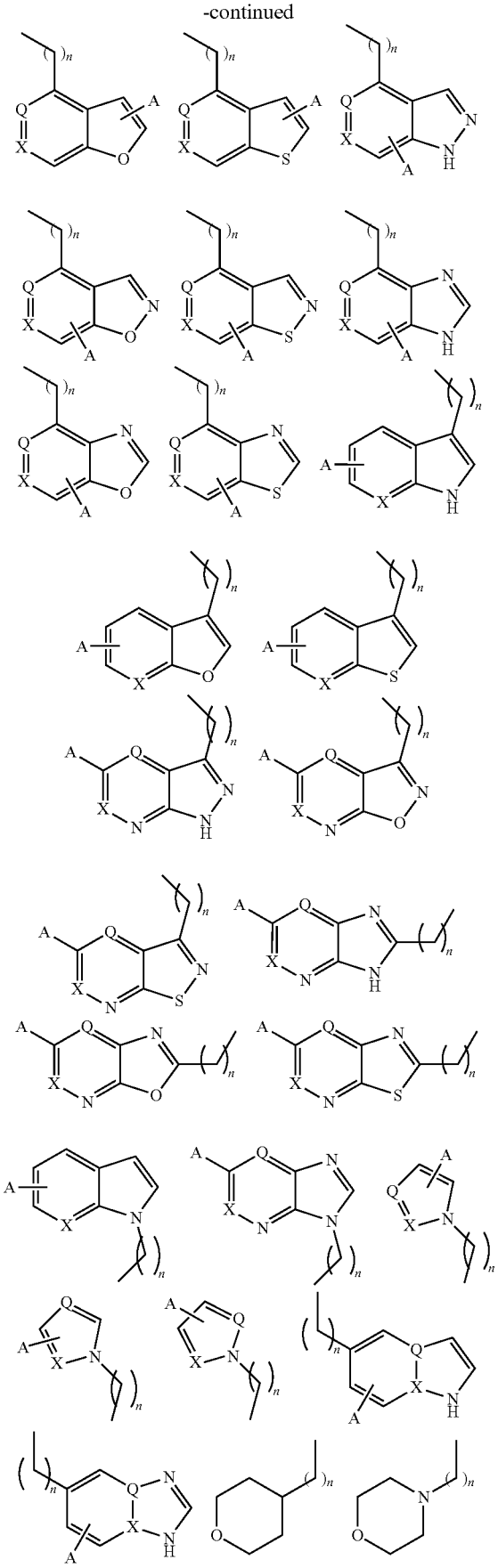

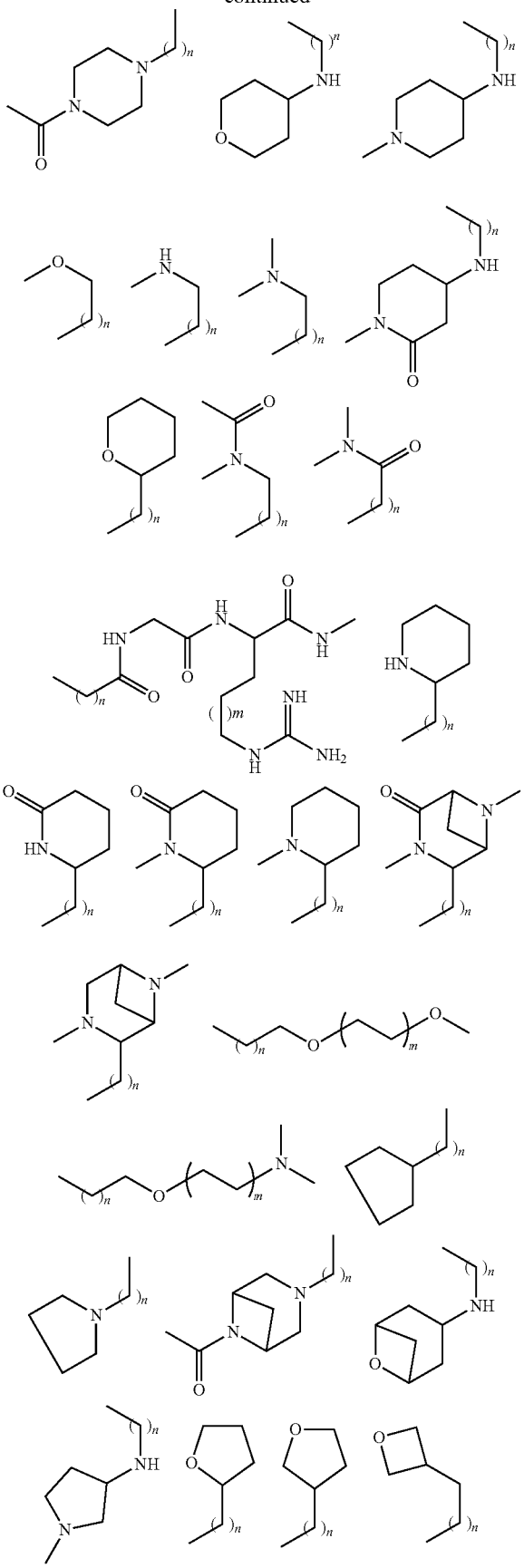

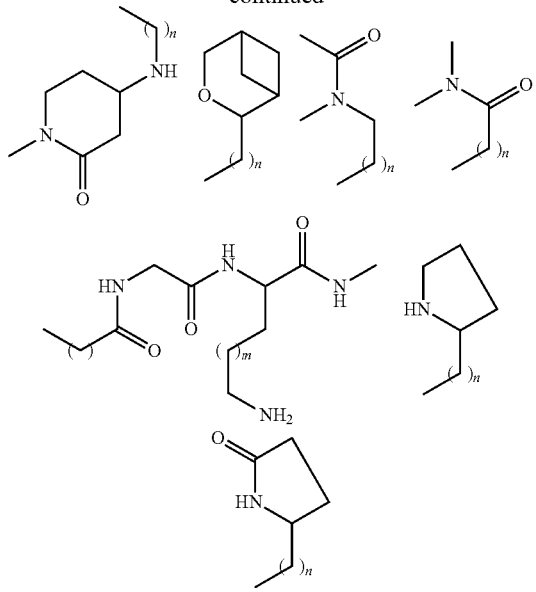

Where:
—A is —H, —Me, —F, —Br, —I, —CF$_3$, —CHF$_2$, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.

n=0, 1, 2, 3 or 4; m=0, 1, 2, 3 or 4

R1, R$_2$, and R3 is a CONH—, O—, CH2_13 , HN—, CC— S-linker connected to a protein binder;

R4 is O, S, NH, NCOY.

In other preferred embodiments, a Rpn11 binding partner is partner is denoted by the formula V

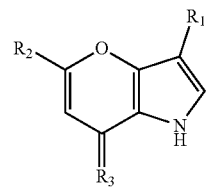

R1 and R2 are selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$—COO—,

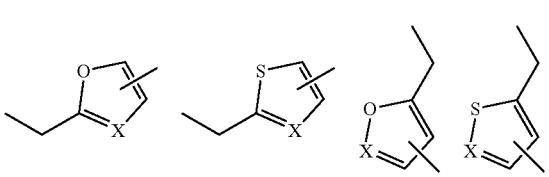

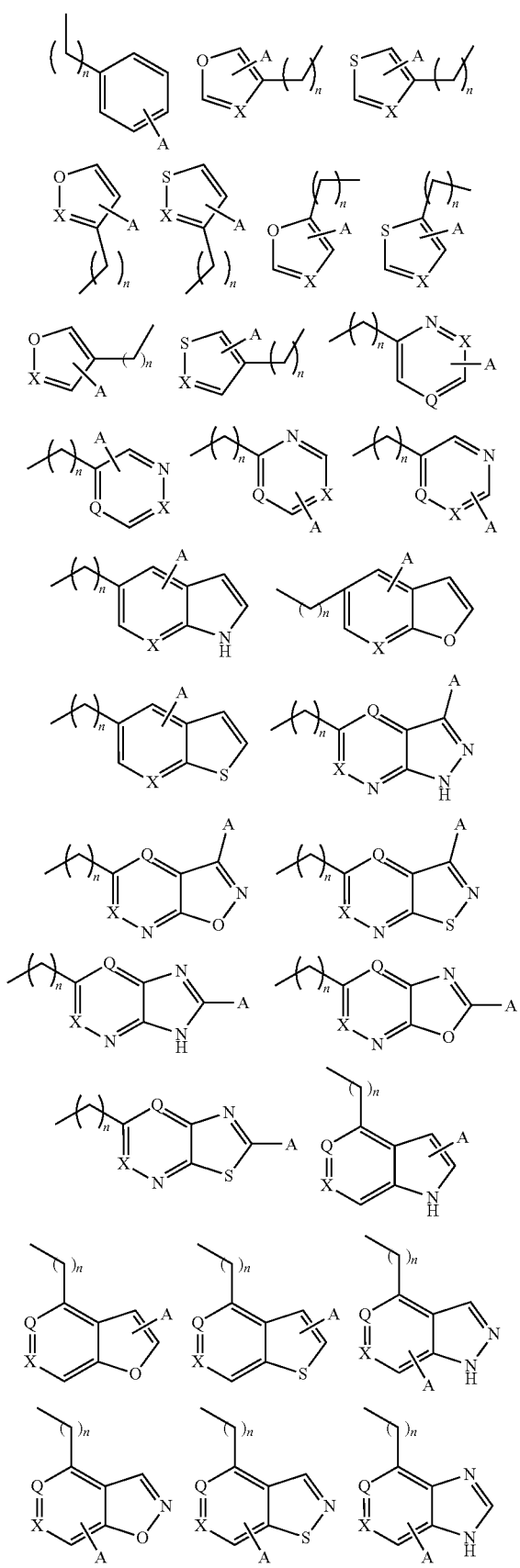
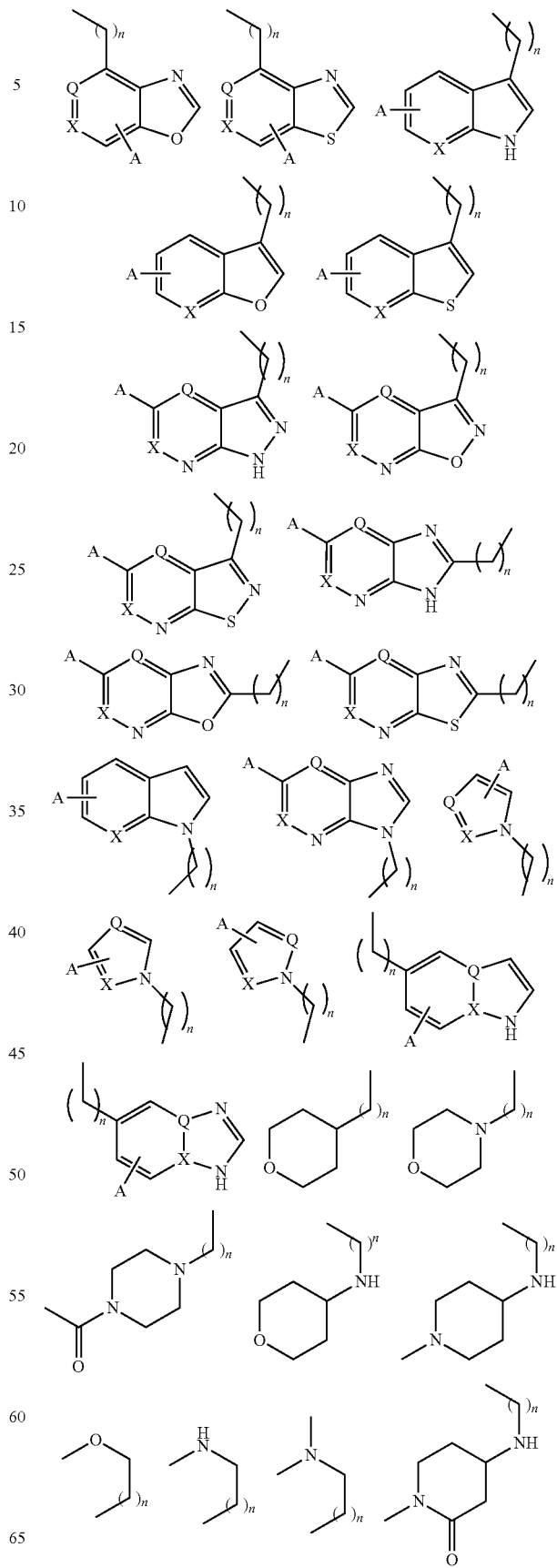

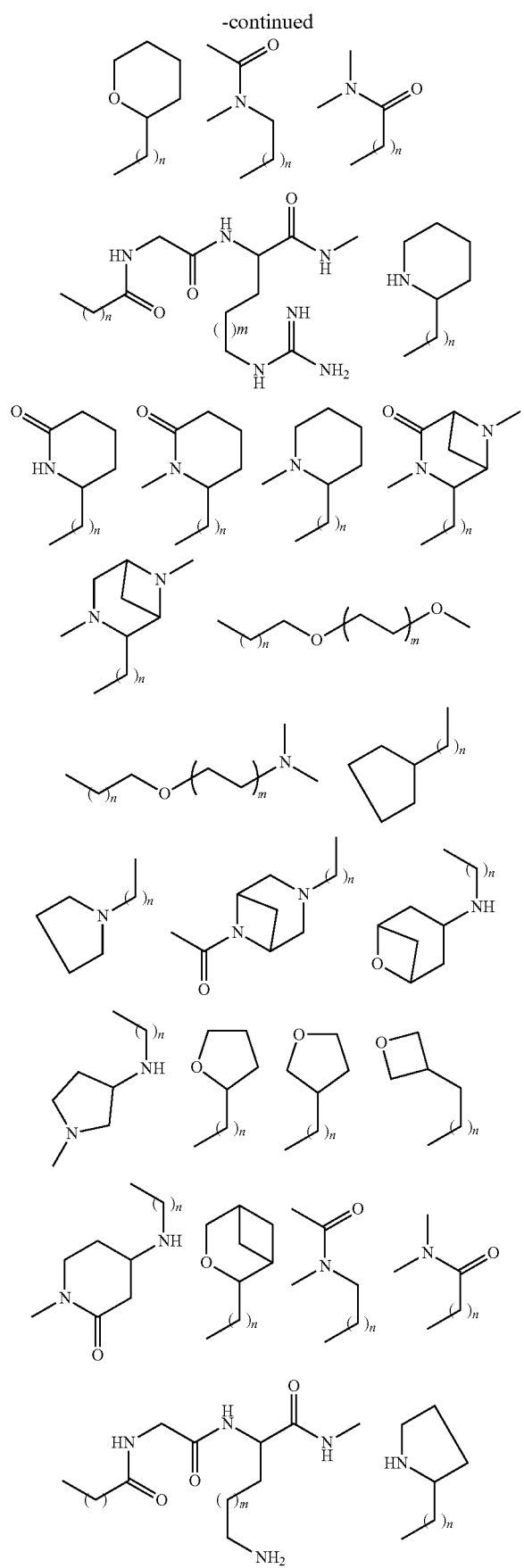

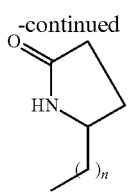

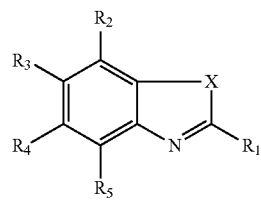

Where:
- A is —H, —Me, —Cl, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
- X and Q are N or CH.
- n=0, 1, 2, 3 or 4; m=0, 1, 2, 3 or 4
- R1, and R$_2$, is a CONH—, O-, CH2—, HN—, CC— S-linker connected to a protein binder; R3 is O, S, NH, NCOY.

In other preferred embodiments, a Rpn11 binding partner is partner is denoted by the formula VI

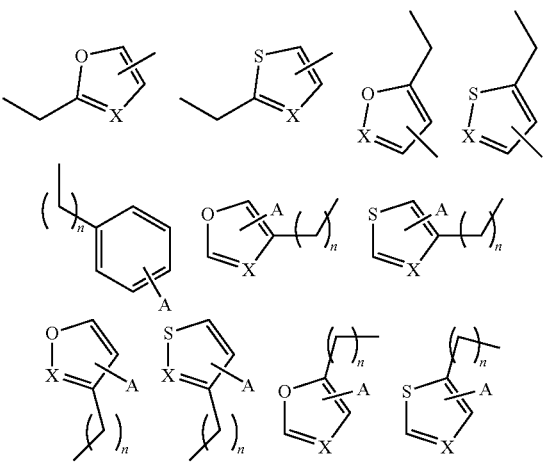

X=NH, O, S, CH2
R1 and R4 are preferentially —H, but also —Me, —F, —Cl, —Br, —I, —CF$_3$, —CHF$_2$, —CH$_2$F, —CN, —OMe, —SMe, —SOMe, —SO$_2$Me —NH$_2$, —NHMe, —NO$_2$, —CHO . . .
R$_2$ and R$_3$ is selected from a group consisting of —CO—Z, OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$—COO—,

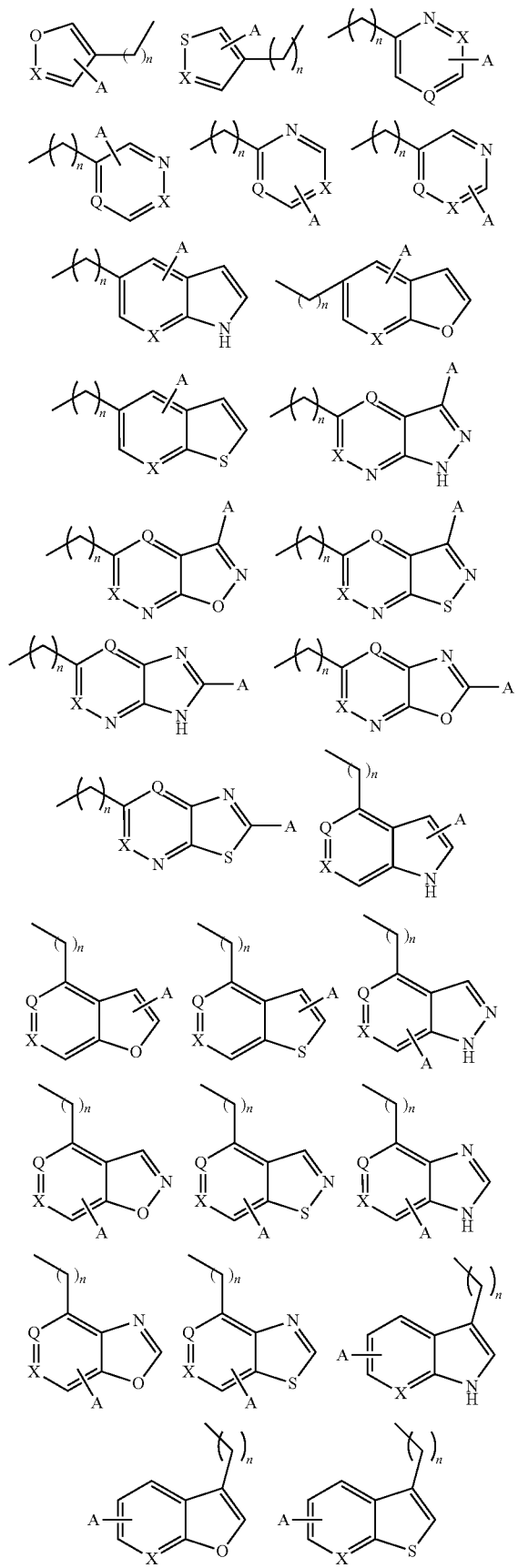
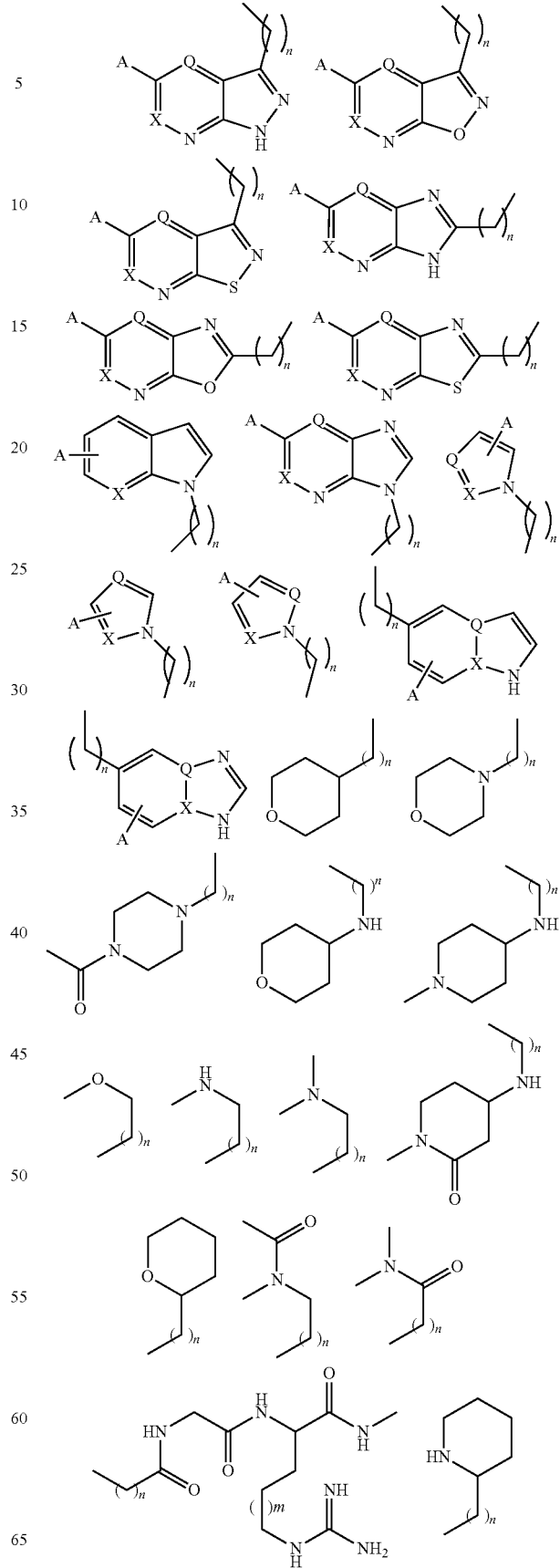

-continued

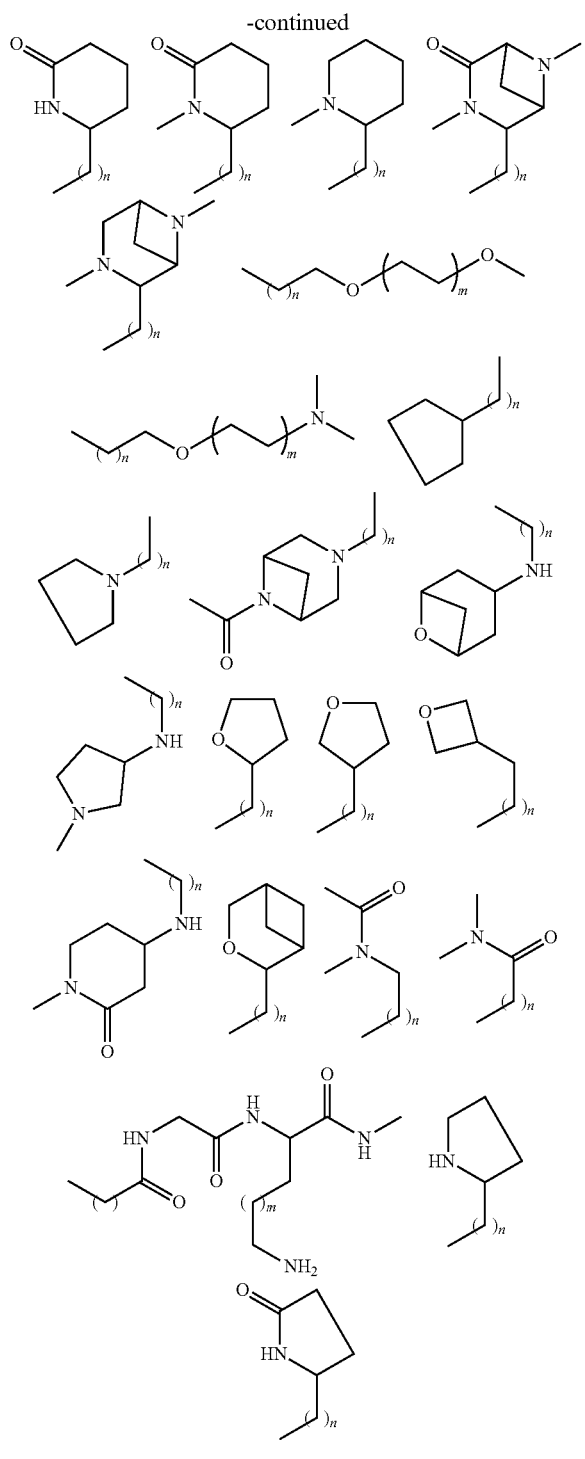

Where:
—A is —H, —Me, —Cl, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$
—X and Q are N or CH.
n=0, 1, 2, 3 or 4; m=0, 1, 2, 3 or 4
R$_2$ and R$_3$ is a CONH—, O—, CH2—, HN—, CC—
S-linker connected to a protein binder;

R5 is selected from a group consisting of —SH, —NH$_2$, —OH, SSY, SCOY, OCOY where Y is described above.

In other preferred embodiments, a Rpn11 binding partner is partner is denoted by the formula VII

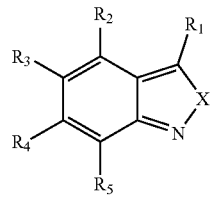

X=NH, O, S, CH$_2$
R$_1$, R$_2$ and R$_3$ is selected from a group consisting of —CO—Z, OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$—COO—,

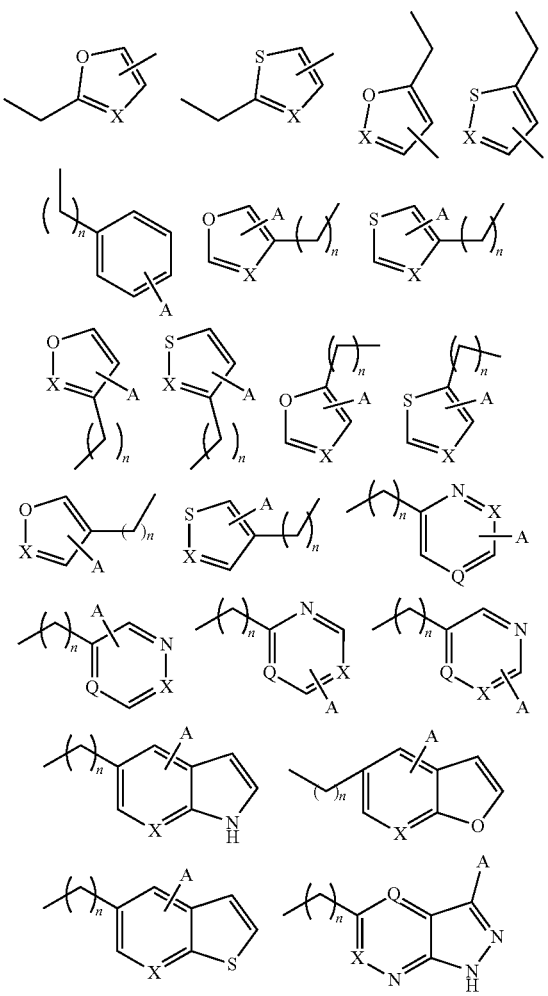

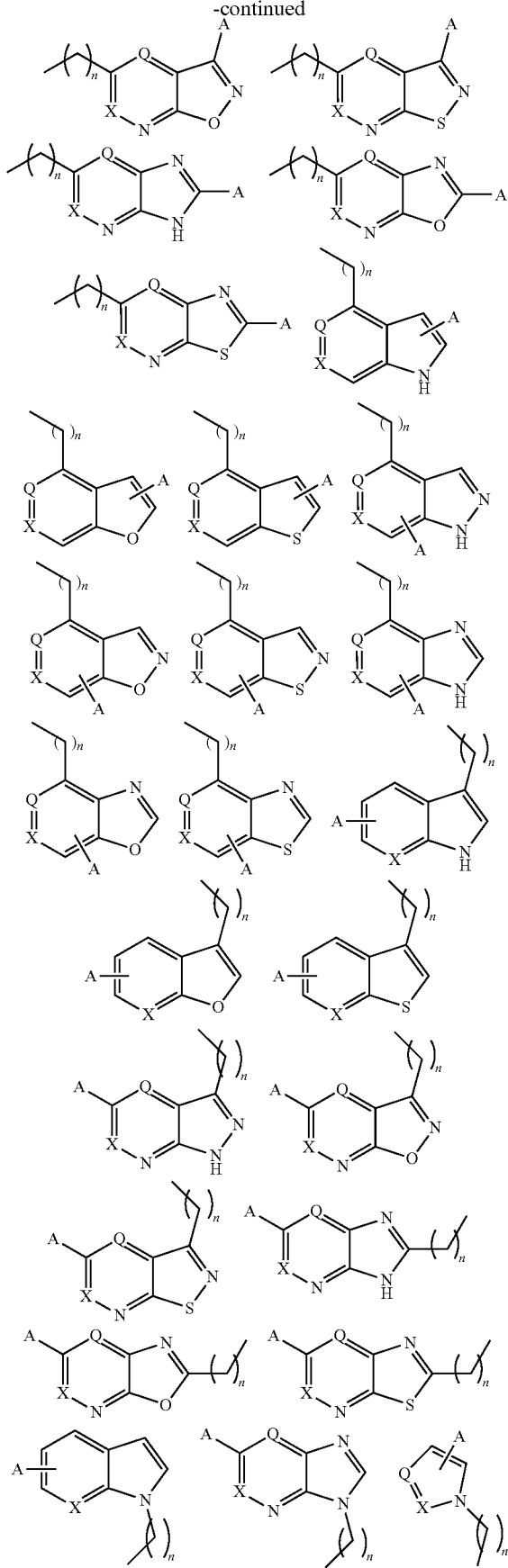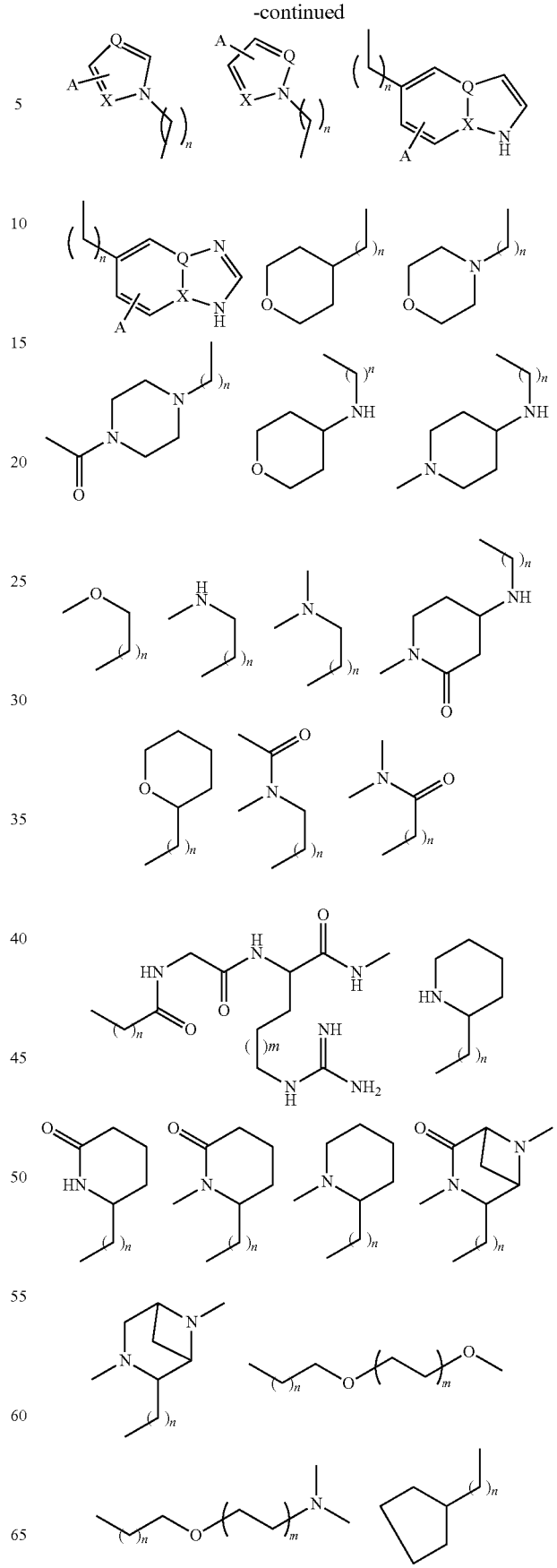

-continued

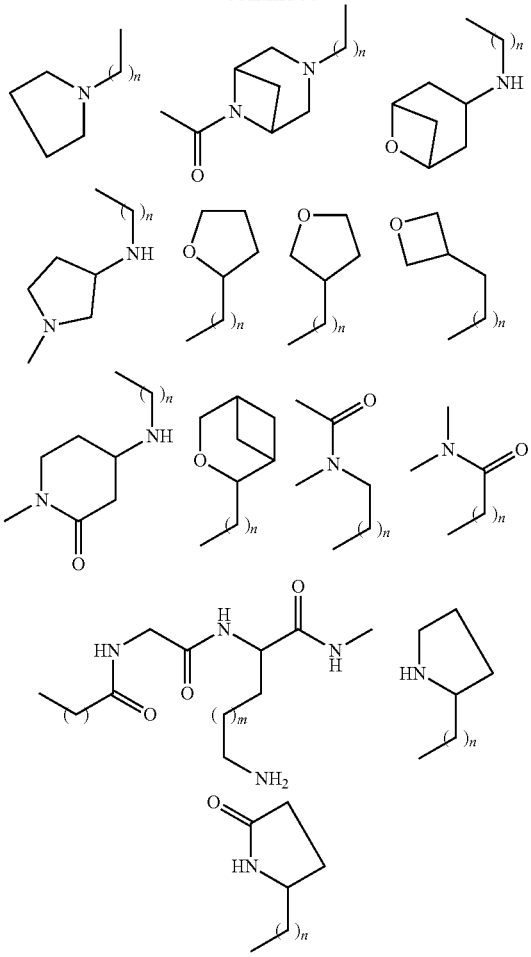

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
—X and Q are N or CH.
n=0, 1, 2, 3 or 4; m=0, 1, 2, 3 or 4
R1, R2, and R3 is a CONH—, O—, CH2—, HN—, CC— S-linker connected to a protein binder;
R4 is are preferentially —H, but also Me, F, Cl, Br, CF$_3$, CHF$_2$, CH$_2$F, CN, OMe, SMe, SOMe, SO$_2$Me NH$_2$, NHMe, NO$_2$, CHO,
R5 is selected from a group consisting of —SH, —NH$_2$, —OH, SSY, SCOY, OCOY where Y is described above.

In other preferred embodiments, a Rpn11 binding partner is partner is denoted by the formula VIII R1 is selected from a group consisting of —SH, —NH$_2$, —OH, —SSY, —SCOY, —OCOY, NHCOY where Y is described above.
R4 is selected from a group consisting of —S, —NH, —O,
R2 and R3 is selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, NO$_2$, CHO; Z is selected from a group consisting of —NH$_2$, —NHY, —OH, and —OY; Y is selected from a group consisting of —CH$_3$, —CH$_2$—COO—,

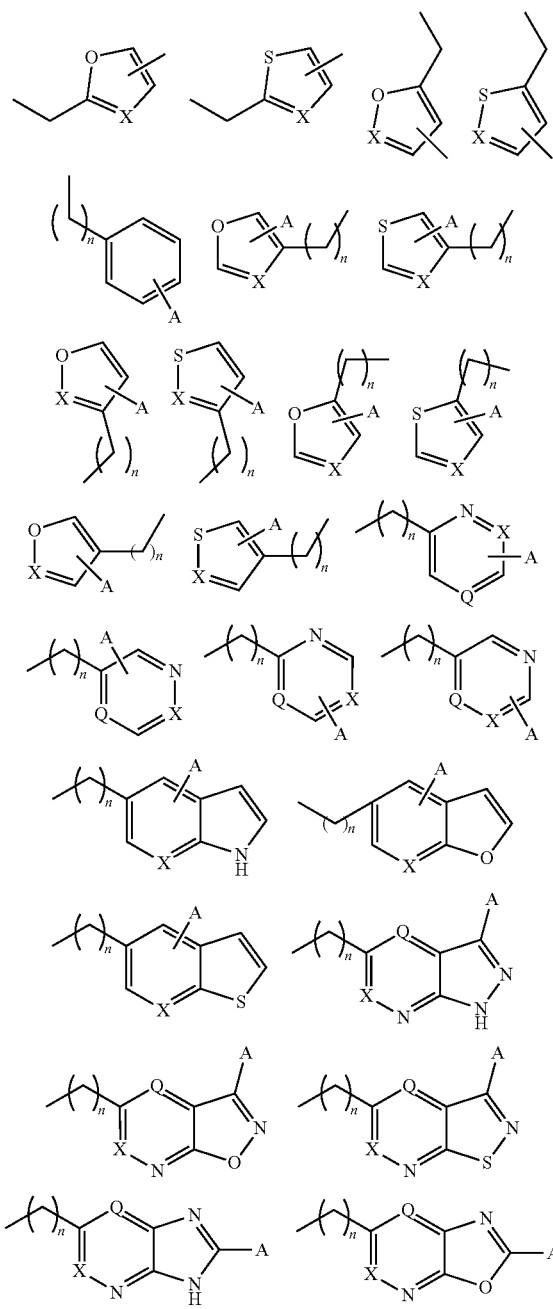

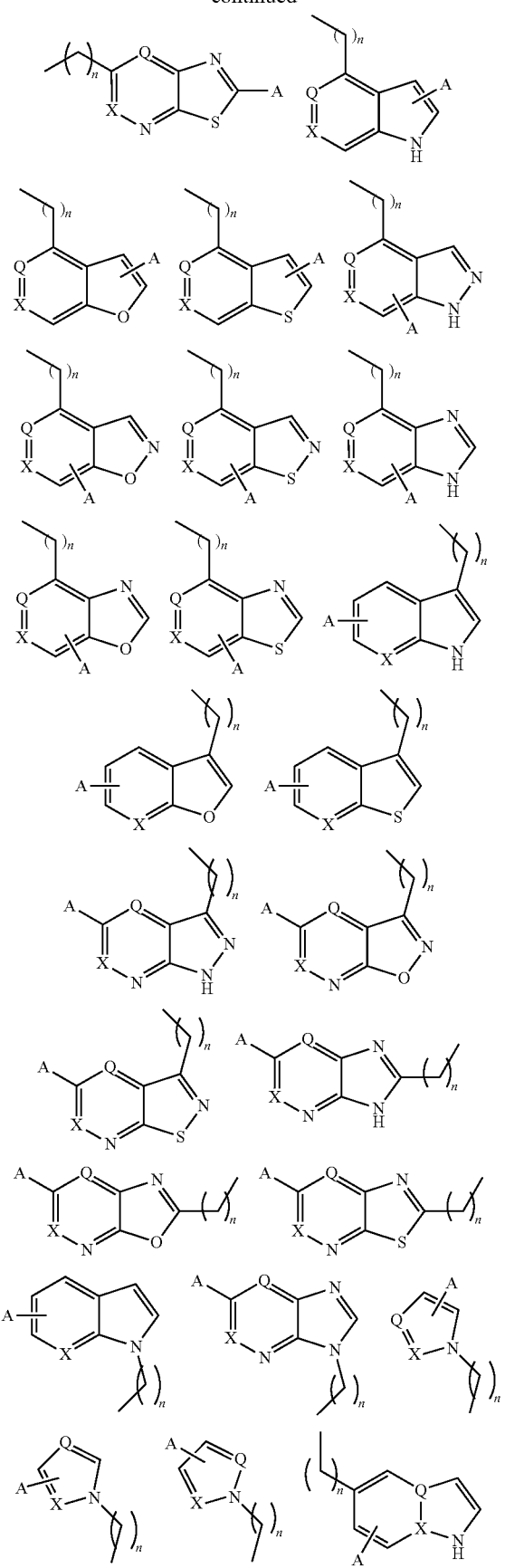
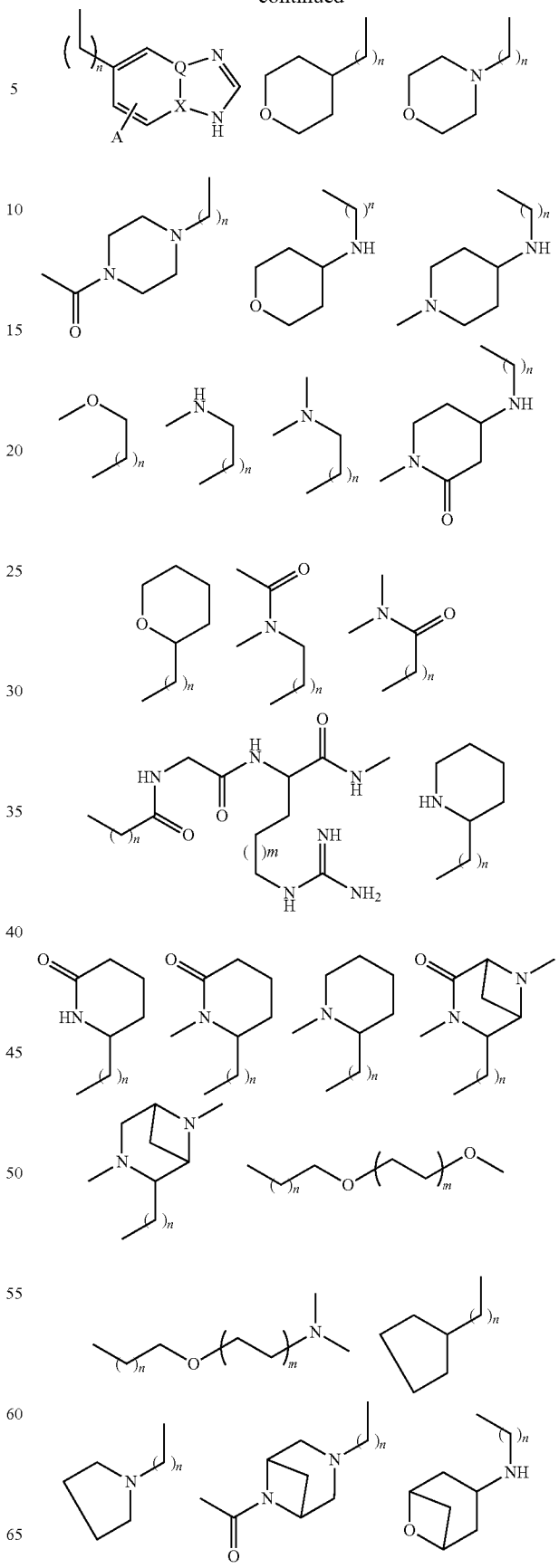

-continued

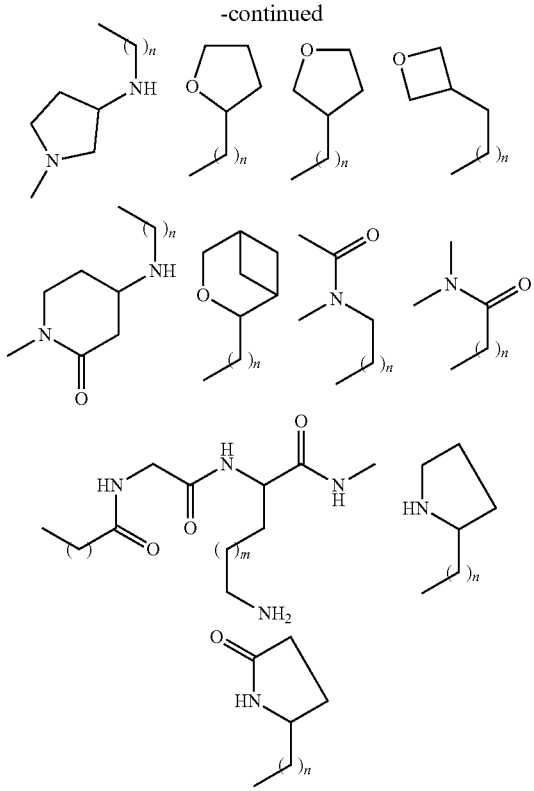

Where:
—A is —H, —Me, —Cl, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
—X and Q are N or CH.
n=0, 1, 2, 3 or 4; m=0, 1, 2, 3 or 4 and R$_4$ is selected from a group consisting of —S, —NH, —O.

The invention also encompasses a compound of formula (IX):

R11L-(CL)-TPL      (IX), wherein — refers to a covalent bond;
wherein R11L is a ligand that binds Rpn11,
wherein CL is a covalent linker
wherein TPL is a ligand that binds to a target protein.

A R11L may be selected from the group of Rpn11 ligands provided in Table 1. Preferably, the Rpn11 ligand binds to Rpn11 with an affinity of at least 10 nM. Preferably, the Rpn11 ligand binds to Rpn11 with a Kd of less than 1 μM. A Rpn11 ligand may be selected from the group of Rpn11 binding molecules provided in Table 1.

Preferably, a target protein ligand may be selected from the group consisting of: kinase inhibitors, phosphatase inhibitors, compounds targeting BET bromodomain-containing proteins, HDM2/MDM2 inhibitors, heat shock protein 90 inhibitors, HDAC inhibitors, human lysine methyltransferase inhibitors and antibodies. In other preferred embodiments, a linker may be a polyethylene glycol (PEG) linker, a hydrocarbon linker, an akyl-ether linker, or a combined PEG, alkyl linker.

The invention also encompasses a compound of the formula (X):

R11L-A-(CL)-B-TPL      (X), wherein — refers to a covalent bond;
wherein R11L is a ligand that binds Rpn11,
wherein CL is a covalent linker having a first end A and a second end B that are different, wherein A and B are, independently, amide, oxime, keto, carbon, ether, ester, or carbamate;
wherein TPL is a ligand that binds to a target protein, and wherein R$_{11}$L is covalently linked to A and TPL is covalently linked to B.

Preferably, a target protein ligand may be selected from the group consisting of: kinase inhibitors, phosphatase inhibitors, compounds targeting BET bromodomain-containing proteins, HDM2/MDM2 inhibitors, heat shock protein 90 inhibitors, HDAC inhibitors, human lysine methyltransferase inhibitors and antibodies. In other preferred embodiments, a linker may be a polyethylene glycol (PEG) linker, a hydrocarbon linker, an akyl-ether linker, or a combined PEG, alkyl linker.

The invention also encompasses a compound of formula XI:

R$_{11}$L-(CL)-Rx      (XI), wherein — refers to a covalent bond;
wherein R11L is a ligand that binds Rpn11,
wherein CL is a covalent linker ending in Rx,
wherein Rx is able to form a covalent chemical bond with a ligand, and
wherein Rx is not PEG.

Preferably, a R$_{11}$L may be selected from the group of Rpn11 ligands provided in Table 1. Preferably, the Rpn11 ligand binds to Rpn11 with an affinity of at least 10 nM. Preferably, the Rpn11 ligand binds to Rpn11 with a Kd of less than 1 μM. A Rpn11 ligand may be selected from the group of Rpn11 binding molecules provided in Table 1.

Preferably, a target protein ligand may be selected from the group consisting of: kinase inhibitors, phosphatase inhibitors, compounds targeting BET bromodomain-containing proteins, HDM2/MDM2 inhibitors, heat shock protein 90 inhibitors, HDAC inhibitors, human lysine methyltransferase inhibitors and antibodies. In other preferred embodiments, a linker may be a polyethylene glycol (PEG) linker, a hydrocarbon linker, an alkyl-ether linker, or a combined PEG, alkyl linker. Preferably, a linker has a first end that is an oxime. Preferably, a linker has a second end that is an amine.

Preferably, a R$_{11}$L is denoted by the formula I

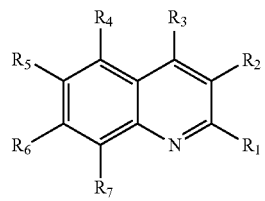

R1 and R6 are preferentially —H, but also —Me, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO . . .
R$_2$, R$_3$, R$_4$ and R5 is selected from a group consisting of —CO—Z, OCH$_3$, —CF$_3$, —COOH, —CH$_2$NH$_2$, —CH₃, —H, —Me, —F, —Cl, —Br, —CF₃, —CHF₂, —CH₂F, —CN, —OH, —OMe, —SMe, —SOMe, —SO₂Me, —NH₂, —NHMe, —NMe₂, NO₂, CHO . . . ; Z is selected from a group consisting of —NH₂, —NHY, —OH, and —OY; Y is selected from a group consisting of —CH₃, —CH₂COO—,
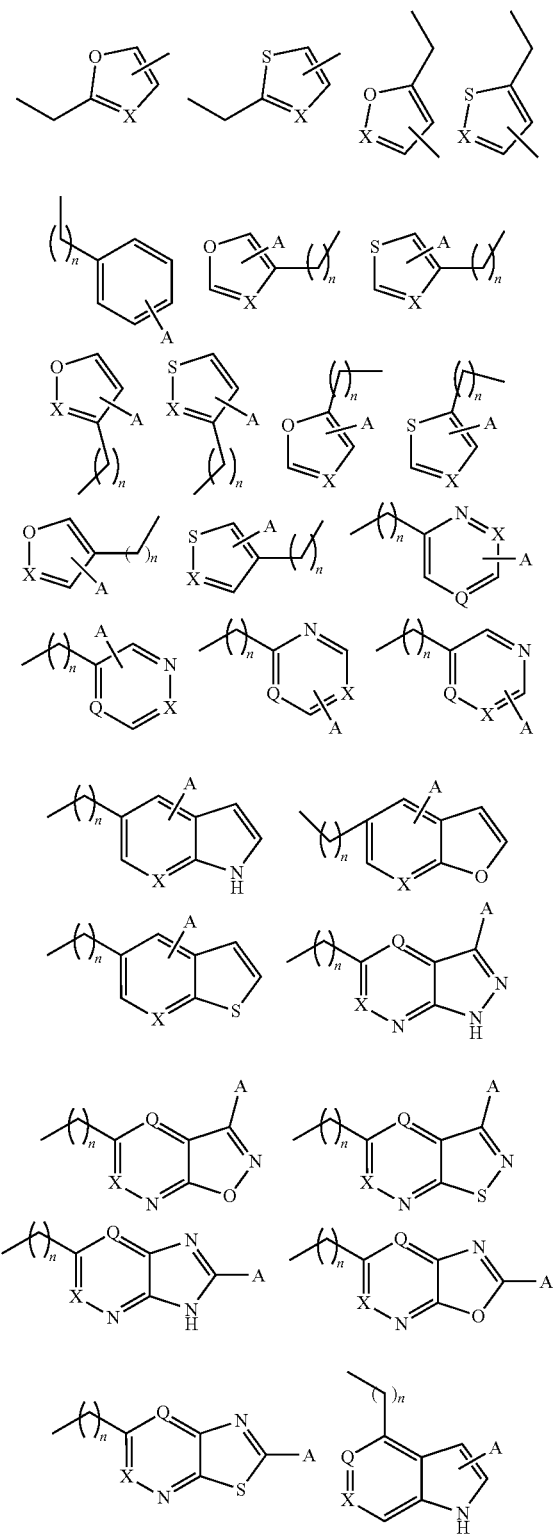
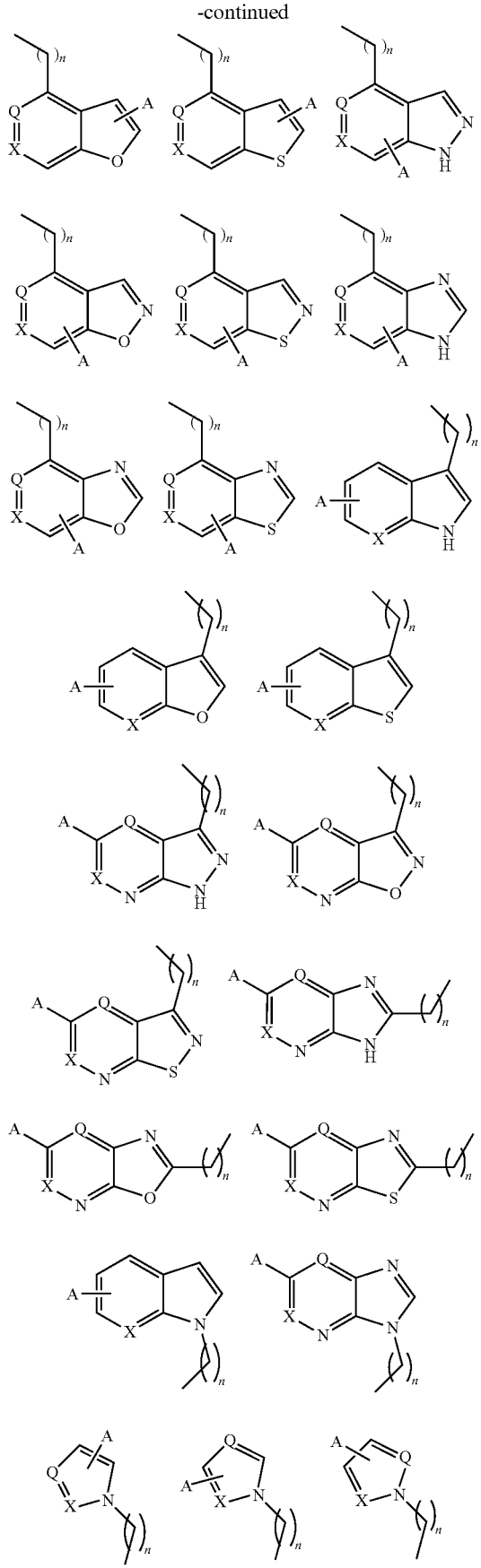

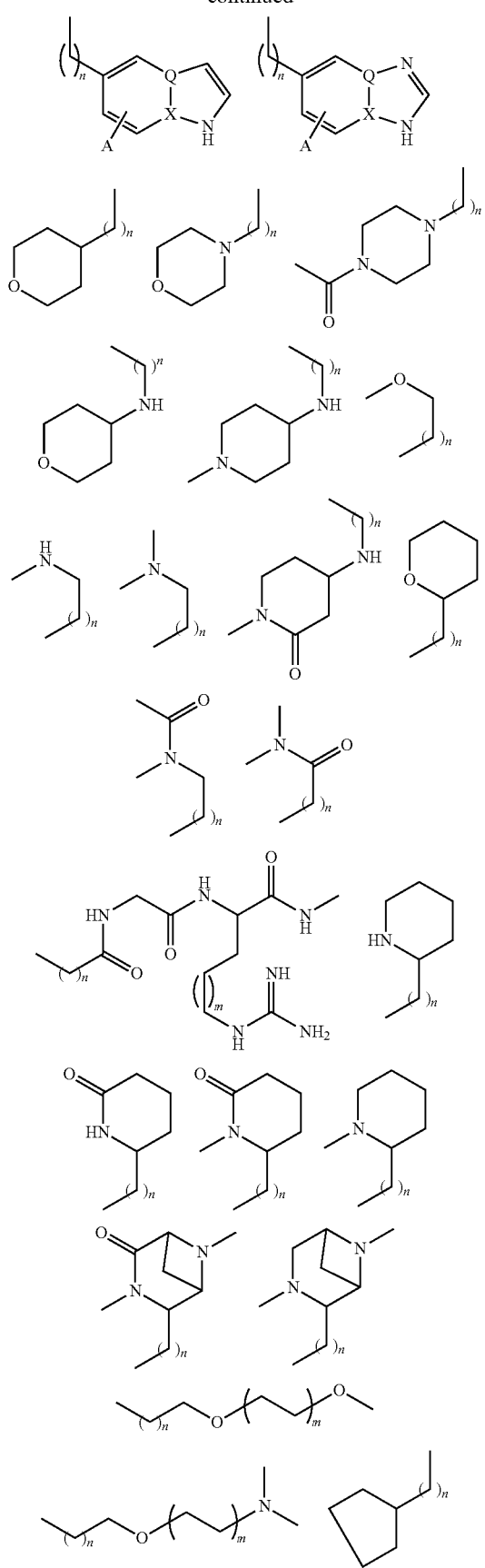
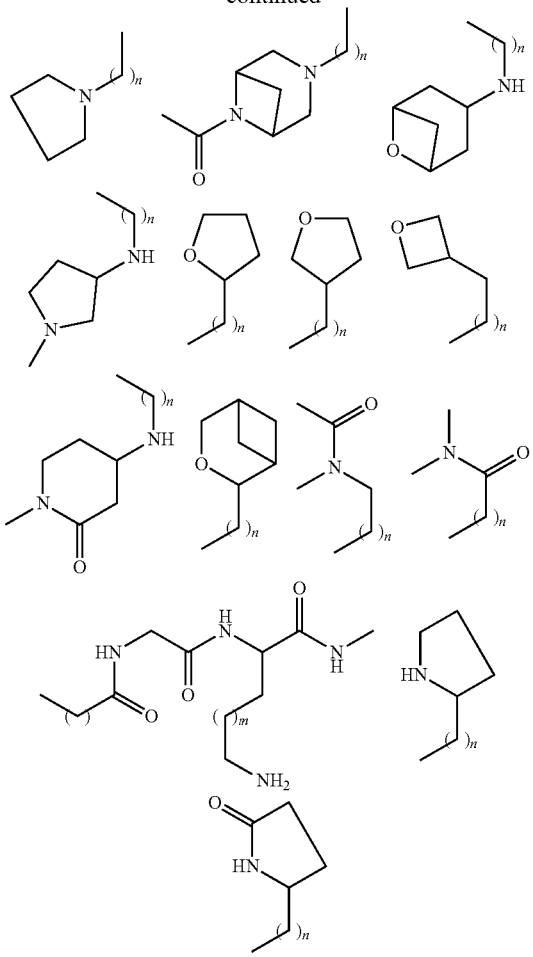

Where:
- —A is —H, —Me, —F, —Cl, —Br, —I, —$CF_3$, —$CHF_2$, —$CH_2F$, —CN, —OH, —OMe, —SMe, —SOMe, —$SO_2Me$, —$NH_2$, —NHMe, —$NMe_2$, —$NO_2$, —CHO, —$COCH_3$, —$CO_2CH_3$, —$OCF_3$, —$OCHF_2$, —$OCH_2F$, —$SCF_3$, —$SCHF_2$, —$SCH_2F$, —$CONH_2$, —$CONHCH_3$, —$CON(CH_3)_2$, —$CSNH_2$, —$SONH_2$, —$SO_2NH_2$, —$SONHNH_2$ . . .
- —X and Q are N or CH.
- n=0, 1, 2, 3 or 4; m=0, 1, 2, 3 or 4
- $R_2$, $R_3$, $R_4$ and R5 is a CONH—, O—, CH2—, HN—, CC— S-linker connected to a protein binder;
- R7 is selected from a group consisting of —SH, —$NH_2$, —OH, SSY, SCOY, OCOY where Y is described above.

Preferably, a $R_{11}L$ is denoted by the formula II

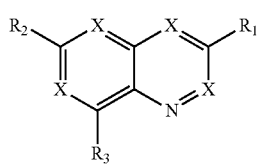

X=CH or N
$R_1$, and R2 is selected from a group consisting of —CO—Z, $OCH_3$, —$CF_3$, —COOH, —$CH_2NH_2$, —$CH_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,
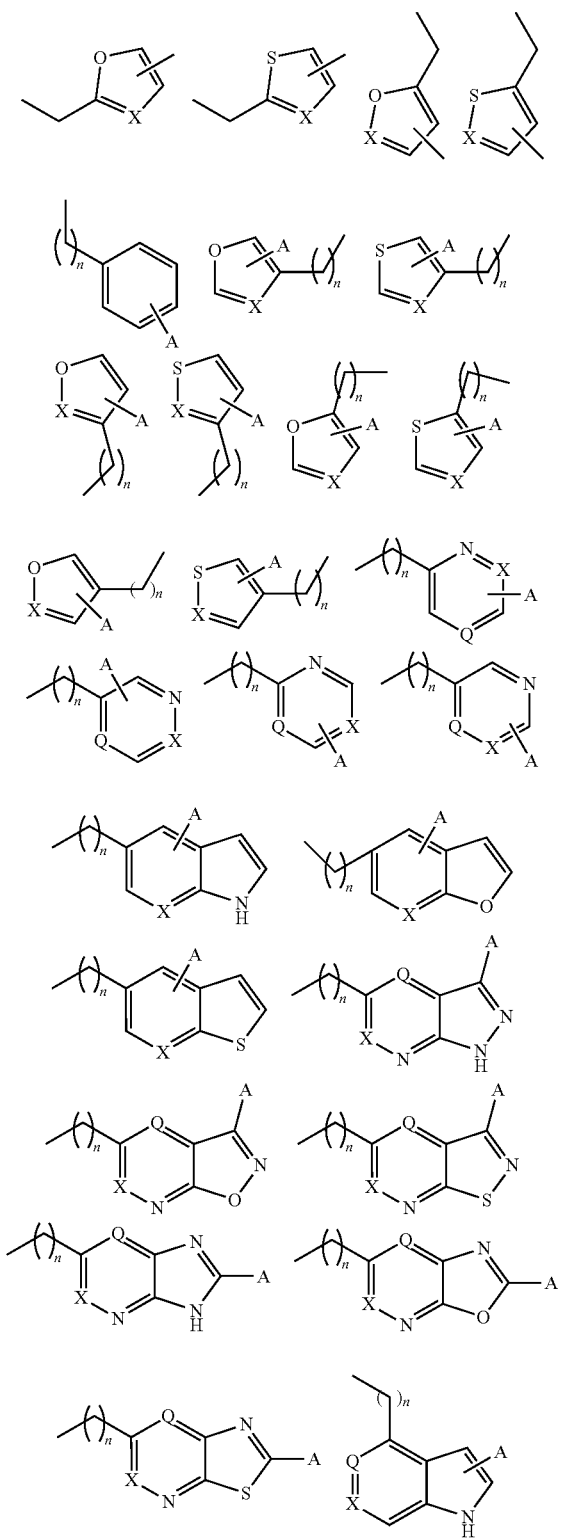
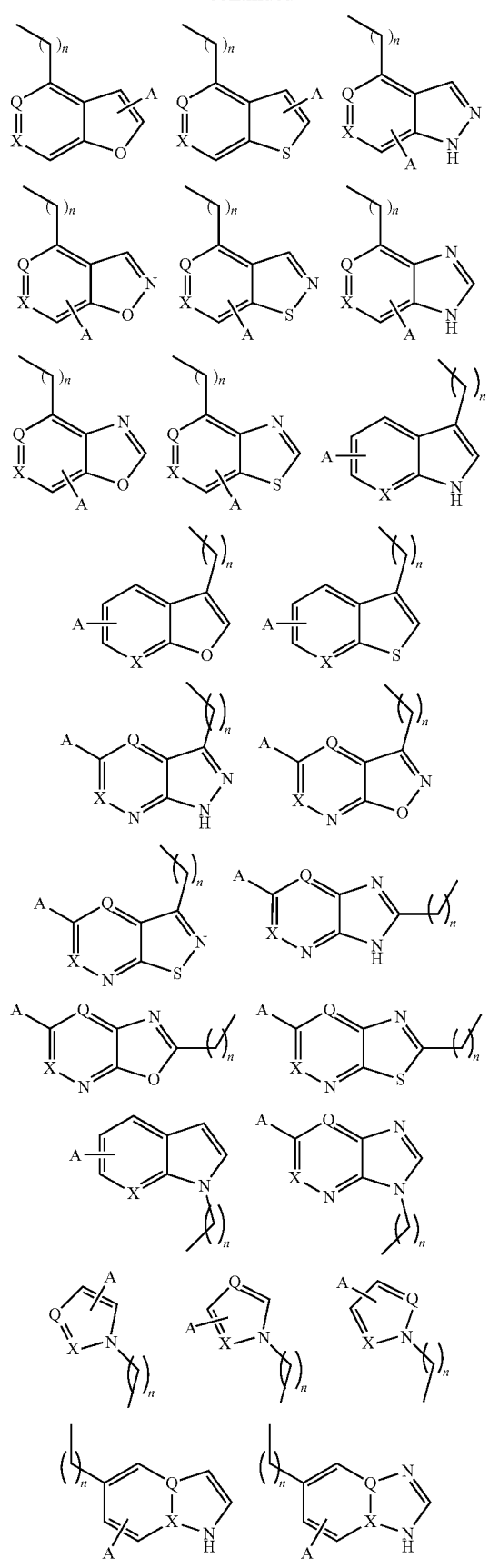

41
-continued

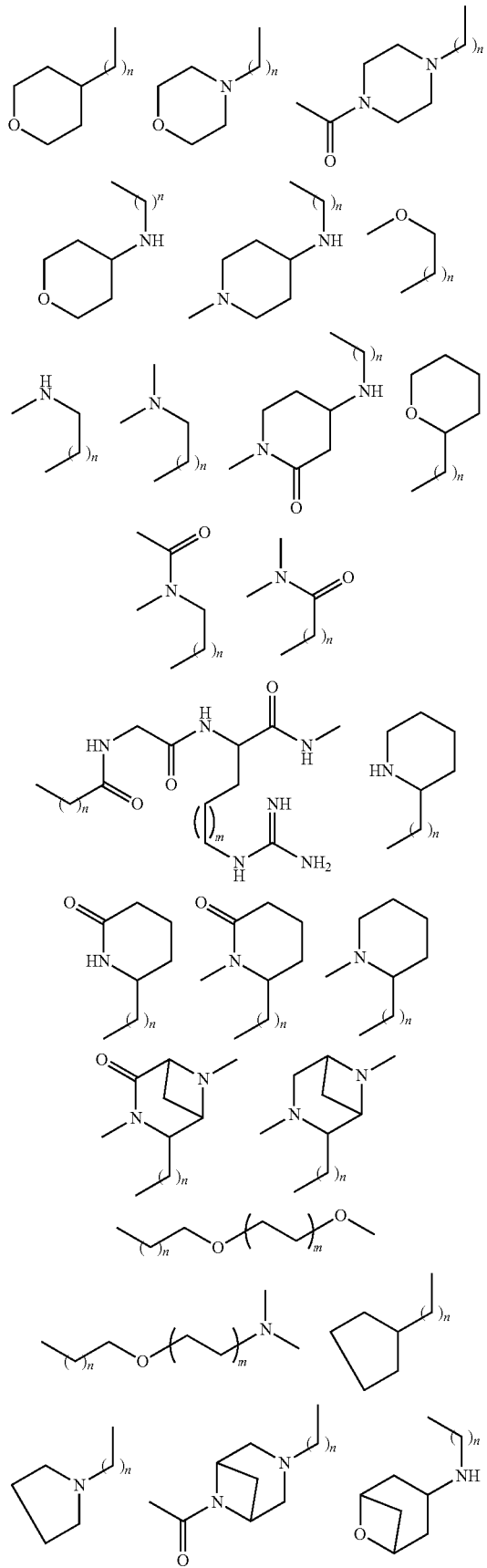

42
-continued

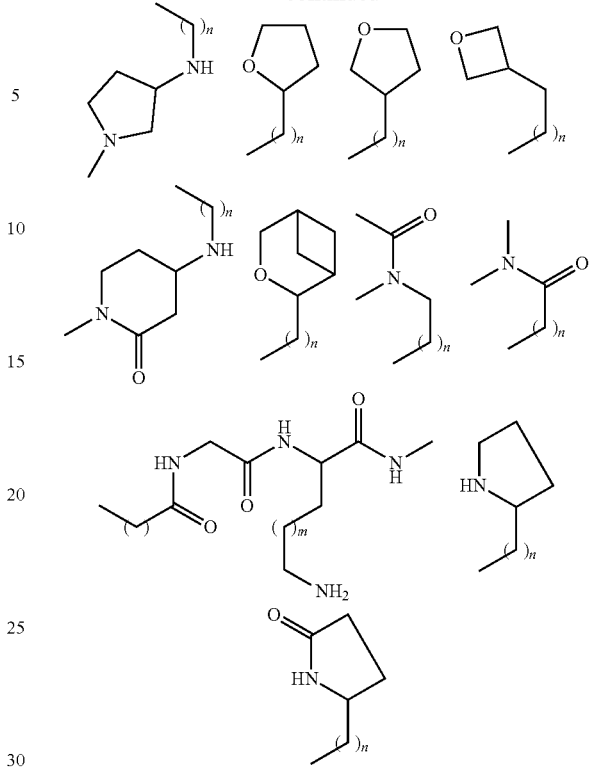

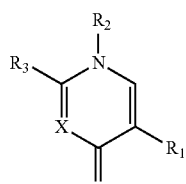

Where:
—A is —H, —Me, —Cl, —F, —Br, —I, —$CF_3$, —CN, —OMe, —SMe, —SOMe, —$SO_2$Me —$NH_2$, —NHMe, —$NO_2$, —COOH, —CHO, —$COCH_3$, —$CO_2CH_3$, —$OCF_3$, —$OCHF_2$, —$OCH_2F$, —$SCF_3$, —$SCHF_2$, —$SCH_2F$, —$CONH_2$, —$CONHCH_3$, —$CON(CH_3)_2$, —$CSNH_2$, —$SONH_2$, —$SO_2NH_2$, —$SONHNH_2$ ...
—X and Q are N or CH.
n=0, 1, 2, 3 or 4; m=0, 1, 2, 3 or 4.
$R_1$, and $R_2$ is a CONH—, O-, CH2—, HN—, CC— S-linker connected to a protein binder;
R3 is selected from a group consisting of —SH, —$NH_2$, —OH, —SSY, —SCOY, —OCOY where Y is described above.
Preferably, a $R_{11}$L is denoted by the formula III $R_1$ is selected from a group consisting of —SH, —$NH_2$, —OH, —SSY, —SCOY, —OCOY where Y is described above.
$R_2$ and $R_3$ is selected from a group consisting of —CO—Z, —$OCH_3$, —$CF_3$, —COOH, —$CH_2NH_2$, —$CH_3$, —H, —F, —Cl, —Br, —$CF_3$, —$CHF_2$, —$CH_2F$, —CN, —OH, —OMe, —SMe, —SOMe, —$SO_2$Me, —$NH_2$, —NHMe, $NO_2$, CHO; Z is selected from a group consisting of —$NH_2$, —NHY, —OH, and —OY; Y is selected from a group consisting of —$CH_3$, —$CH_2COO$—,

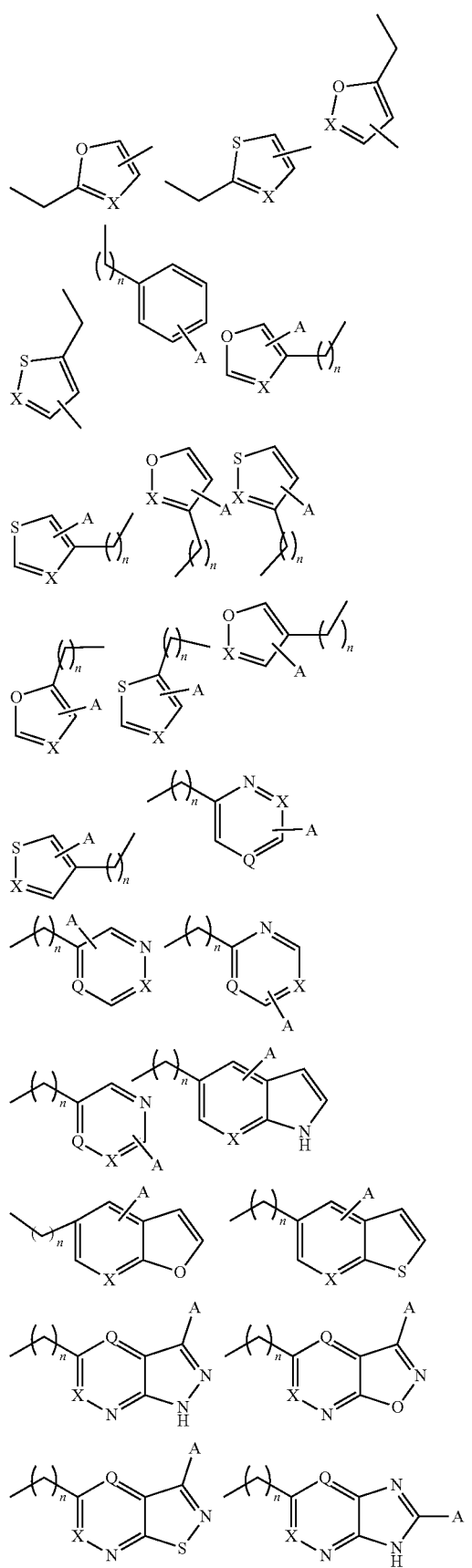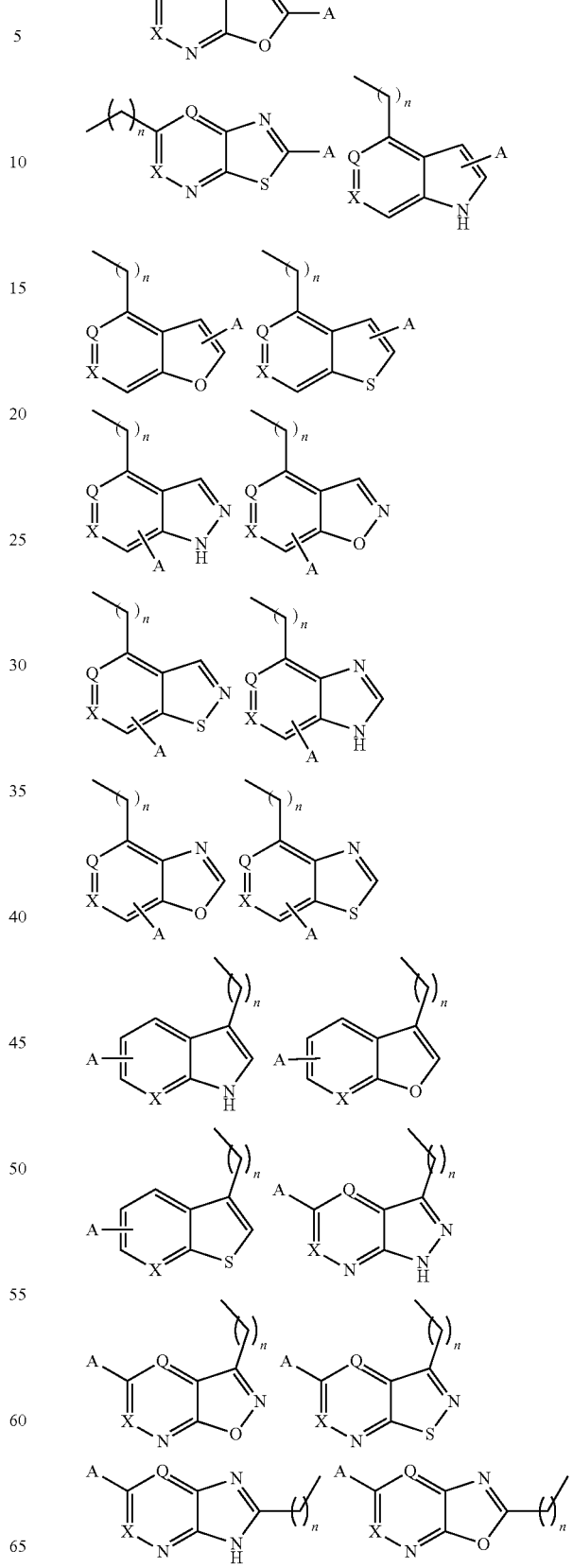

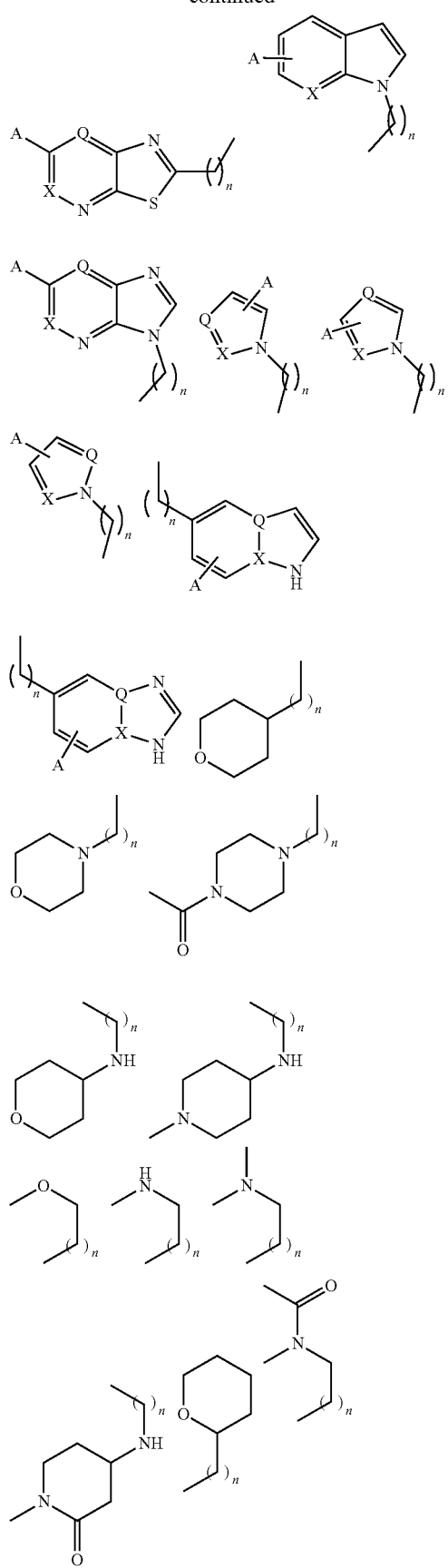
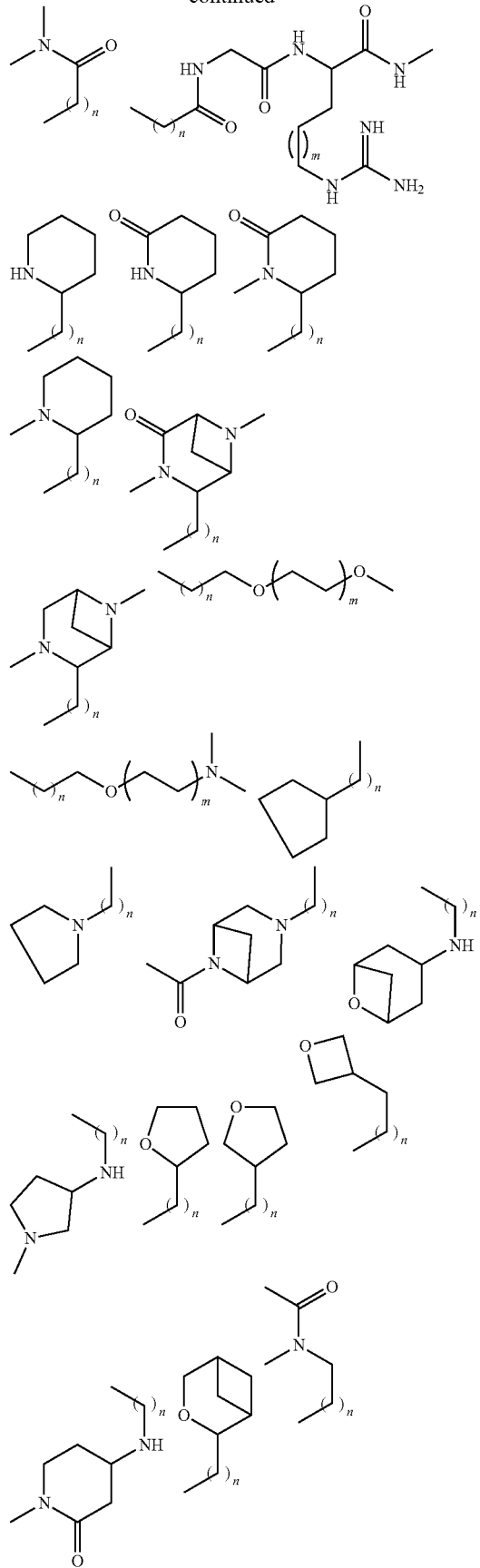

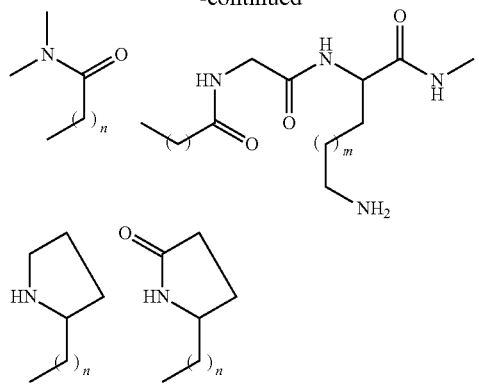
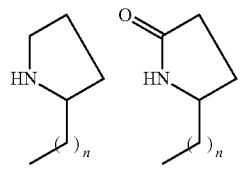

Where:
—A is —H, —Me, —Cl, —F, —Br, —I, —$CF_3$, —$CHF_2$, —$CH_2F$, —CN, —OMe, —SMe, —SOMe, —$SO_2Me$, —$NH_2$, —NHMe, —$NO_2$, —COOH, —CHO, —$COCH_3$, —$CO_2CH_3$, —$OCF_3$, —$OCHF_2$, —$OCH_2F$, —$SCF_3$, —$SCHF_2$, —$SCH_2F$, —$CONH_2$, —$CONHCH_3$, —$CON(CH_3)_2$, —$CSNH_2$, —$SONH_2$, —$SO_2NH_2$, —$SONHNH_2$ ...
—X and Q are N or CH.
n=0, 1, 2, 3 or 4; m=0, 1, 2, 3 or 4
$R_2$, and R3 is CONH—, O—, CH2—, HN—, CC—
S-linker connected to a protein binder; $R_4$ is O, S, NH.
Preferably, a R11L is denoted by the formula IV

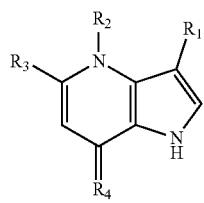

R1, R2 and R3 are selected from a group consisting of —CO—Z, —$OCH_3$, —$CF_3$, —COOH, —$CH_2NH_2$, —$CH_3$, —H, —F, —Cl, —Br, —$CF_3$, —$CHF_2$, —$CH_2F$, —CN, —OH, —OMe, —SMe, —SOMe, —$SO_2Me$, —$NH_2$, —NHMe, —$NMe_2$, $NO_2$, CHO; Z is selected from a group consisting of —$NH_2$, —NHY, —OH, and —OY; Y is selected from a group consisting of —$CH_3$, —$CH_2COO$—,

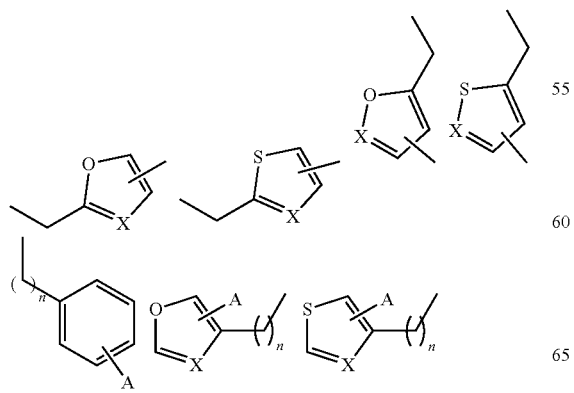
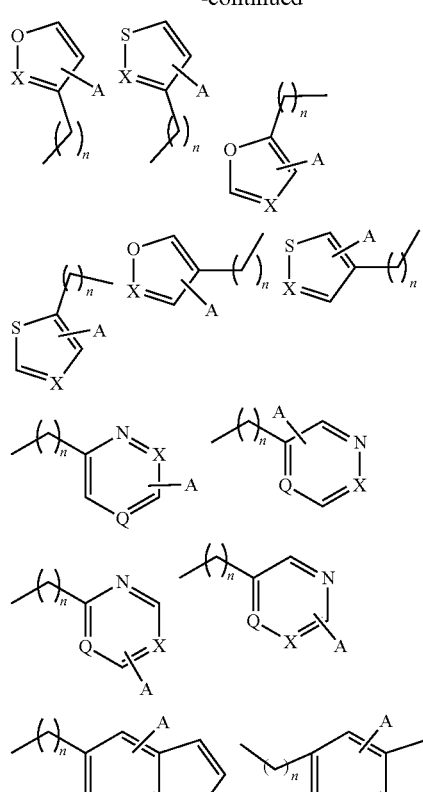
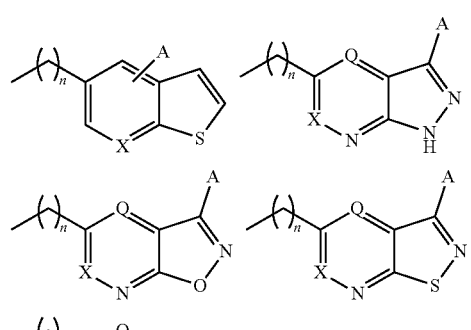
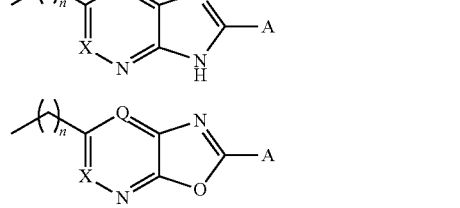
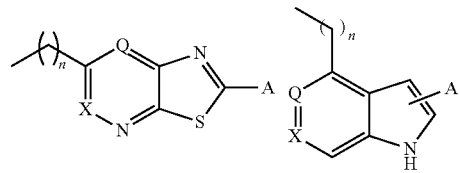
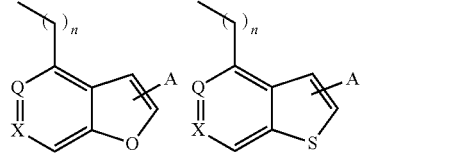

-continued
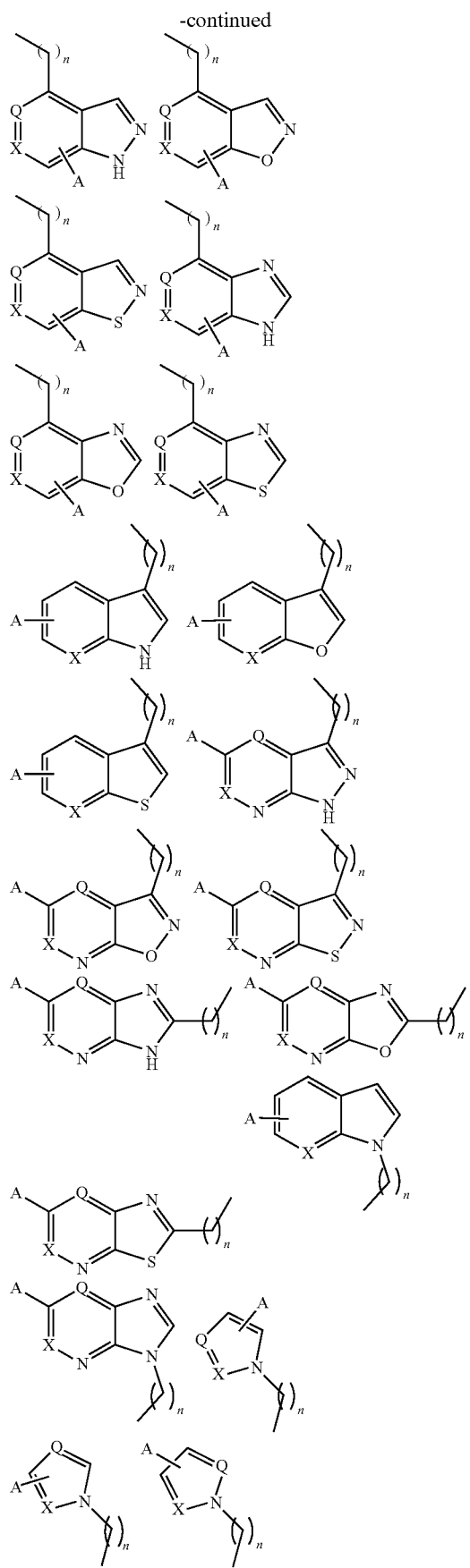
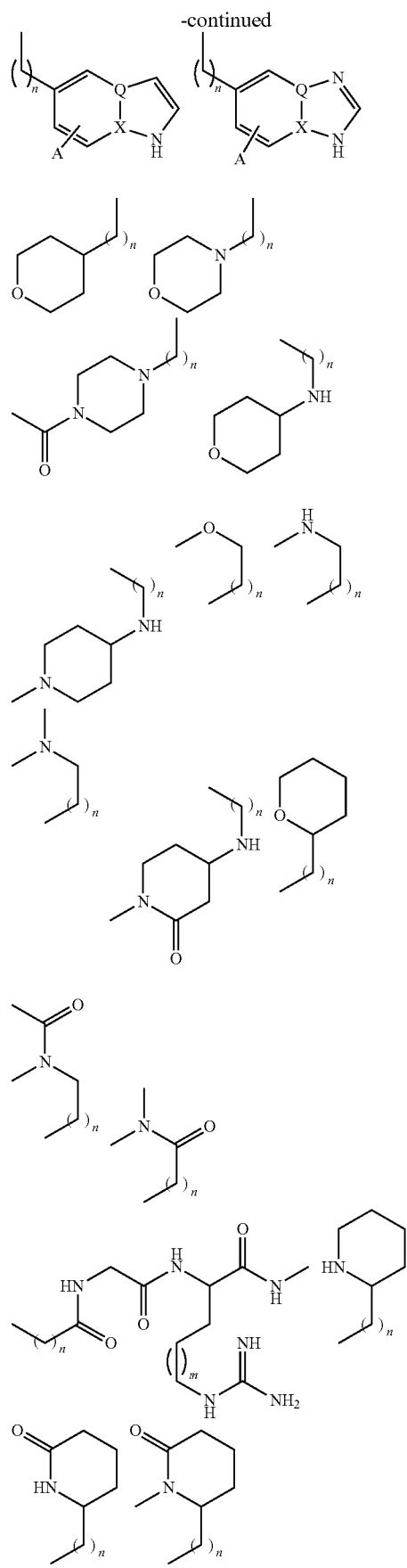

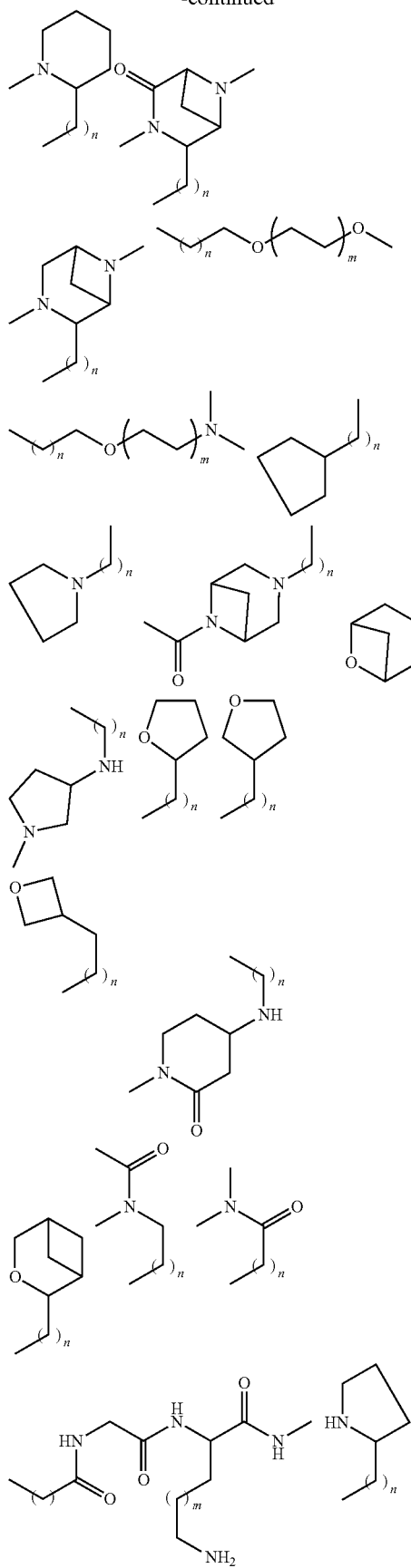

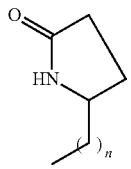

Where:
—A is —H, —Me, —Cl, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . .

—X and Q are N or CH.
n=0, 1, 2, 3 or 4; m=0, 1, 2, 3 or 4
R1, R$_2$, and R3 is a CONH—, O—, CH2—, HN—, CC— S-linker connected to a protein binder;
R4 is O, S, NH, NCOY.
Preferably, a R11L is denoted by the formula V

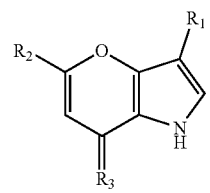

R1 and R2 are selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

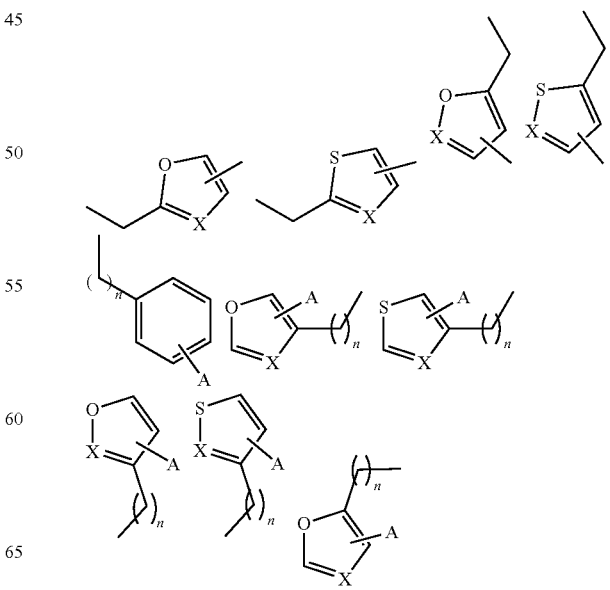

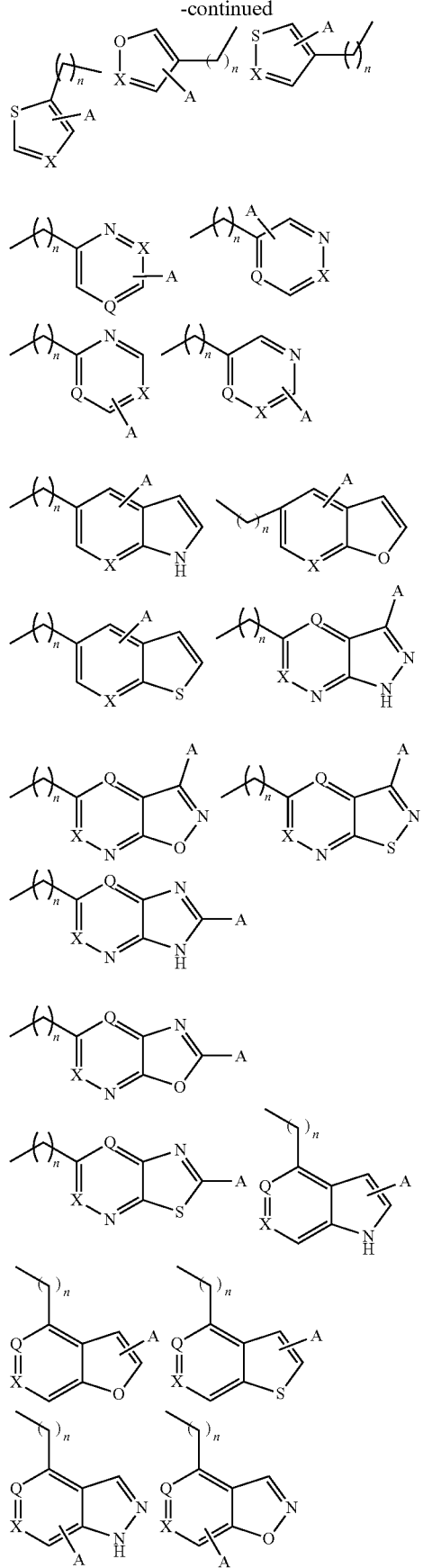

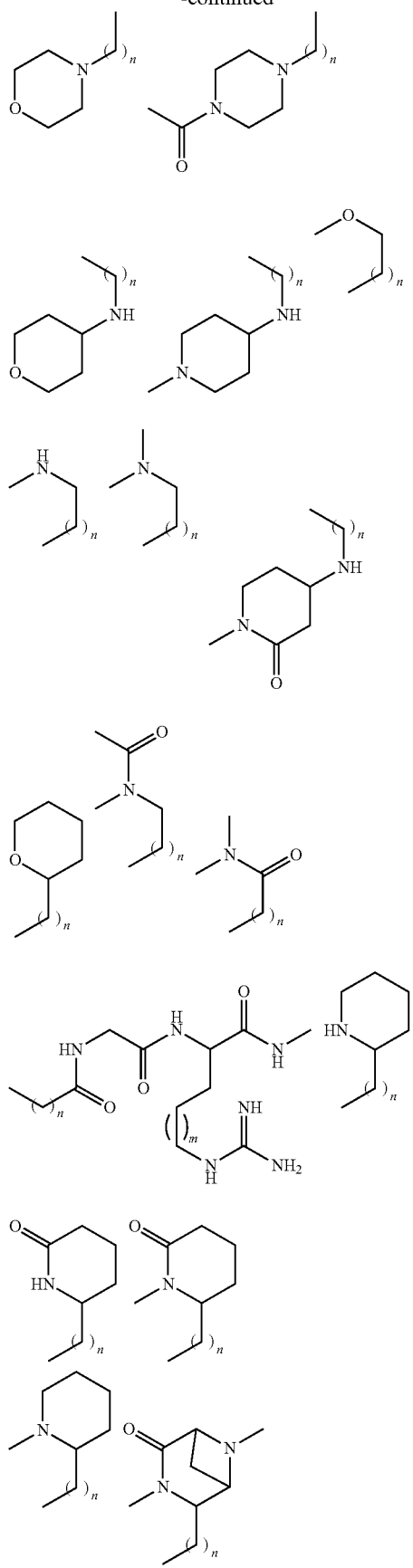
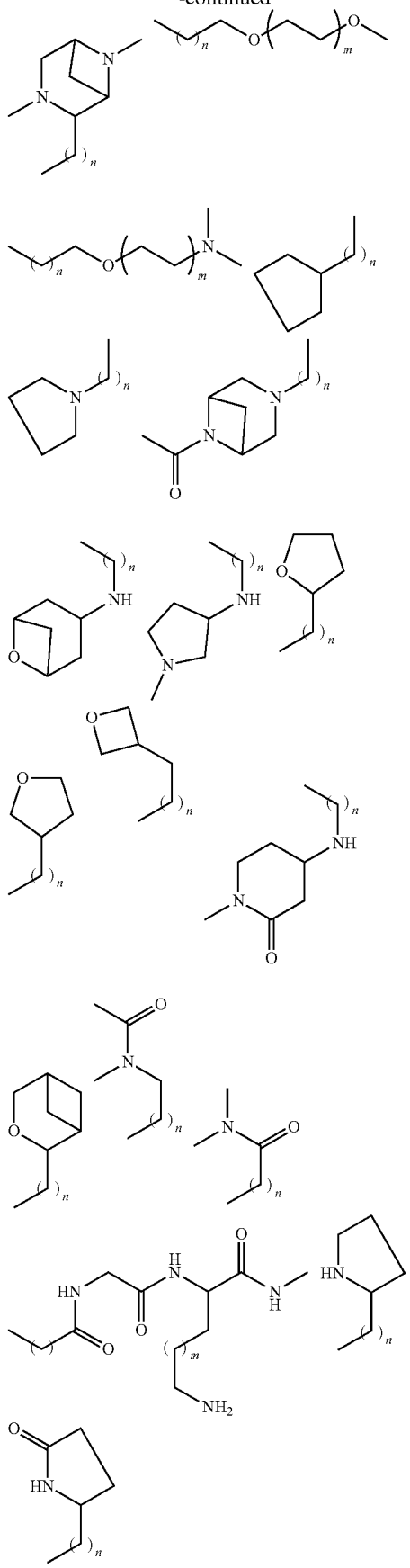

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
—X and Q are N or CH.
n=0, 1, 2, 3 or 4; m=0, 1, 2, 3 or 4
R$_1$, and R$_2$, is a CONH—, O—, CH2—, HN—, CC— S-linker connected to a protein binder;
R$_3$ is O, S, NH, NCOY.
Preferably, a R11L is denoted by the formula VI

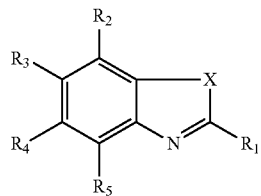

X=NH, O, S, CH$_2$
R1 and R4 are preferentially —H, but also —Me, —F, —Cl, —Br, —I, —CF$_3$, —CHF$_2$, —CH$_2$F, —CN, —OMe, —SMe, —SOMe, —SO$_2$Me —NH$_2$, —NHMe, —NO$_2$, —CHO . . .
R$_2$, and R$_3$ is selected from a group consisting of —CO—Z, OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

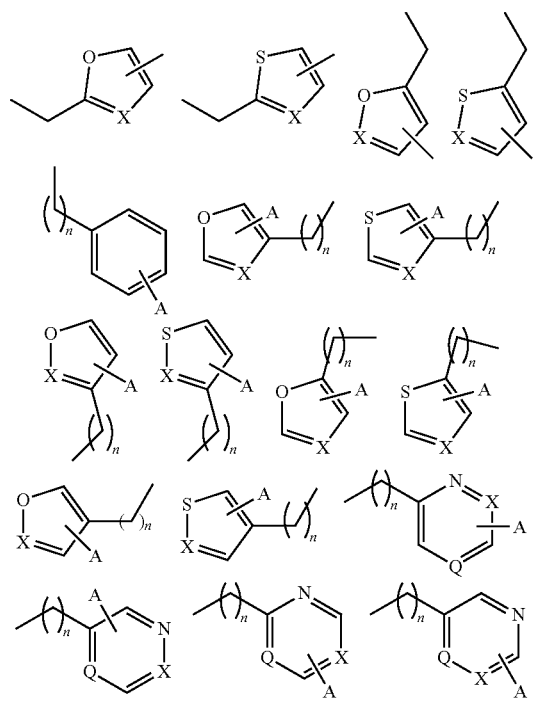

-continued

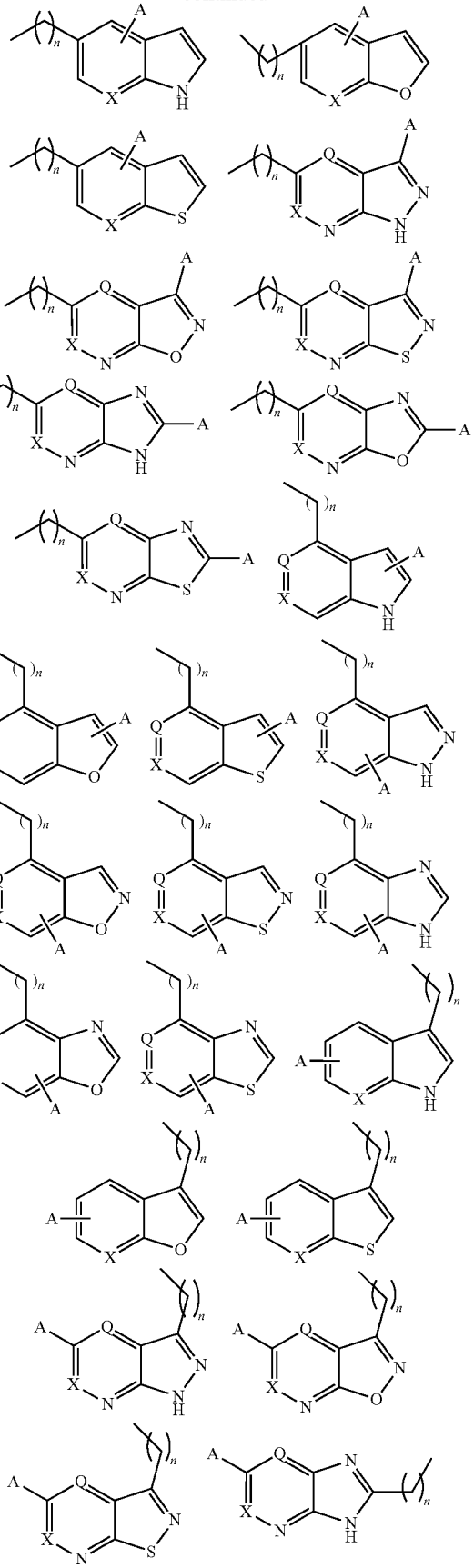

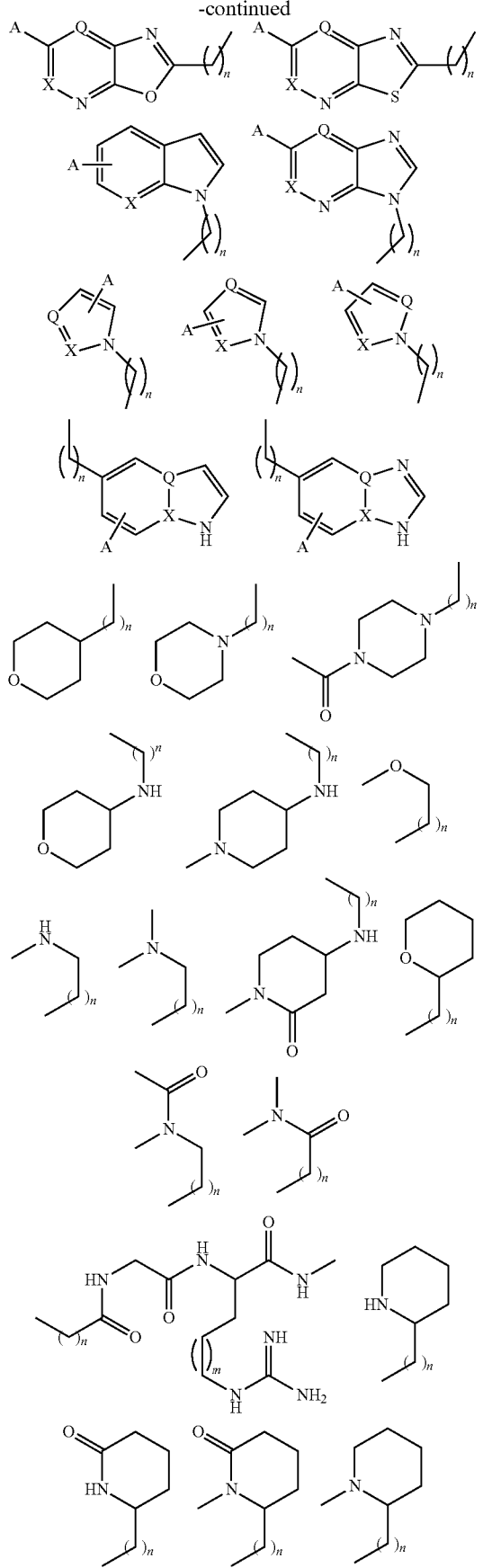
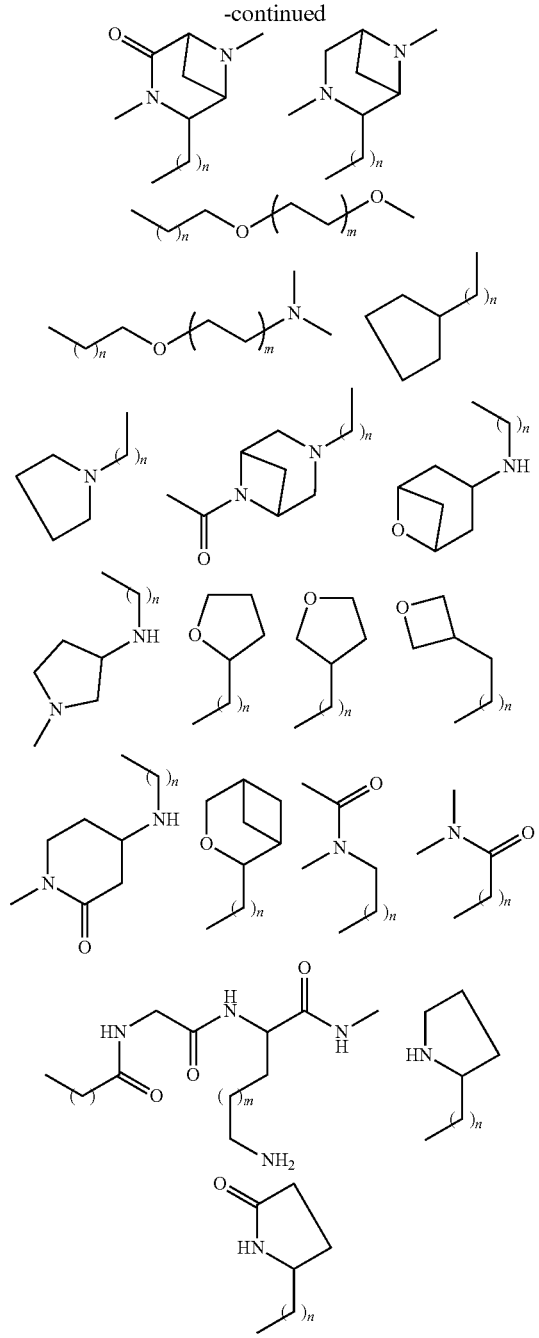

Where:
—A is —H, —Me, —Cl, —F, —Br, —I, —$CF_3$, —$CHF_2$, —$CH_2F$, —CN, —OMe, —SMe, —SOMe, —$SO_2Me$ —$NH_2$, —NHMe, —$NO_2$, —COOH, —CHO, —$COCH_3$, —$CO_2CH_3$, —$OCF_3$, —$OCHF_2$, —$OCH_2F$, —$SCF_3$, —$SCHF_2$, —$SCH_2F$, —$CONH_2$, —$CONHCH_3$, —$CON(CH_3)_2$, —$CSNH_2$, —$SONH_2$, —$SO_2NH_2$, —$SONHNH_2$ —X and Q are N or CH.

n=0, 1, 2, 3 or 4; m=0, 1, 2, 3 or 4

R2 and R3 is a CONH—, O—, CH2—, HN—, CC— S-linker connected to a protein binder;

$R_5$ is selected from a group consisting of —SH, —$NH_2$, —OH, SSY, SCOY, OCOY where Y is described above.

Preferably, a R11L is denoted by the formula VII
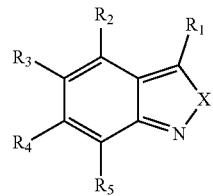
X=NH, O, S, CH₂
R1, R₂ and R₃ is selected from a group consisting of —CO—Z, OCH₃, —CF₃, —COOH, —CH₂NH₂, —CH₃, —H, —F, —Cl, —Br, —CF₃, —CHF₂, —CH₂F, —CN, —OH, —OMe, —SMe, —SOMe, —SO₂Me, —NH₂, —NHMe, —NMe₂, NO₂, CHO; Z is selected from a group consisting of —NH₂, —NHY, —OH, and —OY; Y is selected from a group consisting of —CH₃, —CH₂COO—,
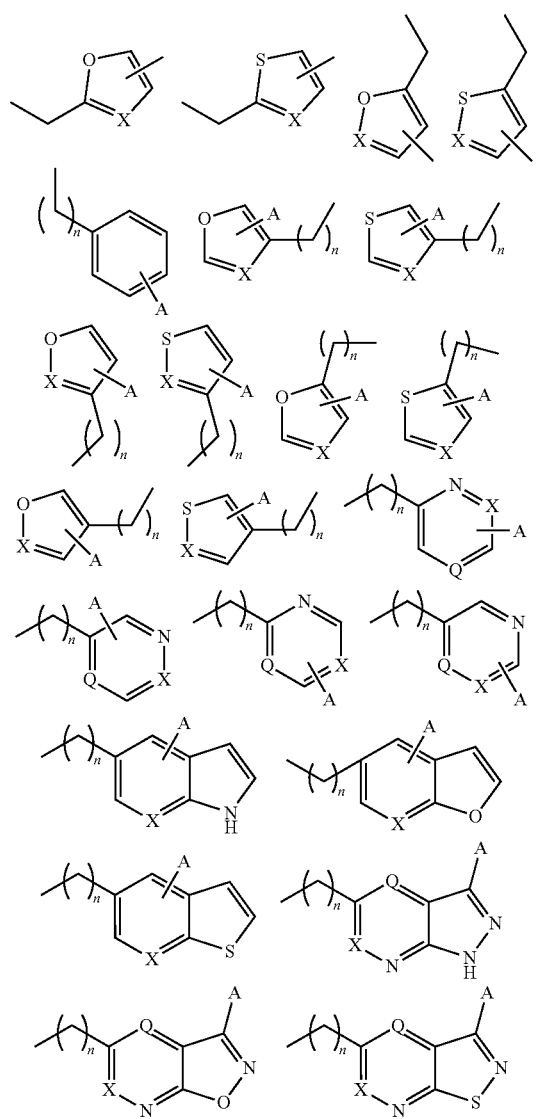
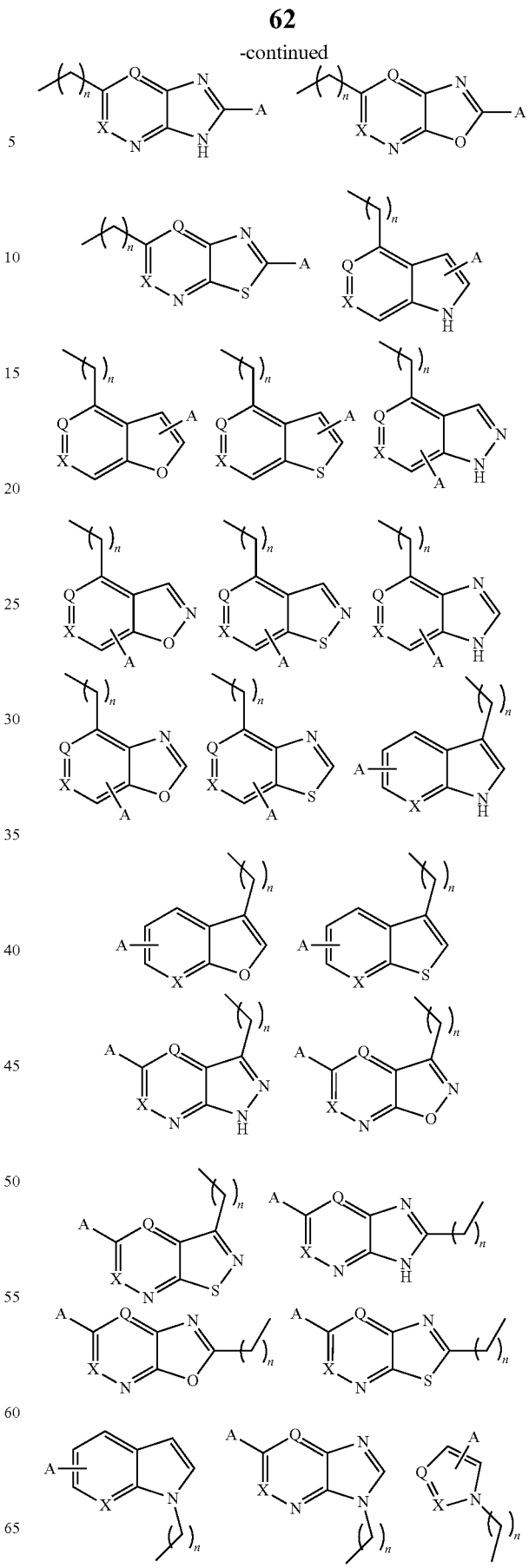

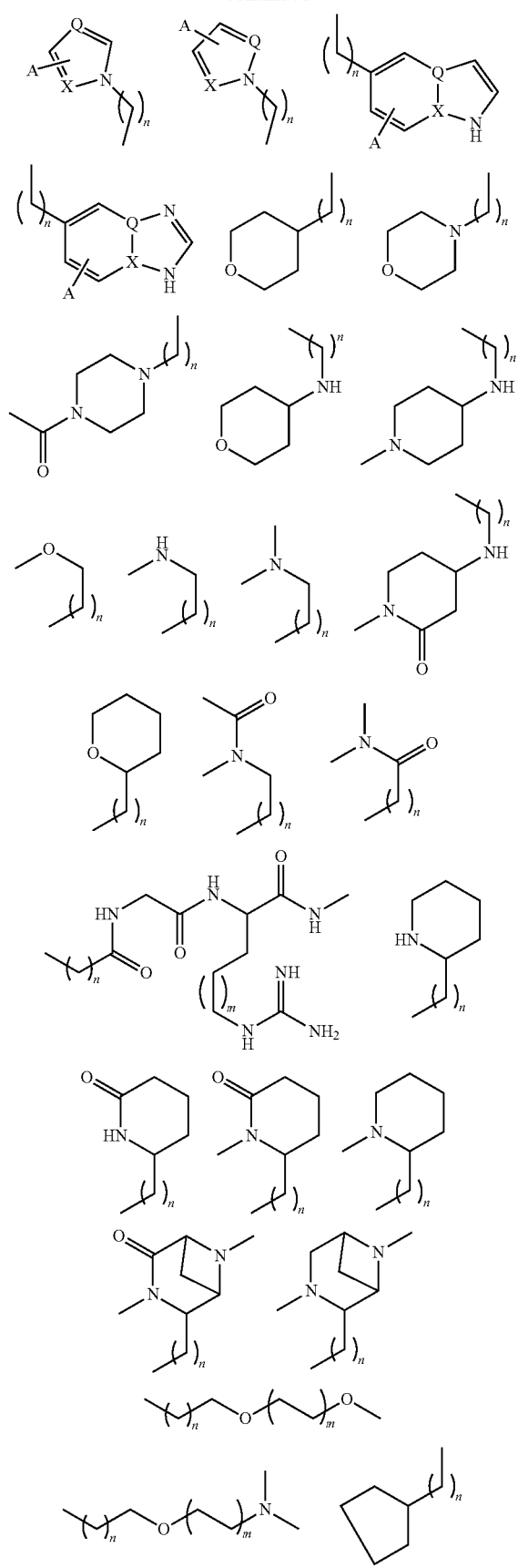
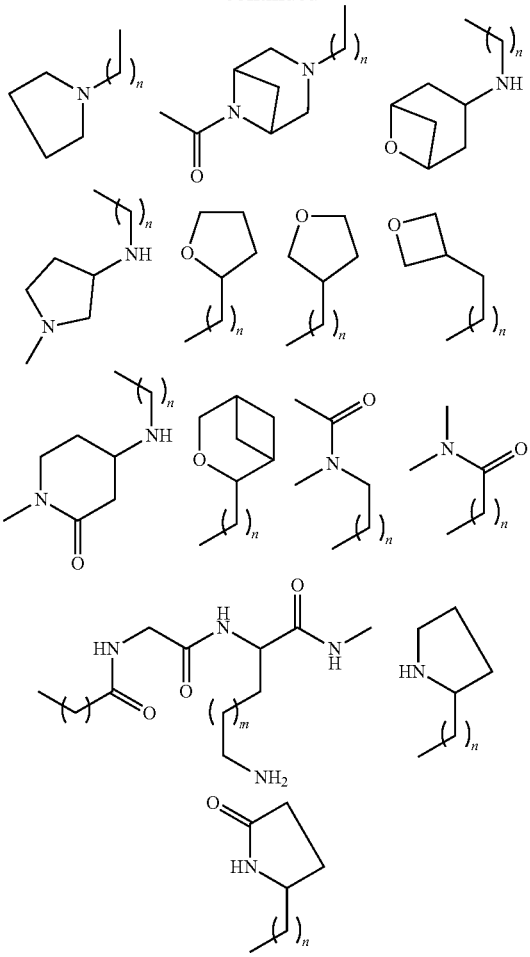

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.

n=0, 1, 2, 3 or 4; m=0, 1, 2, 3 or 4

R1, R2, and R3 is a CONH—, O—, CH2—, HN—, CC—S-linker connected to a protein binder;

R4 is are preferentially —H, but also Me, F, Cl, Br, CF$_3$, CHF$_2$, CH$_2$F, CN, OMe, SMe, SOMe, SO$_2$Me NH$_2$, NHMe, NO$_2$, CHO . . .

R5 is selected from a group consisting of —SH, —NH$_2$, —OH, SSY, SCOY, OCOY where Y is described above.

Preferably, a R11L is denoted by the formula VIII

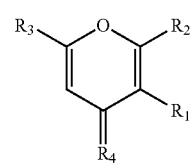

R1 is selected from a group consisting of —SH, —NH$_2$, —OH, —SSY, —SCOY, —OCOY, NHCOY where Y is described above.

R4 is selected from a group consisting of —S, —NH, —O,

R2 and R3 is selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, NO$_2$, CHO; Z is selected from a group consisting of —NH$_2$, —NHY, —OH, and —OY; Y is selected from a group consisting of —CH$_3$, —CH$_2$COO—,

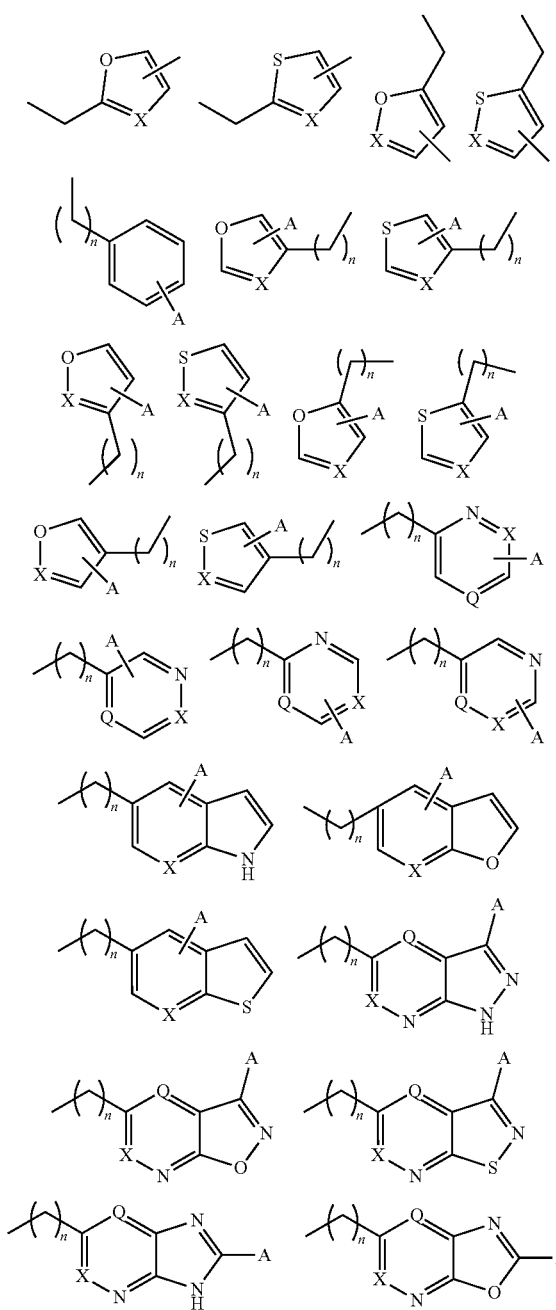

-continued

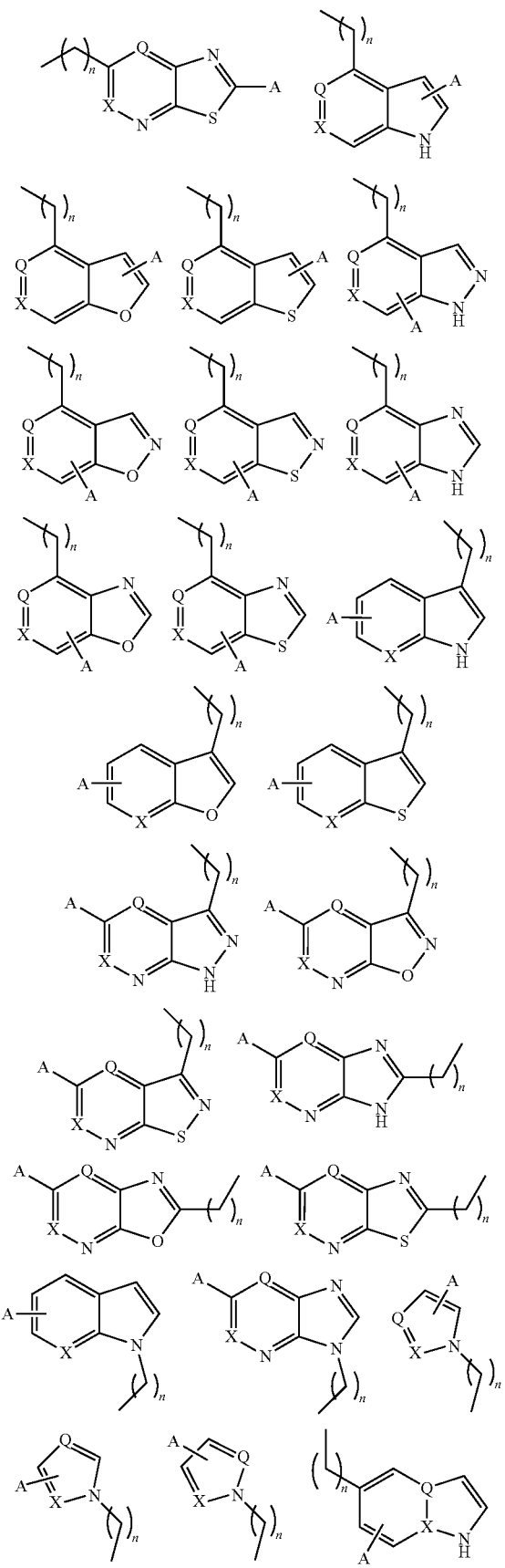

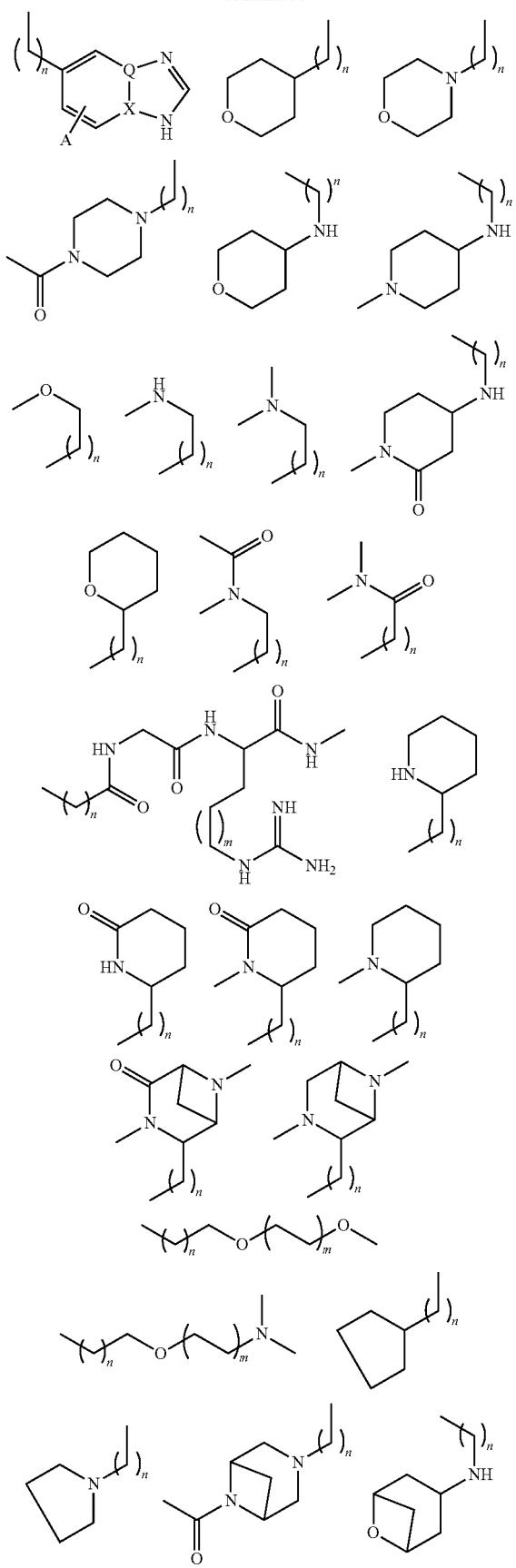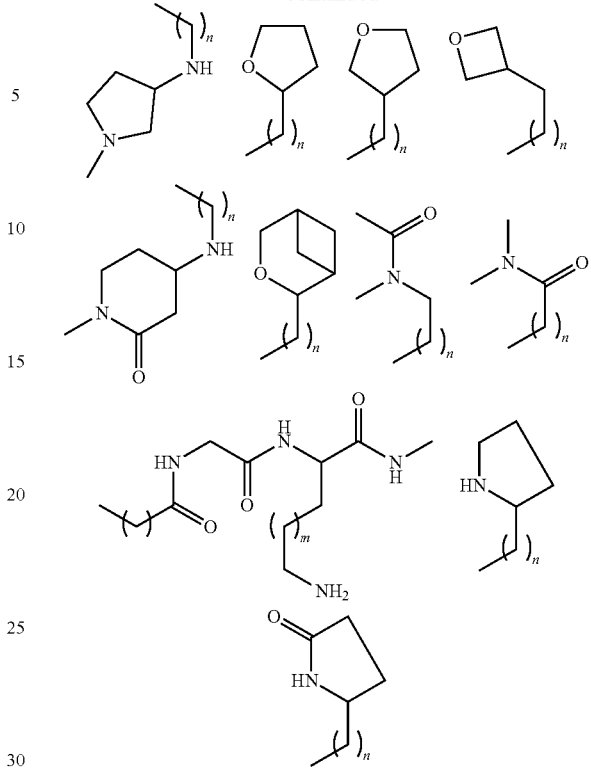

Where:
- A is —H, —Me, —Cl, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
- —X and Q are N or CH.
- n=0, 1, 2, 3 or 4; m=0, 1, 2, 3 or 4
- R$_2$, and R3 is a CONH—, O-, CH2—, HN—, CC— S-linker connected to a protein binder; and R$_4$ is selected from a group consisting of —S, —NH, —O.

The invention also encompasses a method of obtaining increased proteolysis of a target protein in a cell, the method comprising contacting the cell with a bifunctional molecule according to any of aforesaid compounds.

The invention also encompasses a method of obtaining increased proteolysis of a target protein in a subject, the method comprising administering to the subject a bifunctional molecule according to any of aforesaid compounds.

The invention also encompasses a method of providing a bifunctional molecule comprising two covalently linked binding partners, wherein a first binding partner binds to Rpn11 and a second binding partner binds to a selected target protein, the method comprising providing a first and a second binding partners, and covalently linking the first and the second binding partners.

The invention also encompasses a method of selecting a bifunctional molecule that facilitates proteolysis of a target protein:
  a. selecting a first binding partner by providing a candidate first binding partner and determining that said candidate first binding partner binds to Rpn11;

b. selecting a second binding partner by providing a candidate second binding partner and determining that said candidate second binding partner binds to a target protein of interest;
c. covalently attaching said first and second binding partners to form a bifunctional molecule;
d. contacting a cell with said bifunctional molecule;
e. determining if said target protein undergoes proteolysis.

The invention also encompasses a method of selecting a bifunctional molecule capable of facilitating proteolysis of a target protein, comprising:
(a) providing a bifunctional molecule comprising an Rpn11 binding partner covalently linked to a target protein binding partner,
(b) contacting the bifunctional molecule with a cell in vitro or in a mammal, the cell comprising Rpn11 and the target protein, wherein the contacting permits binding of the bifunctional molecule to the Rpn11 and the target protein, and
(c) detecting proteolysis of the target protein in the cell, wherein the detected proteolysis is increased relative to proteolysis of the target protein in the absence of the contacting.

The invention also encompasses any of the aforesaid methods, comprising the step of measuring proteolysis of the target protein in the absence of the bifunctional molecule.

The invention also encompasses a method of inducing protein degradation in vivo in a eukaryote or prokaryote which has RPN11 molecule or its homolog, comprising administering to said eukaryote or prokaryote a compound as set forth herein, without inhibiting de-ubiquitination by said RPN11.

The invention also encompasses a cells, tissue, or organ culture medium, comprising a compound according to any of aforesaid compounds, without inhibiting de-ubiquitination by said RPN11.

The invention also encompasses a method of degrading a target protein, the method comprising a step of inducing degradation of the target protein with a compound according to any of aforesaid compounds, without inhibiting de-ubiquitination by said RPN11.

The invention also encompasses a pharmaceutical composition, comprising a compound according to any of aforesaid compounds and a pharmaceutically acceptable carrier.

Preferably the bifunctional molecule is denoted as Rpn11 binding partner-linker-R, wherein the linker is —[(CH2)n-(V)m-(Z)p-(CH2)q]y Wherein:
n, m, p, q and y=0, 1, 2, 3, 4, 5, 6, 7, 8
V=O, S, NR1, CO, CONR1, CC, CH=CH, where R1=H, alkyl, aryl or heteroaryl
Z=cycloalkyl, aryl, heteroaryl Preferably, the Rpn 11 (R11L) binding partner is denoted by the formula I, in some embodiments, the linker is connected to the Rpn11 binding partner through a position selected from the group consisting of R2, R3, R4 and R5.

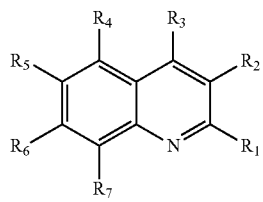

R1 and R6 are preferentially —H, but also —Me, —F, —Cl, —Br, —CF$_3$, —CHF$_2$, —CH$_2$F, —CN, —OH, —OMe, —SMe, —SOMe, —SO$_2$Me, —NH$_2$, —NHMe, NO$_2$, CHO . . .

R$_2$, R$_3$, R$_4$ and R5 is selected from a group consisting of —CO—Z, OCH$_3$, —CF$_3$, —COOH, —CH$_2$NH$_2$, —CH$_3$, —H, —Me, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO . . . ; Z is selected from a group consisting of —NH$_2$, —NHY, —OH, and —OY; Y is selected from a group consisting of —CH$_3$, —CH$_2$COO—,

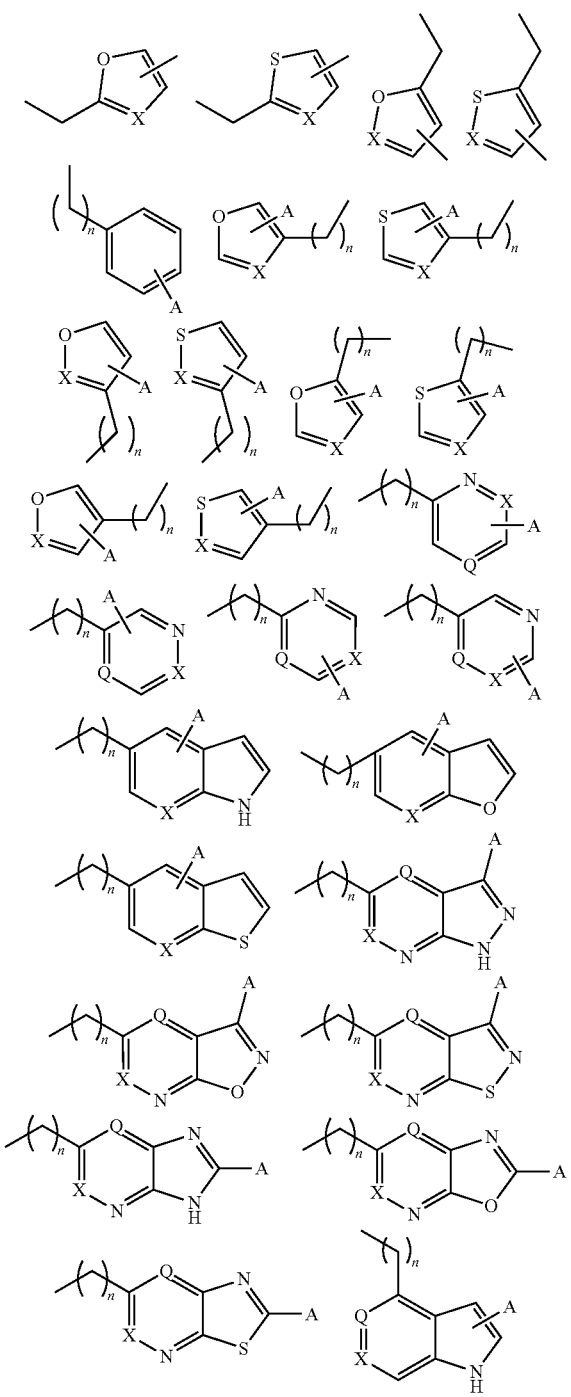

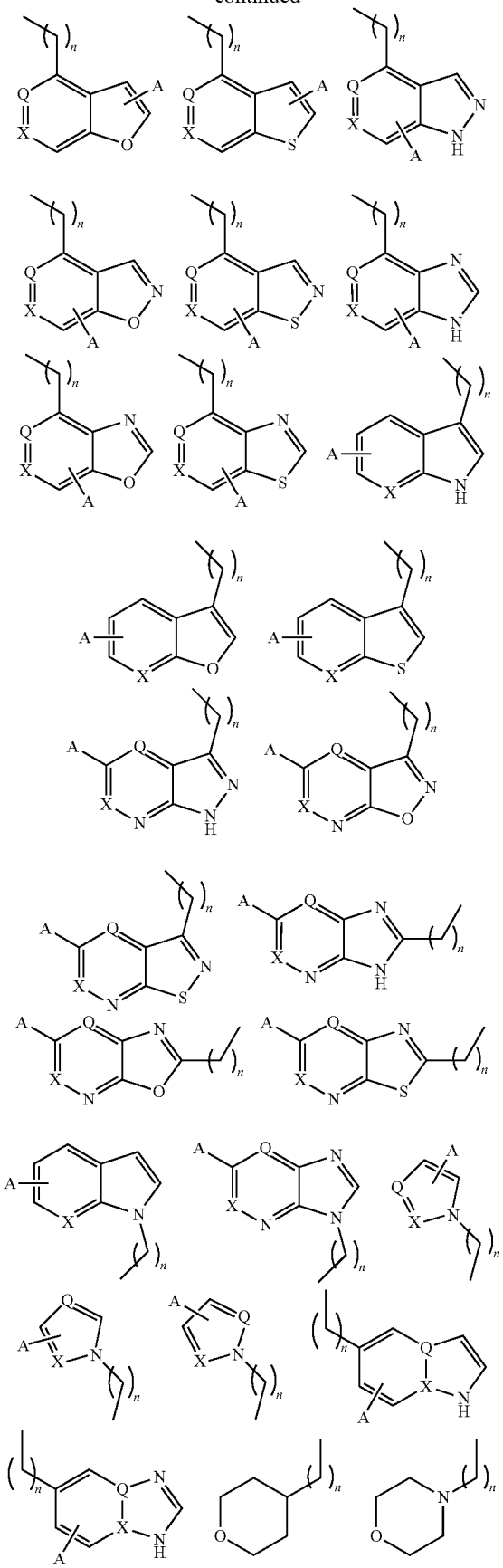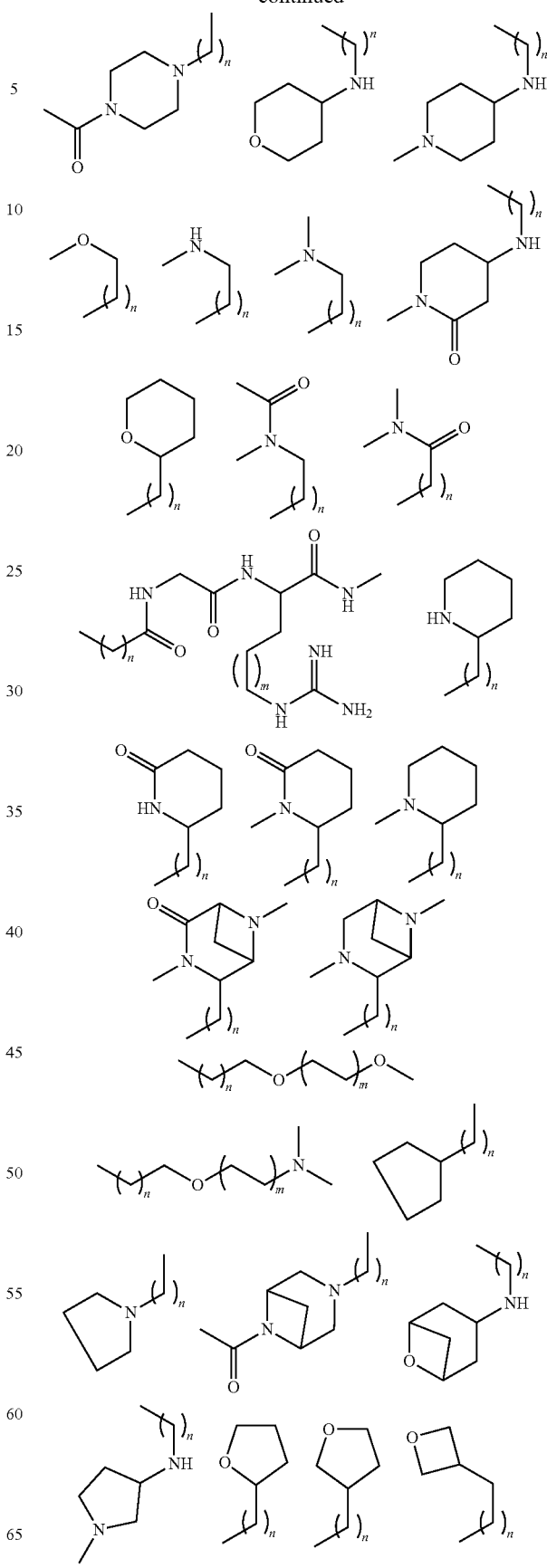

-continued

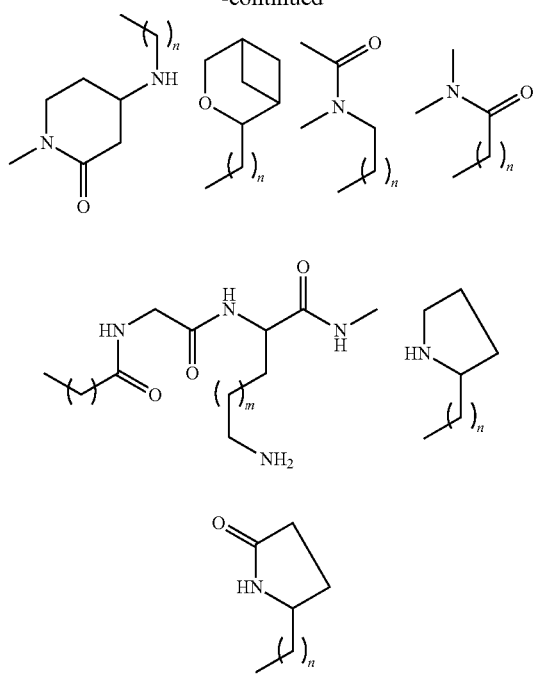

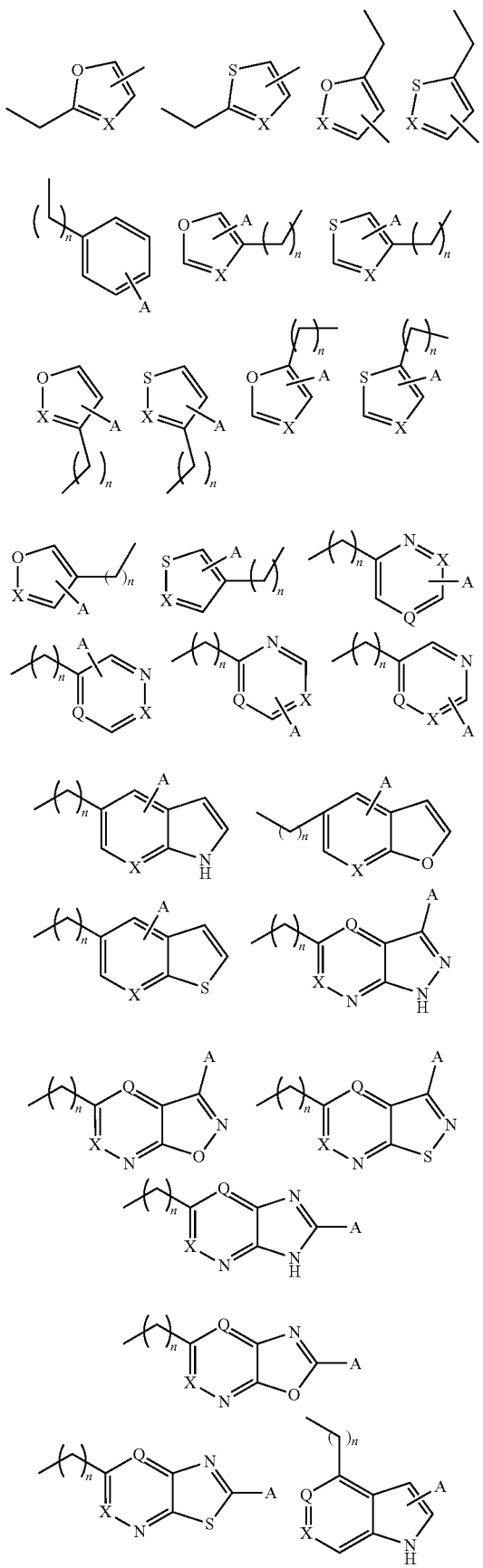

Where:
- —A is —H, —Me, —F, —Br, —I, —CF$_3$, —CHF$_2$, —CH$_2$F, —CN, —OH, —OMe, —SMe, —SOMe, —SO$_2$Me, —NH$_2$, —NHMe, —NO$_2$, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .
- —X and Q are N or CH.
- n=0, 1, 2, 3 or 4; m=0, 1, 2, 3 or 4
- R$_2$, R$_3$, R$_4$ and R5 is a CONH—, O-, CH2—, HN—, CC— S-linker connected to a protein binder;
- R7 is selected from a group consisting of —SH, —NH$_2$, —OH, SSY, SCOY, OCOY where Y is described above.

Preferably, the Rpn 11 binding partner is denoted by the formula II

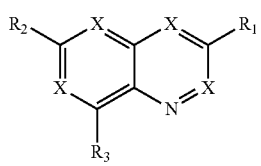

X=CH or N

R$_1$, and R$_2$ is selected from a group consisting of —CO—Z, OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

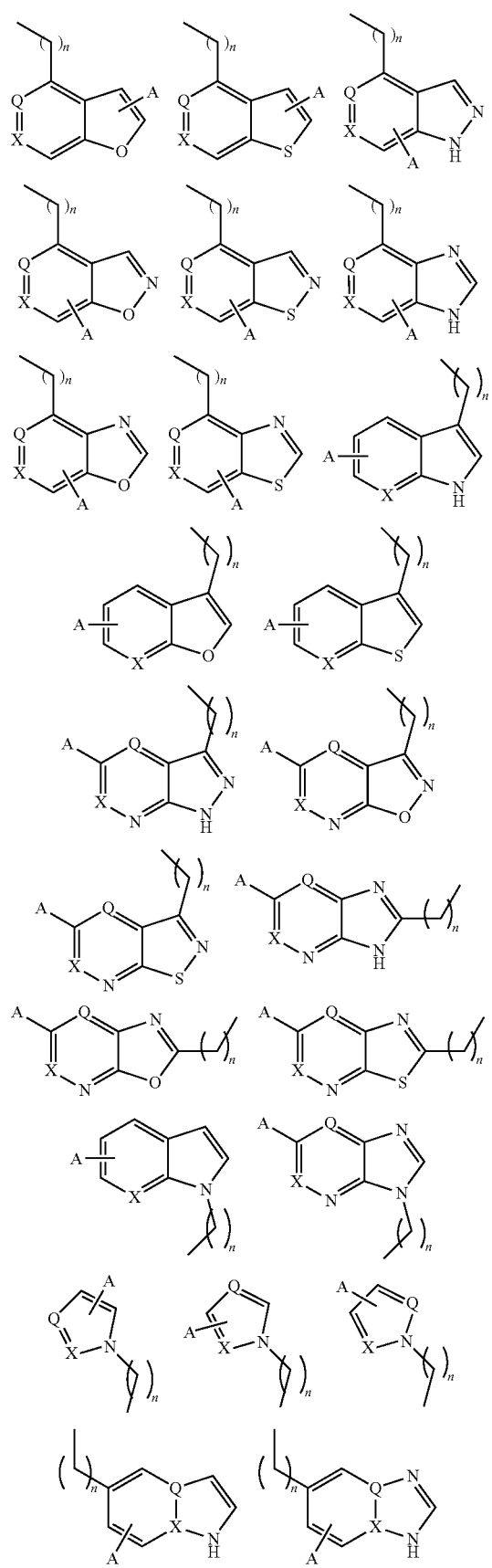
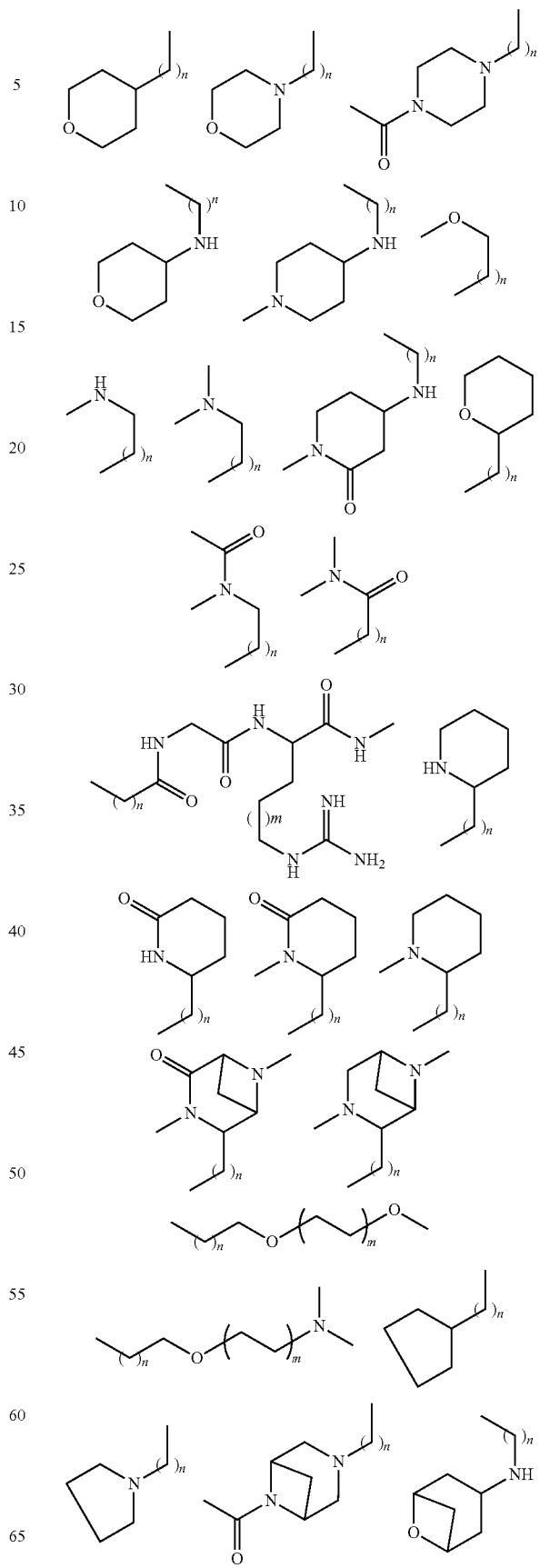

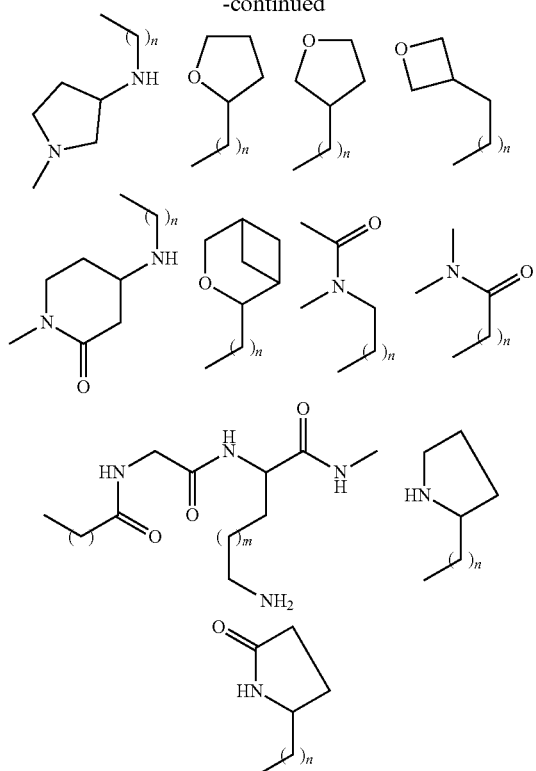

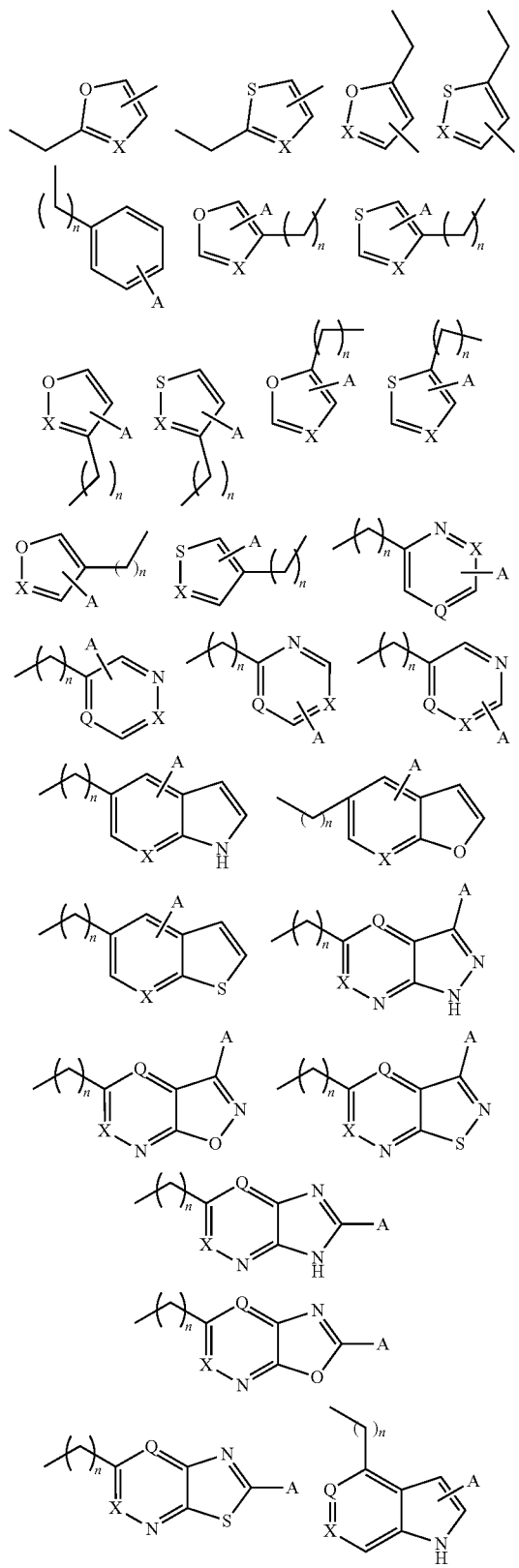

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.
n=0, 1, 2, 3 or 4; m=0, 1, 2, 3 or 4.
R$_1$, and R2 is a CONH—, O—, CH2—, HN—, CC— S-linker connected to a protein binder;
R3 is selected from a group consisting of —SH, —NH$_2$, —OH, —SSY, —SCOY, —OCOY where Y is described above.
Preferably, the Rpn 11 binding partner is denoted by the formula III R1 is selected from a group consisting of —SH, —NH$_2$, —OH, —SSY, —SCOY, —OCOY where Y is described above.
R2 and R3 is selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, NO$_2$, CHO; Z is selected from a group consisting of —NH$_2$, —NHY, —OH, and —OY; Y is selected from a group consisting of —CH$_3$, —CH$_2$COO—,

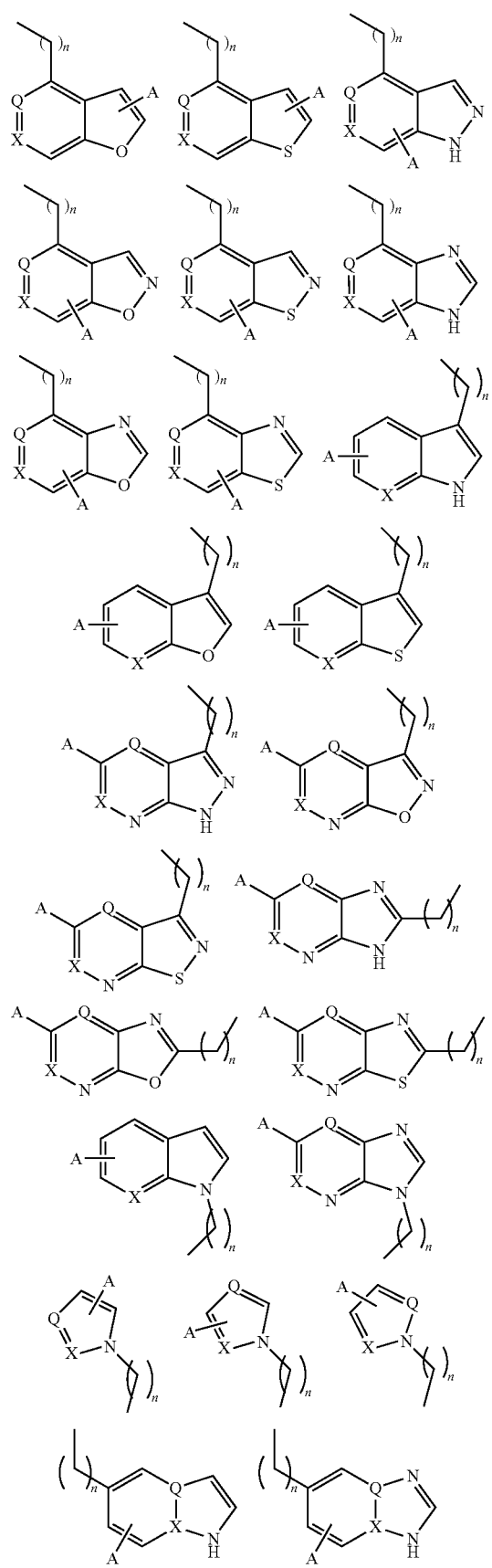
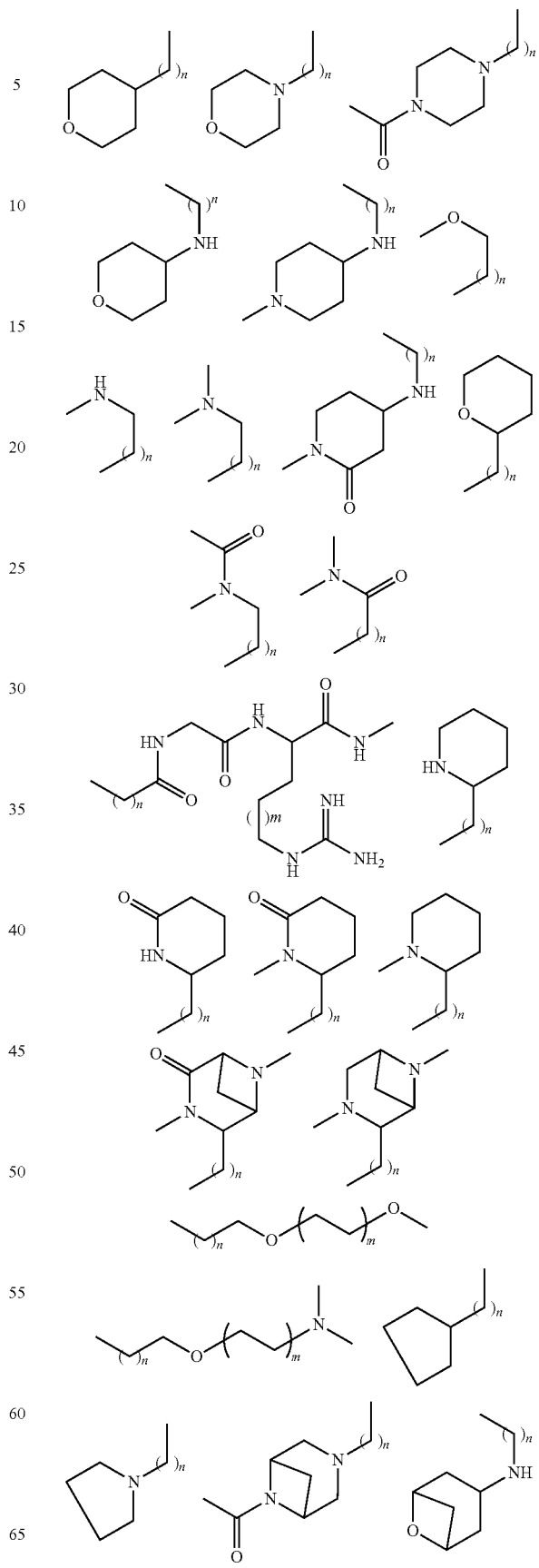

-continued

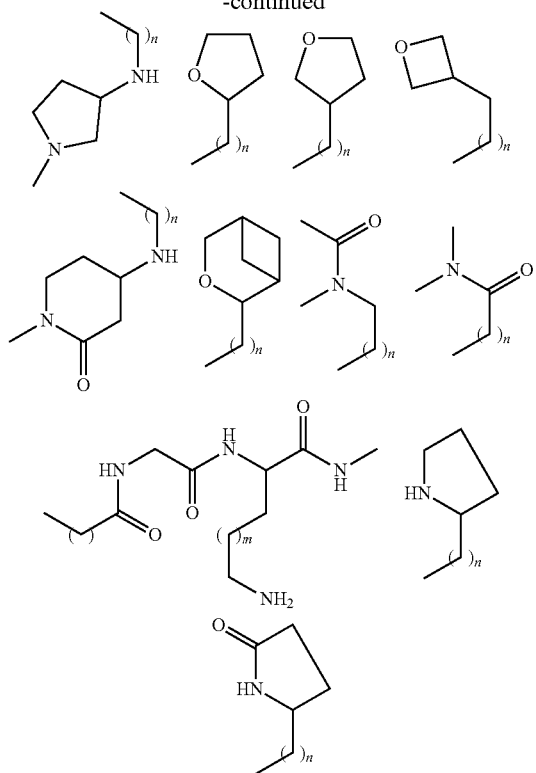

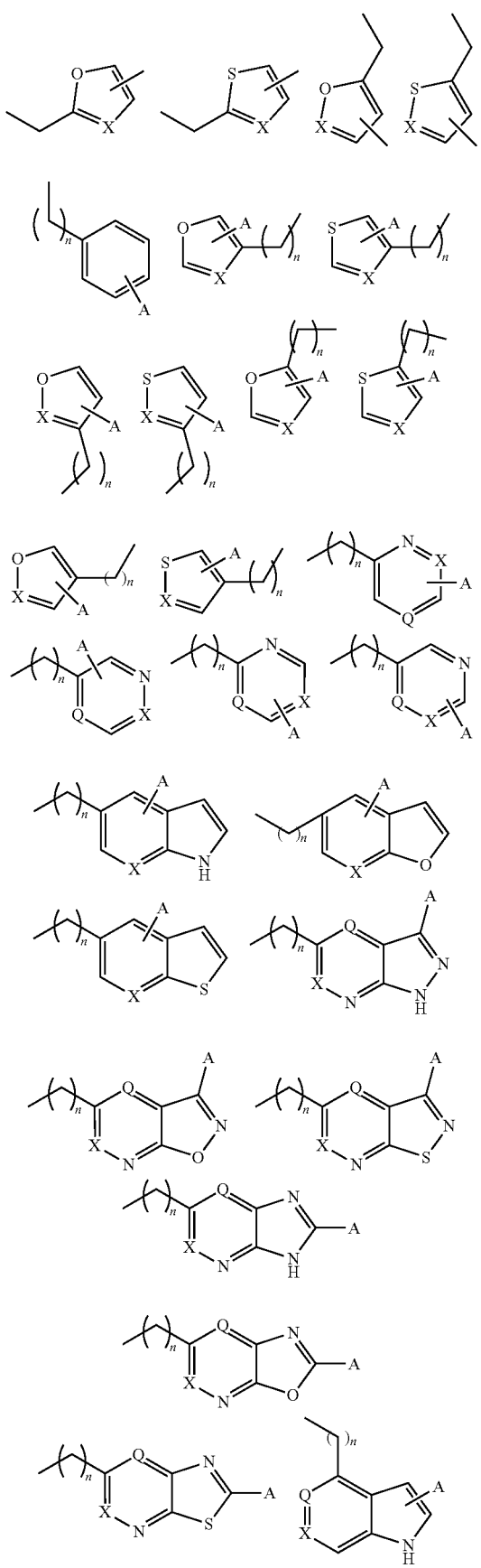

Where:
—A is —H, —Me, —Cl, —F, —Br, —I, —CF$_3$, —CHF$_2$, —CH$_2$F, —CN, —OMe, —SMe, —SOMe, —SO$_2$Me, —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.

n=0, 1, 2, 3 or 4; m=0, 1, 2, 3 or 4

R$_2$, and R$_3$ is a CONH—, O—, CH2—, HN—, CC— S-linker connected to a protein binder;

R$_4$ is O, S, NH

Preferably, the Rpn 11 binding partner is denoted by the formula IV

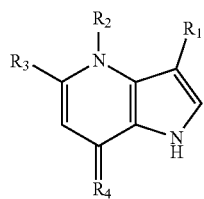

R$_1$, R$_2$ and R$_3$ are selected from a group consisting of —CO—Z, —OCH$_3$, —CF$_3$, —COOH, —CH$_2$NH$_2$, —CH$_3$, —H, —F, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

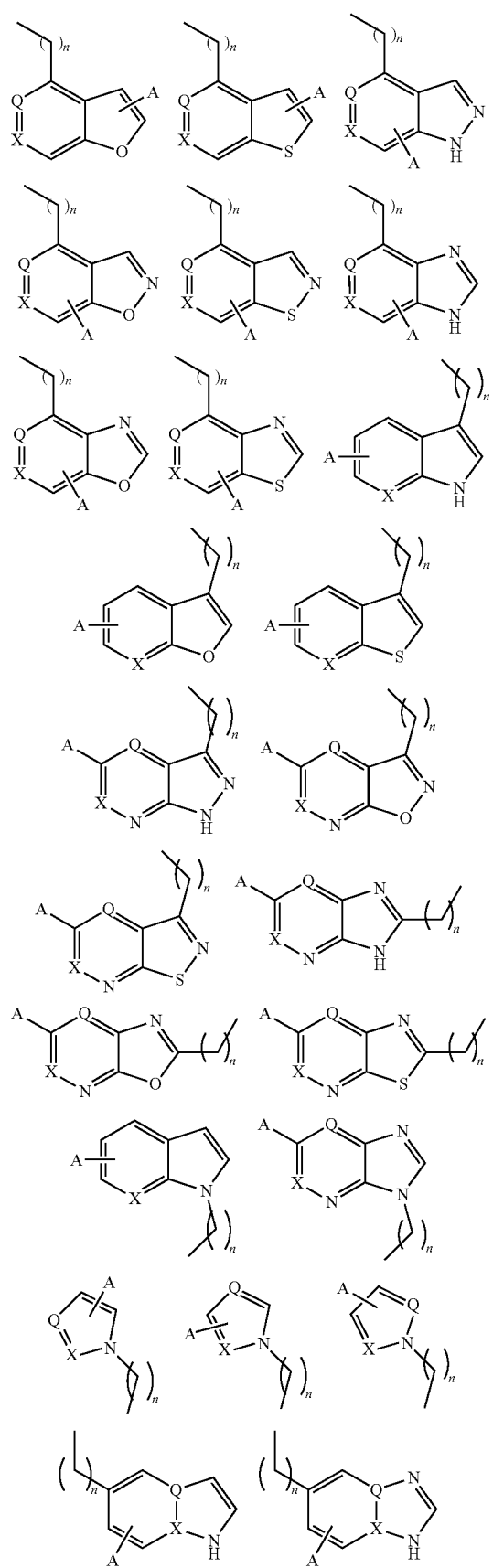
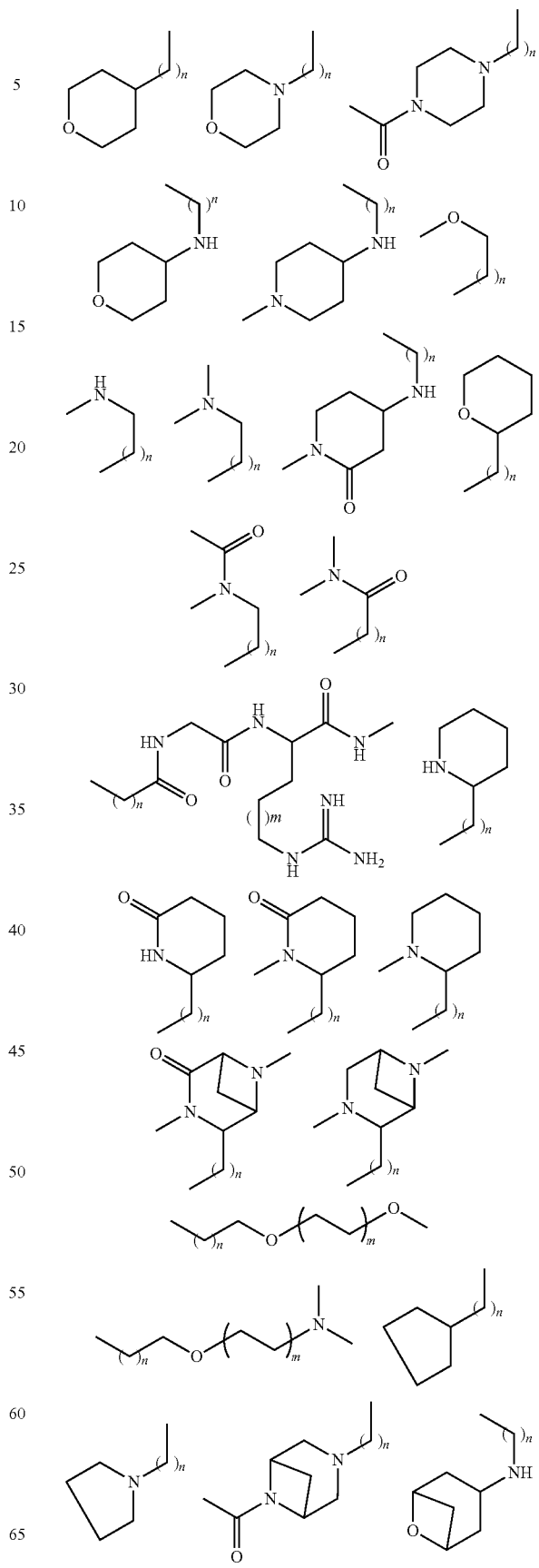

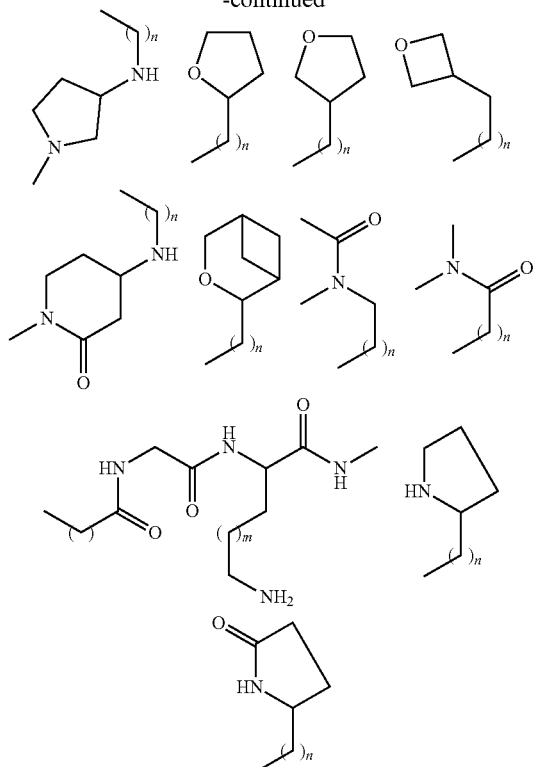

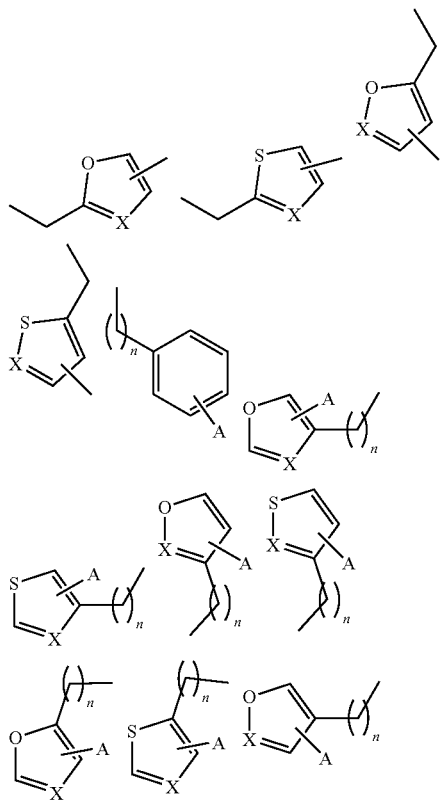

Where:

—A is —H, —Me, —Cl, —F, —Br, —I, —CF$_3$, —CHF$_2$, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.

n=0, 1, 2, 3 or 4; m=0, 1, 2, 3 or 4

R$_1$, R$_2$, and R$_3$ is a CONN-, O-, CH2—, HN—, CC—S-linker connected to a protein binder;

R$_4$ is O, S, NH, NCOY

Preferably, the Rpn 11 binding partner is denoted by the formula V

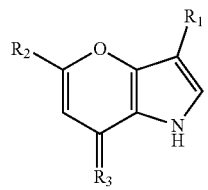

R1 and R$_2$ are selected from a group consisting of —CO—Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

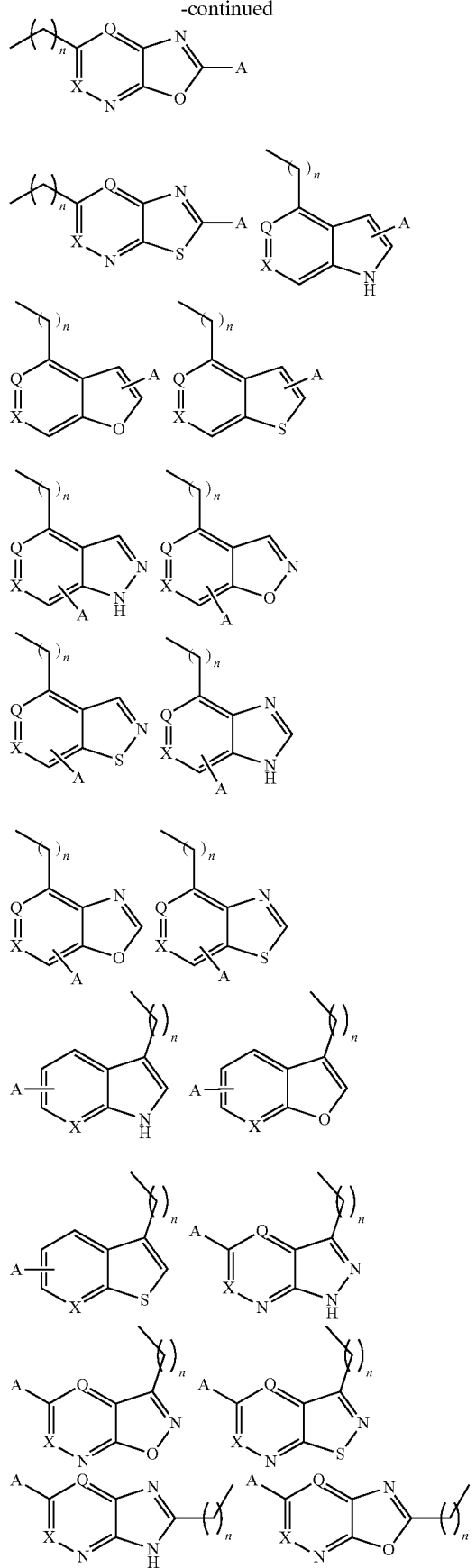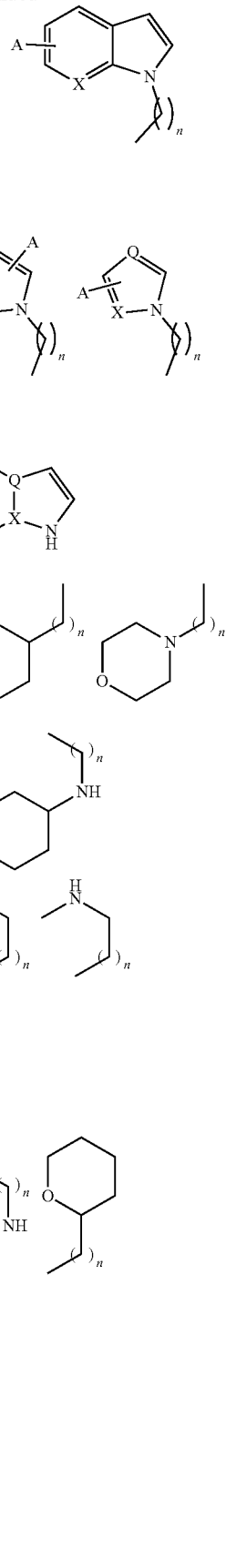

89

-continued

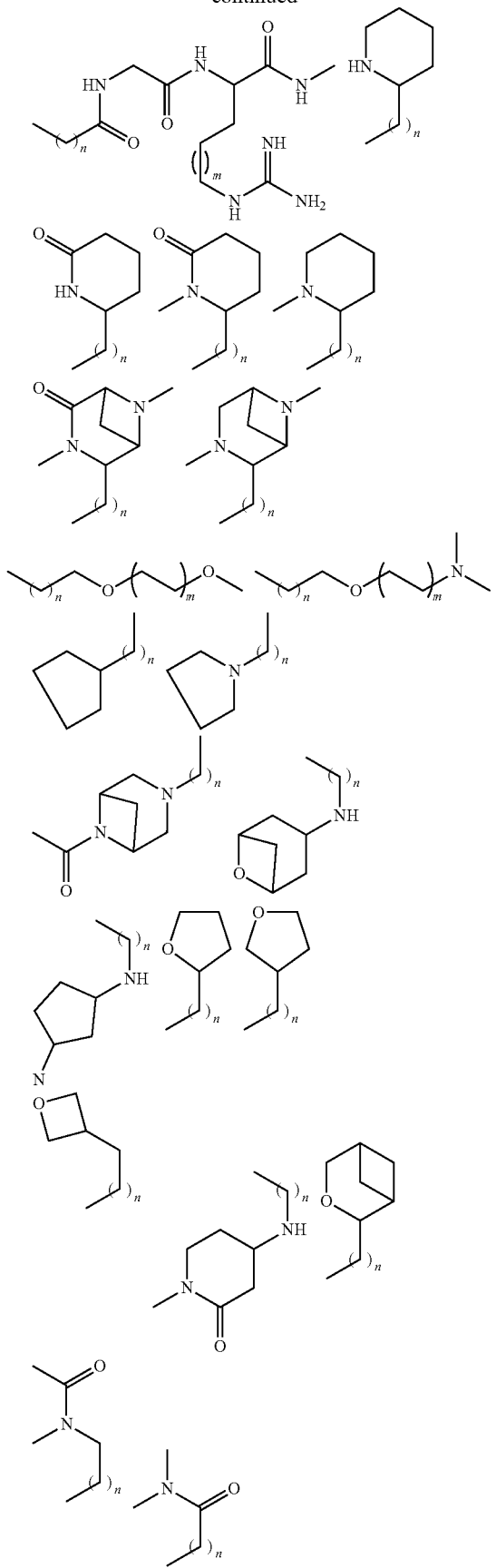

90

-continued

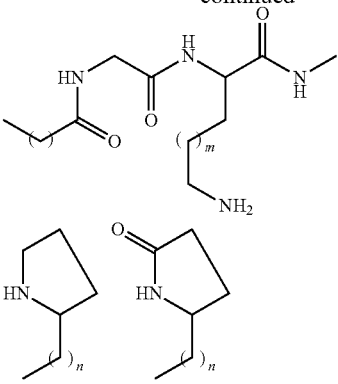

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ ...

—X and Q are N or CH.

n=0, 1, 2, 3 or 4; m=0, 1, 2, 3 or 4

R1, and R$_2$, is a CONH—, O-, CH2—, HN—, CC— S-linker connected to a protein binder;

R3 is O, S, NH, NCOY

Preferably, the Rpn 11 binding partner is denoted by the formula VI

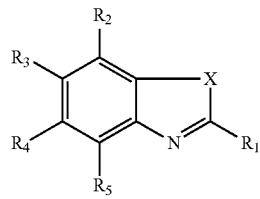

X=NH, O, S, CH$_2$

R1 and R4 are preferentially —H, but also —Me, —F, —Cl, —Br, —I, —CF$_3$, —CHF$_2$, —CH$_2$F, —CN, —OMe, —SMe, —SOMe, —SO$_2$Me —NH$_2$, —NHMe, —NO$_2$, —CHO ...

R$_2$ and R$_3$ is selected from a group consisting of —CO— Z, OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

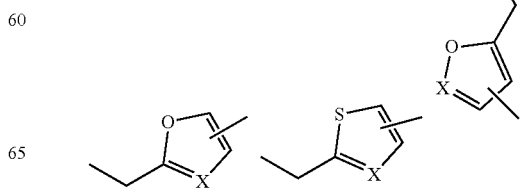

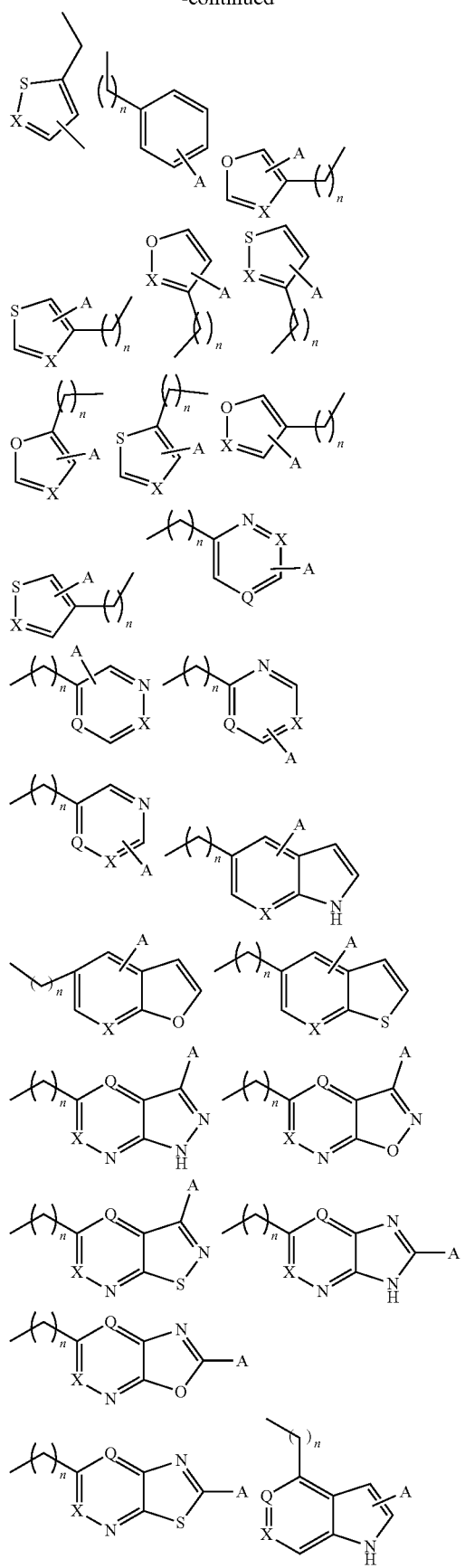
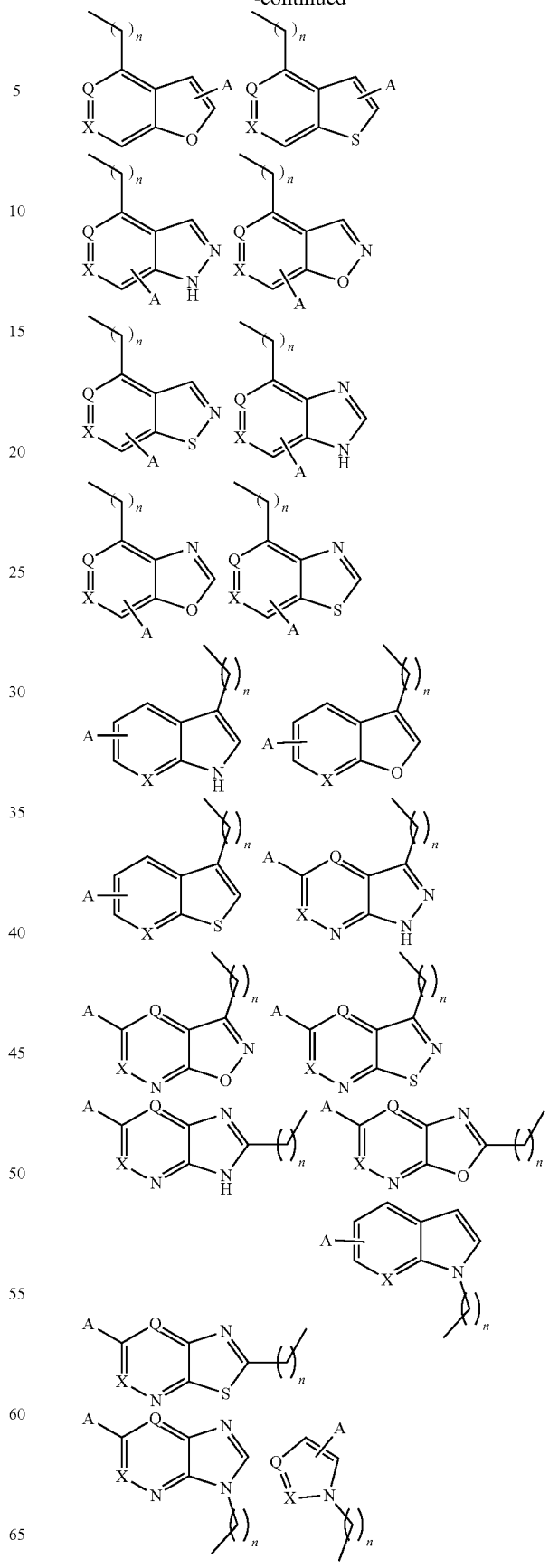

-continued
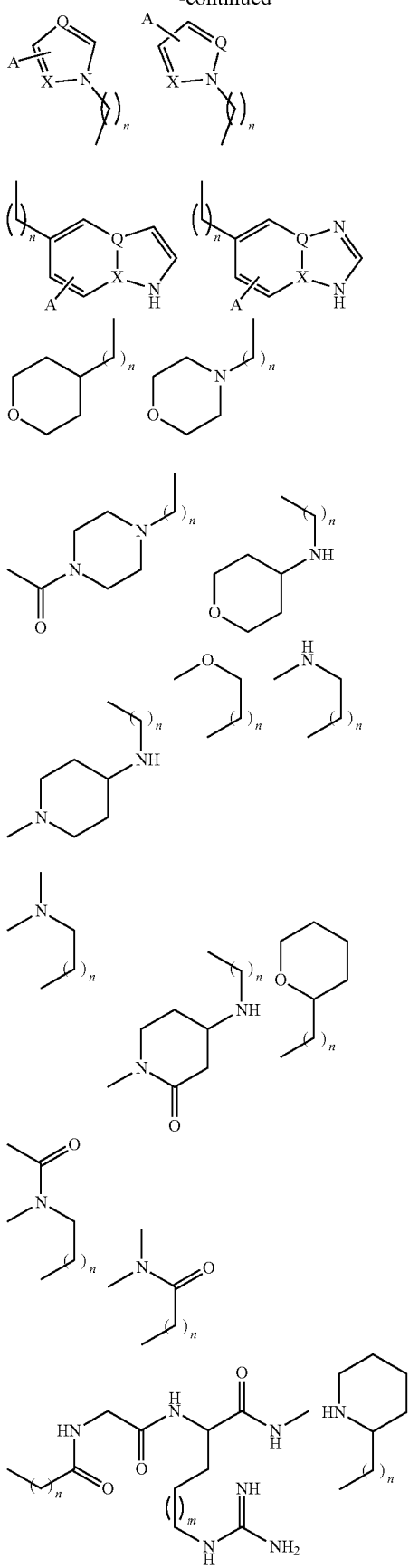
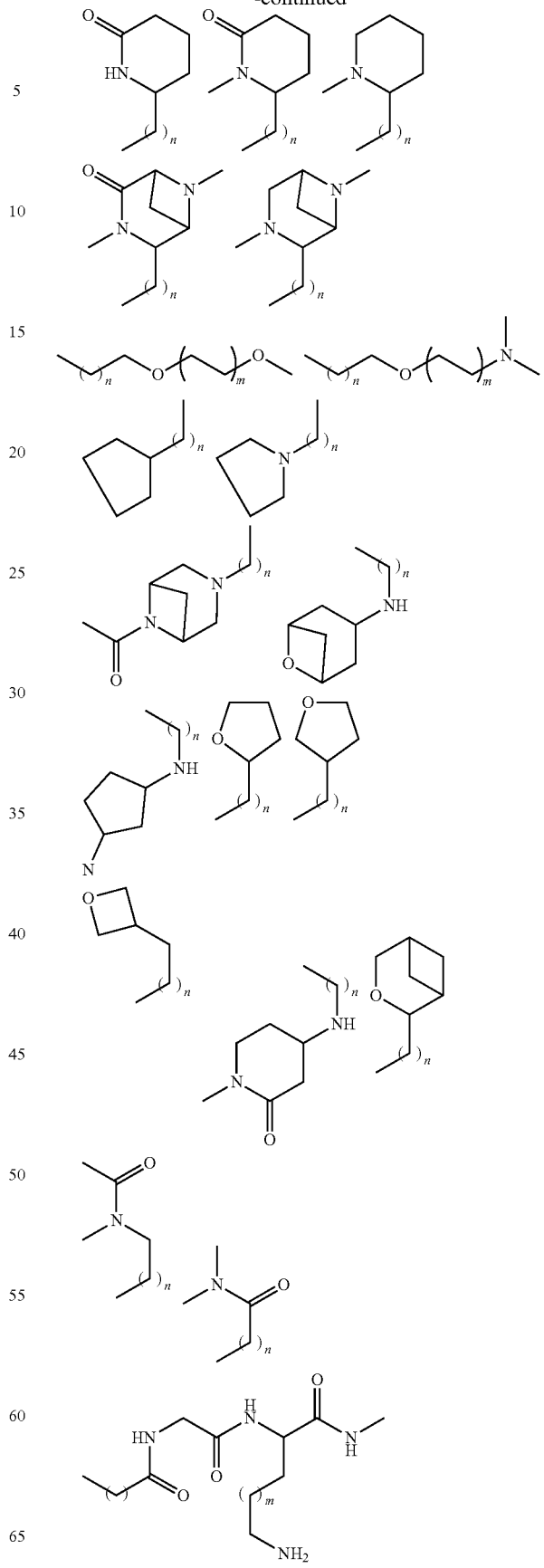

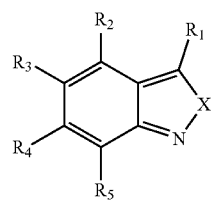

Where:
—A is —H, —Me, —Cl, —F, —Br, —I, —$CF_3$, —$CHF_2$, —$CH_2F$, —CN, —OMe, —SMe, —SOMe, —$SO_2Me$ —$NH_2$, —NHMe, —$NO_2$, —COOH, —CHO, —$COCH_3$, —$CO_2CH_3$, —$OCF_3$, —$OCHF_2$, —$OCH_2F$, —$SCF_3$, —$SCHF_2$, —$SCH_2F$, —$CONH_2$, —$CONHCH_3$, —$CON(CH_3)_2$, —$CSNH_2$, —$SONH_2$, —$SO_2NH_2$, —$SONHNH_2$ —X and Q are N or CH.

n=0, 1, 2, 3 or 4; m=0, 1, 2, 3 or 4

$R_2$, and R3 is a CONH—, O-, CH2—, HN—, CC— S-linker connected to a protein binder;

R5 is selected from a group consisting of —SH, —$NH_2$, —OH, SSY, SCOY, OCOY where Y is described above.

Preferably, the Rpn 11 binding partner is denoted by the formula VII

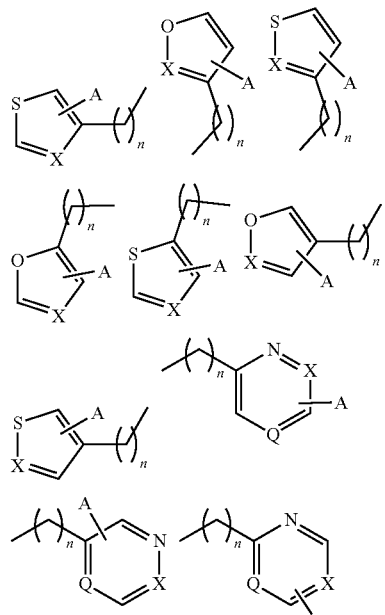

X=NH, O, S, $CH_2$

R1, $R_2$ and $R_3$ is selected from a group consisting of —CO—Z, $OCH_3$, —$CF_3$, —COOH, —$CH_2NH_2$, —$CH_3$, —H, —F, —Cl, —Br, —$CF_3$, —$CHF_2$, —$CH_2F$, —CN, —OH, —OMe, —SMe, —SOMe, —$SO_2Me$, —$NH_2$, —NHMe, $NO_2$, CHO; Z is selected from a group consisting of —$NH_2$, —NHY, —OH, and —OY; Y is selected from a group consisting of —$CH_3$, —$CH_2COO$—,

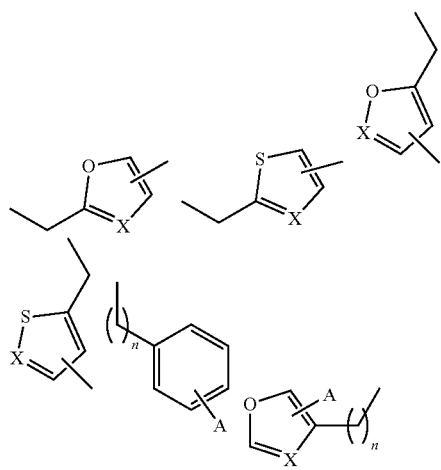

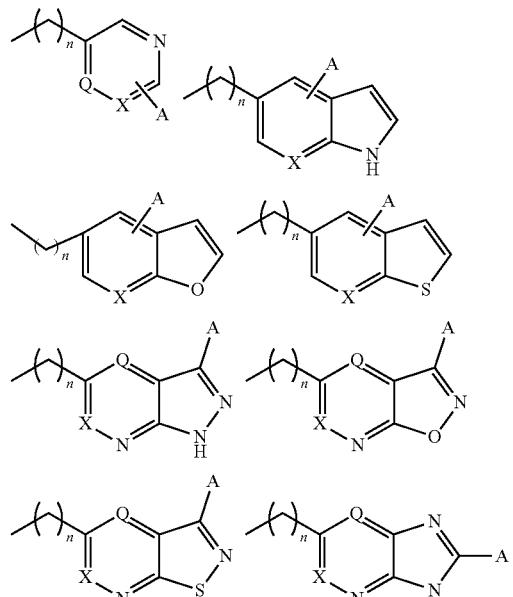

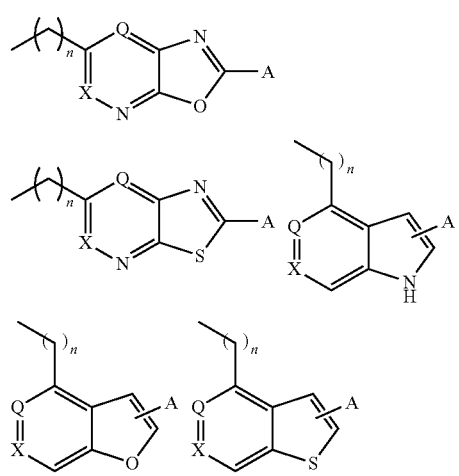

-continued
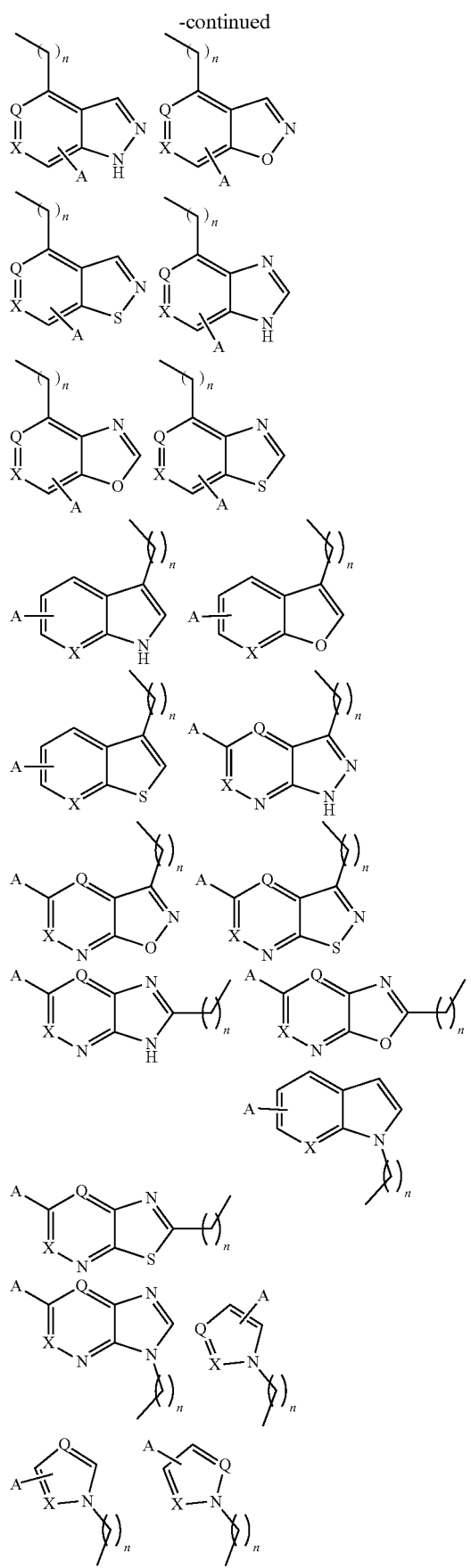
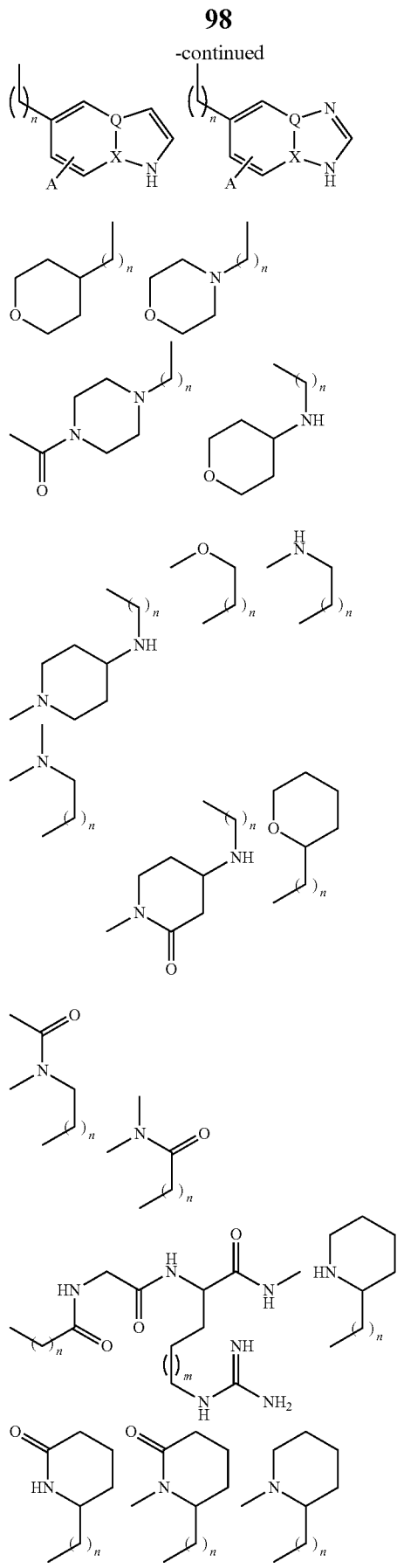

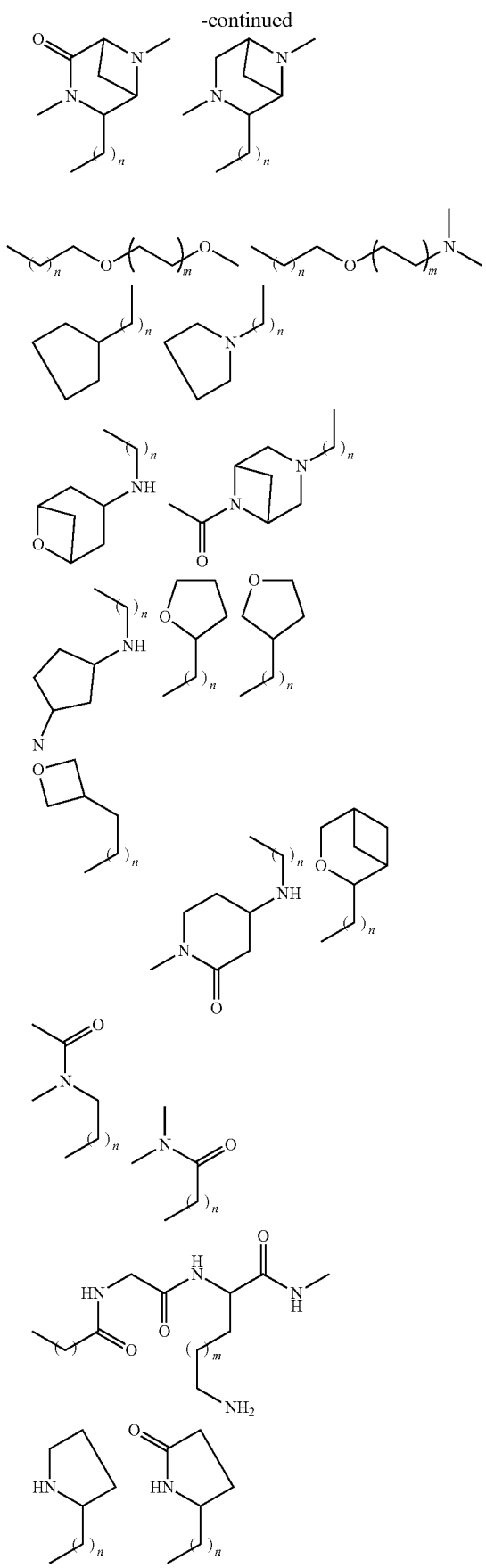

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.

n=0, 1, 2, 3 or 4; m=0, 1, 2, 3 or 4

R1, R2, and R3 is a CONH—, O—, CH2—, HN—, CC— S-linker connected to a protein binder;

R4 is are preferentially —H, but also Me, F, Cl, Br, CF$_3$, CHF$_2$, CH$_2$F, CN, OMe, SMe, SOMe, SO$_2$Me NH$_2$, NHMe, NO$_2$, CHO . . .

R5 is selected from a group consisting of —SH, —NH$_2$, —OH, SSY, SCOY, OCOY where Y is described above.

Preferably, the Rpn 11 binding partner is denoted by the formula VIII

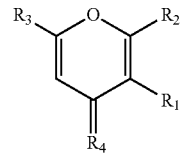

R1 is selected from a group consisting of —SH, —NH$_2$, —OH, —SSY, —SCOY, —OCOY, NHCOY where Y is described above.

R4 is selected from a group consisting of —S, —NH, —O,

R2 and R3 is selected from a group consisting of —CO— Z, —OCH$_3$, —CF$_3$, —COOH, —CH$_2$NH$_2$, —CH$_3$, —H, —F, —Cl, —Br, —CF$_3$, —CHF$_2$, —CH$_2$F, —CN, —OH, —OMe, —SMe, —SOMe, —SO$_2$Me, —NH$_2$, —NHMe, —NMe$_2$, NO$_2$, CHO; Z is selected from a group consisting of —NH$_2$, —NHY, —OH, and —OY; Y is selected from a group consisting of —CH$_3$, —CH$_2$COO—,

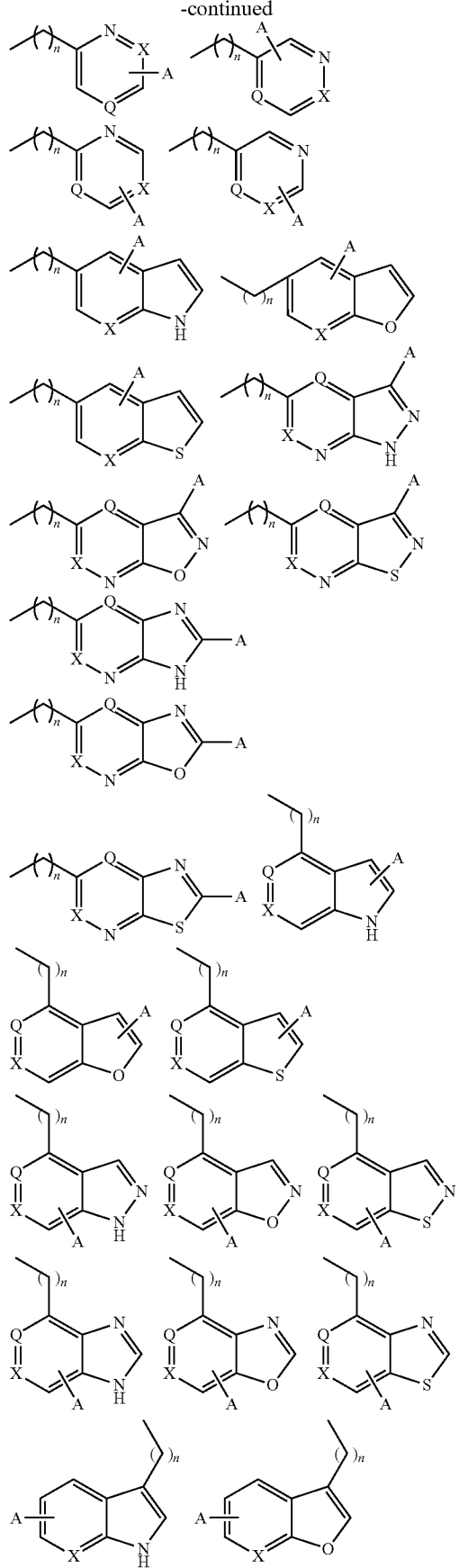
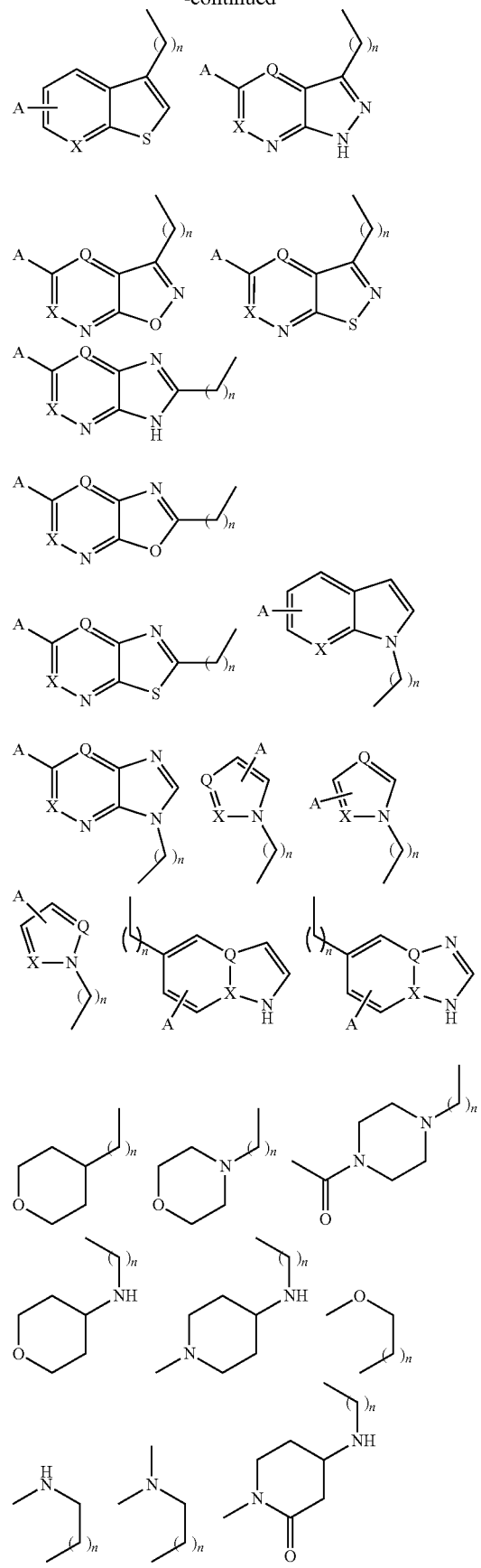

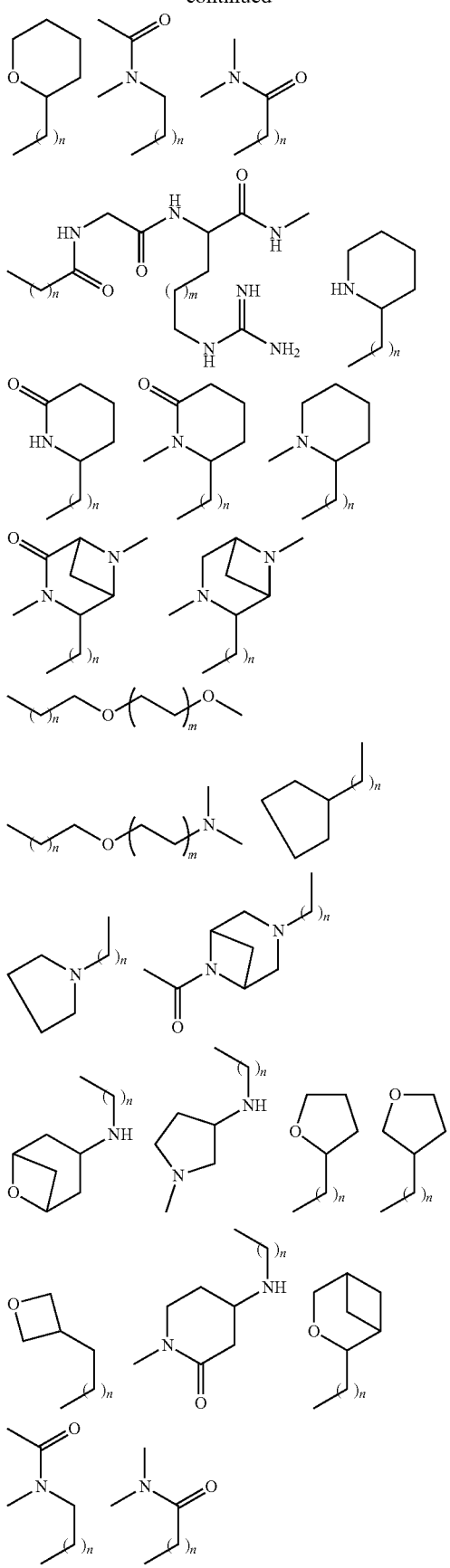

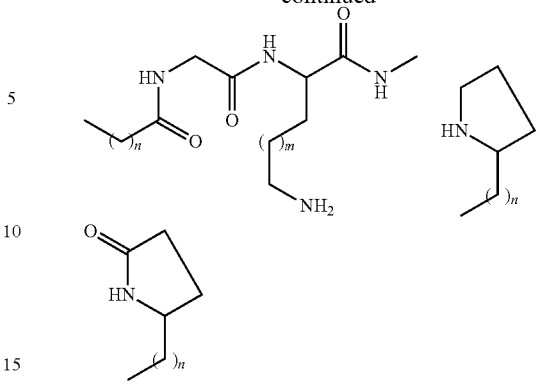

Where:
—A is —H, —Me, —F, —Br, —I, —CF$_3$, —CHF$_2$, —CH$_2$F, —CN, —OMe, —SMe, —SOMe, —SO$_2$Me —NH$_2$, —NHMe, —NO$_2$, —COOH, —CHO, —COCH$_3$, —CO$_2$CH$_3$, —OCF$_3$, —OCHF$_2$, —OCH$_2$F, —SCF$_3$, —SCHF$_2$, —SCH$_2$F, —CONH$_2$, —CONHCH$_3$, —CON(CH$_3$)$_2$, —CSNH$_2$, —SONH$_2$, —SO$_2$NH$_2$, —SONHNH$_2$ . . .

—X and Q are N or CH.
n=0, 1, 2, 3 or 4; m=0, 1, 2, 3 or 4
R$_2$, and R3 is a CONH—, O-, CH2—, HN—, CC— S-linker connected to a protein binder;
R4 is selected from a group consisting of —S, —NH, —O, In one embodiment, the bifunctional molecule is

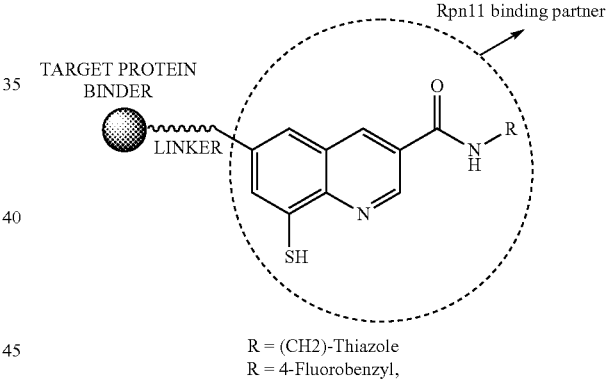

R = (CH2)-Thiazole
R = 4-Fluorobenzyl,
R = Thiazole ...

In one embodiment, the bifunctional molecule is

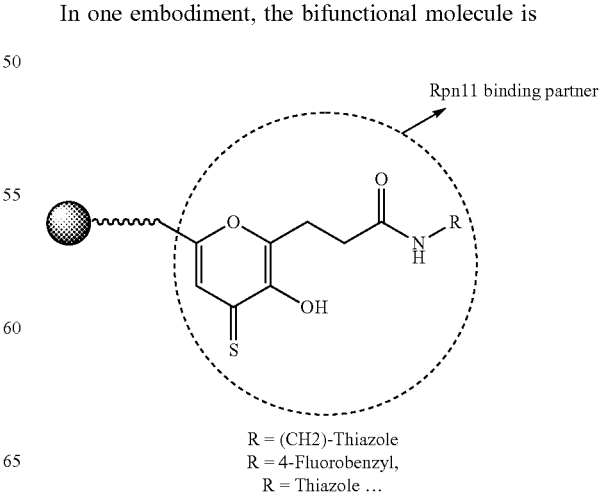

R = (CH2)-Thiazole
R = 4-Fluorobenzyl,
R = Thiazole ...

In one embodiment, the bifunctional molecule is selected from the group consisting of

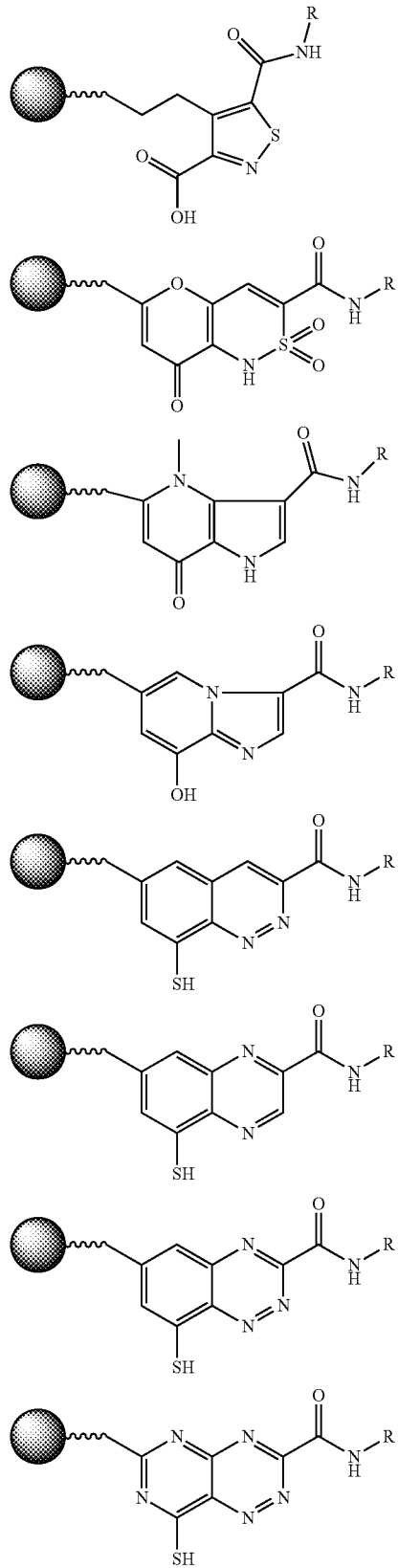

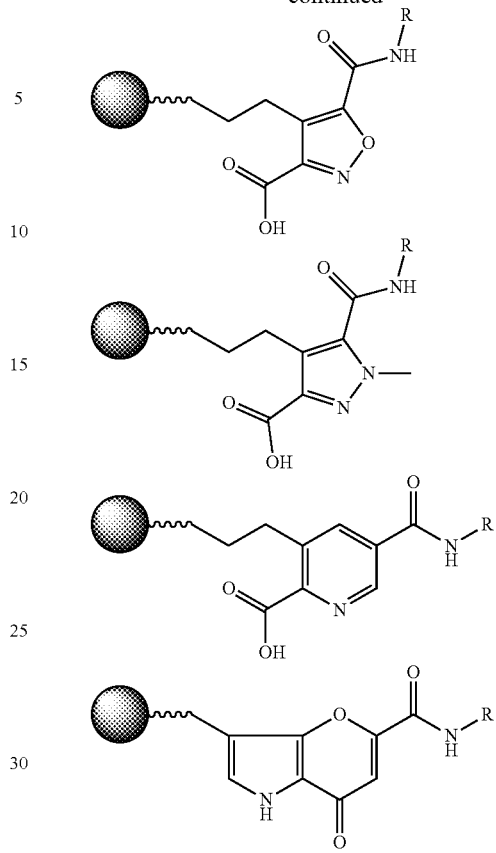

Wherein
R=(CH2)-Thiazole
R=4-Fluorobenzyl,
R=Thiazole . . . .

Preferably, the Rpn11 binding partner, when not covalently bound to the target protein binding partner, binds to Rpn11 with an affinity in the range of 10 nM-10 μM. More preferably, the Rpn11 binding partner, when not covalently bound to the target protein binding partner, binds to Rpn11 with an affinity of at least 10 nM.

Preferably, the Rpn11 binding partner, when not covalently bound to the target protein binding partner, binds to Rpn11 with a dissociation constant (Kd) range of 1 nM-1 μM. More preferably, the Rpn11 binding partner, when not covalently bound to the target protein binding partner, binds to Rpn11 with a Kd of less than 1 μM.

The Rpn11 binding partner may be selected from the group of Rpn11 binding molecules provided in Table 1.

The target protein binding partner may be selected from the group consisting of: kinase inhibitors, phosphatase inhibitors, compounds targeting BET bromodomain-containing proteins, HDM2/MDM2 inhibitors, heat shock protein 90 inhibitors, HDAC inhibitors, human lysine methyltransferase inhibitors and antibodies.

The bifunctional molecule facilitates proteolysis of a target protein.

Preferably, the linker is a polyethylene glycol (PEG) linker, a hydrocarbon linker, or a combined PEG, alkyl linker. Preferably, the linker has a first end that is an oxime and/or the linker has a second end that is an amine. The linker may comprise from 2 to 12 PEG repeats, and/or may comprise from 2 to 12 $(CH_2)n$ repeats.

The invention also includes a binding molecule which comprises an Rpn11 binding partner connected to a linker, where the linker is capable of linking to a second binding partner.

In this binding molecule, the Rpn11 binding partner may bind to Rpn11 with an affinity in the range of 10 nM-10 µM. The Rpn11 binding partner may bind to Rpn11 with an affinity of at least 10 nM.

In this binding molecule, the Rpn11 binding partner may bind to Rpn11 with a dissociation constant (Kd) range of 1 nM-1 µM. The Rpn11 binding partner may bind to Rpn11 with a Kd of less than 1 µM.

The Rpn11 binding partner may be selected from the group of Rpn11 binding molecules provided in Table 1.

Preferably, the linker is a polyethylene glycol (PEG) linker, a hydrocarbon linker, or a combined PEG, alkyl linker. Preferably, the linker has a first end that is an oxime and/or the linker has a second end that is an amine. The linker may comprise from 2 to 12 PEG repeats, and/or may comprise from 2 to 12 $(CH_2)n$ repeats.

The invention also includes a method of obtaining increased proteolysis of a target protein in a cell, the method comprising contacting the cell with a bifunctional molecule comprising an Rpn11 binding partner linked to a target protein binding partner.

The inventive methods also include a method of obtaining increased proteolysis of a target protein in a subject by administering to the subject a bifunctional molecule comprising an Rpn11 binding partner linked to a target protein binding partner.

The invention also includes a method of providing a bifunctional molecule comprising two covalently linked binding partners, wherein a first binding partner binds to Rpn11 and a second binding partner binds to a selected target protein, the method comprising providing the first and the second binding partners, and covalently linking the first and the second binding partners.

The invention also includes a method of selecting a bifunctional molecule that facilitates proteolysis of a target protein:
 a. selecting a first binding partner by providing a candidate first binding partner and determining that the candidate first binding partner binds to Rpn11;
 b. selecting a second binding partner by providing a candidate second binding partner and determining that the candidate second binding partner binds to a target protein of interest;
 c. covalently attaching the first and second binding partners to form a bifunctional molecule;
 d. contacting a cell with the bifunctional molecule;
 e. determining if the target protein undergoes proteolysis.

The inventive methods also include a method of selecting a bifunctional molecule capable of facilitating proteolysis of a target protein, comprising:
 (a) providing a bifunctional molecule comprising an Rpn11 binding partner covalently linked to a target protein binding partner,
 (b) contacting the bifunctional molecule with a cell in vitro or in a mammal, the cell comprising Rpn11 and the target protein, wherein the contacting permits binding of the bifunctional molecule to Rpn11 and the target protein, and
 (c) detecting proteolysis of the target protein in the cell, wherein the detected proteolysis is increased relative to proteolysis of the target protein in the absence of said contacting as in step (b).

The method also may include the step of measuring proteolysis of the target protein in the absence of the bifunctional molecule.

The invention also includes a library of bifunctional molecules, the library comprising a plurality of bifunctional molecules, the plurality of bifunctional molecules comprising a plurality of Rpn11 binding partners covalently linked to a selected target protein binding partner. As such, the target protein binding partner is pre-selected and the Rpn11 binding partner is not determined in advance. The library may be used to determine the activity of a candidate Rpn11 binding partner of a bifunctional molecule in facilitating target protein degradation.

The invention also includes a library of bifunctional molecules, the library comprising a plurality of bifunctional molecules, the plurality of bifunctional molecules comprising a plurality of target protein binding elements and a selected Rpn11 binding partner. As such, the Rpn11 binding partner is preselected and the target protein is not determined in advance. The library may be used to determine the activity of a putative target protein binding partner and its value as a binder of a target protein to facilitate target protein degradation.

The invention also provides a method of screening a library of candidate bifunctional molecules to identify a bifunctional molecule which facilitates proteolysis of a target protein.

The method comprises incubating a cell with a pool of bifunctional molecules from the library; monitoring the amount of target protein in the cell; identifying a subpool of bifunctional molecules that provide a decrease in the amount of target protein in the cell; incubating the cell with a bifunctional molecule from the identified subpool; monitoring the amount of target protein in the cell; and identifying a bifunctional molecule that provides a decrease in the amount of target protein in the cell.

These and additional inventive compositions and methods are found in the following detailed description and claims.

Figure 6A:
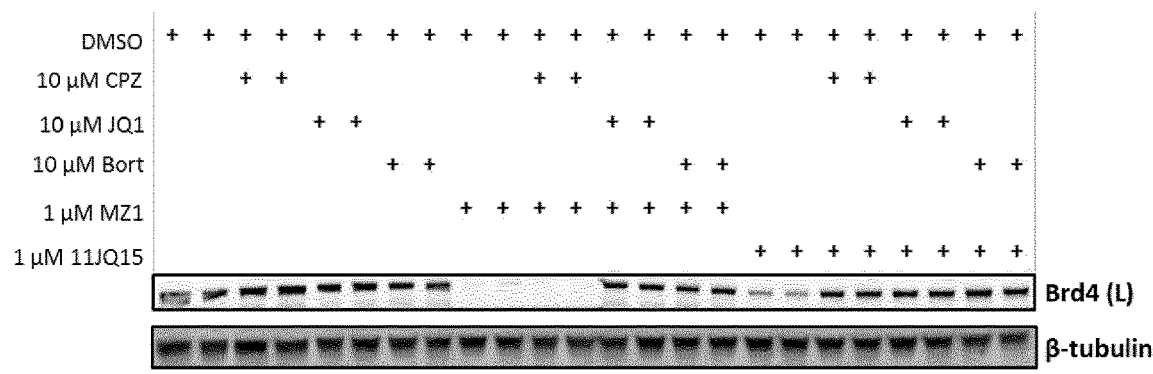
Figure 6B:
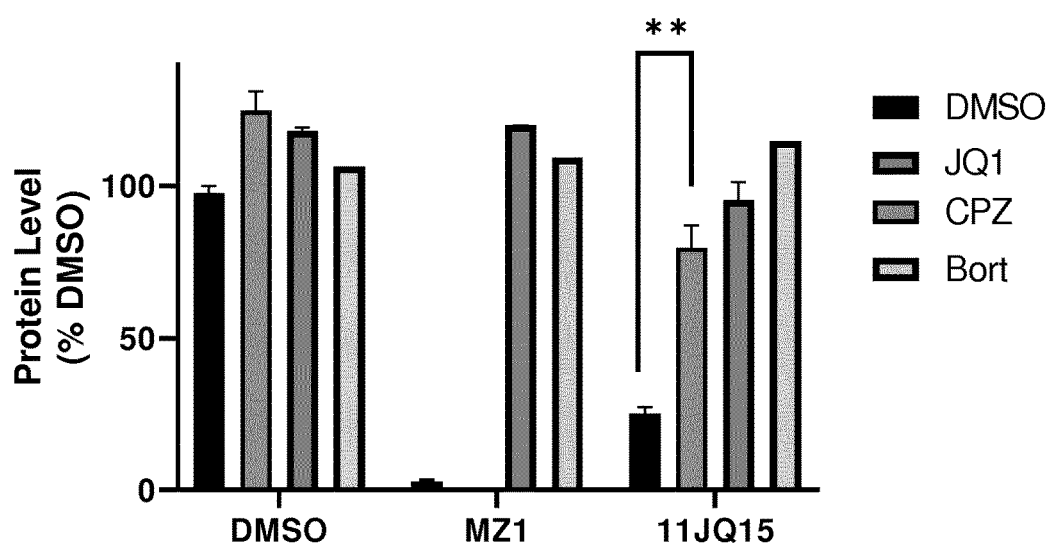
Figure 6C:
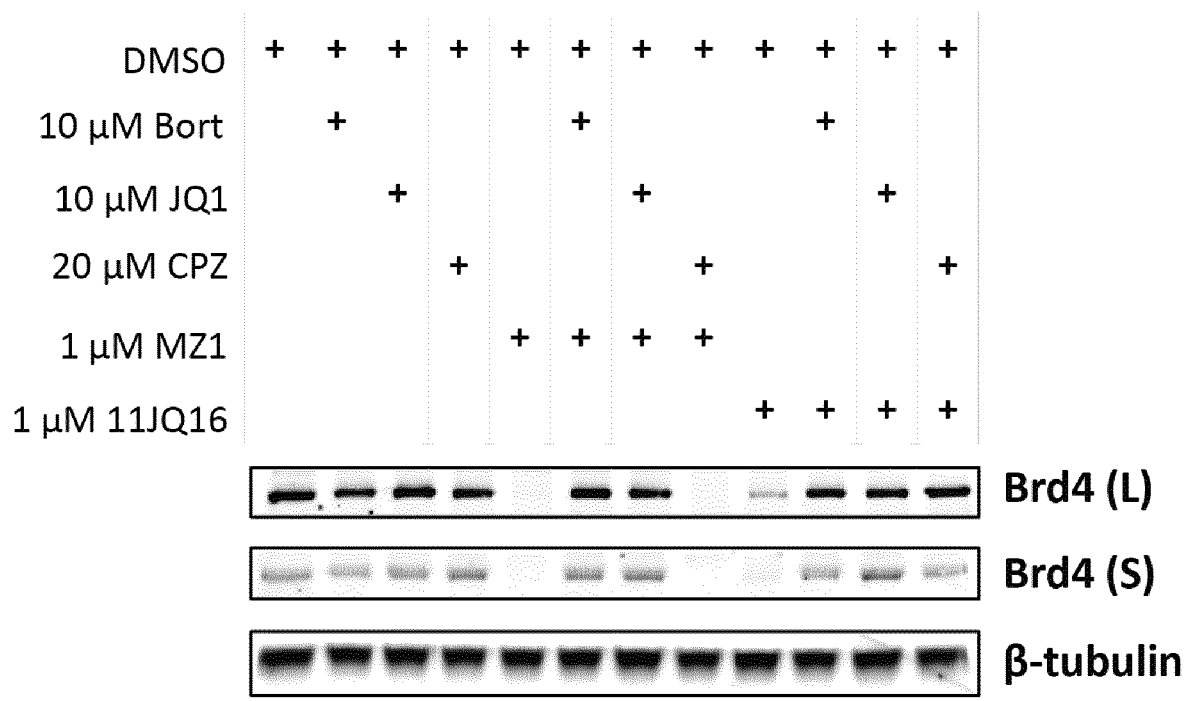

FIG. 6A shows representative immunoblot of Brd4 protein levels following 4 h treatment of HEK293 cells with 1 µM 11JQ15 or MZ1, in the presence and absence of 10 µM bortezomib, 10 µM capzimin, and 10 µM JQ1. In FIG. 6B, Brd4 band intensities were normalized to tubulin loading control and reported as % of the average 0.1% DMSO vehicle intensity. Each bar is mean±SEM of three independent experiments performed in duplicate (n=3). FIG. 6C shows an immunoblot of Brd4 protein levels following 4 h treatment of HeLa cells with 1 µM 11JQ16 or MZ1, in the presence and absence of 10 µM bortezomib, 20 µM capzimin, and 10 µM JQ1.

Figure 7:
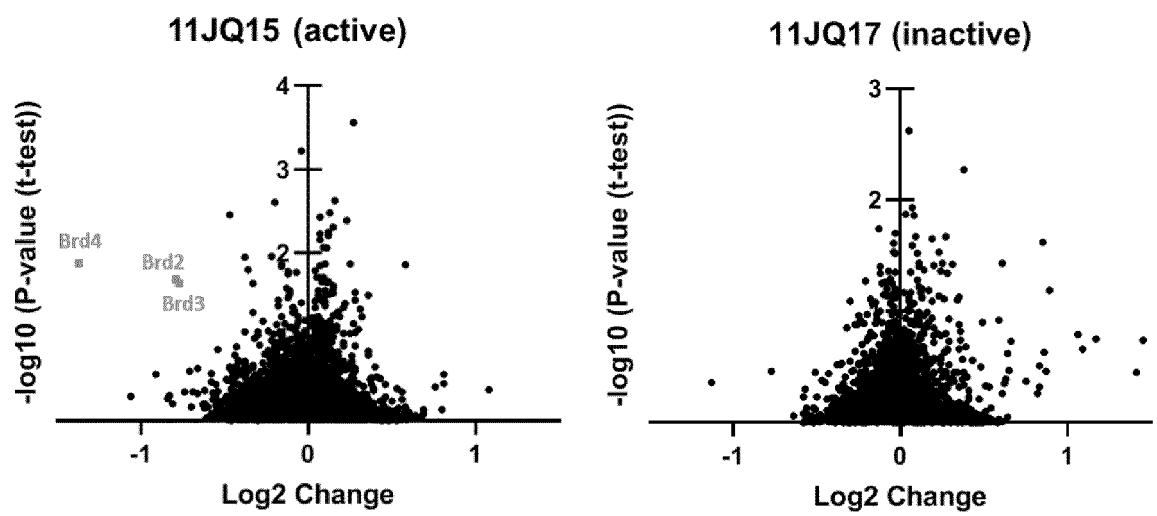

FIG. 7 show selective BET bromodomain degradation by unbiased TMT-labeling proteomics. HEK293 cells were treated for 4 hours with DMSO, 1 µM 11JQ15 or 1 µM 11JQ17. FIG. 7 (left) depicts fold change of abundance of 7882 proteins comparing 11JQ15 to DMSO treatment as well as their respective p-value (t-test; n=3); FIG. 7 (right) depicts fold change of abundance of 7882 proteins comparing 1 µM 11JQ17 to DMSO treatment (n=3)

Figure 8:
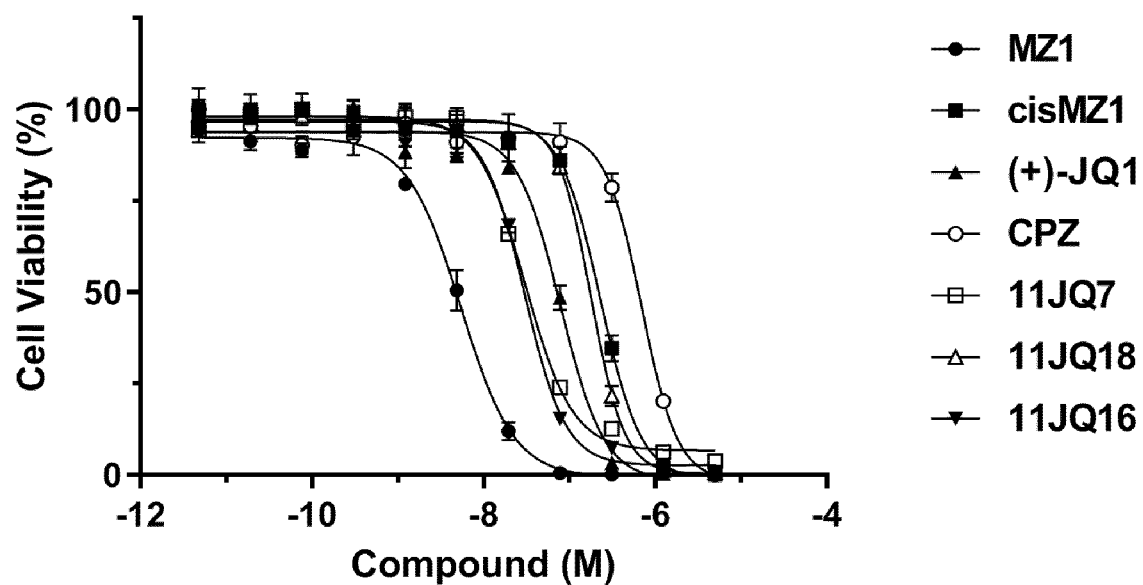

FIG. 8 shows the anti-proliferative effect in MV4-11 cells following treatment with 1 µM capzimin-based representative compounds, as measured using the CellTiter-Glo assay (Promega). JQ1 and capzimin (CPZ) were run in parallel, and MZ1 and 11JQ18 were used as positive and negative controls, respectively.

Figure 9:
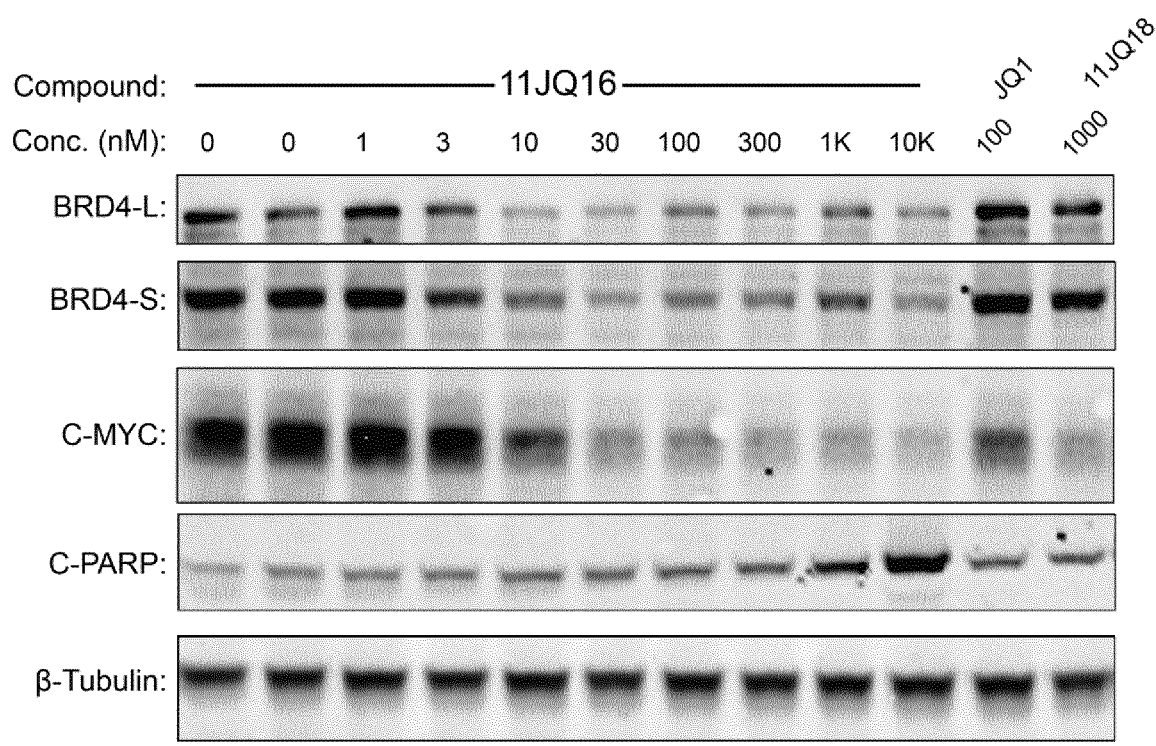

FIG. 9 shows representative immunoblots of Brd4, c-MYC, cleaved PARP (C-PARP) levels in MV4-11 cells following treatment with increasing concentrations of 11JQ16, compared to BET inhibitor JQ1. 11JQ18 was used as a negative control.

Figure 10:
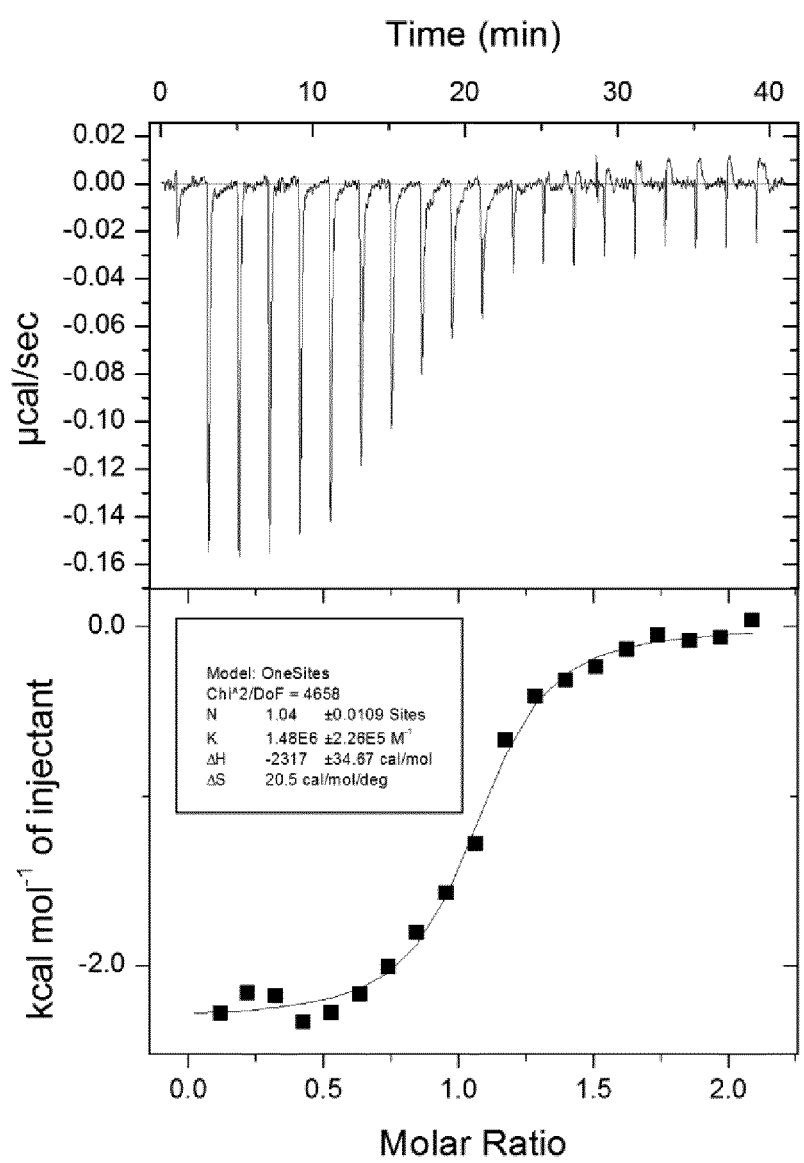

FIG. 10 shows an ITC titration of the capzimin based compounds into purified human Rpn11-Rpn8 heterodimer.

DETAILED DESCRIPTION

The invention provides for a bifunctional molecule that can bind simultaneously to Rpn11 and a selected target protein, thereby facilitating degradation of the target protein by proteolysis.

Compositions and methods are described that relate to recruiting a selected target protein to the proteasome to undergo proteolysis. This is accomplished according to the invention using a bifunctional molecule that binds both Rpn11 and the selected target protein. Accordingly, the present invention provides molecules having dual binding functionality comprising a Rpn11 binding partner linked to a binding partner of a target protein. The present invention facilitates degradation of a selected target protein by the proteasome.

Definitions

As used herein, a "bifunctional molecule" has a functional group at each end, wherein a first functional group is an Rpn11 binding partner, and a second functional group is a target protein binding partner. A bifunctional molecule can bind to Rpn11 and a selected target protein simultaneously.

The term "ubiquitination" refers to the process of ubiquitin ligation of a given protein, whereby the protein undergoes covalent attachment of one ore more ubiquitin molecules to the protein (this occurs via attachment of ubiquitin typically to a surface lysine residue of the protein, or to its N-terminus). The covalent attachment of ubiquitin molecules marks the protein for proteasomal degradation, whereupon the protein is digested into small peptides.

The term "ubiquitin-independent degradation" means proteolysis of a selected target protein which does not require ubiquitination of the target protein prior to its proteolysis.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "solvate" refers to a pharmaceutically acceptable form of a specified compound, with one or more solvent molecules, that retains the biological effectiveness of such compound. Examples of solvates include compounds of the invention in combination with solvents such, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents, and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e., six carbons or less). For example, "lower alkyl" refers to an alkyl group containing 1-6 carbons, and "lower alkenyl" refers to an alkyenyl group containing 2-6 carbons.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged). "Monocyclic" refers to compounds and/or groups with one ring; and "bicyclic" refers to compounds/and or groups with two rings.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 20, 1 to 15, or 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, 1-(1-ethylcyclopropyl)ethyl and 1-cyclohexylethyl.

The term "cycloalkyl" is a subset of alkyl which refers to cyclic hydrocarbon radical containing from 3 to 15, 3 to 10, or 3 to 7 carbon atoms. Representative examples of cycloalkyl include, but are not limited to, cyclopropyl and cyclobutyl.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon 15 radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene," is art-recognized, and as used herein pertains to a diradical obtained by removing two hydrogen atoms of an alkyl group, as defined above.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein refers to a radical of a non-aromatic, ring system, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfoni acid, alkylsulfonyl, haloalkylsulfonyl, fluroralkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, allwxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "aryl," as used herein means a phenyl, naphthyl, phenanthrenyl, or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluroralkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, halo alkylcarbonyl, fluoroalkylcarbonyl, alkenylcarbonyl, alkynylcarbonyl, carboxyl, alkoxycarbonyl halo alkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluroralkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyan, nitro, azido, phosphinyl, phosphoryl, silyl, silyloxy, and any of said substituents bound to the heterocyclyl group through an alkylene moiety (e.g., methylene).

The term "arylene," is art-recognized, and as used herein pertains to a diradical obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl) phenyl and 4-(4-methoxyphenyl)pyridinyl.

The term "heteroaryl" as used herein include radicals of aromatic ring systems, including, but not limited to, monocyclic, bicyclic and tricyclic rings, which have 3 to 12 atoms including at least one heteroatom, such as nitrogen, oxygen, or sulfur. For purposes of exemplification, which should not be construed as limiting the scope of this invention: aminobenzimidazole, benzimidazole, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkyenyloxy, alkynyloxy, carbocyclyloxy, heterocyclyloxy, halo alkoxy, fluoroalkyloxy, sulfhydryl, alkylthio, halo alkylthio, fluoroalkylthio, alkyenylthio, alkynylthio, sulfonic acid, alkylsulfonyl, haloalkylsulfonyl, fluroralkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, halo alkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluroralkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g., methylene).

The term "heteroarylene," is art-recognized, and as used herein pertains to a diradical obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "fused bicyclyl" as used herein means the radical of a bicyclic ring system wherein the two rings are ortho-fused, and each ring, contains a total of four, five, six or seven atoms (i.e., carbons and heteroatoms) including the two fusion atoms, and each ring can be completely saturated, can contain one or more units of unsaturation, or can be completely unsaturated (e.g., in some case, aromatic). For the avoidance of doubt, the degree of unsaturation in the fused bicyclyl does not result in an aryl or heteroaryl moiety. The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein some or all of the hydrogens are replaced with fluorines.

The term "haloalkylene," as used herein pertains to diradical obtained by removing two hydrogen atoms of an haloalkyl group, as defined above.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclylthio", and "heterocyclylthio" are likewise defined.

The term "arylthio" as used herein means an aryl group, as defined herein, appended to the parent molecular moiety through a sulfur. The term "heteroarylthio" is likewise defined.

The term "arylalkylthio" or "aralkylthio" as used herein means an arylalkyl group, as defined herein, appended to the parent molecular moiety through a sulfur. The term "heteroarylalkylthio" is likewise defined.

The term "sulfonyl" as used herein refers to —S(=O)2- group.

The term "sulfonic acid" as used herein refers to —S(=O)2OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluororalkylsulfonyl","alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein.

Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O) hydrogen group.

The term "acyl" as used herein refers to any group or radical of the form —C(=O)R, where R is an organic group. An example of the acyl group is the acetyl group (—C(=O)CH3).

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxop entyl. The terms "halo alky lc arb onyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxyl" as used herein means a —CO₂H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The terms "haloalkoxycarbonyl","fluoroalkoxycarbonyl","alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy","fluoroalkylcarbonyloxy", "alkenylcarbonyloxy", "a lkynylcarbonyloxy", "carbocyc lylcarbonyloxy", "heterocyclylcarbonyloxy", "arylcarbonyloxy","aralkylcarbonyloxy", "heteroarylcarbonyloxy", and "heteroaralkylcarbonyloxy" are likewise defined.

The term "alkylsulfonyloxy" as used herein means an alkylsulfonyl group, as 10 defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "arylsulfonyloxy", "heteroaralkylsulfonyloxy","alkenyloxysulfonyloxy", "heterocyclyloxysulfonyloxy" "carbocyclylsulfonyloxy", "aralkylsulfonyloxy", "haloalkoxysulfonyloxy", "alkynyloxysulfonyloxy", "aryloxysulfonyloxy", "heterocyclylsulfonyloxy", "heteroarylsulfonyloxy", "fluoroalkoxysulfonyloxy", "carbocyclyloxysulfonyloxy","aralkyloxysulfonyloxy", heteroaryloxysulfonyloxy" and "heteroaralkyloxysulfonyloxy" are likewise defined.

The term "amino" or "amine" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyan" as used herein means a —CN group.

The term "nitro" as used herein means a —NO2 group.

The term "azido" as used herein means a —N3 group.

The term "phosphinyl" or "phosphino" as used herein includes —PH3 and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH2 and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H3Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl methanesulfonyl, carbobenzyloxy, and tert-butyloxycarbonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

By "protein-expression related disease" is meant a disease or disorder whose pathology is related at least in part to inappropriate protein expression (e.g., expression at the wrong time and/or in the wrong cell), excessive protein expression or expression of a mutant protein. In one embodiment, a mutant protein disease is caused when a mutant protein interferes with the normal biological activity of a cell, tissue, or organ.

By "mutant protein" is meant a protein having an alteration that affects its primary, secondary or tertiary structure relative to a reference (wild type) protein.

By "enhances" is meant a positive alteration of at least about 10%, 15%, 25%, 50%, 75%, or 100%.

By "reduces" is meant a negative alteration of at least about 10%, 25%, 50%, 75%, or 100%.

By "selective degradation" is meant degradation that preferentially affects a targeted protein, such that other proteins are substantially unaffected. In various embodiments, less than about 45%, 35%, 25%, 15%, 10%, or 5% of non-targeted proteins are degraded.

Rpn11 is a deubiquitinating enzyme which assists in removing the polyubiquitin chain from a ubiquitinated substrate by cutting at the junction between the ubiquitin chain and the substrate to release the ubiquitin for recycling. The ubiquitin recycling step catalyzed by Rpn11 is necessary for protein degradation. Rpn11 is a metalloprotease. (Perez et al. 2017 J. Med. Chem. 60:1343-1361 and US2017050931). Rpn11 presents the metalloproteases activity to hydrolyze the ubiquitin molecules from the poly-ubiquitin chain before protein substrates are unfolded and degraded. Human Rpn11 is also known as PSMD14 and POH1.

```
Rpn11 Nucleotide and Amino Acid Sequences (Human)
PSMD14 - 000487
Rpn11 Nucleotide sequence
atggacagacttcttagacttggaggaggtatgcctggactgggccaggg gccacctacagatgctcctgcagtggacacagcagaacaagtctatatct cttccctggcactgttaaaaatgttaaaacatggccgtgctggagttcca atggaagttatgggtttgatgcttggagaatttgttgatgattataccgt cagagtgattgatgtgtttgctatgccacagtcaggaacaggtgtcagtg tggaggcagttgatccagtgttccaagctaaaatgttggatatgttgaag cagacaggaaggccggagatggttgttggttggtatcacagtcaccctgg ctttggttgttggctttctggtgtggatatcaacactcagcagagctttg aagccttgtcggagagagctgtggcagtggttgtggatcccattcagagt gtaaaaggaaaggttgttattgatgccttcagattgatcaatgctaatat gatggtcttaggacatgaaccaagacaaacaacttcgaatctgggtcact taaacaagccatctatccaggcattaattcatggactaaacagacattat tactccattactattaactatcggaaaaatgaactggaacagaagatgtt gctaaatttgcataagaagagttggatggaaggtttgacacttcaggact acagtgaacattgtaaacacaatgaatcagtggtaaaagagatgttggaa ttagccaagaattacaataaggctgtagaagaagaagataagatgacacc tgaacagctggcaataaagaatgttggcaagcaggaccccaaacgtcatt tggaggaacatgtggatgtacttatgacctcaaatattgtccagtgttta gcagctatgttggatactgtcgtatttaaataa Rpn11 Amino Acid Sequence
MDRLLRLGGGMPGLGQGPPTDAPAVDTAEQVYISSLALLKMLKHGRAGVP

MEVMGLMLGEFVDDYTVRVIDVFAMPQSGTGVSVEAVDPVFQAKMLDMLK

QTGRPEMVVGWYHSHPGFGCWLSGVDINTQQSFEALSERAVAVVVDPIQS
```

-continued
VKGKVVIDAFRLINANMMVLGHEPRQTTSNLGHLNKPSIQALIHGLNRHY

YSITINYRKNELEQKMLLNLHKKSWMEGLTLQDYSEHCKHNESVVKEMLE

LAKNYNKAVEEEDKMTPEQLAIKNVGKQDPKRHLEEHVDVLMTSNIVQCL

AAMLDTVVFK

A "selected target protein" is a protein that the skilled practitioner wishes to selectively degrade and/or inhibit in a cell or a mammal, e g, a human subject. According to the invention, degradation of the target protein will occur when the target protein is subjected to a bifunctional molecule, as set forth herein. Degradation of the target protein will reduce protein levels and reduce the effects of the target protein in the cell. The control of protein levels afforded by the present invention provides treatment of a disease state or condition, which is modulated through the target protein by lowering the level of that protein in the cells of a patient.

A "target protein binding partner" refers to a partner which binds to a selected target protein. A target protein binding partner is a molecule which selectively binds a target protein. A bifunctional molecule according to the invention contains a target protein binding partner which binds to the target protein with sufficient binding affinity such that the target protein is more susceptible to proteolysis than if unbound by the bifunctional molecule.

The term "selected target protein" refers to a protein which is selected by one of skill in the art to be targeted for protein degradation.

The term "linker" refers to, in its simplest foil 1, an alkyl linker comprising, a repeating subunit of —$CH_2$—; where the number of repeats is from 1 to 50, for example, 1-50, 1-40, 1-30, 1-1-19, 1-18, 1-17, 1-16, 1-15, 1-14, 1-13, 1-12, 1-11, 1-10, 1-9. 1-8, 1-7, 1-6, 1-5, 1-4, 1-3 and 1-2. The term "linker" also refers a polyethylene glycol (PEG) linker comprising repeating subunits of ethylene glycol ($C_2H_4O$), for example, having from about 1-50 ethylene glycol subunits, for example where the number of repeats is from 1 to 100, for example, 1-50, 1-40, 1-1-20, 1-19, 1-18, 1-17, 1-16, 1-15, 1-14, 1-13, 1-12, 1-11, 1-10, 1-9, 1-8, 1-7, 1-6, 1-5, 1-4, 1-3 and 1-2. A "linker" is desired to be of a length and flexibility such that the target protein binding partner and the Rpn11 binding partner are within a particular distance. For example, an Rpn11 binding paltrier and a target protein binding partner of a bifunctional molecule of the invention connected via a linker, may be separated by a distance of 18-95 Å, for example, 18-25 Å for a linker comprising 2-4 ethylene glycol subunits, 25-33 Å for a linker comprising 4-6 ethylene glycol subunits, 33-39 Å for a linker comprising 6-8 ethylene glycol subunits, 39-53 Å for a linker comprising 8-12 ethylene glycol subunits and, 53 to 95 Å for a linker comprising 12-24 ethylene glycol subunits. In one embodiment, an Rpn11 binding partner and a target protein binding partner of a bifunctional molecule of the invention connected via a linker may be separated by a distance of 7 to 80 atoms, for example, 7-13 atoms for a linker comprising 2-4 ethylene glycol subunits, 13-19 atoms for a linker comprising 4-6 ethylene glycol subunits, 19-atoms for a linker comprising 6-8 ethylene glycol subunits, 25-41 atoms for a linker comprising 8-12 ethylene glycol subunits and, 41-80 atoms for a linker comprising 12-24 ethylene glycol subunits. In some embodiments, the linker is a single atom, for example —$CH_2$— or —O—. In some embodiments, the linker is a peptide linker.

A linker of the invention can have a degree of flexibility that corresponds to the number of rotatable bonds in the linker. A rotatable bond is defined as a single non-ring bond, bound to a nonterminal heavy atom. An amide (C—N) bond is not considered rotatable because of the high rotational energy barrier. The invention provides for linkers having a particular degree or range of flexibility. Such linkers can be designed by including rings, double bonds and amides to reduce the flexibility of the linker. A linker having a high degree of flexibility would be an unsubstituted PEG or alkyl linker.

The present invention also includes pro-drugs. As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)2H or a moiety that contains a carboxylic acid) wherein the free hydrogen is replaced by (Ci-C4)alkyl, (C2-Ci2)alkanoyloxymethyl, (C4-C9)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-(Ci-C2)alkylamino(C2-C3)alkyl (such dimethylamino ethyl), carbamoyl-(Ci-C2)alkyl, N,N-di(Ci-C2)-alkylc arbamoyl-(Ci-C2)alkyl and piperidino-, pyrrolidino- or morpholino (C2-C3)alkyl.

Other exemplary pro-drugs release an alcohol or amine of a compound of the invention wherein the free hydrogen of a hydroxyl or amine substituent is replaced by (C1-C6) alkanoyloxymethyl, 1((C1-C6)alkanoyloxy)ethyl, 1-methy1-14 (Ci-C6)alkanoyloxy)ethyl, (C1-C6)alkoxycarbonyl-oxymethyl, N-(Ci-C6)alkoxycarbonylamino-methyl, succinoyl, (C1-C6)alkanoyl, a-amino(C1-C4)alkanoyl, arylactyl and a-aminoacyl, or a-aminoacyl-a-aminoacyl wherein said a-aminoacyl moieties are independently any of the naturally occurring L-amino acids found in proteins, —P(O)(OH)$_2$, —P(O)(O(C1-C6)alkyl)2 or glycosyl (the radical resulting from detachment of the hydroxyl of the hemiacetal of a carbohydrate).

The phrase "protecting group" as used herein means temporary substituents which protect a potentially reactive functional group from undesired chemical transfonnations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)CH3, —OAc).

For example, an aldehyde or ketone group may be protected as an acetal or ketal, respectively, in which the carbonyl group (C(═O)) is converted to a diether (C(OR)2), by reaction with, for example, a primary alcohol. The aldehyde or ketone group is readily regenerated by hydrolysis using a large excess of water in the presence of acid.

For example, an amine group may be protected, for example, as an amide (—NRC(═O)R) or a urethane (—NRC(═O)OR), for example, as: a methyl amide (—NHC(═O)CH3); a benzyloxy amide (—NHC(═O)OCH2C6H5NHCbz); as a t-butoxy amide (—NHC═(═O)OC(CH3)3, —NHBoc); a 2-biphenyl-2-propoxy amide (—NHC(═O)OC(CH3)$_2$C6H4C6H5NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide. For example, a thiol group may be protected as a thioether (—SR), for example, as: a benzyl thioether; or an acetamidomethyl ether (—SCH2NHC(═O)CH3).

Some representative examples of pro-drugs that are activated by the cleavage or hydrolysis of a chemical protective group is shown below.

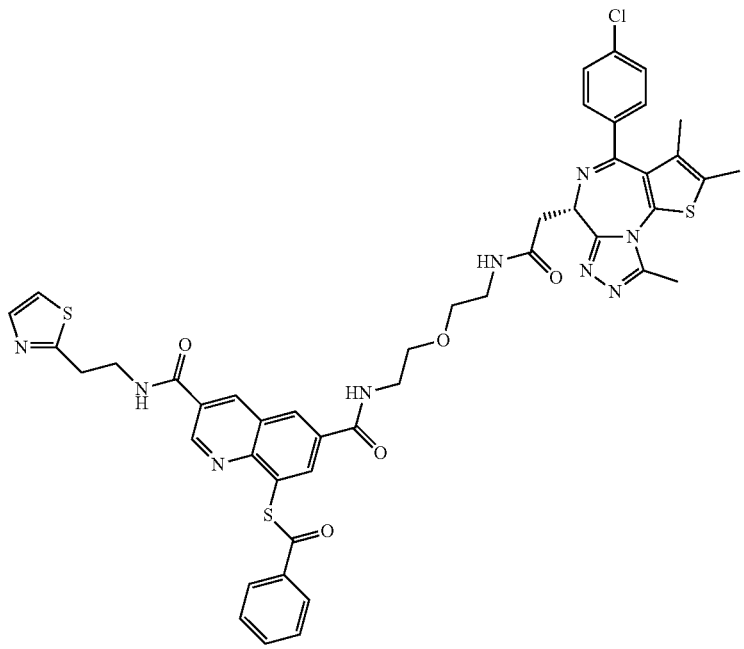

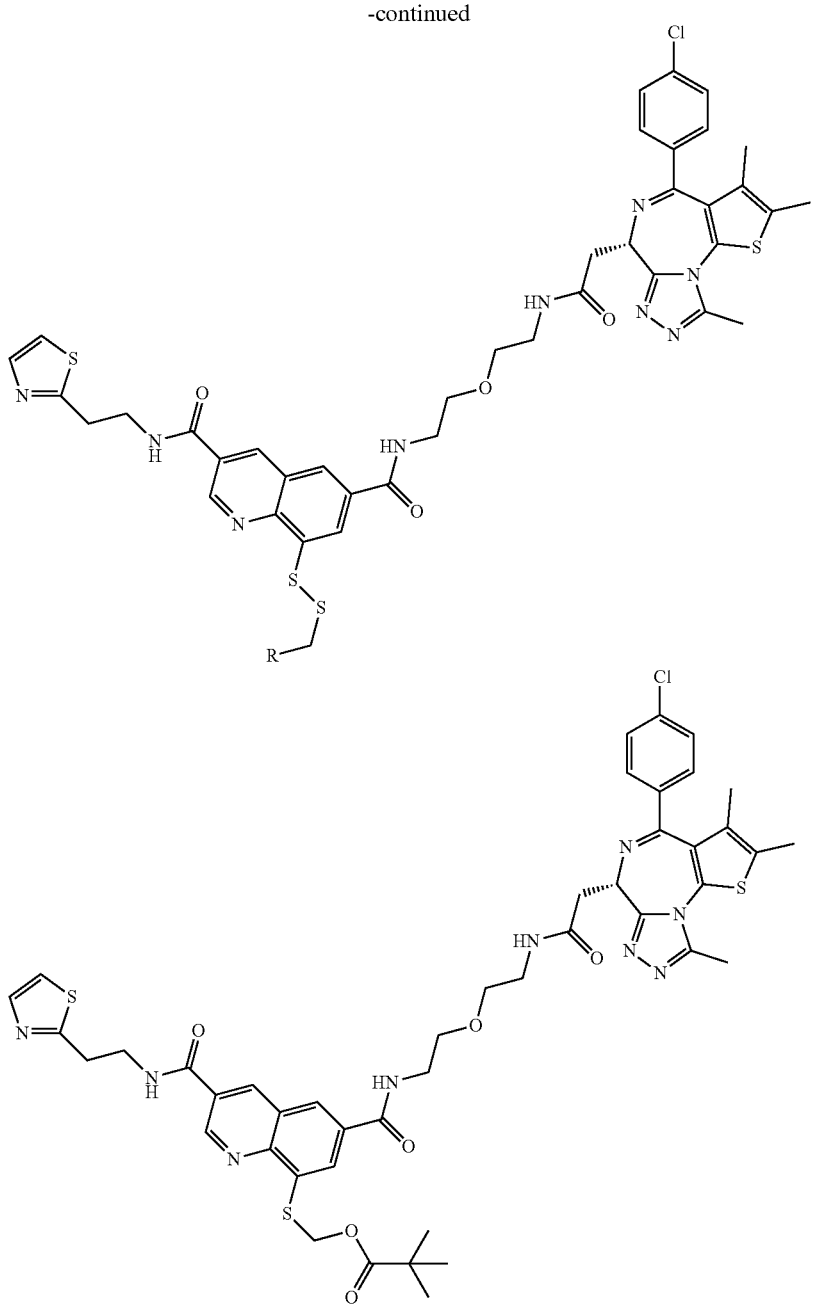

Hypoxia Activated Pro-Drugs

Prodrugs of the invention may also include hypoxia-activated prodrugs. Regions of low oxygen (hypoxia) occur in a diverse range of biological contexts, including in disease states, bacterial infections and tumor environments. During tumor development, oxygen supply quickly becomes a growth-limiting factor, because of the high number of metabolically active tumor cells. In response to the problem of inadequate oxygen supply, the process of angiogenesis is initiated to create a tumor vasculature. However, this vasculature has many aberrant features, and although it manages to sustain the tumor it also results in regions of hypoxia, in which only the most aggressive fraction of the tumor cells can survive. These hypoxic regions occur at distances >100 μm from a functional vessel, and they can be both chronic and acute. Hypoxic cells are resistant to radiotherapy, as the DNA damage induced by radiation, which is required for cell killing, occurs in an oxygen dependent manner Hypoxic cells comprise the most aggressive tumor fraction, and they are the most important to treat in order to improve patient prognosis. Pro-drugs of the invention harness the substantial differences in chemical environment between hypoxia and normoxia to target drug compounds of the invention to these therapeutically challenging tumor regions.

As used herein, the term "Hypoxia activated prodrug" or "HAP" refers to a prodrug wherein the prodrug is less active or inactive, relative to the corresponding drug, and comprises the drug and one or more bioreducible groups. HAPs include prodrugs that are activated by a variety of reducing agents and reducing enzymes, including without limitation single electron transferring enzymes (such as cytochrome P450 reductases) and two electron transferring (or hydride transferring) enzymes. In some embodiments, HAPs are 2-nitroimidazole triggered hypoxia-activated prodrugs.

Examples of HAPs include, without limitation, TH-302 and TH-281. Methods of synthesizing TH-302 are described in US 2010/0137254 and US 2010/0183742, incorporated herein by reference.

The target drugs of the invention can be readily converted to hypoxia activated pro-drugs by using techniques that are well known to a person of skill in art. For instance, O' Connor et al., has shown that a hypoxia sensitive prodrug of a Chk1 and Aurora A kinase inhibitor can be created by adding bioreductive 4-nitrobenzyl group to a known Chk1 and Aurora A kinase inhibitor thereby achieving the goal of targeting the relevant therapeutic compound to areas of hypoxia. Many hypoxia activated prodrugs use the 1-methyl-2-nitroimidazole group as the bioreductive functionality. Five distinct chemical moieties, nitro groups, quinones, aromatic N-oxides, aliphatic N-oxides and transition metals, have been identified as being sensitive to bioreduction. Given their widespread use, the nitroaryl-based compounds are among the most amenable for use in the development of a bioreductive prodrug. In addition to the 4-nitrobenzyl and 1-methyl-2-nitroimidazole groups, nitrofuran- and nitrothiophene-based groups have also been used as the basis of bioreductive compounds. In principle, the most important considerations when choosing which bioreductive group to use are its propensity to undergo bioreduction and the oxygen concentration at which this process occurs. In addition, the propensity of the drug component to be a good leaving group has a role in the rate of its release from pro-drug. The reagents required to attach the 4-nitrobenzyl, nitrofuran- and nitrothiophene-based groups to biologically active compounds are readily available from commercial sources. Connor et al also describes an optimized protocol for the synthesis of a range of derivatives with useful synthetic handles for attachment to biologically active compounds (O' Connor et al., Nat Protoc. 2016 April; 11(4):781-94, contents of which are herein incorporated in its entirety by reference).

Sun et al., (Clip Cancer Res. 2012 Feb. 1; 18(3):758-70, contents of which are herein incorporated in its entirety by reference) describes the design criteria for an optimized hypoxia activated pro-drug and it may include pharmacokinetic properties to ensure adequate tumor delivery and penetration; stability to oxygen concentration-independent activating or inactivating reductases; high hypoxia selectivity with activation only in severely hypoxic tumor tissues and not moderately hypoxic normal tissues. and a bystander effect, where adjacent tumor cells, not hypoxic enough to activate the prodrug, are nonetheless targeted by the diffusible effector moiety. Some early examples are pro-drugs include quinone bioreductive drugs such as porfiromycin, N-oxides such as tirapazamine, and nitroaromatic agents such as CI-1010. Some examples of pro-drugs that have advanced to clinical trials include tirapazamine, PR104, AQ4N, and TH-302 (28-31). TH-302 (1-methyl-2-nitro-1H-imidazole5-yl) N, N0-bis (2-bromoethyl) diamidophosphate is a 2-nitroimidazole-linked prodrug of a brominated version of isophosphoramide mustard. The 2-nitroimidazole moiety of TH-302 is a substrate for intracellular 1-electron reductases and, when reduced in deeply hypoxic conditions, releases Br-IPM. In vitro cytotoxicity and clonogenic assays employing human cancer cell lines show that TH-302 has little cytotoxic activity under normoxic conditions and greatly enhanced cytotoxic potency under hypoxic conditions. The nitroimidazole moiety of TH-302 may be incorporated into the target drug compounds to generate the prodrug compounds of the invention.

Rui Zhu et al., (J. Med. Chem. 2011, 54, 7720-7728; contents of which are herein incorporated in its entirety by reference) describes the use of 4-Nitrobenzyloxycarbonyl Derivatives as moieties for the development of hypoxia-activated pro-drug compounds. Rui Zhu et al. discloses three different moieties that can be attached to a target drug in order to generate hypoxia sensitive or hypoxia activated prodrugs. They include 4-nitrobenzyl (6-(benzyloxy)-9H-purin-2-yl)carbamate (1) and its monomethyl (2) and gem-dimethyl analogues. Rui Zhu et al. also teaches about desirable traits for selecting moieties that are used for the generation of prodrugs. They include (a) the ease and extent of reduction of the nitro group, (b) the relative position of the nitro group with respect to the side chain, and (c) the ease of fragmentation of the C O bond, where C is the benzylic carbon, once the nitro group is converted to the hydroxy-lamino or amino function.

Some representative examples of pro-drugs that are activated by hypoxia found in tumor microenvironment are shown below.

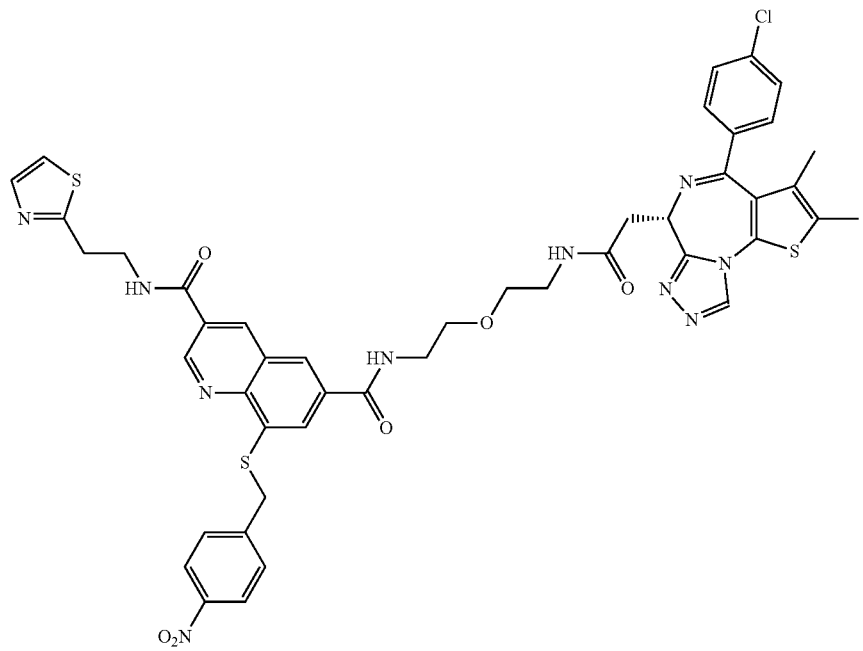

-continued
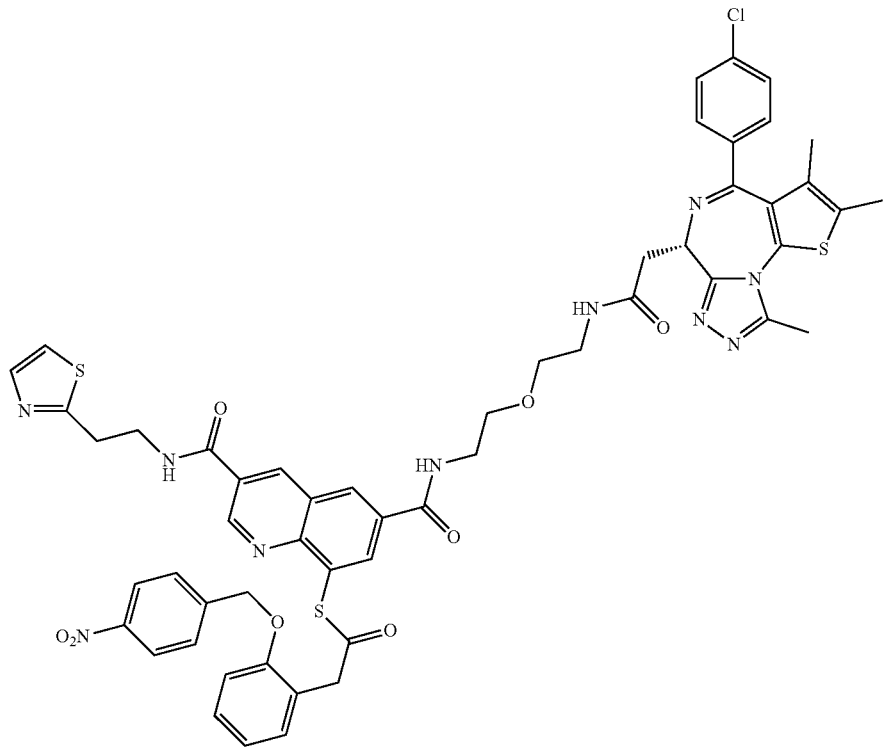
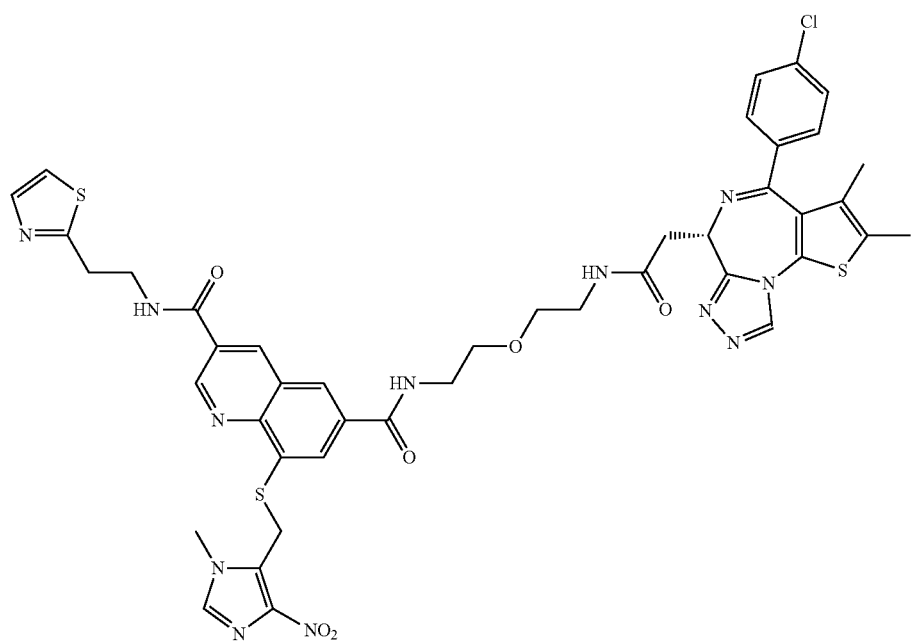

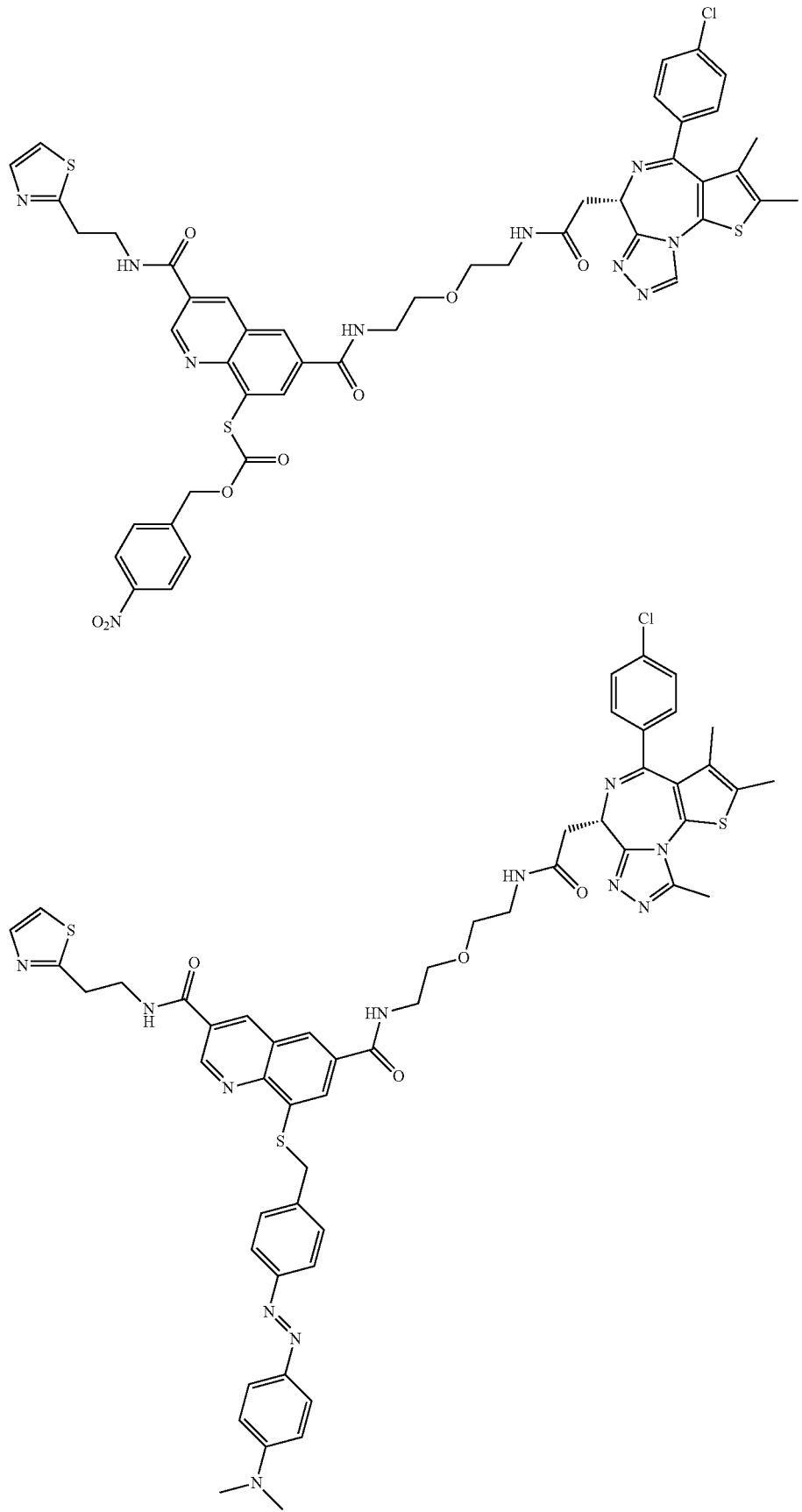

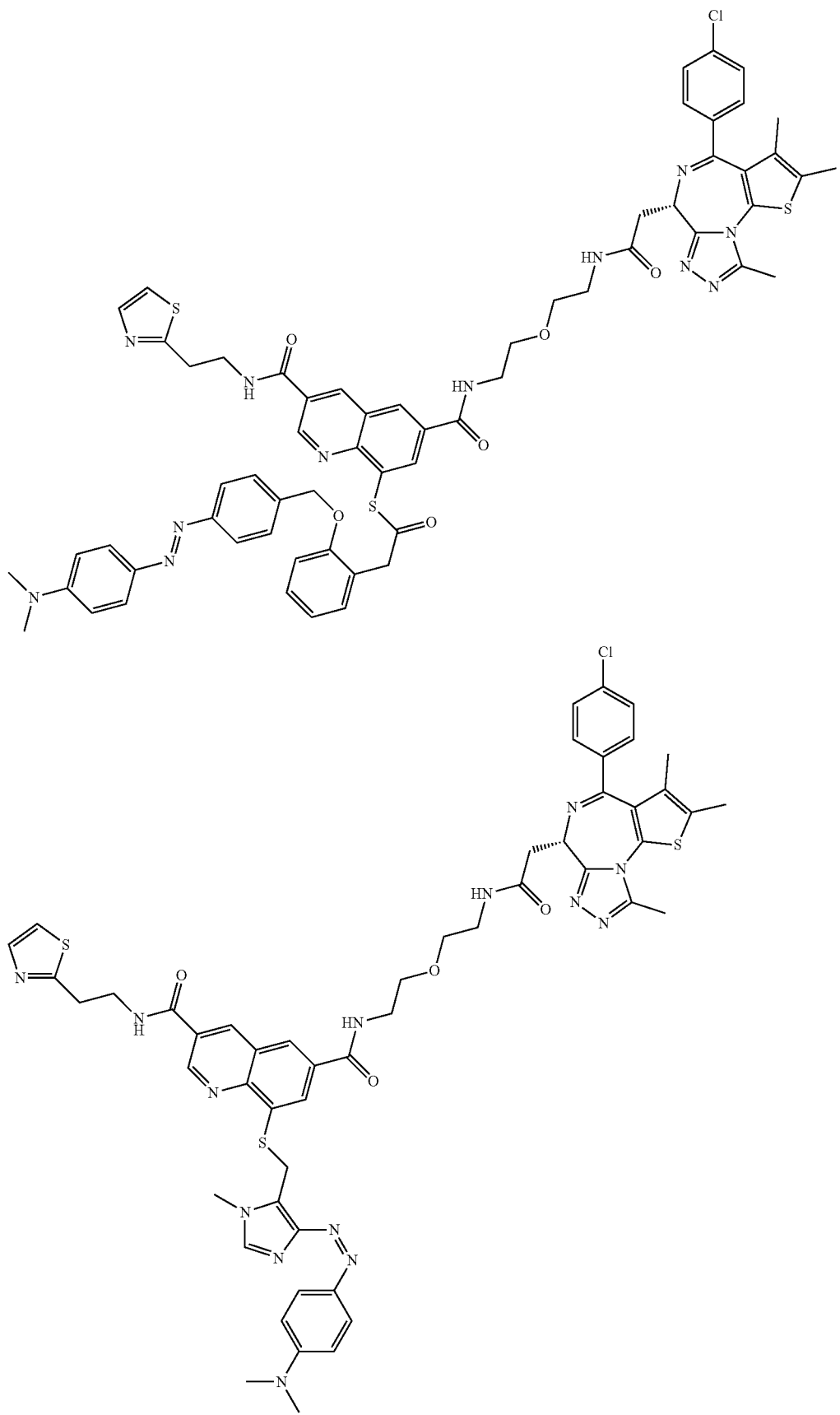

-continued

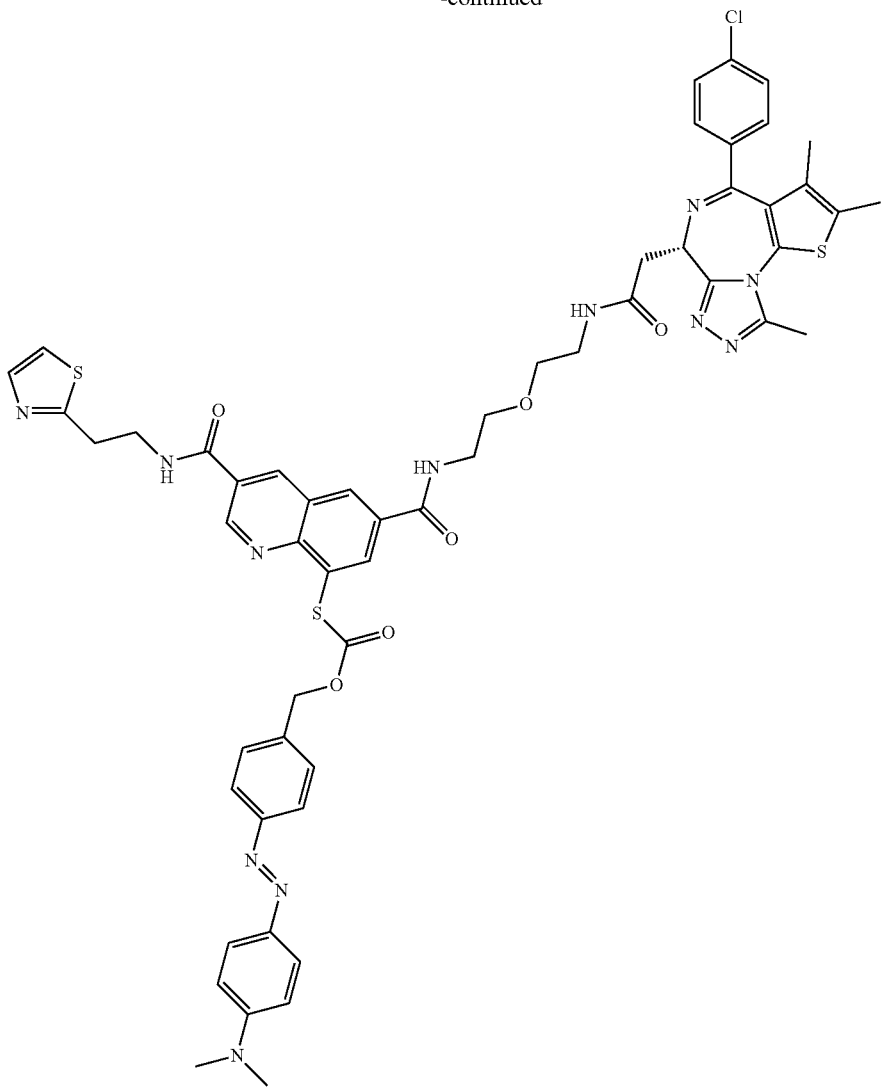 [SMILES: Cc1sc2c(c1C)C(c1ccc(Cl)cc1)=N[C@@H](CC(=O)NCCOCCNC(=O)c1cc(SC(=O)OCc3ccc(/N=N/c4ccc(N(C)C)cc4)cc3)c3ncc(C(=O)NCCc4nccs4)cc3c1)c1nnc(C)n1-2]

pH Sensitive Pro-Drugs

Pro-drugs of the invention may also include pH Sensitive pro-drugs. As used herein, the term "pH sensitive prodrug" refers to a prodrug wherein the prodrug is less active or inactive, relative to the corresponding drug, and comprises the drug and one or more pH labile groups. The pH sensitive pro-drug when exposed to an acidic micro environment undergoes cleavage of the pH labile groups thereby activating the target drug and facilitating site directed release. The pH sensitive pro-drug may comprise gastro-retentive properties adapted for oral administration comprising one or more pH sensitive moieties and a therapeutic agent, wherein the pH sensitive moieties allows for release of the therapeutic target drug in the increased pH of the small intestine or acidic tumor microenvironment or endosomal or lysosomal environment (~pH 5).

The pH-triggered drug release is an eminent type of therapy against cancer and has been extensively exploited. It is well known that the pH value in endosomes (pH 5.0-6.5) and lysosomes (pH 4.5-5.0) of cancer cells is more acidic than the physiological pH of 7.4. With introduction of the pH-sensitive linkage, target drug can be conjugated to polymer backbone, which can serve as a reservoir when they are internalized into cancer cells. Upon degradation, the therapeutic payload can be directly released in its original active form serves therapeutic effect.

Photothermal therapy (PTT) with near-infrared (NIR) light has been considered as a powerful supplement to chemotherapy to provide combined effects in destroying cancer tissues. In addition, heat generated from PTT can aggrandize cell metabolism and the permeability of the cell membrane, which facilitates drug intake of cancer cells to enhance treatment effects.

The target drugs of the invention can be readily converted to pH sensitive pro-drugs by using techniques that are well known to a person of skill in art. For example, Sun et al., (*Mol. Pharmaceutics* 2018, 15, 3343-3355; contents of which are herein incorporated in its entirety by reference) describes a simple method to fabricate the cargo-free and pH-responsive nanomedicine for codelivery of DOX (Doxorubicin) and 5N38 (7-ethyl-10-hydroxyl camptothecin) to cancer cells. This cargo-free nanomedicine was composed of prodrug (PEG-CH=N-DOX) and SN38. The pH sensitive moiety or imine linker between PEG and DOX facilitated a rapid drug release in acidic conditions. Such pH sensitive pro-drugs exhibit effective cellular uptake capacity, high tumor penetrating ability, and enhanced passive targeting ability through the enhanced permeability and retention (EPR) effect. Such pH sensitive imine linkers can be attached to the target drugs of the invention to generate pH sensitive prodrugs using standard synthetic chemistry processes known to a person of skill in the art.

Similarly Zhang et al., (*European Journal of Pharmaceutics and Biopharmaceutics* 128 (2018) 260-271, contents of which are herein incorporated in its entirety by reference) describes a pH-sensitive prodrug conjugated polydopamine for NIR-triggered synergistic chemo-photothermal therapy. Combination of chemotherapy with photothermal therapy (PTT) demonstrate highly desirable for efficient medical treatment of tumor. Zhang et al. teaches that camptothecin (CPT)-containing polymeric prodrug (PCPT) can be fabricated by polymerization of a pH-sensitive camptothecin (CPT) prodrug monomer and MPC using reversible addition-fragmentation transfer (RAFT) strategy. The pH-sensitive polymeric prodrug was tethered onto surface of polydopamine (PDA) nanoparticles by amidation chemistry for combination of chemotherapy with photothermal therapy. The active CPT quickly released from the multifunctional nanoparticles in acidic microenvironment ascribe to the cleavage of bifunctional silyl ether linkage. Meanwhile, the PDA could convert the near infrared (NIR) light energy into heat with high efficiency, which makes the resulted nanoparticles an effective platform for photothermal therapy. In vitro analysis confirmed that the PDA@PCPT nanoparticles could be efficiently taken up by HeLa cells and deliver CPT into the nuclei of cancer cells. The cell viability assays indicated an evident in vitro cytotoxicity to HeLa cancer cells under 808 nm light irradiation. Significant tumor regression was also observed in the tumor-bearing mice model with the combinational therapy provided from the PDA@PCPT nanoparticles.

The pH sensitive pro-drug of the invention generated from the target drug of the invention would display the following distinctive features. (1) the prodrug-based polymersome avoids the issue of premature release; (2) besides playing a drug-carrier role, the PDA core possesses intrinsic photostability and excellent photothermal conversion efficiency; (3) target drug of the invention would be linked to the polymers via the pH-sensitive silyl ether bond, which could be cleaved under lower pH, especially under the microenvironment of cancer cells; and (4) produced local hyperthermia and released drug can synergistically kill cancer cells and suppress tumor growth. Thus, a person of skill in the art could generate pH sensitive prodrugs using standard synthetic chemistry processes known to a person of skill in the art by attaching pH labile linkers or pH labile moieties like silyl ether bond or imine linkers to the target drugs.

Some representative examples of pro-drugs that are activated by pH changes found in tumor microenvironment or lysomes or endosomes are shown below.

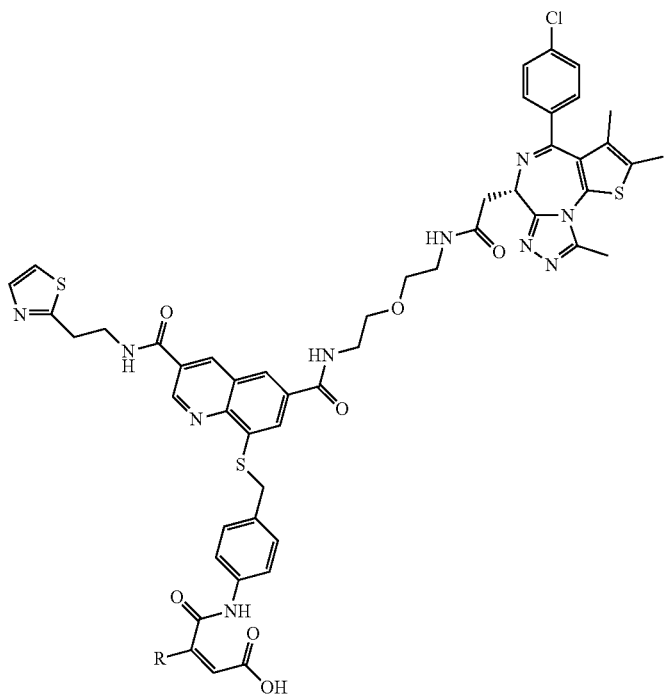

-continued

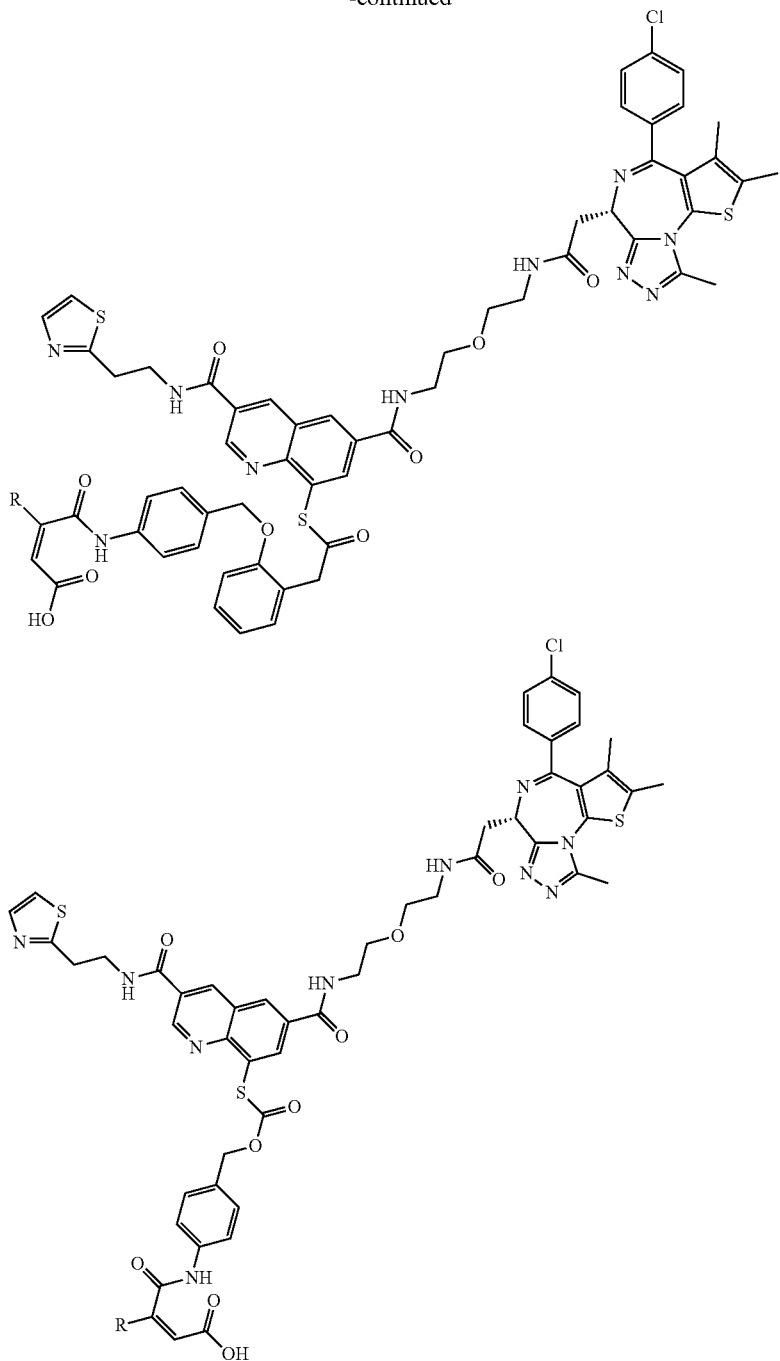

Other examples of pro-drug can reveal an activated double bond (as Michael acceptor) join metabolic activation. Examples include Mannich bases, beta sulfones, sulfoxides or sulfonamide derivatives, beta carbamates and carbonates derivatives and other leaving groups beta to an electron withdrawing group.

The terms "patient" and "subject" are used interchangeably throughout the specification to describe a mammal, in certain embodiments a human or a domesticated animal, to whom treatment, including prophylactic treatment, with the compositions according to the present invention is provided. In certain embodiments, in the present invention, the term patient refers to a human patient unless otherwise stated or implied from the context of the use of the term.

The term "effective" is used to describe an amount of a compound, composition or component that, when used within the context of its intended use, effects an intended result. The term effective subsumes all other effective amount or effective concentration terms, which are otherwise described or used in the present application.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The present invention can be understood more readily by reference to the following detailed description of the invention and the Examples included therein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Rpn11 Binding Partner

An Rpn11 binding partner of the invention binds to Rpn11 with an IC50 in the range of 1 pM-1 mM, or in the subranges of 100 nM-100 µM, 100 nM-1 µM, 100 nM-10 µM, 10 nM-100 µM, 10 nM-50 µM, 10 nM-10 µM, 10 nM-5 µM, 10 nM-1 µM, 10 nM-100 nM. 1 nM-100 µM, 1 nM-10 µM, 1 nM-1 µM, 1 nM-100 nM, 1 nM-10 nM, 1 µM-100 µM, and 1 µM-10 An IC50 is determined according to methods well known in the art, for example a ubiquitin-rhodamine 110 hydrolysis assay.

The Kd of an Rpn11 binding partner of the invention and Rpn11 is in the range of 1 pM-1 mM, or in the subranges of 100 nM-100 µM, 100 nM-1 µM, 100 nM-10 µM, 10 nM-100 µM, 10 nM-10 µM, 10 nM-504, 10 nM-1 µM, 10 nM-100 nM, 1 nM-100 µM, 1 nM-10 µM, 1 nM-1 µM, 1 nM-100 nM, 1 nM-10 nM, 1 µM-100 and 1 µM-10 µM. Kd is determined according to methods well known in the art for example, isothermal calorimetry (ITC) and surface plasmon resonance (SPR) to directly assess the binding.

The binding of an Rpn11 binding partner to Rpn11 may be reversible.

The binding of an Rpn11 binding partner to Rpn11 may be irreversible.

Rpn11 binding partners useful according to the invention include molecules as set forth in Table 1 below.

TABLE 1

Table 1-Rpn11 Binding Partners include but are not limited to the following:

| Publication | Disclosed Compounds |
|---|---|
| US 2017/0050931 |  |

8TQ

TABLE 1-continued
Table 1-Rpn11 Binding Partners include but are not limited to the following:
| Publication | Disclosed Compounds |
| --- | --- |
| |  |
| | 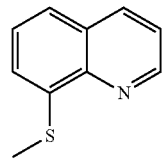 |
| | 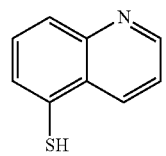 |
| |  |
| | 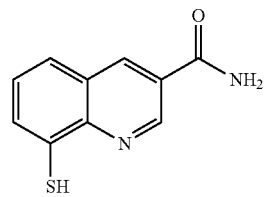 [SMILES: NC(=O)c1cnc2c(S)cccc2c1] |
| | 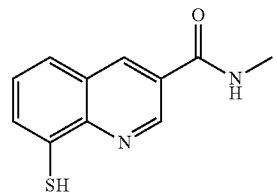 |
| | 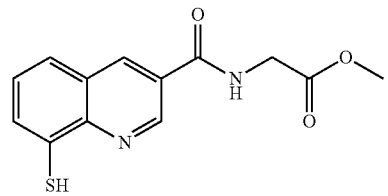 [SMILES: COC(=O)CNC(=O)c1cnc2c(S)cccc2c1] |
| | 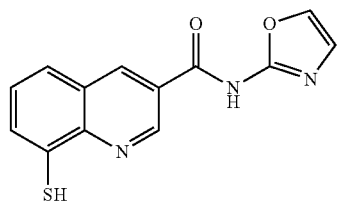 [SMILES: O=C(Nc1nccs1)c1cnc2c(S)cccc2c1] |

TABLE 1-continued

Table 1-Rpn11 Binding Partners include but are not limited to the following:

| Publication | Disclosed Compounds |
| --- | --- |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
| --- | --- |
| | 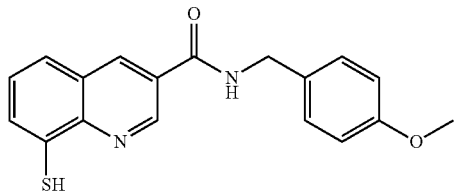 [SMILES: COc1ccc(CNC(=O)c2cnc3c(S)cccc3c2)cc1] |
| | 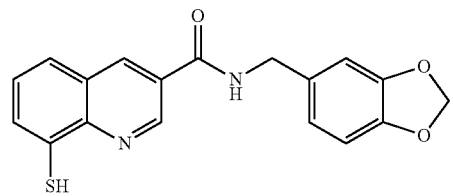 [SMILES: O=C(NCc1ccc2c(c1)OCO2)c1cnc2c(S)cccc2c1] |
| | 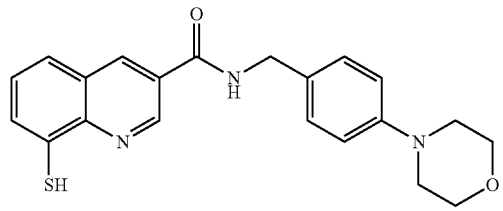 [SMILES: O=C(NCc1ccc(N2CCOCC2)cc1)c1cnc2c(S)cccc2c1] |
| | 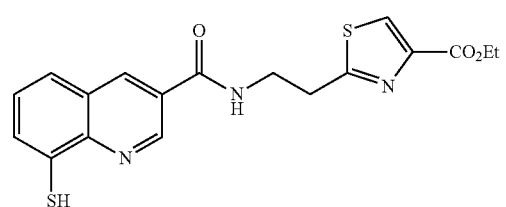 [SMILES: CCOC(=O)c1csc(CCNC(=O)c2cnc3c(S)cccc3c2)n1] |
| | 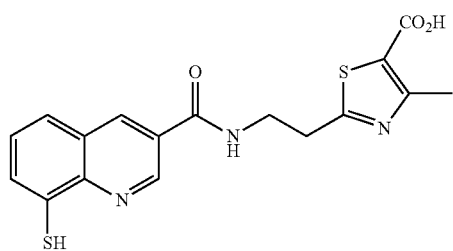 [SMILES: Cc1nc(CCNC(=O)c2cnc3c(S)cccc3c2)sc1C(=O)O] |
| | 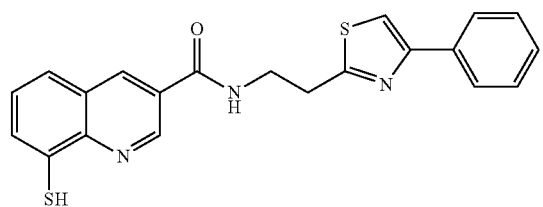 [SMILES: O=C(NCCc1nc(-c2ccccc2)cs1)c1cnc2c(S)cccc2c1] |
| | 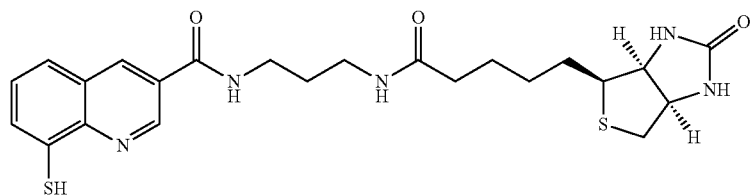 [SMILES: O=C(CCCC[C@@H]1SC[C@@H]2NC(=O)N[C@@H]21)NCCCNC(=O)c1cnc2c(S)cccc2c1] |

TABLE 1-continued
Table 1-Rpn11 Binding Partners include but are not limited to the following:
| Publication | Disclosed Compounds |
|---|---|
| | 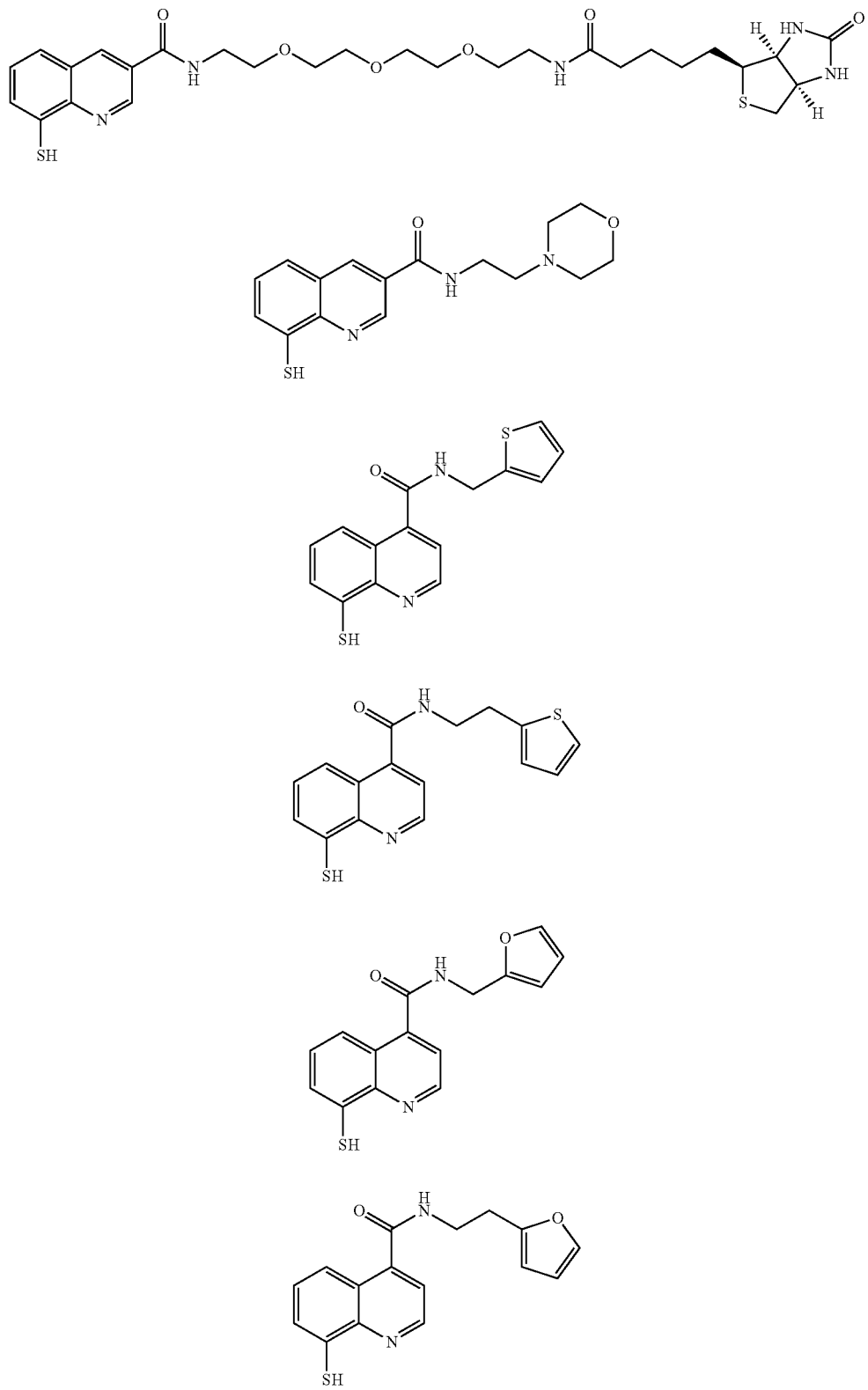 |

TABLE 1-continued
Table 1-Rpn11 Binding Partners include but are not limited to the following:
| Publication | Disclosed Compounds |
|---|---|
| US 2014/0235548 | 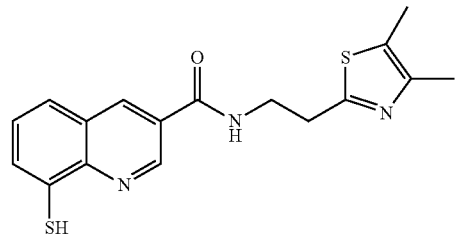 [SMILES: Cc1nc(CCNC(=O)c2cnc3c(S)cccc3c2)sc1C]<br>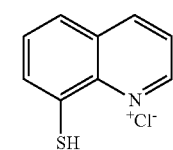<br>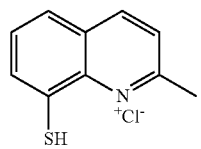<br>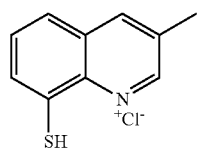<br>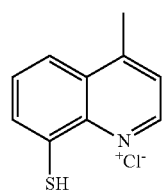<br>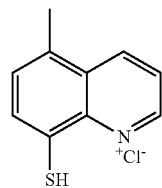<br>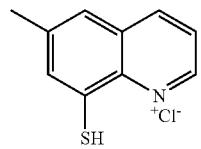<br>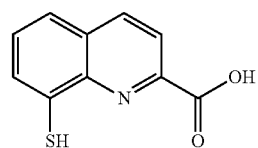 [SMILES: O=C(O)c1ccc2cccc(S)c2n1] |

TABLE 1-continued
Table 1-Rpn11 Binding Partners include but are not limited to the following:
| Publication | Disclosed Compounds |
|---|---|
| | 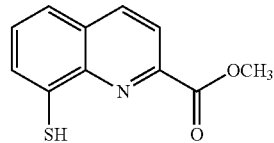 [SMILES: COC(=O)c1ccc2cccc(S)c2n1] |
| | 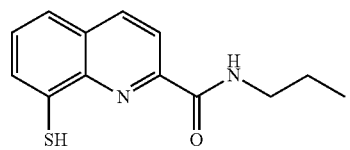 [SMILES: CCCNC(=O)c1ccc2cccc(S)c2n1] |
| | 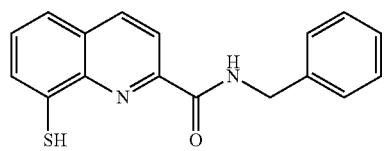 [SMILES: O=C(NCc1ccccc1)c1ccc2cccc(S)c2n1] |
| | 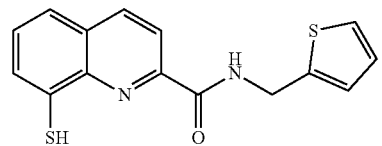 [SMILES: O=C(NCc1cccs1)c1ccc2cccc(S)c2n1] |
| | 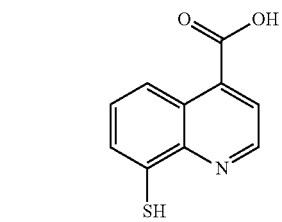 [SMILES: O=C(O)c1ccnc2c(S)cccc12] |
| | 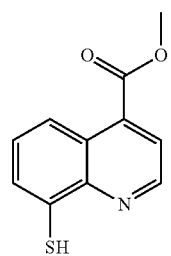 |
| | 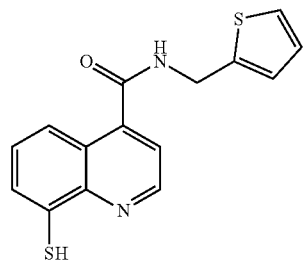 [SMILES: O=C(NCc1cccs1)c1ccnc2c(S)cccc12] |

157 158
TABLE 1-continued
Table 1-Rpn11 Binding Partners include but are not limited to the following:
| Publication | Disclosed Compounds |
|---|---|
| | 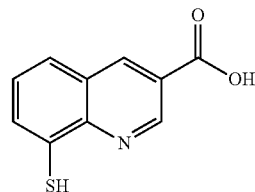 [SMILES: O=C(O)c1cnc2c(S)cccc2c1] |
| | 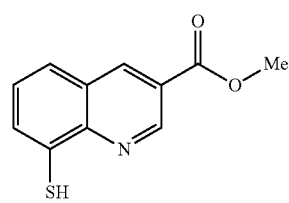 [SMILES: COC(=O)c1cnc2c(S)cccc2c1] |
| | 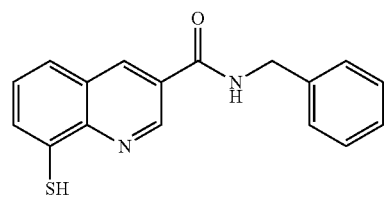 [SMILES: O=C(NCc1ccccc1)c1cnc2c(S)cccc2c1] |
| | 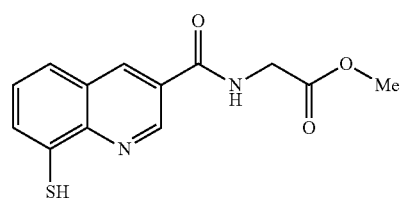 [SMILES: COC(=O)CNC(=O)c1cnc2c(S)cccc2c1] |
| | 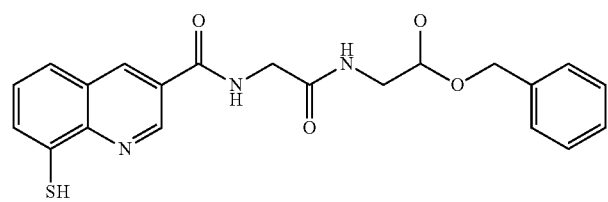 [SMILES: O=C(CNC(=O)c1cnc2c(S)cccc2c1)NCC(O)OCc1ccccc1] |
| | 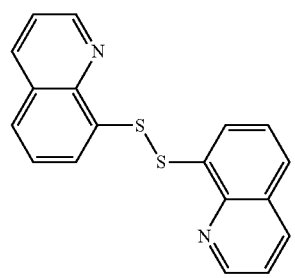 [SMILES: c1cnc2c(SSc3cccc4cccnc34)cccc2c1] |

TABLE 1-continued
Table 1-Rpn11 Binding Partners include but are not limited to the following:
| Publication | Disclosed Compounds |
|---|---|
| | 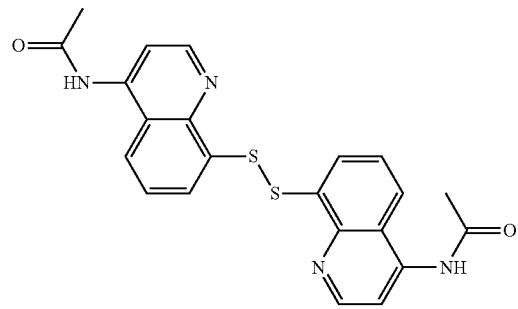 [SMILES: CC(=O)Nc1ccnc2c(SSc3cccc4c(NC(C)=O)ccnc34)cccc12] |
| | 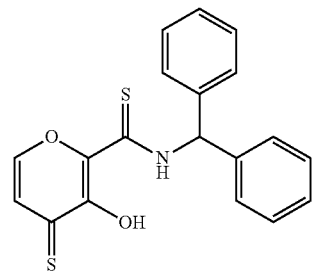 [SMILES: Oc1c(C(=S)NC(c2ccccc2)c2ccccc2)occc1=S] |
| | 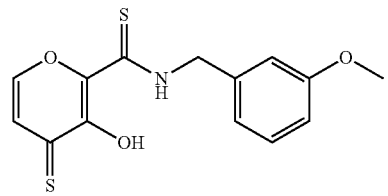 [SMILES: COc1cccc(CNC(=S)c2occc(=S)c2O)c1] |
| | 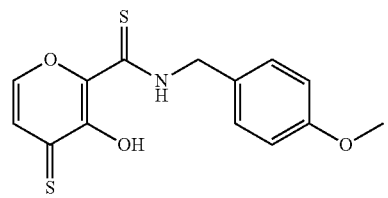 [SMILES: COc1ccc(CNC(=S)c2occc(=S)c2O)cc1] |
| | 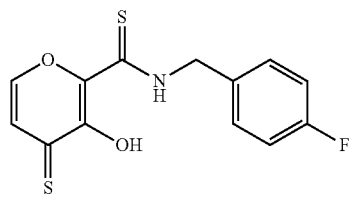 [SMILES: Oc1c(C(=S)NCc2ccc(F)cc2)occc1=S] |
| | 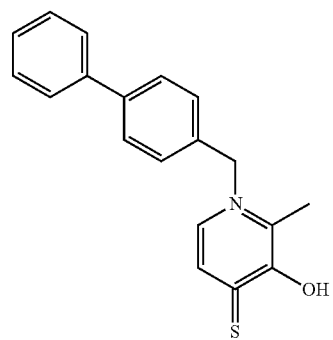 |

TABLE 1-continued
Table 1-Rpn11 Binding Partners include but are not limited to the following:
| Publication | Disclosed Compounds |
|---|---|
| | 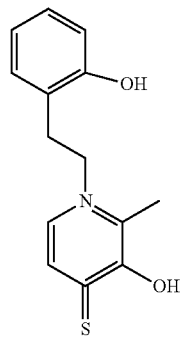 |
| | 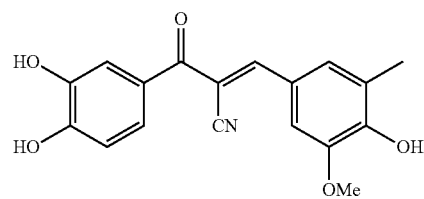 [SMILES: COc1cc(/C=C(\C#N)C(=O)c2ccc(O)c(O)c2)cc(C)c1O] |
| | 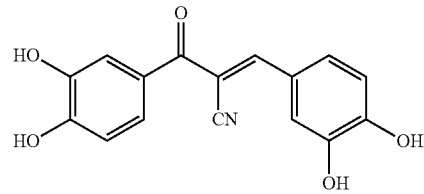 [SMILES: N#C/C(=C\c1ccc(O)c(O)c1)C(=O)c1ccc(O)c(O)c1] |
| | 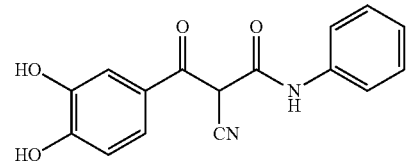 [SMILES: N#CC(C(=O)Nc1ccccc1)C(=O)c1ccc(O)c(O)c1] |
| | 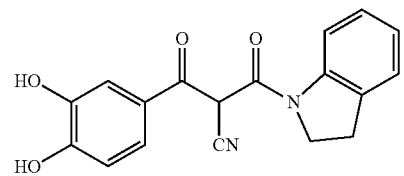 [SMILES: N#CC(C(=O)c1ccc(O)c(O)c1)C(=O)N1CCc2ccccc21] |
| |  |
| | 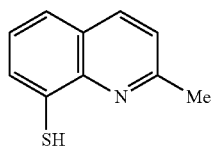 [SMILES: Cc1ccc2cccc(S)c2n1] |

TABLE 1-continued
Table 1-Rpn11 Binding Partners include but are not limited to the following:
| Publication | Disclosed Compounds |
|---|---|
| | 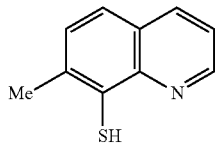 [SMILES: Cc1ccc2cccnc2c1S] |
| | 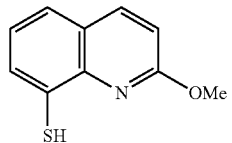 [SMILES: COc1ccc2cccc(S)c2n1] |
| | 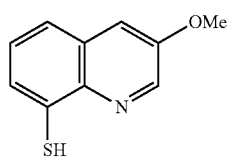 [SMILES: COc1cnc2c(S)cccc2c1] |
| | 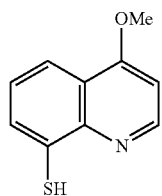 [SMILES: COc1ccnc2c(S)cccc12] |
| | 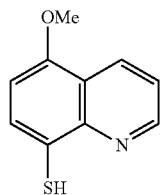 [SMILES: COc1ccc(S)c2ncccc12] |
| | 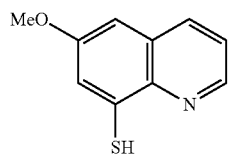 [SMILES: COc1cc(S)c2ncccc2c1] |
| | 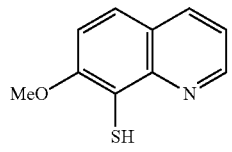 |
| | 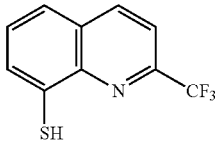 |
| | 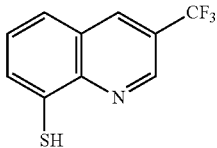 [SMILES: FC(F)(F)c1cnc2c(S)cccc2c1] |

TABLE 1-continued
Table 1-Rpn11 Binding Partners include but are not limited to the following:
| Publication | Disclosed Compounds |
|---|---|
| | 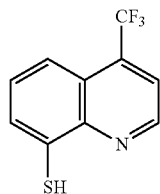 [SMILES: FC(F)(F)c1ccnc2c(S)cccc12] |
| | 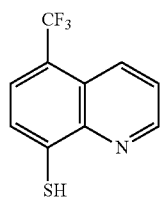 [SMILES: FC(F)(F)c1ccc(S)c2ncccc12] |
| |  |
| | 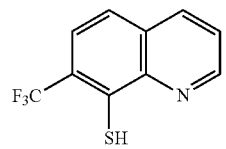 [SMILES: FC(F)(F)c1ccc2cccnc2c1S] |
| | 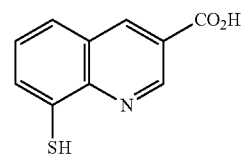 [SMILES: O=C(O)c1cnc2c(S)cccc2c1] |
| | 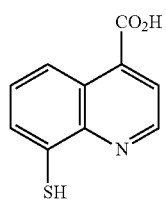 [SMILES: O=C(O)c1ccnc2c(S)cccc12] |
| | 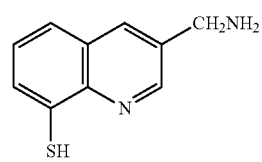 |
| | 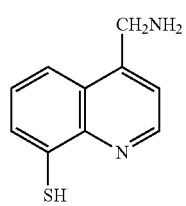 |

TABLE 1-continued
Table 1-Rpn11 Binding Partners include but are not limited to the following:
| Publication | Disclosed Compounds |
|---|---|
| | 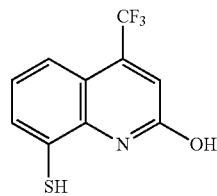 [SMILES: Oc1cc(C(F)(F)F)c2cccc(S)c2n1] |
| | 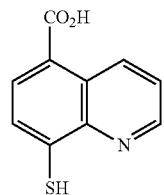 [SMILES: O=C(O)c1ccc(S)c2ncccc12] |
| | 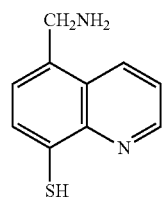 |
| | 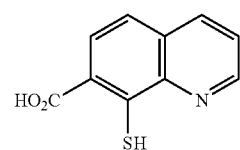 |
| | 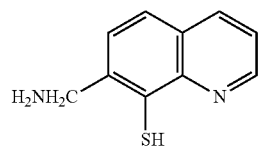 |
| | 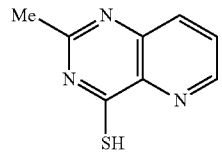 [SMILES: Cc1nc(S)c2ncccc2n1] |
| | 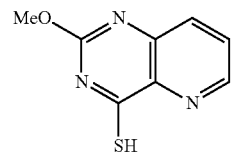 [SMILES: COc1nc(S)c2ncccc2n1] |
| | 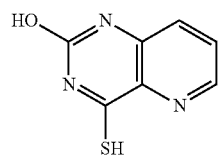 [SMILES: Oc1nc(S)c2ncccc2n1] |
| | 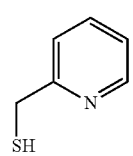 |

TABLE 1-continued
Table 1-Rpn11 Binding Partners include but are not limited to the following:
| Publication | Disclosed Compounds |
|---|---|
| | 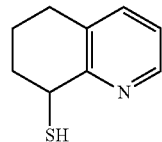 [SMILES: SC1CCCc2cccnc21] |
| | 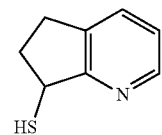 |
| | 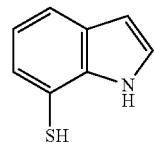 |
| | 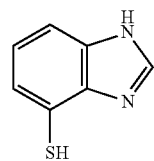 |
| |  |
| |  |
| | 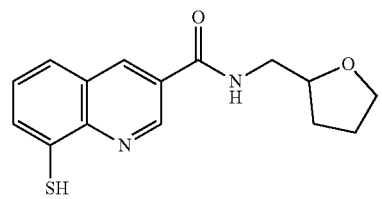 [SMILES: O=C(NCC1CCCO1)c1cnc2c(S)cccc2c1] |
| | 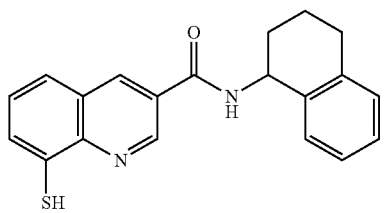 [SMILES: O=C(NC1CCCc2ccccc21)c1cnc2c(S)cccc2c1] |

TABLE 1-continued
Table 1-Rpn11 Binding Partners include but are not limited to the following:
| Publication | Disclosed Compounds |
|---|---|
| | 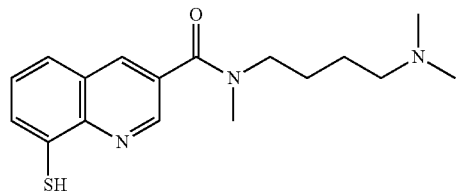 [SMILES: CN(C)CCCCN(C)C(=O)c1cnc2c(S)cccc2c1] |
| | 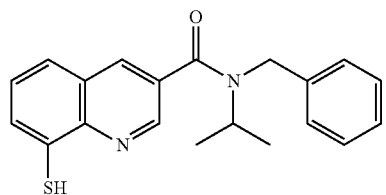 [SMILES: CC(C)N(Cc1ccccc1)C(=O)c1cnc2c(S)cccc2c1] |
| | 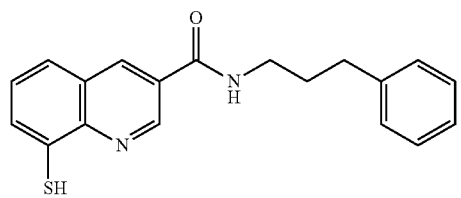 [SMILES: O=C(NCCCc1ccccc1)c1cnc2c(S)cccc2c1] |
| | 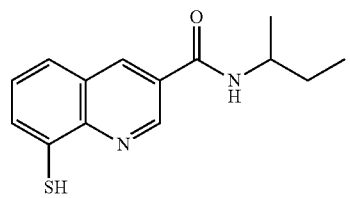 [SMILES: CCC(C)NC(=O)c1cnc2c(S)cccc2c1] |
| | 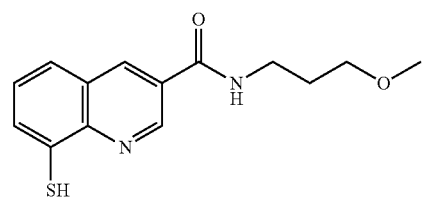 [SMILES: COCCCNC(=O)c1cnc2c(S)cccc2c1] |
| | 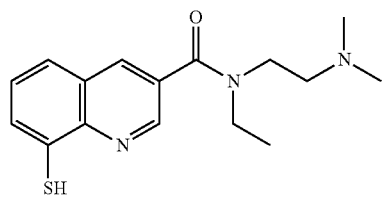 [SMILES: CCN(CCN(C)C)C(=O)c1cnc2c(S)cccc2c1] |
| | 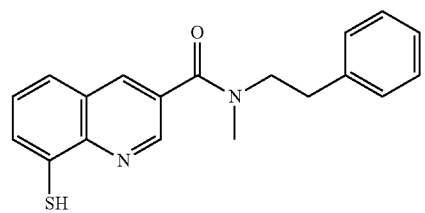 [SMILES: CN(CCc1ccccc1)C(=O)c1cnc2c(S)cccc2c1] |

TABLE 1-continued
Table 1-Rpn11 Binding Partners include but are not limited to the following:
| Publication | Disclosed Compounds |
|---|---|
| | 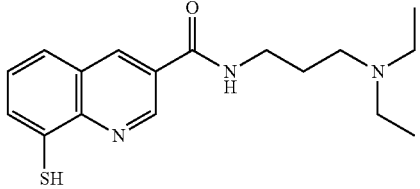 [SMILES: CCN(CC)CCCNC(=O)c1cnc2c(S)cccc2c1] |
| | 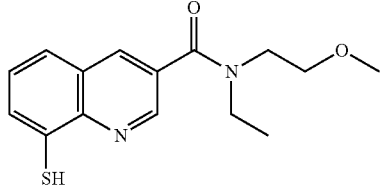 [SMILES: CCN(CCOC)C(=O)c1cnc2c(S)cccc2c1] |
| | 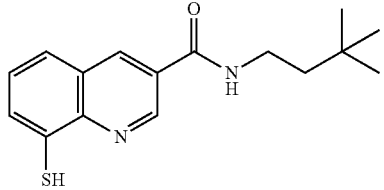 [SMILES: CC(C)(C)CCNC(=O)c1cnc2c(S)cccc2c1] |
| | 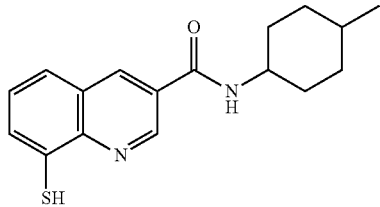 [SMILES: CC1CCC(NC(=O)c2cnc3c(S)cccc3c2)CC1] |
| | 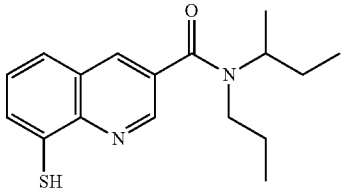 [SMILES: CCCN(C(=O)c1cnc2c(S)cccc2c1)C(C)CC] |
| | 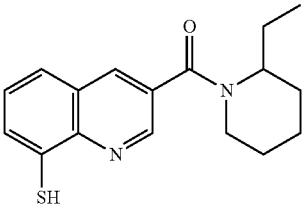 [SMILES: CCC1CCCCN1C(=O)c1cnc2c(S)cccc2c1] |
| | 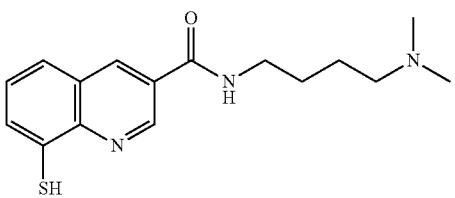 [SMILES: CN(C)CCCCNC(=O)c1cnc2c(S)cccc2c1] |

TABLE 1-continued
Table 1-Rpn11 Binding Partners include but are not limited to the following:
| Publication | Disclosed Compounds |
| --- | --- |
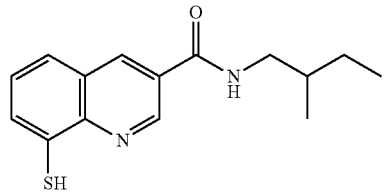 [SMILES: CCC(C)CNC(=O)c1cnc2c(S)cccc2c1]
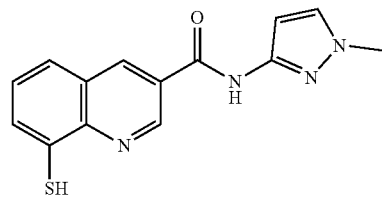 [SMILES: Cn1ccc(NC(=O)c2cnc3c(S)cccc3c2)n1]
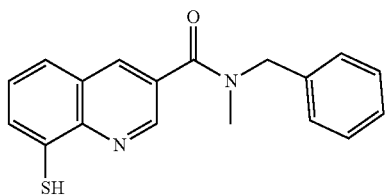 [SMILES: CN(Cc1ccccc1)C(=O)c1cnc2c(S)cccc2c1]
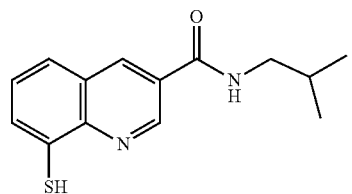 [SMILES: CC(C)CNC(=O)c1cnc2c(S)cccc2c1]
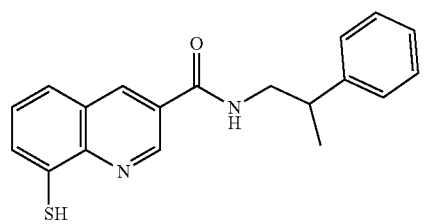 [SMILES: CC(CNC(=O)c1cnc2c(S)cccc2c1)c1ccccc1]
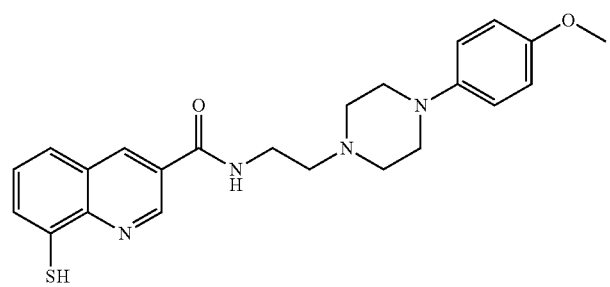 [SMILES: COc1ccc(N2CCN(CCNC(=O)c3cnc4c(S)cccc4c3)CC2)cc1]
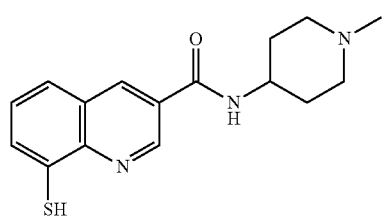 [SMILES: CN1CCC(NC(=O)c2cnc3c(S)cccc3c2)CC1]

TABLE 1-continued
Table 1-Rpn11 Binding Partners include but are not limited to the following:
| Publication | Disclosed Compounds |
|---|---|
| | 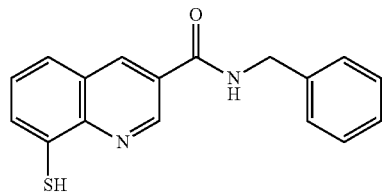 [SMILES: O=C(NCc1ccccc1)c1cnc2c(S)cccc2c1] |
| | 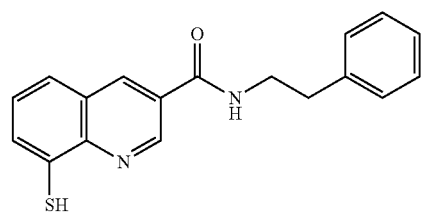 [SMILES: O=C(NCCc1ccccc1)c1cnc2c(S)cccc2c1] |
| | 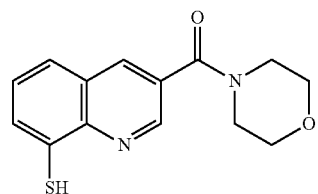 [SMILES: O=C(c1cnc2c(S)cccc2c1)N1CCOCC1] |
| | 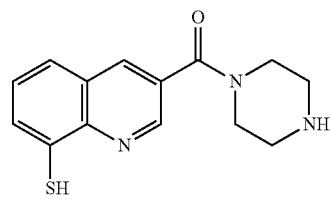 [SMILES: O=C(c1cnc2c(S)cccc2c1)N1CCNCC1] |
| | 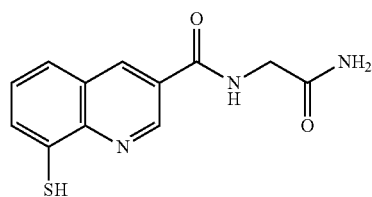 [SMILES: NC(=O)CNC(=O)c1cnc2c(S)cccc2c1] |
| | 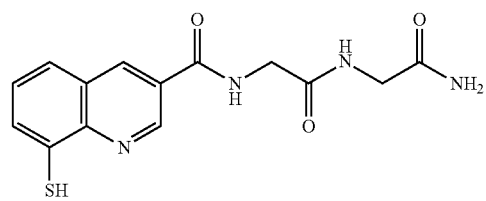 [SMILES: NC(=O)CNC(=O)CNC(=O)c1cnc2c(S)cccc2c1] |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
|---|---|
| | 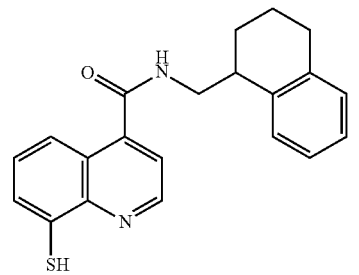 [SMILES: O=C(NCC1CCCc2ccccc21)c1ccnc2c(S)cccc12] |
| | 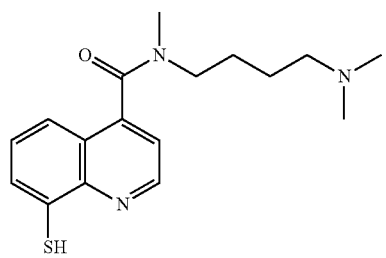 [SMILES: CN(C)CCCCN(C)C(=O)c1ccnc2c(S)cccc12] |
| | 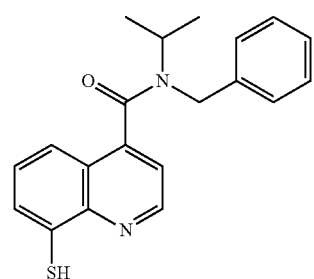 [SMILES: CC(C)N(Cc1ccccc1)C(=O)c1ccnc2c(S)cccc12] |
| | 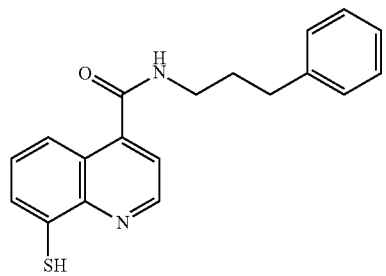 [SMILES: O=C(NCCCc1ccccc1)c1ccnc2c(S)cccc12] |
| | 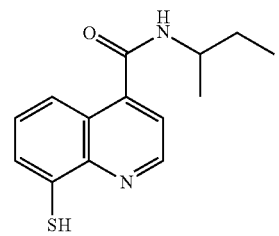 [SMILES: CCC(C)NC(=O)c1ccnc2c(S)cccc12] |
| | 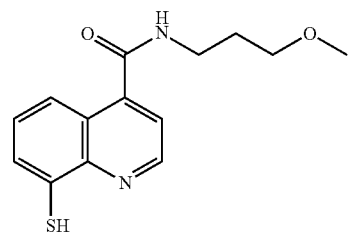 [SMILES: COCCCNC(=O)c1ccnc2c(S)cccc12] |

183 184
TABLE 1-continued
Table 1-Rpn11 Binding Partners include but are not limited to the following:
| Publication | Disclosed Compounds |
|---|---|
| | 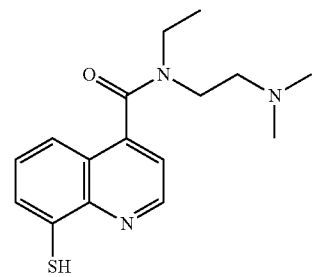 [SMILES: CCN(CCN(C)C)C(=O)c1ccnc2c(S)cccc12] |
| | 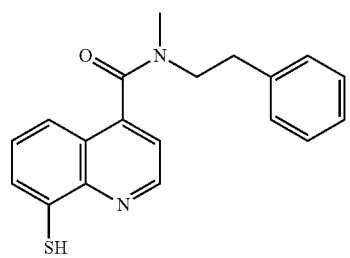 [SMILES: CN(CCc1ccccc1)C(=O)c1ccnc2c(S)cccc12] |
| | 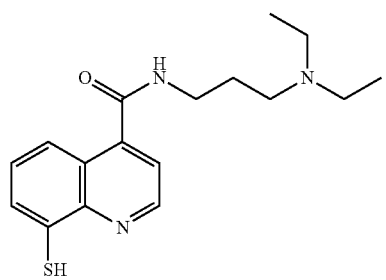 [SMILES: CCN(CC)CCCNC(=O)c1ccnc2c(S)cccc12] |
| | 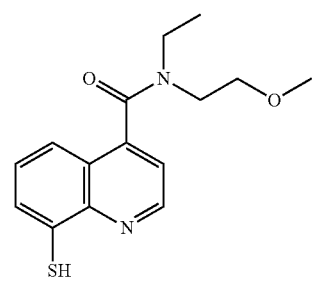 [SMILES: CCN(CCOC)C(=O)c1ccnc2c(S)cccc12] |
| | 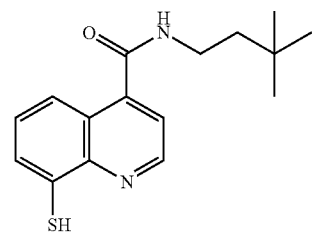 [SMILES: CC(C)(C)CCNC(=O)c1ccnc2c(S)cccc12] |
| | 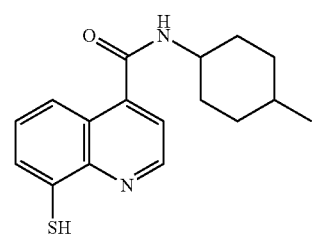 [SMILES: CC1CCC(NC(=O)c2ccnc3c(S)cccc23)CC1] |

TABLE 1-continued
Table 1-Rpn11 Binding Partners include but are not limited to the following:
| Publication | Disclosed Compounds |
|---|---|
| | 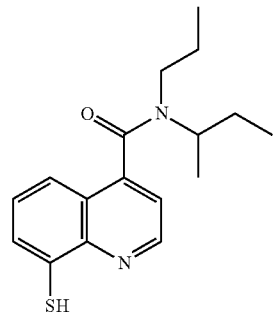 [SMILES: CCCN(C(=O)c1ccnc2c(S)cccc12)C(C)CC] |
| | 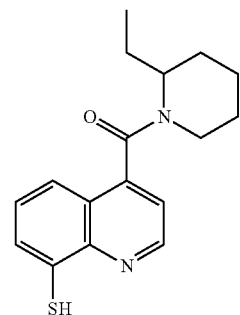 [SMILES: CCC1CCCCN1C(=O)c1ccnc2c(S)cccc12] |
| | 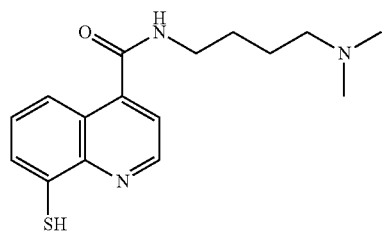 [SMILES: CN(C)CCCCNC(=O)c1ccnc2c(S)cccc12] |
| | 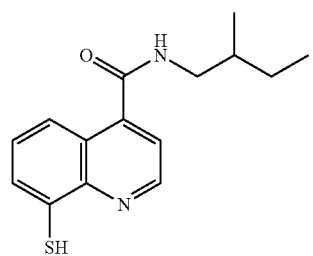 [SMILES: CCC(C)CNC(=O)c1ccnc2c(S)cccc12] |
| | 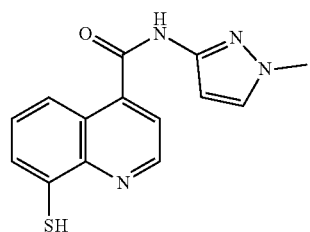 [SMILES: Cn1ccc(NC(=O)c2ccnc3c(S)cccc23)n1] |

… TABLE 1-continued
Table 1-Rpn11 Binding Partners include but are not limited to the following:
| Publication | Disclosed Compounds |
|---|---|
| | 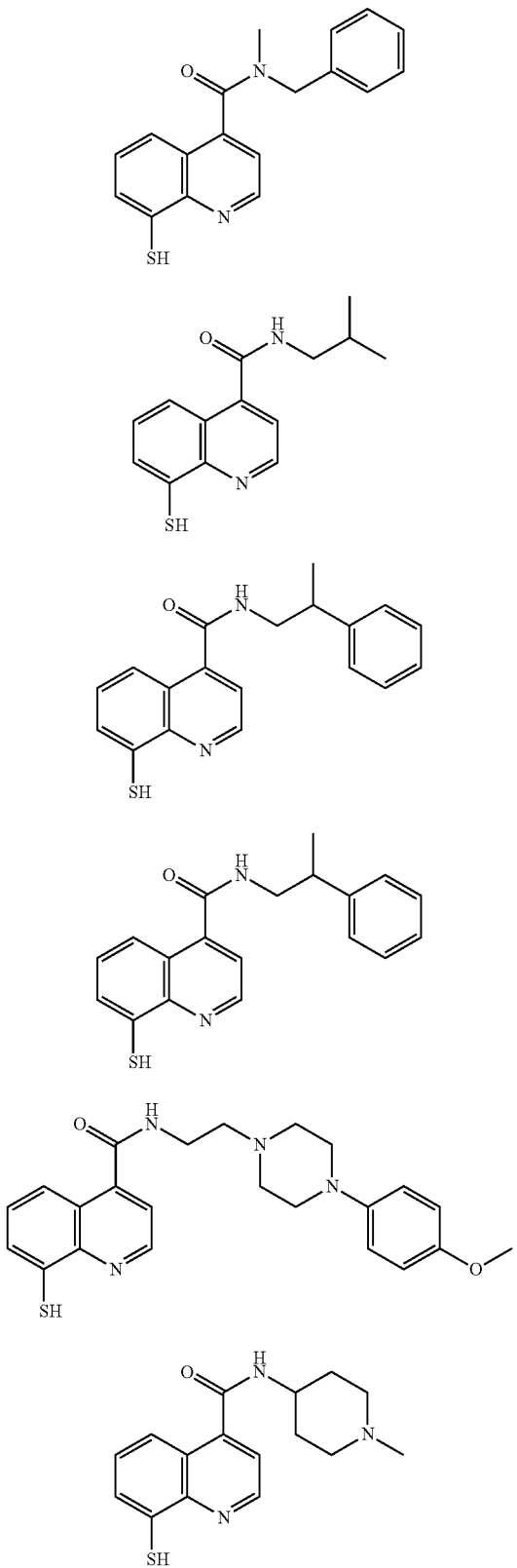 |

TABLE 1-continued
Table 1-Rpn11 Binding Partners include but are not limited to the following:
| Publication | Disclosed Compounds |
|---|---|
| | 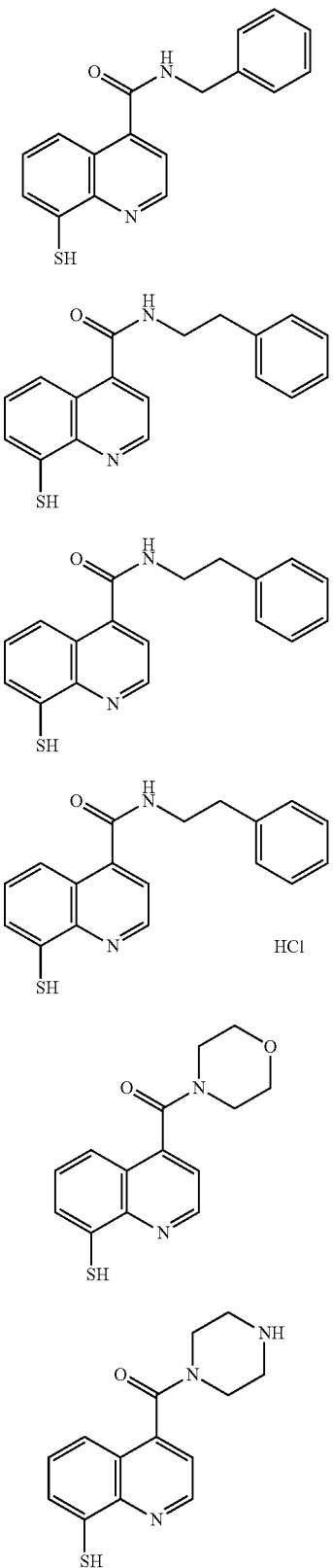 |

TABLE 1-continued
Table 1-Rpn11 Binding Partners include but are not limited to the following:
| Publication | Disclosed Compounds |
|---|---|
| | 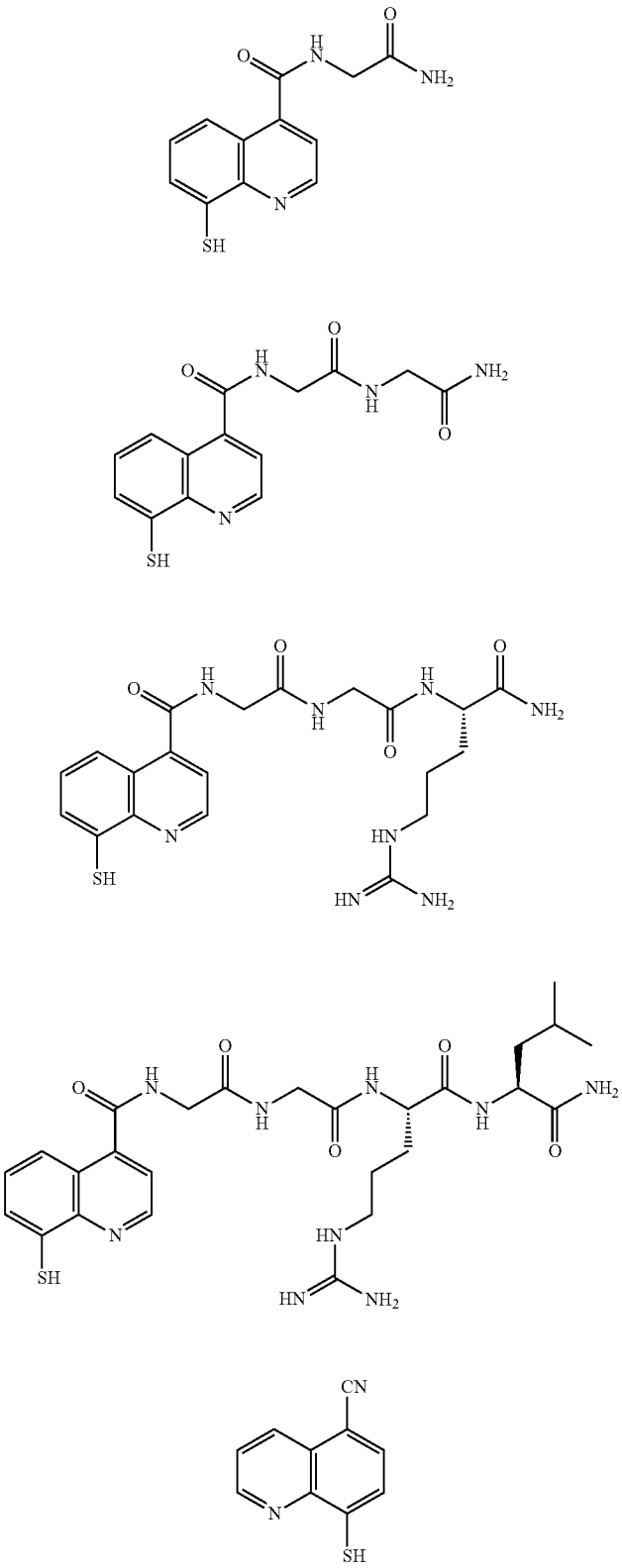 |

TABLE 1-continued
Table 1-Rpn11 Binding Partners include but are not limited to the following:
| Publication | Disclosed Compounds |
|---|---|
| | 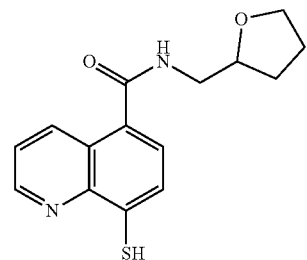 [SMILES: O=C(NCC1CCCO1)c1ccc(S)c2ncccc12] |
| | 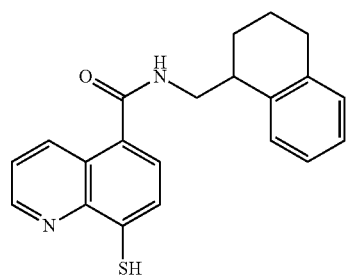 [SMILES: O=C(NCC1CCCc2ccccc21)c1ccc(S)c2ncccc12] |
| | 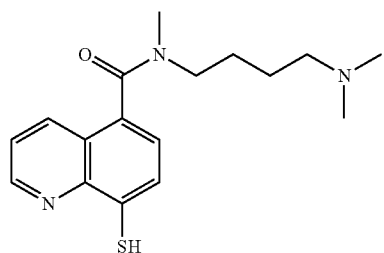 [SMILES: CN(C)CCCCN(C)C(=O)c1ccc(S)c2ncccc12] |
| | 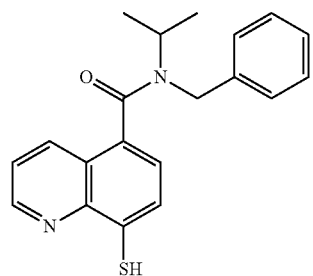 [SMILES: CC(C)N(Cc1ccccc1)C(=O)c1ccc(S)c2ncccc12] |
| | 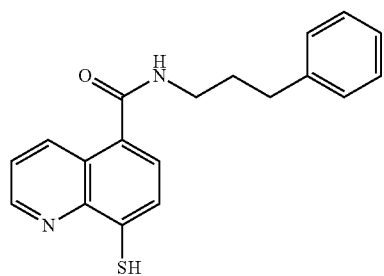 [SMILES: O=C(NCCCc1ccccc1)c1ccc(S)c2ncccc12] |

TABLE 1-continued
Table 1-Rpn11 Binding Partners include but are not limited to the following:
| Publication | Disclosed Compounds |
|---|---|
| | 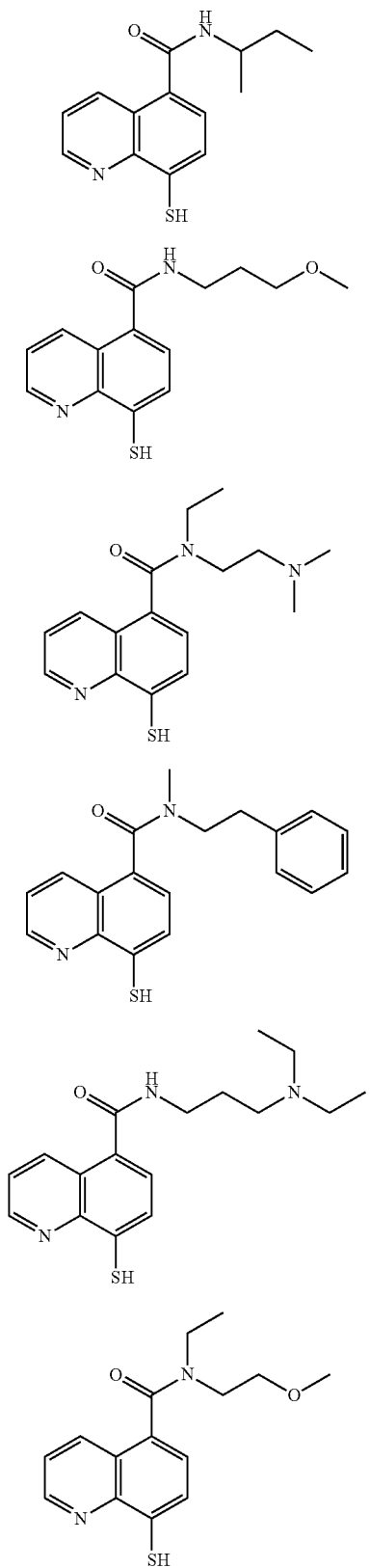 |

TABLE 1-continued
Table 1-Rpn11 Binding Partners include but are not limited to the following:
| Publication | Disclosed Compounds |
|---|---|
| | 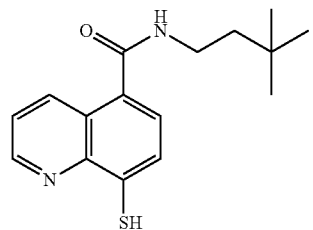 [SMILES: CC(C)(C)CCNC(=O)c1ccc(S)c2ncccc12] |
| | 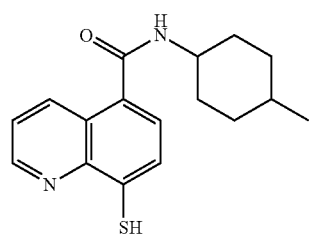 [SMILES: CC1CCC(NC(=O)c2ccc(S)c3ncccc23)CC1] |
| | 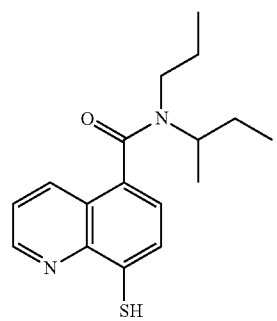 [SMILES: CCCN(C(=O)c1ccc(S)c2ncccc12)C(C)CC] |
| | 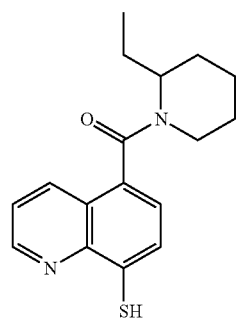 [SMILES: CCC1CCCCN1C(=O)c1ccc(S)c2ncccc12] |
| | 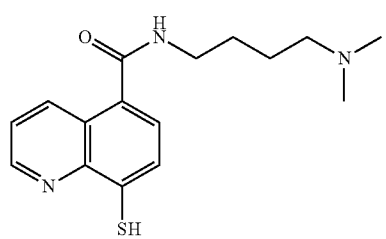 [SMILES: CN(C)CCCCNC(=O)c1ccc(S)c2ncccc12] |

TABLE 1-continued
Table 1-Rpn11 Binding Partners include but are not limited to the following:
| Publication | Disclosed Compounds |
|---|---|
| | 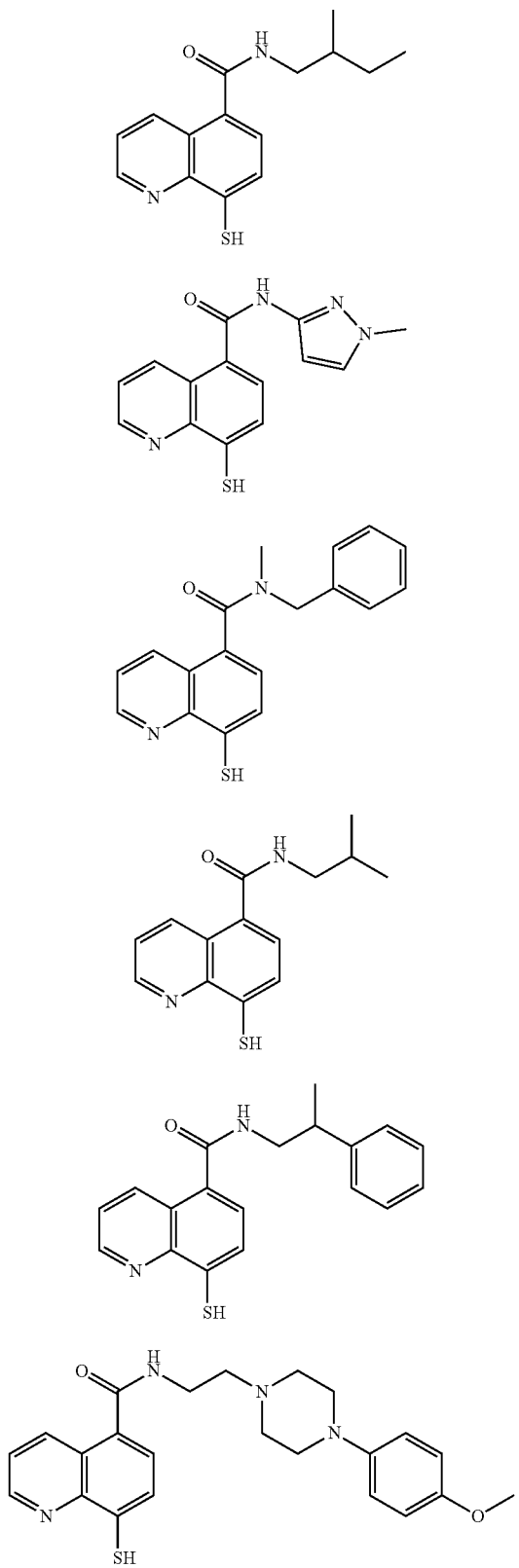 |

TABLE 1-continued
Table 1-Rpn11 Binding Partners include but are not limited to the following:
| Publication | Disclosed Compounds |
|---|---|
| | 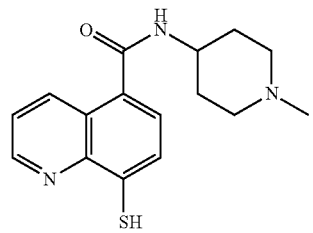 [SMILES: CN1CCC(NC(=O)c2ccc(S)c3ncccc23)CC1] |
| | 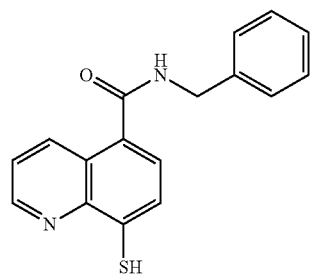 [SMILES: O=C(NCc1ccccc1)c1ccc(S)c2ncccc12] |
| | 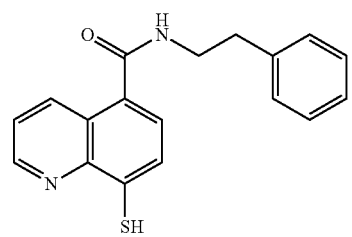 [SMILES: O=C(NCCc1ccccc1)c1ccc(S)c2ncccc12] |
| | 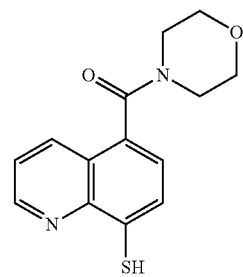 [SMILES: O=C(c1ccc(S)c2ncccc12)N1CCOCC1] |
| | 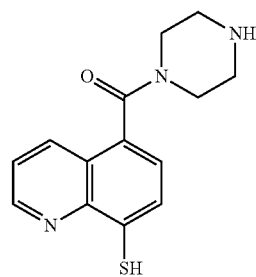 [SMILES: O=C(c1ccc(S)c2ncccc12)N1CCNCC1] |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
|---|---|
| | 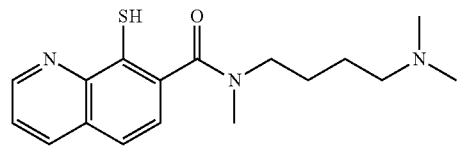 [SMILES: CN(C)CCCCN(C)C(=O)c1ccc2cccnc2c1S] |
| | 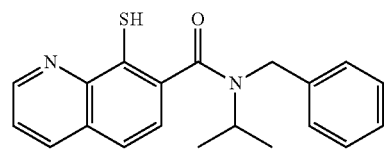 [SMILES: CC(C)N(Cc1ccccc1)C(=O)c1ccc2cccnc2c1S] |
| | 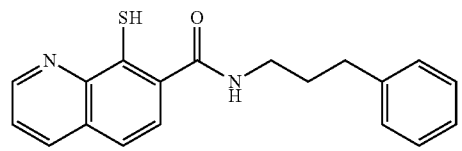 [SMILES: O=C(NCCCc1ccccc1)c1ccc2cccnc2c1S] |
| | 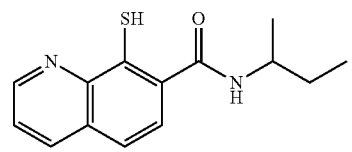 [SMILES: CCC(C)NC(=O)c1ccc2cccnc2c1S] |
| | 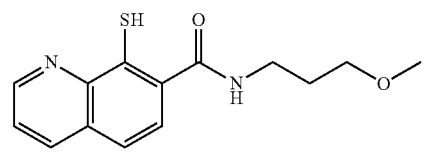 [SMILES: COCCCNC(=O)c1ccc2cccnc2c1S] |
| | 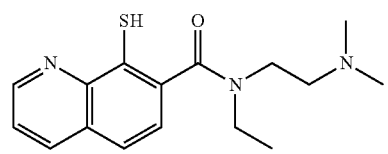 [SMILES: CCN(CCN(C)C)C(=O)c1ccc2cccnc2c1S] |
| | 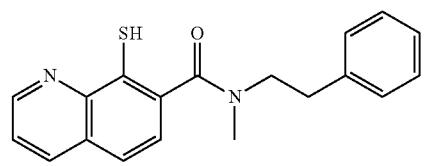 [SMILES: CN(CCc1ccccc1)C(=O)c1ccc2cccnc2c1S] |
| | 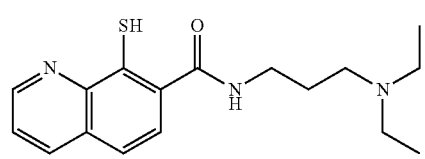 [SMILES: CCN(CC)CCCNC(=O)c1ccc2cccnc2c1S] |
| | 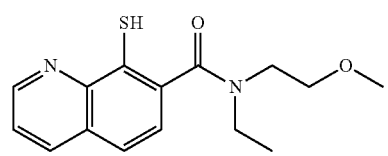 [SMILES: CCN(CCOC)C(=O)c1ccc2cccnc2c1S] |

TABLE 1-continued
Table 1-Rpn11 Binding Partners include but are not limited to the following:
| Publication | Disclosed Compounds |
|---|---|
| | 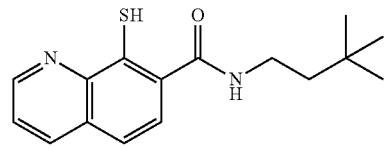 [SMILES: CC(C)(C)CCNC(=O)c1ccc2cccnc2c1S] |
| | 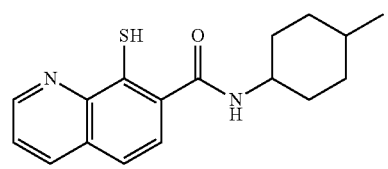 [SMILES: CC1CCC(NC(=O)c2ccc3cccnc3c2S)CC1] |
| | 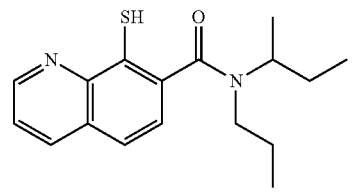 [SMILES: CCCN(C(=O)c1ccc2cccnc2c1S)C(C)CC] |
| | 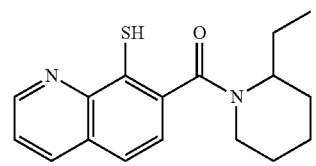 [SMILES: CCC1CCCCN1C(=O)c1ccc2cccnc2c1S] |
| | 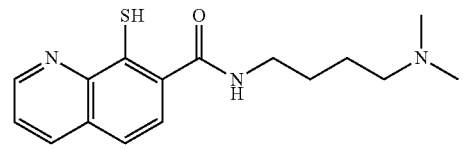 [SMILES: CN(C)CCCCNC(=O)c1ccc2cccnc2c1S] |
| | 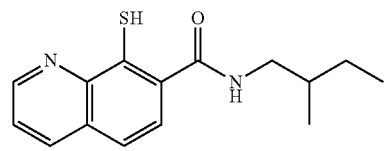 [SMILES: CCC(C)CNC(=O)c1ccc2cccnc2c1S] |
| | 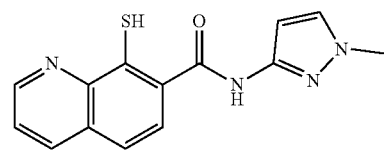 [SMILES: Cn1ccc(NC(=O)c2ccc3cccnc3c2S)n1] |
| | 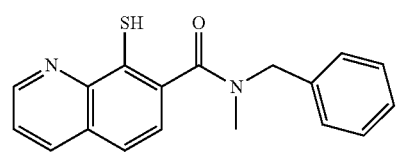 [SMILES: CN(Cc1ccccc1)C(=O)c1ccc2cccnc2c1S] |
| | 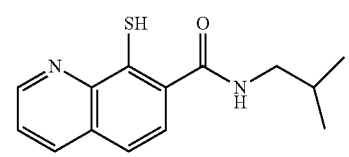 [SMILES: CC(C)CNC(=O)c1ccc2cccnc2c1S] |

TABLE 1-continued
Table 1-Rpn11 Binding Partners include but are not limited to the following:
| Publication | Disclosed Compounds |
|---|---|
| | 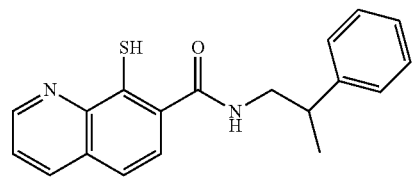 [SMILES: CC(CNC(=O)c1ccc2cccnc2c1S)c1ccccc1] |
| | 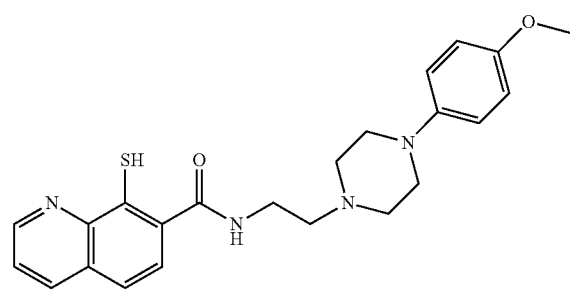 [SMILES: COc1ccc(N2CCN(CCNC(=O)c3ccc4cccnc4c3S)CC2)cc1] |
| | 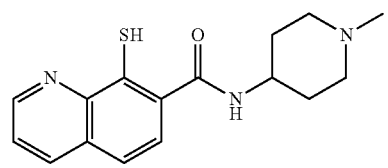 [SMILES: CN1CCC(NC(=O)c2ccc3cccnc3c2S)CC1] |
| | 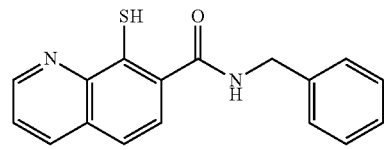 [SMILES: O=C(NCc1ccccc1)c1ccc2cccnc2c1S] |
| | 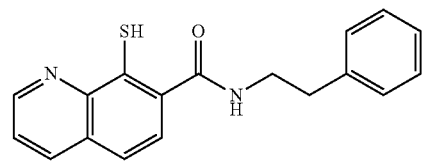 [SMILES: O=C(NCCc1ccccc1)c1ccc2cccnc2c1S] |
| | 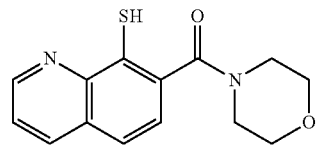 [SMILES: O=C(c1ccc2cccnc2c1S)N1CCOCC1] |
| | 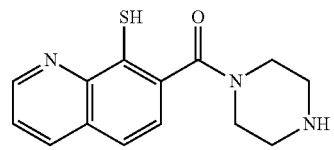 [SMILES: O=C(c1ccc2cccnc2c1S)N1CCNCC1] |
| | 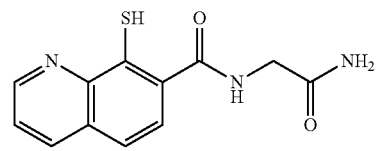 [SMILES: NC(=O)CNC(=O)c1ccc2cccnc2c1S] |

TABLE 1-continued

Table 1-Rpn11 Binding Partners include but are not limited to the following:

| Publication | Disclosed Compounds |
| --- | --- |

TABLE 1-continued
Table 1-Rpn11 Binding Partners include but are not limited to the following:
| Publication | Disclosed Compounds |
|---|---|
| | 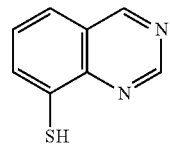 [SMILES: Sc1cccc2cncnc12] |
| | 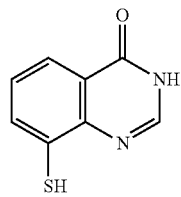 [SMILES: O=c1[nH]cnc2c(S)cccc12] |
| | 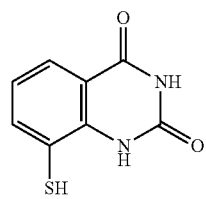 [SMILES: O=c1[nH]c(=O)c2cccc(S)c2[nH]1] |
| | 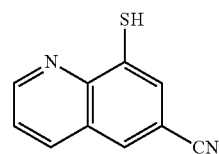 [SMILES: N#Cc1cc(S)c2ncccc2c1] |
| | 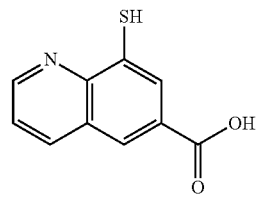 [SMILES: O=C(O)c1cc(S)c2ncccc2c1] |
| | 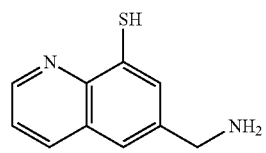 [SMILES: NCc1cc(S)c2ncccc2c1] |
| | 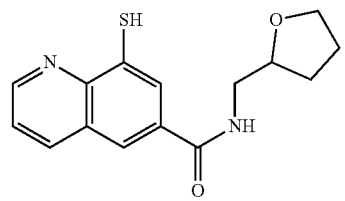 [SMILES: O=C(NCC1CCCO1)c1cc(S)c2ncccc2c1] |
| | 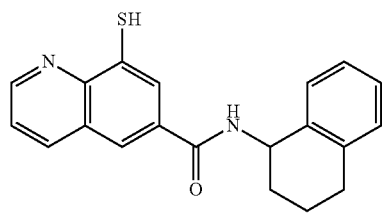 [SMILES: O=C(NC1CCCc2ccccc21)c1cc(S)c2ncccc2c1] |

TABLE 1-continued
Table 1-Rpn11 Binding Partners include but are not limited to the following:
| Publication | Disclosed Compounds |
|---|---|
| | 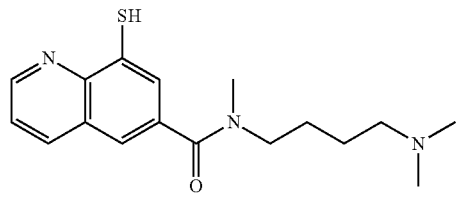 [SMILES: CN(C)CCCCN(C)C(=O)c1cc(S)c2ncccc2c1] |
| | 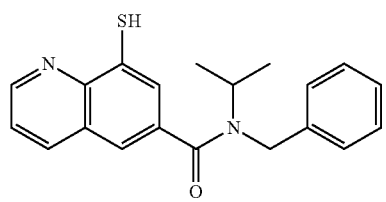 [SMILES: CC(C)N(Cc1ccccc1)C(=O)c1cc(S)c2ncccc2c1] |
| | 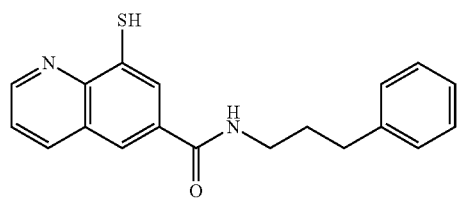 [SMILES: O=C(NCCCc1ccccc1)c1cc(S)c2ncccc2c1] |
| | 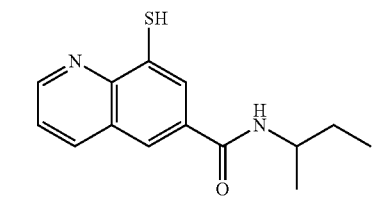 [SMILES: CCC(C)NC(=O)c1cc(S)c2ncccc2c1] |
| | 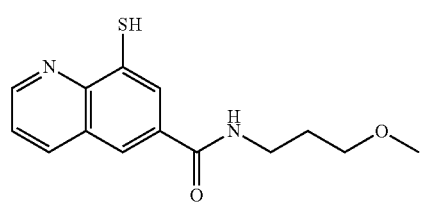 [SMILES: COCCCNC(=O)c1cc(S)c2ncccc2c1] |
| | 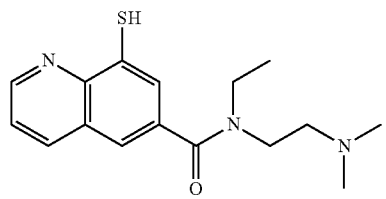 [SMILES: CCN(CCN(C)C)C(=O)c1cc(S)c2ncccc2c1] |
| | 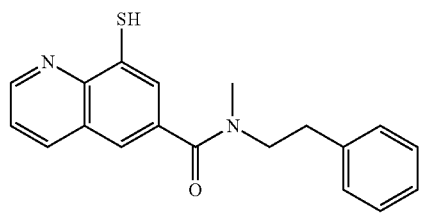 [SMILES: CN(CCc1ccccc1)C(=O)c1cc(S)c2ncccc2c1] |

TABLE 1-continued
Table 1-Rpn11 Binding Partners include but are not limited to the following:
| Publication | Disclosed Compounds |
|---|---|
| | 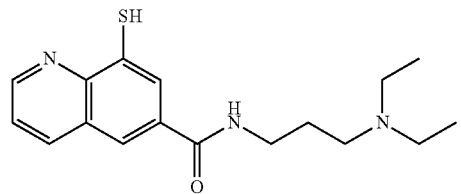 [SMILES: CCN(CC)CCCNC(=O)c1cc(S)c2ncccc2c1] |
| | 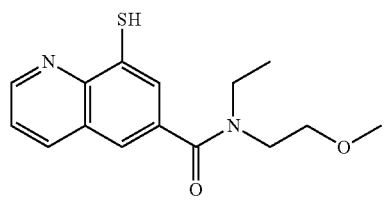 [SMILES: CCN(CCOC)C(=O)c1cc(S)c2ncccc2c1] |
| | 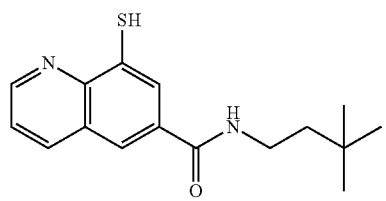 [SMILES: CC(C)(C)CCNC(=O)c1cc(S)c2ncccc2c1] |
| | 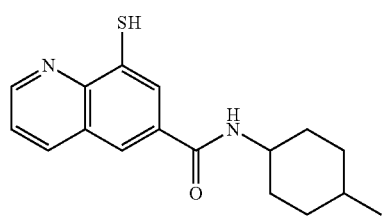 [SMILES: CC1CCC(NC(=O)c2cc(S)c3ncccc3c2)CC1] |
| | 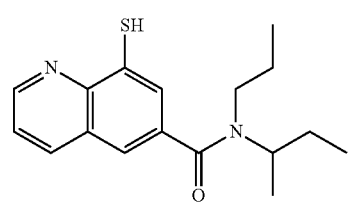 [SMILES: CCCN(C(=O)c1cc(S)c2ncccc2c1)C(C)CC] |
| | 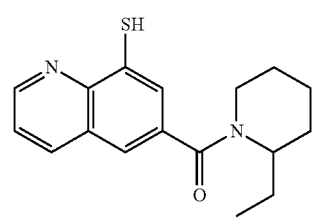 [SMILES: CCC1CCCCN1C(=O)c1cc(S)c2ncccc2c1] |
| | 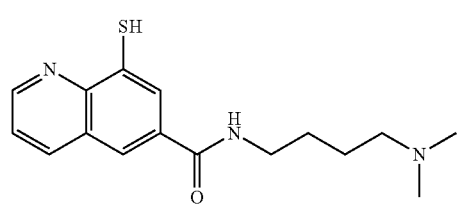 [SMILES: CN(C)CCCCNC(=O)c1cc(S)c2ncccc2c1] |

TABLE 1-continued
Table 1-Rpn11 Binding Partners include but are not limited to the following:
| Publication | Disclosed Compounds |
| --- | --- |
| | 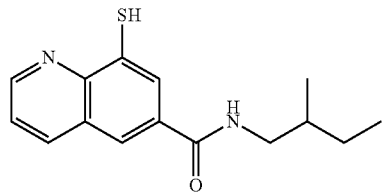 [SMILES: CCC(C)CNC(=O)c1cc(S)c2ncccc2c1] |
| | 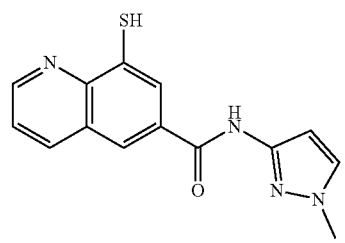 [SMILES: Cn1ccc(NC(=O)c2cc(S)c3ncccc3c2)n1] |
| | 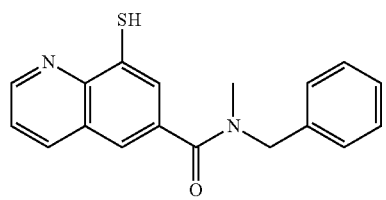 [SMILES: CN(Cc1ccccc1)C(=O)c1cc(S)c2ncccc2c1] |
| | 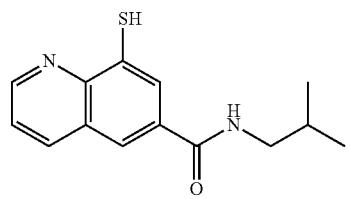 [SMILES: CC(C)CNC(=O)c1cc(S)c2ncccc2c1] |
| | 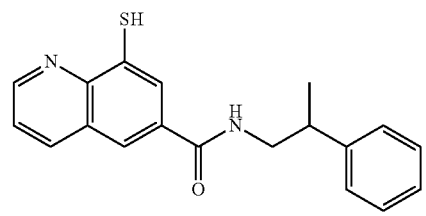 [SMILES: CC(CNC(=O)c1cc(S)c2ncccc2c1)c1ccccc1] |
| | 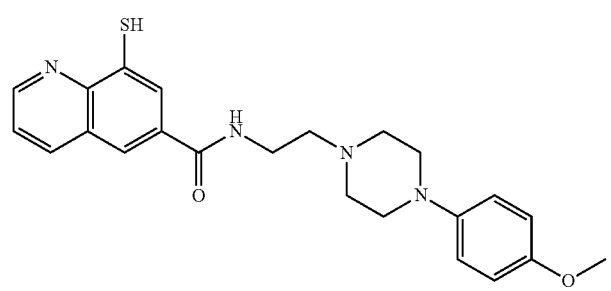 [SMILES: COc1ccc(N2CCN(CCNC(=O)c3cc(S)c4ncccc4c3)CC2)cc1] |

TABLE 1-continued
Table 1-Rpn11 Binding Partners include but are not limited to the following:
| Publication | Disclosed Compounds |
|---|---|
| | 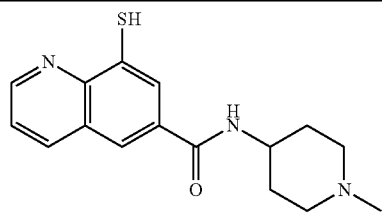 |
| | 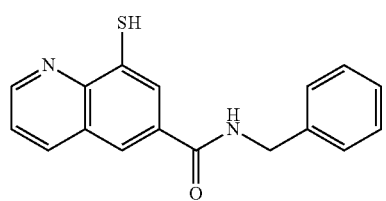 [SMILES: O=C(NCc1ccccc1)c1cc(S)c2ncccc2c1] |
| | 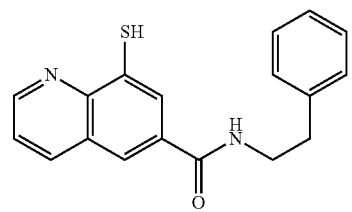 [SMILES: O=C(NCCc1ccccc1)c1cc(S)c2ncccc2c1] |
| | 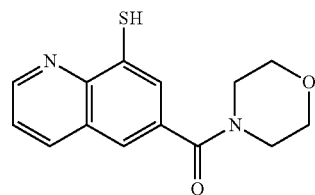 [SMILES: O=C(c1cc(S)c2ncccc2c1)N1CCOCC1] |
| | 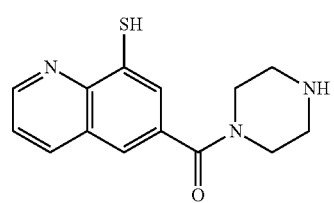 [SMILES: O=C(c1cc(S)c2ncccc2c1)N1CCNCC1] |
| | 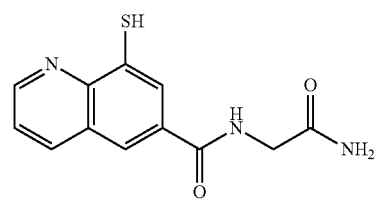 [SMILES: NC(=O)CNC(=O)c1cc(S)c2ncccc2c1] |
| | 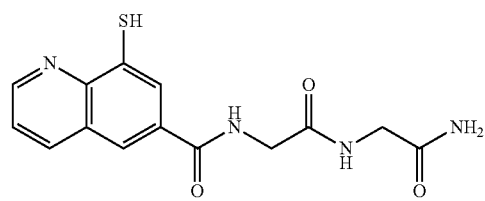 [SMILES: NC(=O)CNC(=O)CNC(=O)c1cc(S)c2ncccc2c1] |

US 11,925,690 B2
TABLE 1-continued
Table 1-Rpn11 Binding Partners include but are not limited to the following:
| Publication | Disclosed Compounds |
| --- | --- |
| | 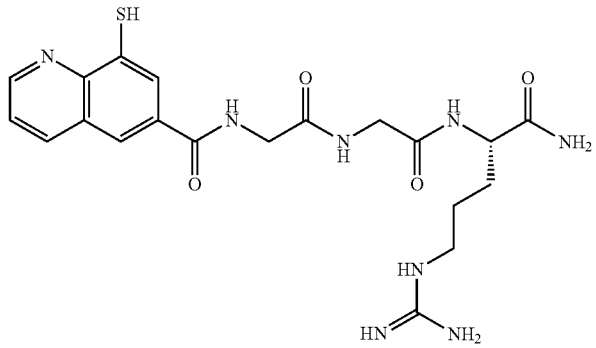 [SMILES: N=C(N)NCCC[C@H](NC(=O)CNC(=O)CNC(=O)c1cc(S)c2ncccc2c1)C(N)=O] |
| | 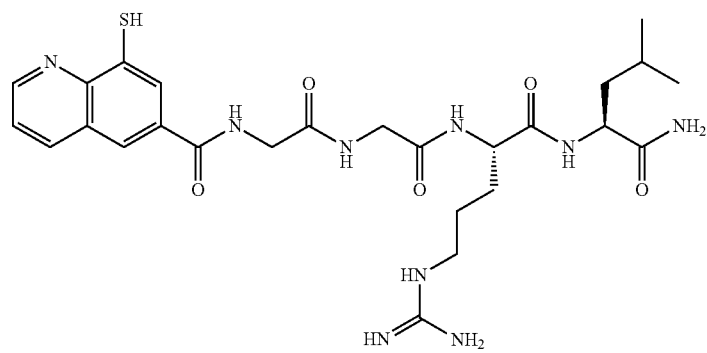 [SMILES: CC(C)C[C@H](NC(=O)[C@H](CCCNC(=N)N)NC(=O)CNC(=O)CNC(=O)c1cc(S)c2ncccc2c1)C(N)=O] |
| | 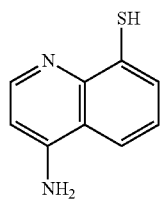 [SMILES: Nc1ccnc2c(S)cccc12] |
| | 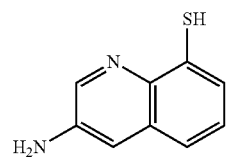 |
| | 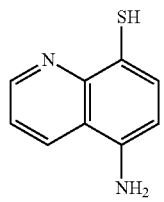 |
| | 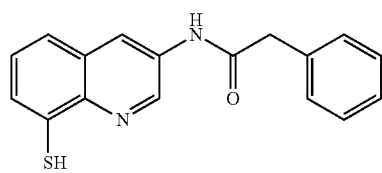 [SMILES: O=C(Cc1ccccc1)Nc1cnc2c(S)cccc2c1] |

TABLE 1-continued
Table 1-Rpn11 Binding Partners include but are not limited to the following:
| Publication | Disclosed Compounds |
|---|---|
| | 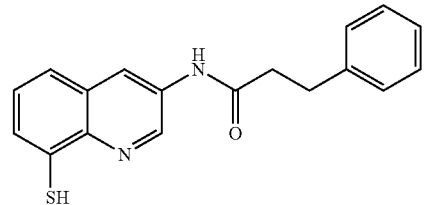 [SMILES: O=C(CCc1ccccc1)Nc1cnc2c(S)cccc2c1] |
| | 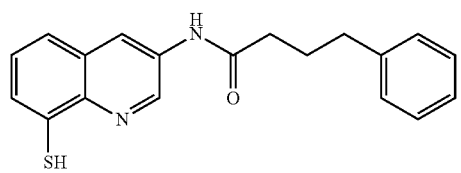 [SMILES: O=C(CCCc1ccccc1)Nc1cnc2c(S)cccc2c1] |
| | 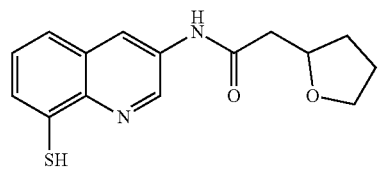 [SMILES: O=C(CC1CCCO1)Nc1cnc2c(S)cccc2c1] |
| | 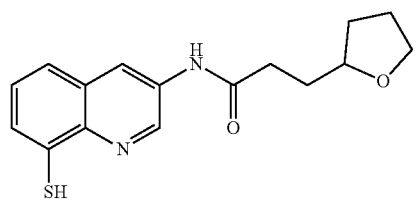 [SMILES: O=C(CCC1CCCO1)Nc1cnc2c(S)cccc2c1] |
| | 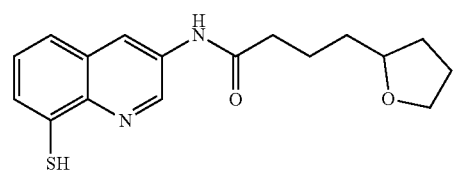 [SMILES: O=C(CCCC1CCCO1)Nc1cnc2c(S)cccc2c1] |
| | 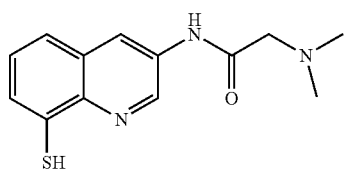 [SMILES: CN(C)CC(=O)Nc1cnc2c(S)cccc2c1] |
| | 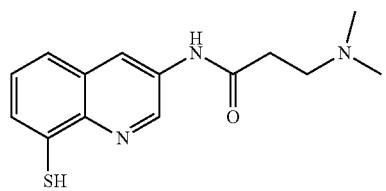 [SMILES: CN(C)CCC(=O)Nc1cnc2c(S)cccc2c1] |
| | 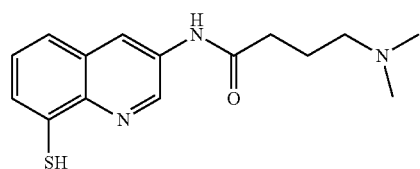 [SMILES: CN(C)CCCC(=O)Nc1cnc2c(S)cccc2c1] |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
|---|---|
| | 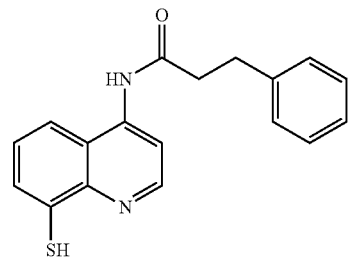 [SMILES: O=C(CCc1ccccc1)Nc1ccnc2c(S)cccc12] |
| | 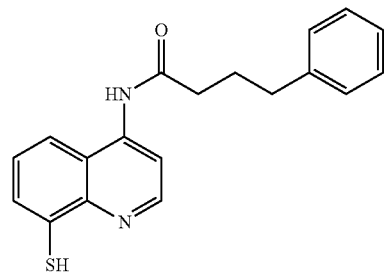 [SMILES: O=C(CCCc1ccccc1)Nc1ccnc2c(S)cccc12] |
| | 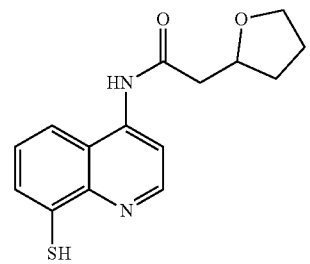 [SMILES: O=C(CC1CCCO1)Nc1ccnc2c(S)cccc12] |
| | 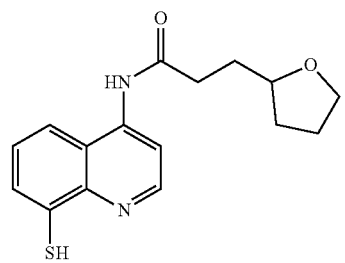 [SMILES: O=C(CCC1CCCO1)Nc1ccnc2c(S)cccc12] |
| | 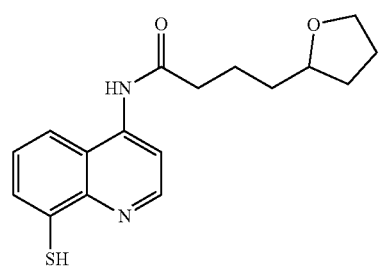 [SMILES: O=C(CCCC1CCCO1)Nc1ccnc2c(S)cccc12] |

TABLE 1-continued
Table 1-Rpn11 Binding Partners include but are not limited to the following:
| Publication | Disclosed Compounds |
|---|---|
| | 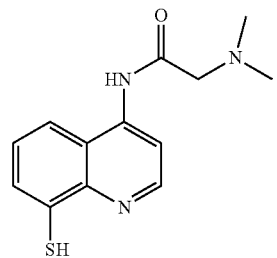 [SMILES: CN(C)CC(=O)Nc1ccnc2c(S)cccc12] |
| | 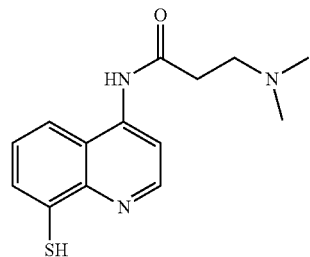 [SMILES: CN(C)CCC(=O)Nc1ccnc2c(S)cccc12] |
| | 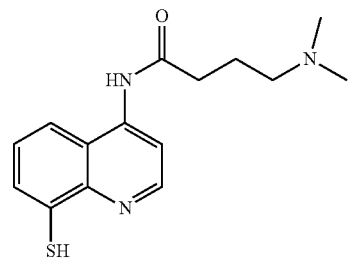 [SMILES: CN(C)CCCC(=O)Nc1ccnc2c(S)cccc12] |
| | 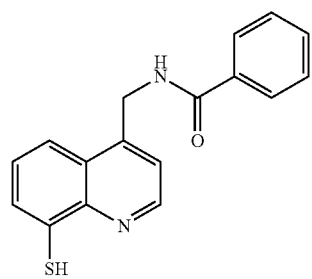 [SMILES: O=C(NCc1ccnc2c(S)cccc12)c1ccccc1] |
| | 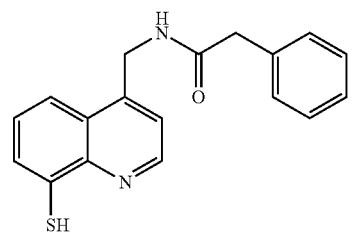 [SMILES: O=C(Cc1ccccc1)NCc1ccnc2c(S)cccc12] |

233
234
TABLE 1-continued
Table 1-Rpn11 Binding Partners include but are not limited to the following:
| Publication | Disclosed Compounds |
|---|---|
| | 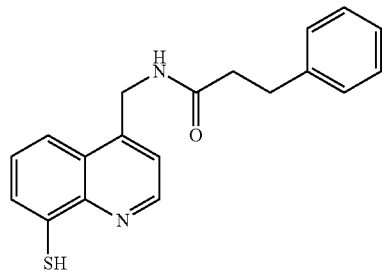 [SMILES: O=C(CCc1ccccc1)NCc1ccnc2c(S)cccc12] |
| | 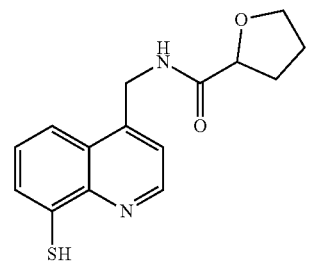 [SMILES: O=C(NCc1ccnc2c(S)cccc12)C1CCCO1] |
| | 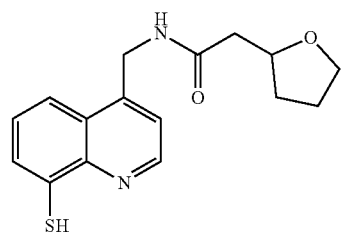 [SMILES: O=C(CC1CCCO1)NCc1ccnc2c(S)cccc12] |
| | 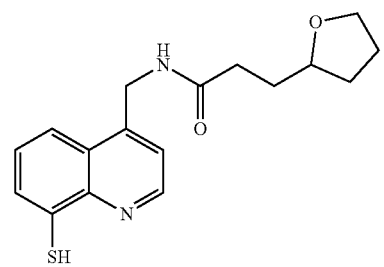 [SMILES: O=C(CCC1CCCO1)NCc1ccnc2c(S)cccc12] |
| | 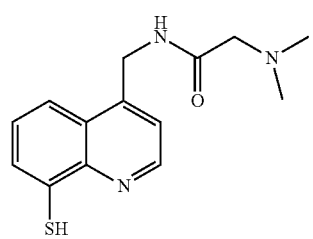 [SMILES: CN(C)CC(=O)NCc1ccnc2c(S)cccc12] |
| | 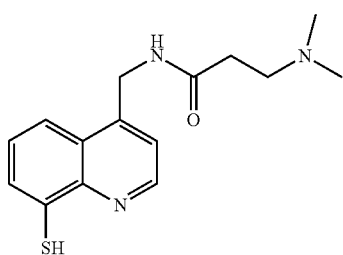 [SMILES: CN(C)CCC(=O)NCc1ccnc2c(S)cccc12] |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
|---|---|
| | 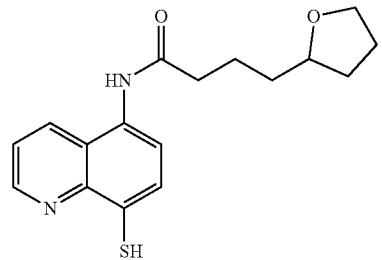 [SMILES: O=C(CCCC1CCCO1)Nc1ccc(S)c2ncccc12] |
| | 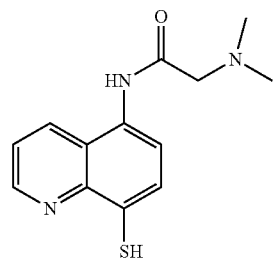 [SMILES: CN(C)CC(=O)Nc1ccc(S)c2ncccc12] |
| | 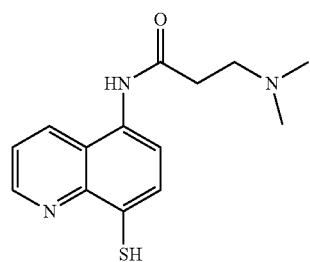 [SMILES: CN(C)CCC(=O)Nc1ccc(S)c2ncccc12] |
| | 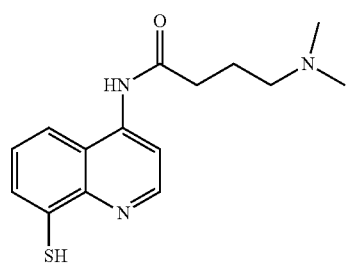 [SMILES: CN(C)CCCC(=O)Nc1ccnc2c(S)cccc12] |
| | 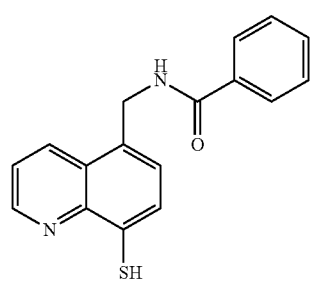 [SMILES: O=C(NCc1ccc(S)c2ncccc12)c1ccccc1] |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
|---|---|
| | 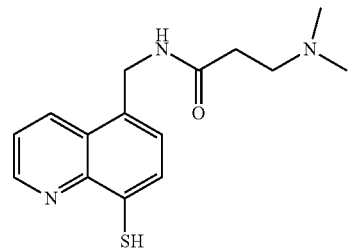 [SMILES: CN(C)CCC(=O)NCc1ccc(S)c2ncccc12] |
| | 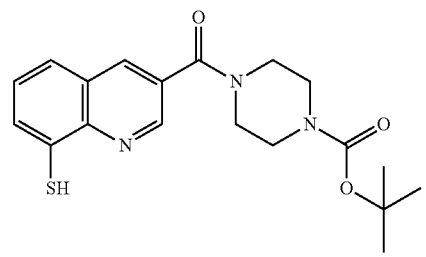 [SMILES: CC(C)(C)OC(=O)N1CCN(C(=O)c2cnc3c(S)cccc3c2)CC1] |
| | 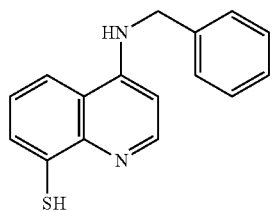 [SMILES: Sc1cccc2c(NCc3ccccc3)ccnc12] |
| | 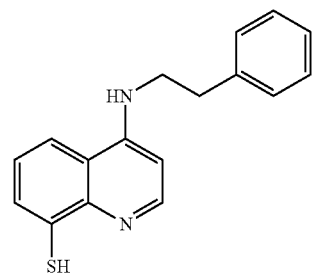 [SMILES: Sc1cccc2c(NCCc3ccccc3)ccnc12] |
| | 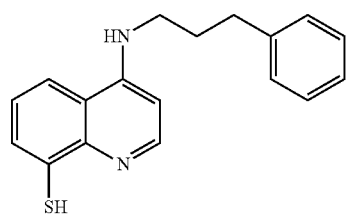 [SMILES: Sc1cccc2c(NCCCc3ccccc3)ccnc12] |
| | 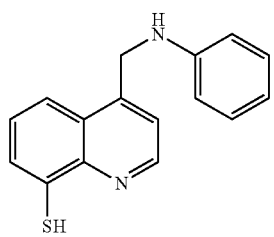 [SMILES: Sc1cccc2c(CNc3ccccc3)ccnc12] |

TABLE 1-continued
Table 1-Rpn11 Binding Partners include but are not limited to the following:
| Publication | Disclosed Compounds |
| --- | --- |
| | 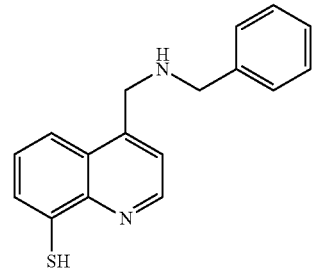 [SMILES: Sc1cccc2c(CNCc3ccccc3)ccnc12] |
| | 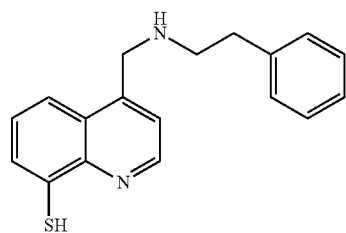 [SMILES: Sc1cccc2c(CNCCc3ccccc3)ccnc12] |
| | 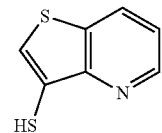 |
| | 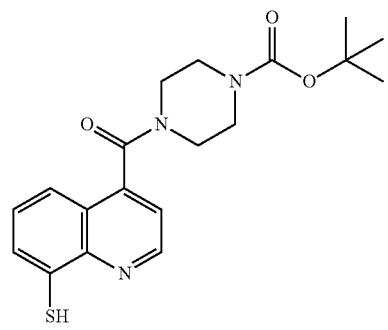 [SMILES: CC(C)(C)OC(=O)N1CCN(C(=O)c2ccnc3c(S)cccc23)CC1] |
| | 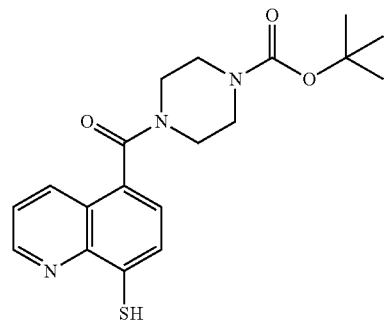 [SMILES: CC(C)(C)OC(=O)N1CCN(C(=O)c2ccc(S)c3ncccc23)CC1] |

TABLE 1-continued
Table 1-Rpn11 Binding Partners include but are not limited to the following:
| Publication | Disclosed Compounds |
|---|---|
| | 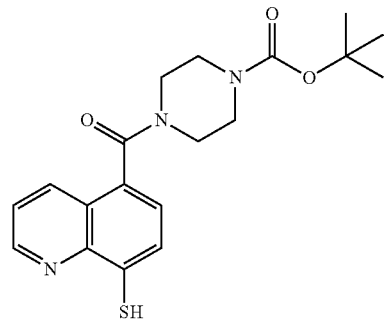 [SMILES: CC(C)(C)OC(=O)N1CCN(C(=O)c2ccc(S)c3ncccc23)CC1] |
| | 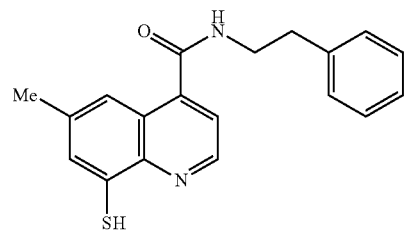 [SMILES: Cc1cc(S)c2nccc(C(=O)NCCc3ccccc3)c2c1] |
| | 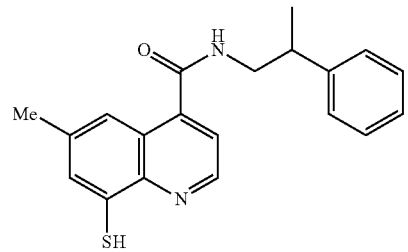 [SMILES: Cc1cc(S)c2nccc(C(=O)NCC(C)c3ccccc3)c2c1] |
| | 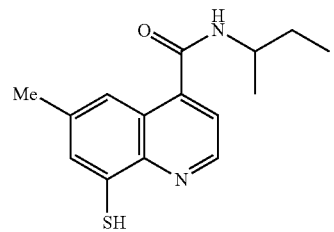 [SMILES: CCC(C)NC(=O)c1ccnc2c(S)cc(C)cc12] |
| | 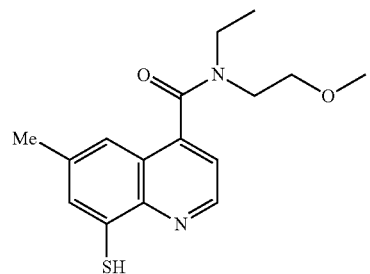 [SMILES: CCN(CCOC)C(=O)c1ccnc2c(S)cc(C)cc12] |

TABLE 1-continued
Table 1-Rpn11 Binding Partners include but are not limited to the following:
| Publication | Disclosed Compounds |
|---|---|
| | 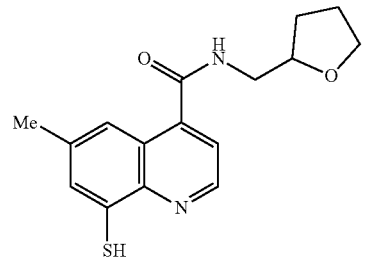 [SMILES: Cc1cc(S)c2nccc(C(=O)NCC3CCCO3)c2c1] |
| | 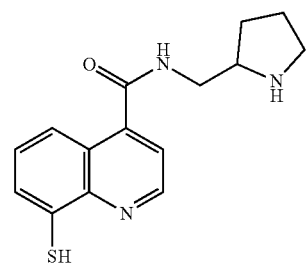 [SMILES: O=C(NCC1CCCN1)c1ccnc2c(S)cccc12] |
| | 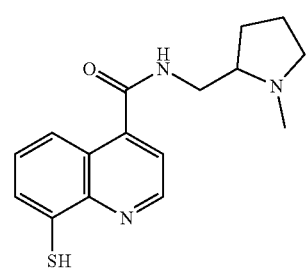 [SMILES: CN1CCCC1CNC(=O)c1ccnc2c(S)cccc12] |
| | 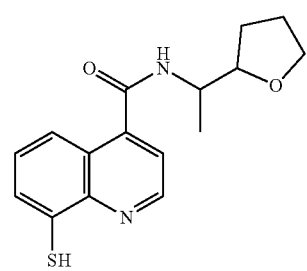 [SMILES: CC(NC(=O)c1ccnc2c(S)cccc12)C1CCCO1] |
| | 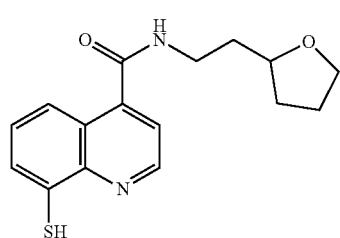 [SMILES: O=C(NCCC1CCCO1)c1ccnc2c(S)cccc12] |

TABLE 1-continued

Table 1-Rpn11 Binding Partners include but are not limited to the following:

| Publication | Disclosed Compounds |
|---|---|

TABLE 1-continued
Table 1-Rpn11 Binding Partners include but are not limited to the following:
| Publication | Disclosed Compounds |
|---|---|
| | 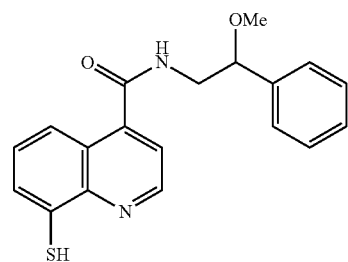 [SMILES: COC(CNC(=O)c1ccnc2c(S)cccc12)c1ccccc1] |
| | 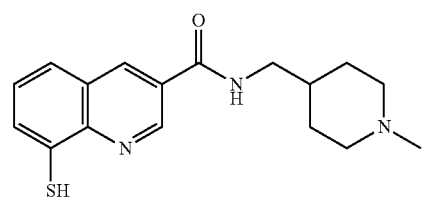 [SMILES: CN1CCC(CNC(=O)c2cnc3c(S)cccc3c2)CC1] |
| | 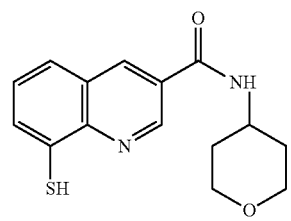 [SMILES: O=C(NC1CCOCC1)c1cnc2c(S)cccc2c1] |
| | 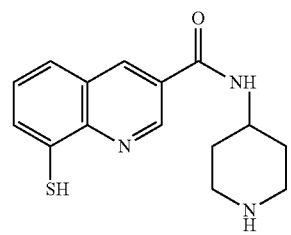 [SMILES: O=C(NC1CCNCC1)c1cnc2c(S)cccc2c1] |
| | 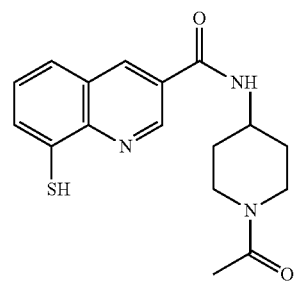 [SMILES: CC(=O)N1CCC(NC(=O)c2cnc3c(S)cccc3c2)CC1] |
| | 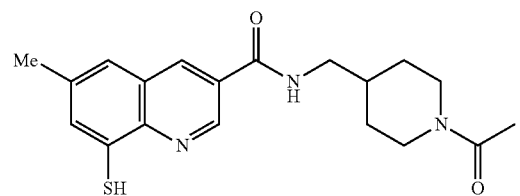 [SMILES: CC(=O)N1CCC(CNC(=O)c2cnc3c(S)cc(C)cc3c2)CC1] |

TABLE 1-continued
Table 1-Rpn11 Binding Partners include but are not limited to the following:
| Publication | Disclosed Compounds |
|---|---|
| | 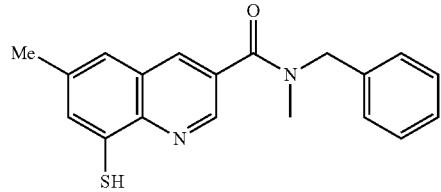 [SMILES: Cc1cc(S)c2ncc(C(=O)N(C)Cc3ccccc3)cc2c1]<br>Carfilzomib<br>MLN-4924 |
| Li et al. Nat Chem Biol. 2017 May;13(5): 486-493<br>Lauinger et al. Nat Chem Biol. 2017 Jul;13(7): 709-714<br>Perez et al. J Med Chem. 2017 Feb 23;60(4): 1343-1361 | Quinilone-8-thiol (8TQ)<br>Capzimin<br><br>Thiolutin<br><br><br><br>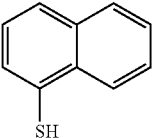 [SMILES: Sc1cccc2ccccc12]<br><br>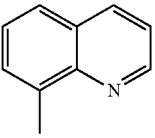<br><br>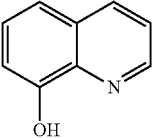 [SMILES: Oc1cccc2cccnc12]<br><br>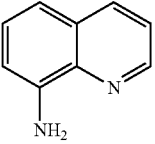 [SMILES: Nc1cccc2cccnc12]<br><br>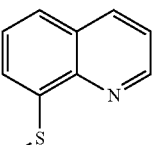<br><br>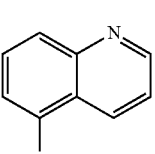 |

TABLE 1-continued

Table 1-Rpn11 Binding Partners include but are not limited to the following:

| Publication | Disclosed Compounds |
|---|---|
| Chen et al. Cancer Metastasis Rev. 2017 Dec;36(4): 655-668. | 8TQ<br>capzimin<br>Thiolutin |

The invention also provides for Rpn11 binding partners which are anti-Rpn11 antibodies and fragments thereof, such as Fv antibodies, diabodies, single domain antibodies, such as a VH and/or VL polypeptide, and antibody fragments, so long as they exhibit the desired biological activity, which is to bind to Rpn11. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., (*Nature*, 1990 348: 552-554).

A bifunctional molecule comprising an antibody that binds to Rpn11 linked to a target protein binding partner can be prepared according to methods known in the art, for example, as provided in Tsuchikama et al. (*Protein Cell*, 2018, 9(1): 33-46).

Anti-Rpn11 antibodies useful according to the invention include but are not limited to:

| Product | Company | Catalog Number |
|---|---|---|
| Proteasome 19S Rpn11/S13 subunit (human) polyclonal antibody | Enzo Life Sciences, Inc. | BML-PW9625-0100 |
| Anti-26S proteasome regulatory subunit Rpn11 Antibody | MilliporeSigma | ABE390 |
| Anti-26S proteasome regulatory subunit Rpn11, clone 7C7.1 | MilliporeSigma | MABE881 |
| Antibody combination against N terminus of P43588 (Yeast ubiquitin carboxyl-terminal hydrolase Rpn11) | Abmart | X1-P43588 |

The invention also provides for Rpn11 binding partners which are aptamers. A bifunctional molecule comprising an aptamer that binds to Rpn11 linked to a target protein binding partner can be prepared according to methods known in the art, for example, as provided in Wang et al., dx.doi.org/10.1021/ja4117395|*J. Am. Chem. Soc.* 2014, 136, 2731-2734.

In one embodiment, a bifunctional molecule comprising an Rpn11 binding partner, that is an aptamer, connected to a target protein binding partner via a linker, has the general structure shown below:

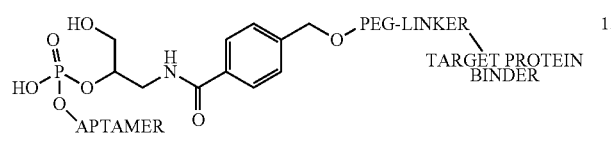

The invention also provides for Rpn11 binding partners that are bicyclic or multispecific peptide molecules, for example as described in U.S. Pat. No. 9,670,482. Such bicyclic peptide molecules are low molecular weight (1.5-2 kDa), are flexible, and are chemically synthesized.

Structures shown below allow for covalent binding of first and second binding partners to produce a bifunctional molecule according to the invention: In the structures set forth below, X represents an Rpn11 binding partner.

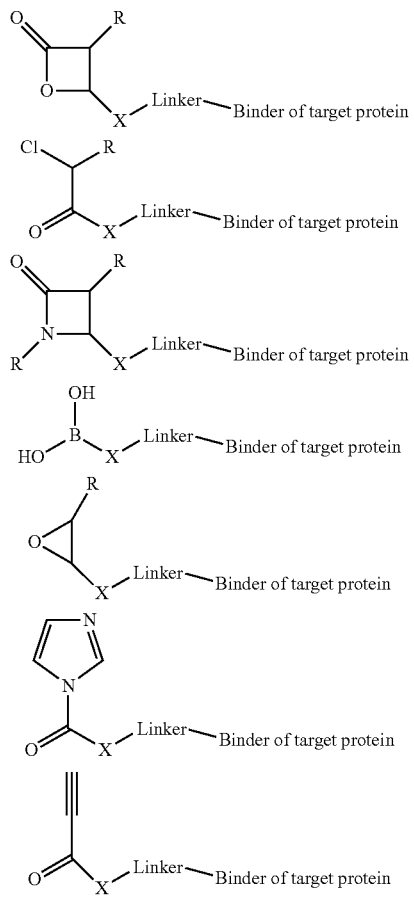

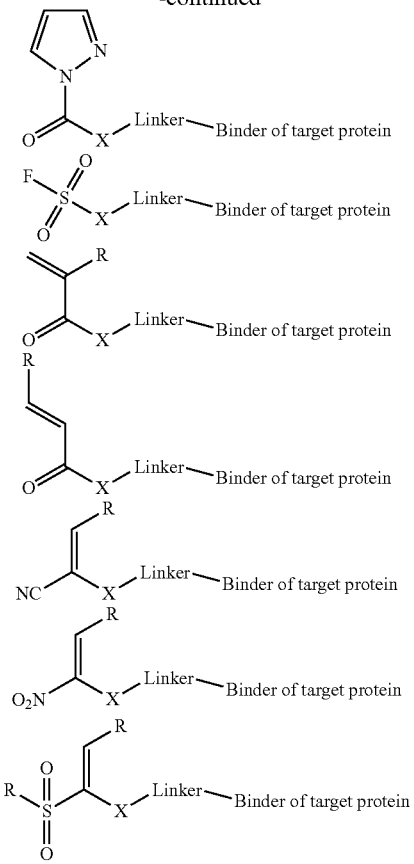

Target Protein Binding Partner

A target protein binding partner is a molecule (a protein, a peptide, a ligand of the protein, a nucleic acid such as a DNA or RNA or combined DNA/RNA molecule) that binds to a selected target protein with an affinity or a Kd as set forth hereinabove.

The term "target protein binding partner" includes a molecule, for example a small molecule, an antibody, an aptamer, a peptide, a ligand of the target protein, which binds to a target protein. A target binding partner is directly covalently linked or connected via a linker to an Rpn11 binding partner to form a bifunctional molecule that facilitates degradation of the target protein.

A target protein binding partner according to the invention binds to a protein, and can be a small molecule. A small molecule that is known to inhibit activity of a given target protein is useful according to the invention, including but not limited to kinase inhibitors, compounds targeting Human BET Bromodomain-containing proteins, Hsp90 inhibitors, HDM2 and MDM2 inhibitors, HDAC inhibitors, human lysine methyltransferase inhibitors, angiogenesis inhibitors, nuclear hormone receptor compounds, immunosuppressive compounds, and compounds targeting the aryl hydrocarbon receptor (AHR). Exemplary small molecule inhibitor target protein moieties useful for the invention are provided below.

A target protein partner also includes an antibody that binds specifically to a target protein of interest. The term "antibody" (Ab) as used herein includes monoclonal antibodies, polyclonal antibodies, multispecific antibodies (e.g., bispecific antibodies), humanized or human antibodies, Fv antibodies, diabodies, single domain (VH, VL domains)

antibodies, and antibody fragments, so long as they exhibit the desired binding activity. "Antibody" refers to a polypeptide that specifically binds an epitope of a protein. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the Willi antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al, 1990, *Nature*, 348:552-554).

The invention also provides for a target protein binding partner that is a haloalkyl group, wherein the alkyl group generally ranges in size from about 1 or 2 carbons to about 12 carbons in length, for example, 2 to 10 carbons in length, 3 carbons to about 8 carbons in length, and 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure —(CH$_2$)v-Halo where v is an integer from 2 to about 12, often about 3 to about 8, more often about 4 to about 6. Halo may be a halogen, but is preferably Cl or Br, more often Cl.

The invention also includes include pharmaceutically acceptable salts, enantiomers, solvates and polymorphs of the target protein binding partner.

A target protein binding partner that is a kinase inhibitor includes but is not limited to any one of the molecules shown below and derivatives thereof:

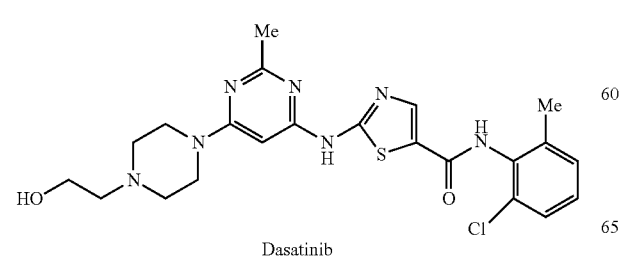

Dasatinib

-continued

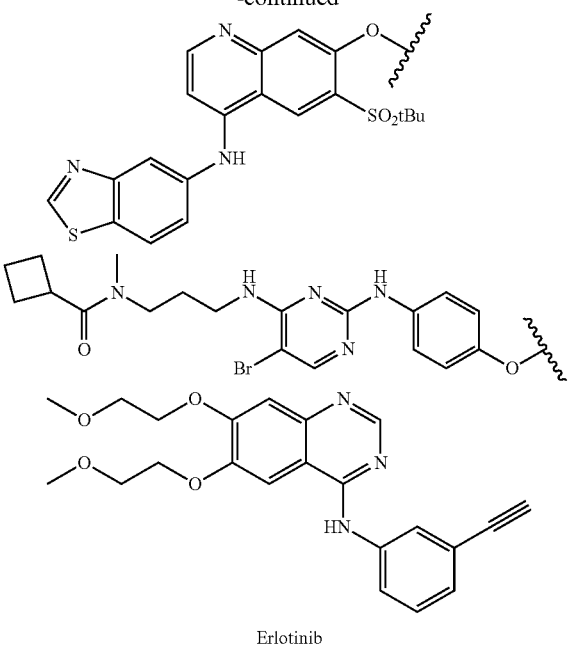

Erlotinib

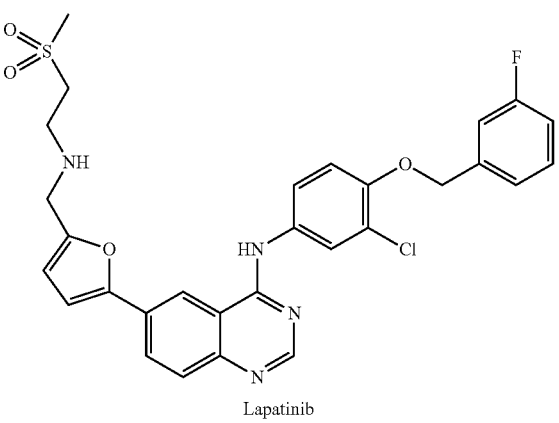

Lapatinib

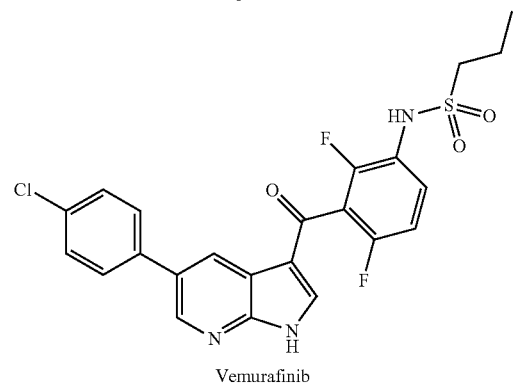

Vemurafinib

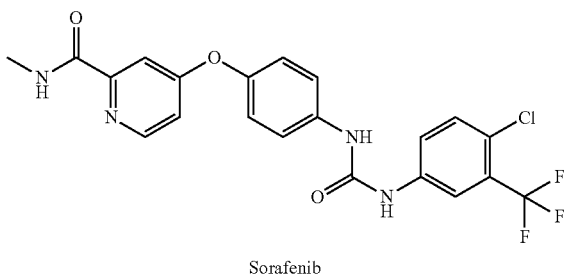

Sorafenib

-continued
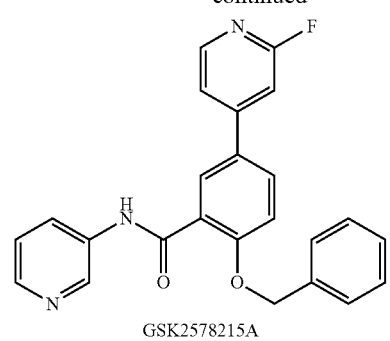
GSK2578215A
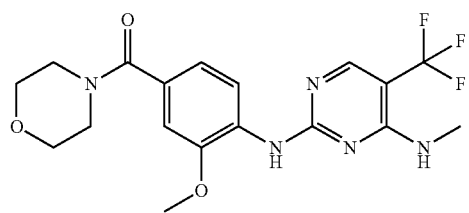
GNE1023
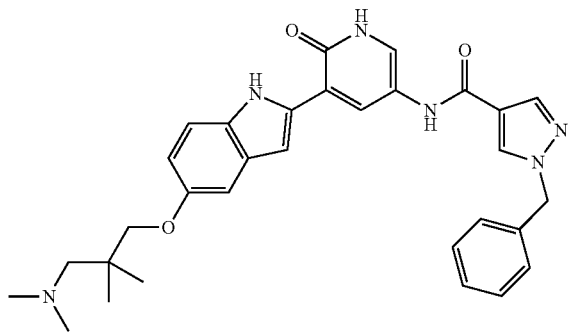
V158411
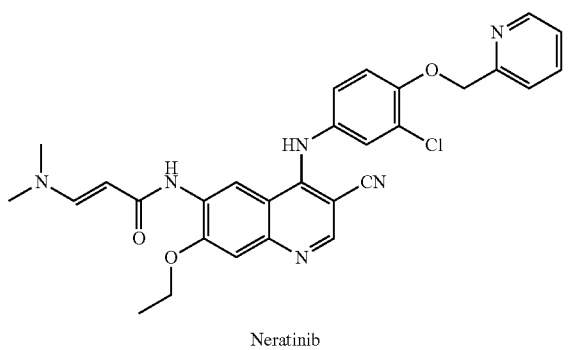
Neratinib
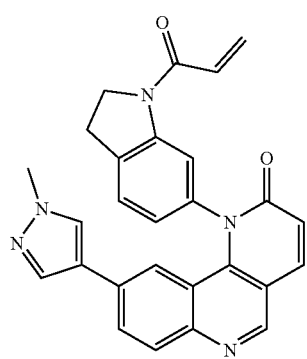
QL47
-continued
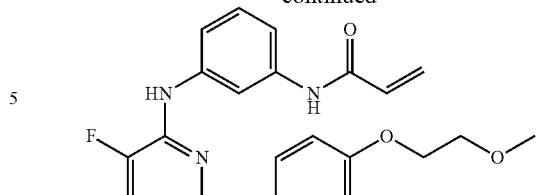
AVL-292
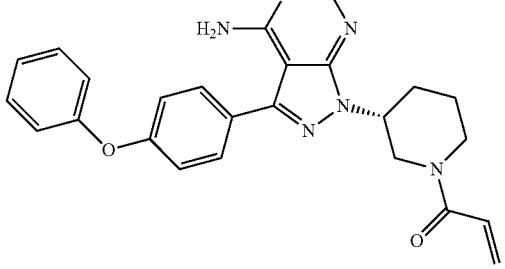
Ibrutinib
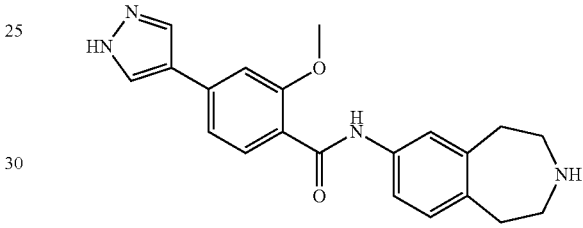
MELK-T1
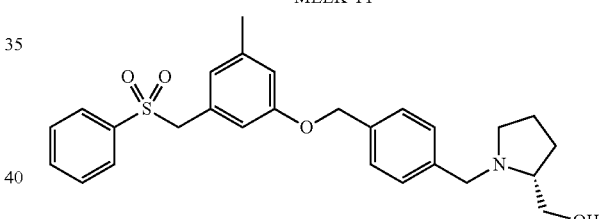
PF-543
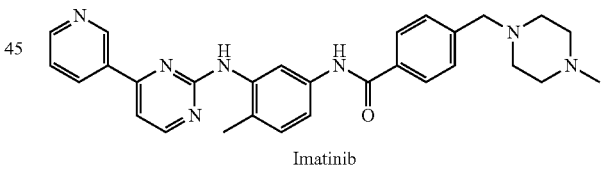
Imatinib
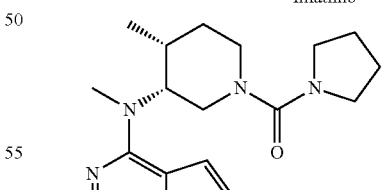
PF-956980
See Jones et al. Small-Molecule Kinase Downregulators, 2017, *Cell Chem. Biol.*, 25: 30-35.
A target protein binding partner that targets a BET protein includes but is not limited to the molecule shown below and derivatives thereof:

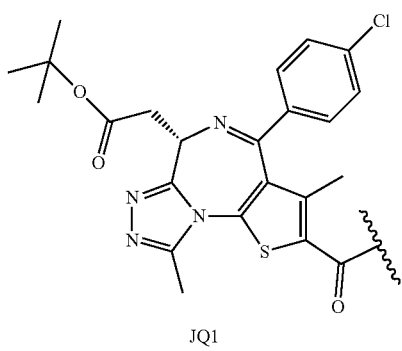 [SMILES: *C(=O)c1sc2c(c1C)C(c1ccc(Cl)cc1)=N[C@@H](CC(=O)OC(C)(C)C)c1nnc(C)n1-2]

JQ1

Additional BET inhibitors are described in Romero, F. A., Taylor, A. M., Crawford, T. D., Tsui, V., Cote, A., Magnuson, S. *Disrupting Acetyl-Lysine Recognition: Progress in the Development of Bromodomain Inhibitors* (2016 *J. Med. Chem.*, 59(4), 1271-1298).

I. Kinase and Phosphatase Inhibitors:

Kinase inhibitors as used herein include, but are not limited to:

1. Erlotinib Derivative Tyrosine Kinase Inhibitor:

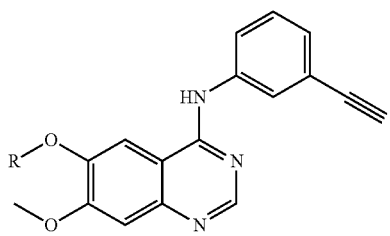

where R is a linker attached, for example, via an ether group;

2. The kinase inhibitor sunitinib (derivatized):

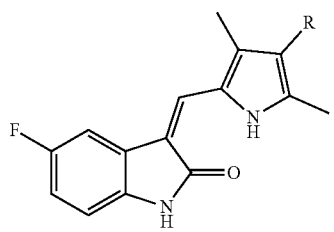

(derivatized where R is a linker attached, for example, to the pyrrole moiety);

3. Kinase Inhibitor sorafenib (derivatized):

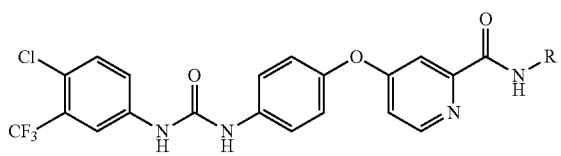

(derivatized where R is a linker attached, for example, to the amide moiety);

4. The kinase inhibitor desatinib (derivatized):

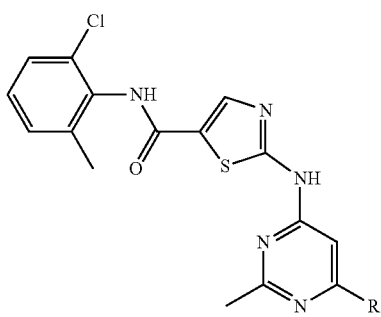

(derivatized where R is a linker attached, for example, to the pyrimidine);

5. The kinase inhibitor lapatinib (derivatized):

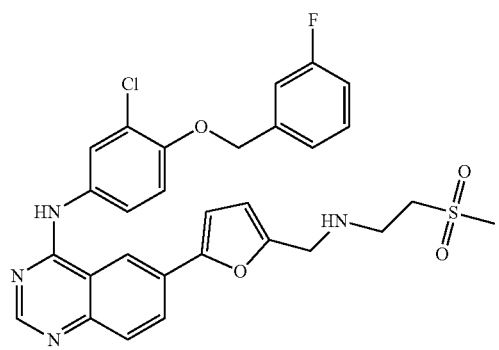 [SMILES: CS(=O)(=O)CCNCc1ccc(-c2ccc3ncnc(Nc4ccc(OCc5cccc(F)c5)c(Cl)c4)c3c2)o1]

(derivatized where a linker is attached, for example, via the terminal methyl of the sulfonyl methyl group);

6. The kinase inhibitor U09-CX-5279 (derivatized):

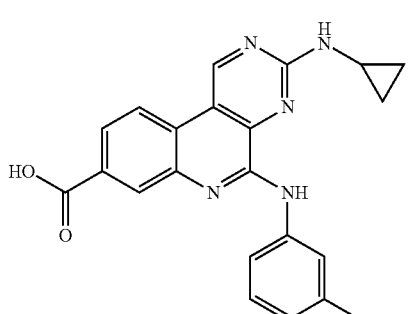

derivatized where a linker is attached, for example, via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, (2011, *J. Med. Chem.* 54:7797), including the kinase inhibitors Y1W and Y1X (Derivatized) having the structures:

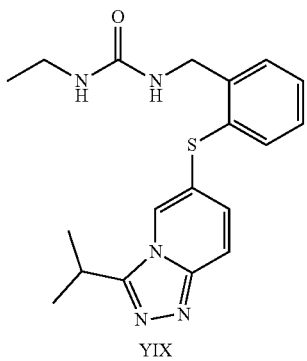

YIX (1-ethyl-3-(2-{[3-(1-methylethyl) [1,2,4]triazolo[4,3-a]pyridine-6-yl] sulfanyl}benzyl)urea
derivatized where a linker is attached, for example, via the ipropyl group;

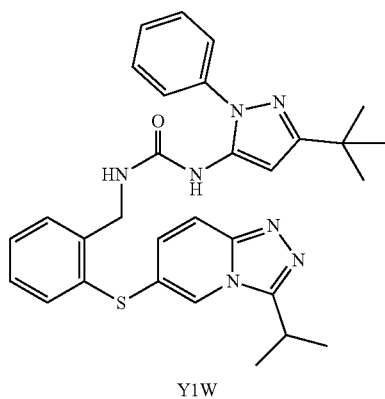 [SMILES: CC(C)c1nnc2ccc(Sc3ccccc3CNC(=O)Nc3cc(C(C)(C)C)nn3-c3ccccc3)cn12 ; "Y1W"]

Y1W 1-(3-tert-butyl-1-phenyl-1H-pyrazol-5-yl)-3-(2-{[3-(1-methylethyl)[1,2,4]triazolo[4,3-a]pyridin-6-yl]sulfanyl}benzyl)urea
derivatized where a linker is attached, for example, preferably via either the i-propyl group or the t-butyl group;

8. The kinase inhibitors identified in Schenkel, et al., Discovery of Potent and Highly Selective Thienopyridine Janus Kinase 2 Inhibitors (2011, *J. Med. Chem.*, 54(24):8440-8450), including the compounds 6TP and OTP (Derivatized) having the structures:

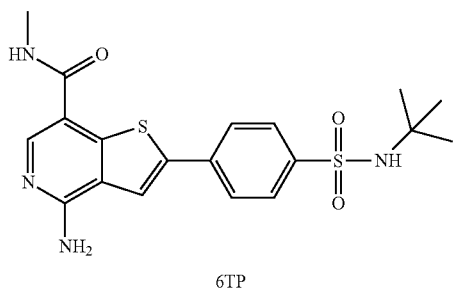 [SMILES: CNC(=O)c1cnc(N)c2cc(-c3ccc(S(=O)(=O)NC(C)(C)C)cc3)sc12]

6TP 4-amino-2-[4-(tert-butylsulfamoyl)phenyl]-N-methylthieno[3,2-c]pyridine-7-carboxamide Thienopyridine 19
derivatized where a linker is attached, for example, via the terminal methyl group bound to amide moiety;

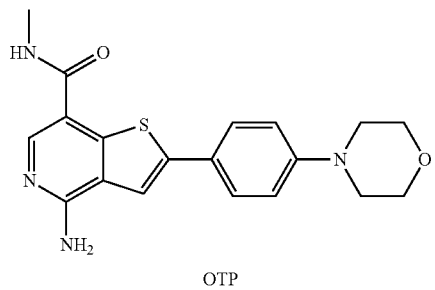 [SMILES: CNC(=O)c1cnc(N)c2cc(-c3ccc(N4CCOCC4)cc3)sc12 ; "OTP"]

OTP 4-amino-N-methyl-2-[4-(morpholin-4-yl)phenyl]thieno[3,2-c]pyridine-7-carboxamide Thienopyridine 8
derivatized where a linker is attached, for example, via the terminal methyl group bound to the amide moiety;

9. The kinase inhibitors identified in Van Eis, et al., "2,6-Naphthyridines as potent and selective inhibitors of the novel protein kinase C isozymes", (2011 December, *Biorg. Med. Chem. Lett.*, 15, 21(24): 7367-72), including the kinase inhibitor 07U having the structure:

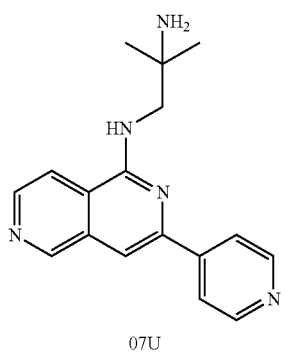 [SMILES: CC(C)(N)CNc1nc(-c2ccncc2)cc2cnccc12]

07U 2-methyl-N-1-[3-(pyridin-4-yl)-2,6-naphthyridin-1-yl]propane-1,2-diamine
derivatized where a linker is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", (2011, *J. Struct.. Biol.*, 176:292), including the kinase inhibitor YCF having the structure:

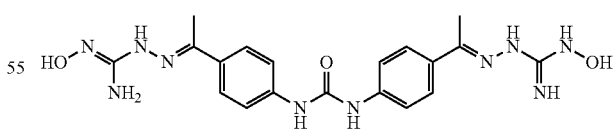

derivatized where a linker is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", (2011, *J. Struct. Biol.* 176292), including the kinase inhibitors XK9 and NXP (derivatized) having the structures:

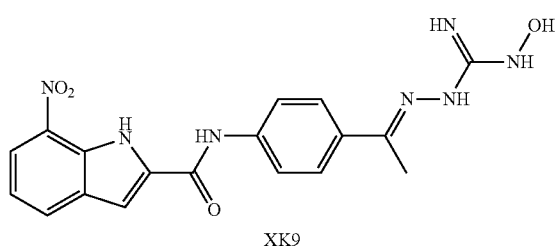

XK9

N-{4-[(1E)-N-(N-hydroxycarbamimidoyl)ethanehydrazonoyl]phenyl}-7-nitro-1H-indole-2-carboxamide;

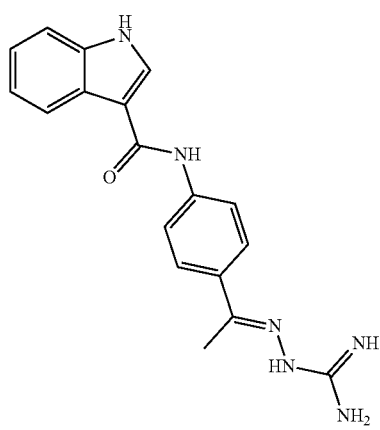

NXP

N-{4-[(1E)-N-carbamimidoylethanehydrazonoyl]phenyl}-1H-indole-3-carboxamide
derivatized where a linker is attached, for example, via the terminal hydroxyl group (XK9) or the hydrazone group (NXP);

12. The kinase inhibitor afotinib (derivatized) (N-[4-[(3-chloro-4-fluorophenyl)amino]-7-[[(3S)-tetrahydro-3-furanyl]oxy]-6-quinazolinyl]-4(dimethylamino)-2-butenamide) (Derivatized where a linker is attached, for example, via the aliphatic amine group);
13. The kinase inhibitor fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker is attached, for example, via a methoxy group);
14. The kinase inhibitor gefitinib (derivatized) (N-(3-chloro-4-fluoro-phenyl)-7-methoxy-6-(3-morpholin-4-ylpropoxy)quinazolin-4-amine)

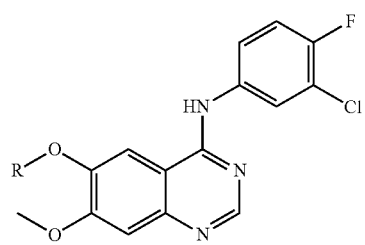

(derivatized where a linker is attached, for example, via a methoxy or ether group);

15. The kinase inhibitor lenvatinib (derivatized) (4-[3-chloro-4-(cyclopropylcarbamoylamino)phenoxy]-7-methoxy-quinoline-6-carboxamide) (derivatized where a linker is attached, for example, via the cyclopropyl group);
16. The kinase inhibitor vandetanib (derivatized) (N-(4-bromo-2-fluorophenyl)-6-methoxy-7-[(1-methylpiperidin-4-yl)methoxy]quinazolin-4-amine) (derivatized where a linker is attached, for example, via the methoxy or hydroxyl group);
17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide) (derivatized where a linker is attached, for example, via the sulfonyl propyl group);
18. The kinase inhibitor Gleevec (also known as Imatinib) (derivatized):

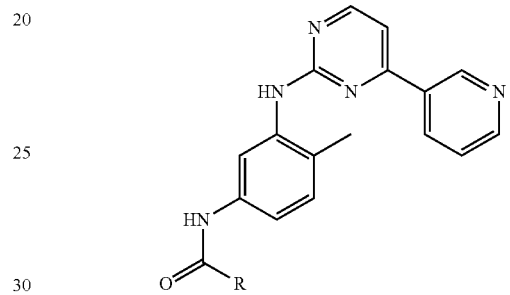

(derivatized where R is a linker attached, for example, via the amide group or via the aniline amine group);

19. The kinase inhibitor pazopanib (derivatized) (VEGFR3 inhibitor):

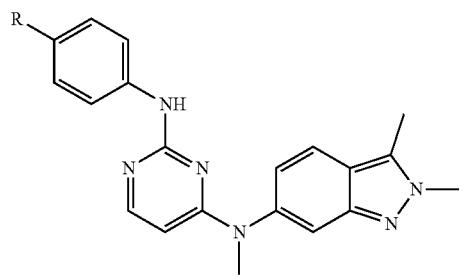

(derivatized where R is a linker attached, for example, to the phenyl moiety or via the aniline amine group);

20. The kinase inhibitor AT-9283 (Derivatized) Aurora Kinase Inhibitor

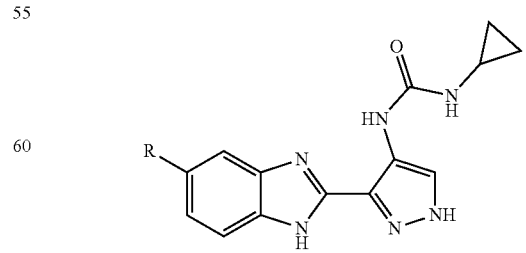

(where R is a linker attached, for example, to the phenyl moiety);

21. The kinase inhibitor TAE684 (derivatized) ALK inhibitor

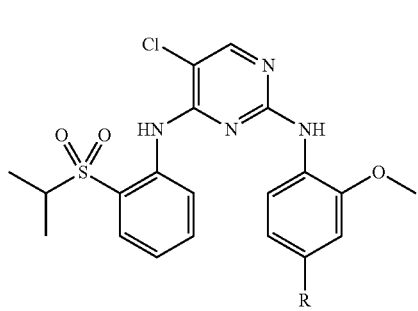

(where R is a linker attached, for example, to the phenyl moiety);

22. The kinase inhibitor nilotanib (derivatized) Abl inhibitor:

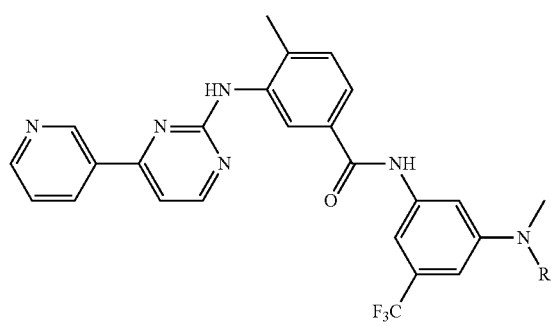

(derivatized where R is a linker attached, for example, to the phenyl moiety or the aniline amine group);

23. Kinase Inhibitor NVP-BSK805 (derivatized) JAK2 Inhibitor

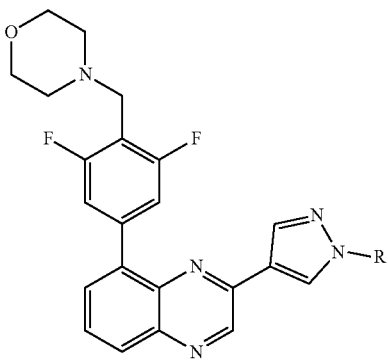

(derivatized where R is a linker attached, for example, to the phenyl moiety or the diazole group);

24. Kinase Inhibitor crizotinib Derivatized Alk Inhibitor

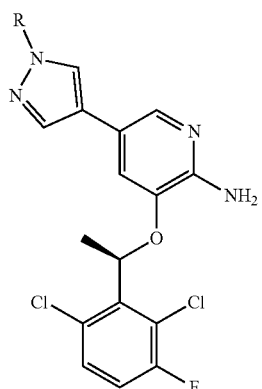

(derivatized where R is a linker attached, for example, to the phenyl moiety or the diazole group);

25. Kinase Inhibitor JNJ FMS (derivatized) Inhibitor

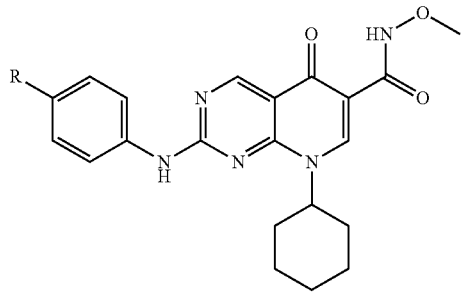

(derivatized where R is a linker attached, for example, to the phenyl moiety);

26. The kinase inhibitor foretinib (derivatized) Met Inhibitor

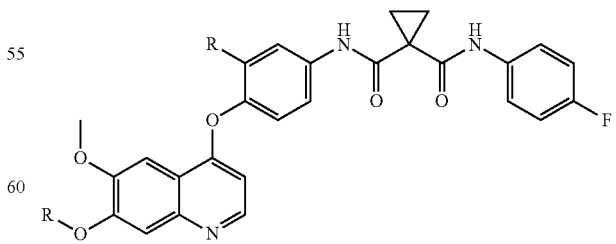

(derivatized where R is a linker attached, for example, to the phenyl moiety or a hydroxyl or ether group on the quinoline moiety);

27. The allosteric Protein Tyrosine Phosphatase Inhibitor PTP1B (derivatized):

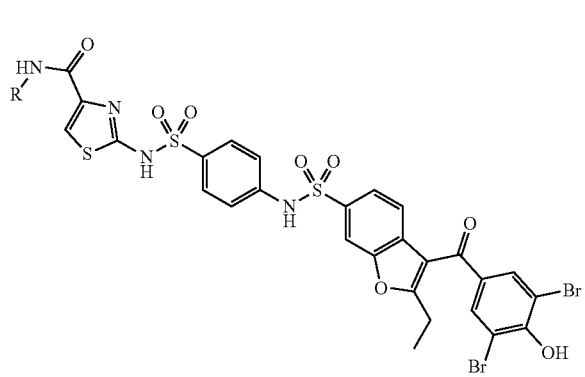

derivatized where a linker is attached, for example, at R, as indicated;

28. The inhibitor of SHP-2 Domain of Tyrosine Phosphatase (derivatized):

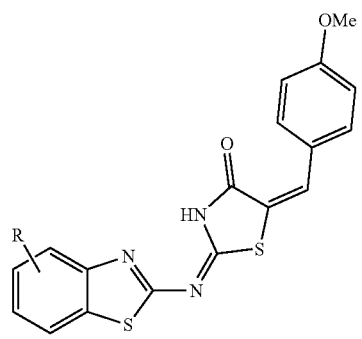

derivatized where a linker is attached, for example, at R;

29. The inhibitor (derivatized) of BRAF (BRAF$^{V600E}$)/mEK:

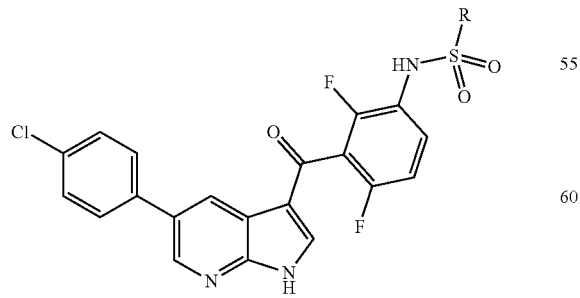

derivatized where a linker group is attached, for example, at R;

30. Inhibitor (derivatized) of Tyrosine Kinase ABL

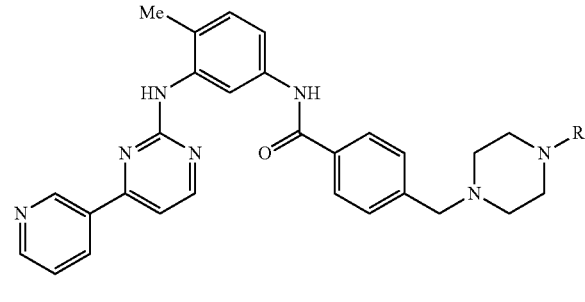

derivatized where a linker is attached, for example, at R;

31. The kinase inhibitor OSI-027 (derivatized) mTORCl/2 inhibitor

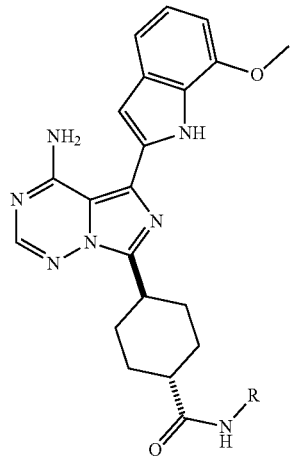

derivatized where a linker is attached, for example, at R;

32. The kinase inhibitor OSI-930 (derivatized) c-Kit/KDR inhibitor

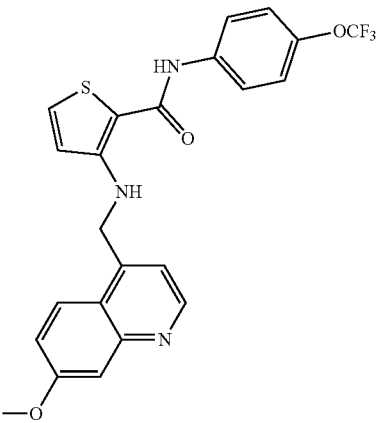

derivatized where a linker is attached, for example, at R; and

33. The kinase inhibitor OSI-906 (derivatized) IGF1R/IR inhibitor

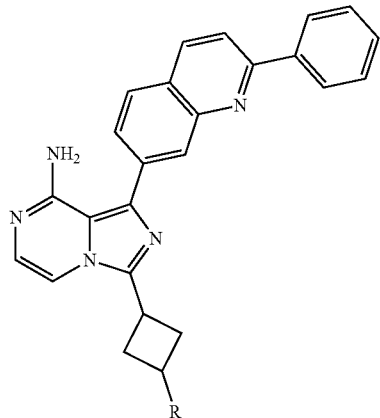

derivatized where a linker is attached, for example, at R; (derivatized where "R" designates a site for attachment of a linker on the piperazine moiety).

II. Compounds Targeting Human BET Bromodomain-Containing Proteins:

Compounds targeting Human BET Bromodomain-containing proteins include, but are not limited to the compounds associated with the targets as described below, where "R" designates a site for linker attachment, for example:

JQ1, Filippakopoulos et al. Selective inhibition of BET bromodomains. *Nature* (2010):

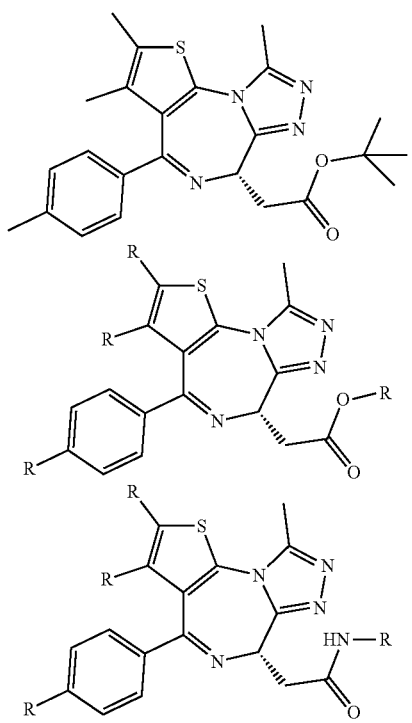

2. I-BET, Nicodeme et al. Supression of Inflammation by a Synthetic Histone Mimic *Nature* (2010). Chung et al. Discovery and Characterization of Small Molecule Inhibitors of the BET Family Bromodomains J. Med Chem. (2011):

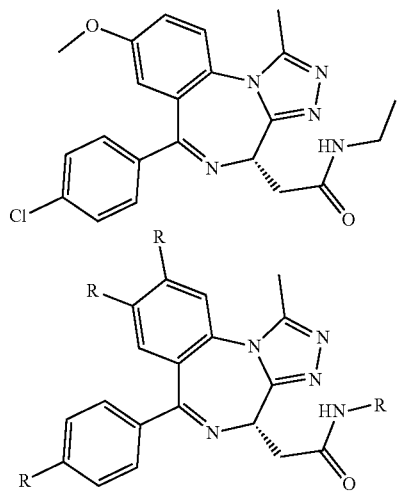

3. Compounds described in Hewings et al. 3,5-Dimethylisoxazoles Act as Acetyl-lysine Bromodomain Ligands. (2011, *J. Med. Chem.*54:6761-6770).

4. I-BET151, Dawson et al Inhibition of BET Recruitment to Chromatin as an Effective Treatment for MLL-fusion Leukemia. *Nature* (2011):

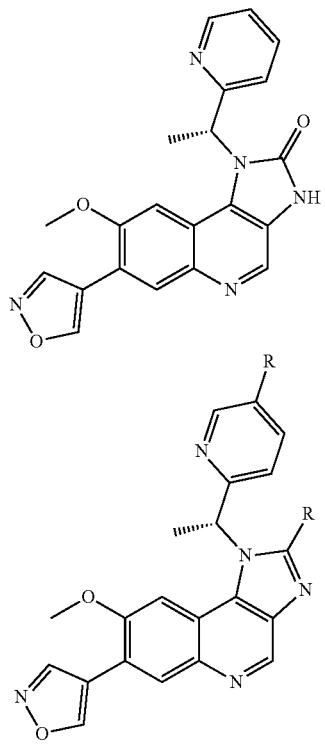

(Where R, in each instance, designates a site for attachment of a linker)

III. HDM2/MDM2 Inhibitors:

HDM2/MDM2 inhibitors of the invention include, but are not limited to:

1. The HDM2/MDM2 inhibitors identified in Vassilev, et al., *In vivo activation of the p53 pathway by small-molecule antagonists of MDM2*, (2004, *Science*, 303844-848), and Schneekloth, et al., *Targeted intracellular protein degradation induced by a small molecule: En route to chemical proteomics*, (2008, *Biorg. Med. Chem. Lett.*, 18:5904-5908), including (or additionally) the compounds nutlin-3, nutlin-2, and nutlin-1 (derivatized) as described below, as well as all derivatives and analogs thereof:

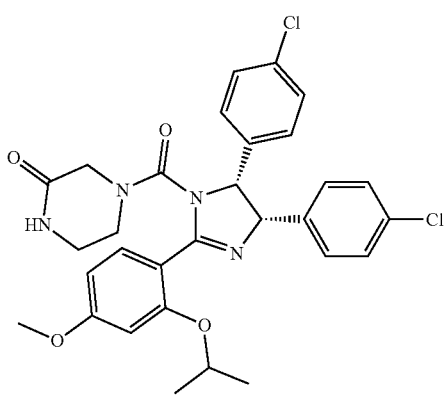 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker is attached, for example, at the methoxy group or as a hydroxyl group);

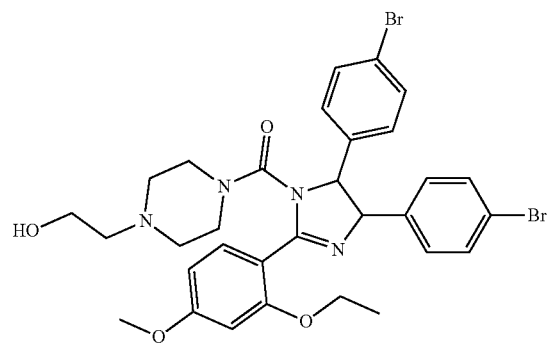 [SMILES: CCOc1cc(OC)ccc1C1=NC(c2ccc(Br)cc2)C(c2ccc(Br)cc2)N1C(=O)N1CCN(CCO)CC1]

(derivatized where a linker is attached, for example, at the methoxy group or hydroxyl group);

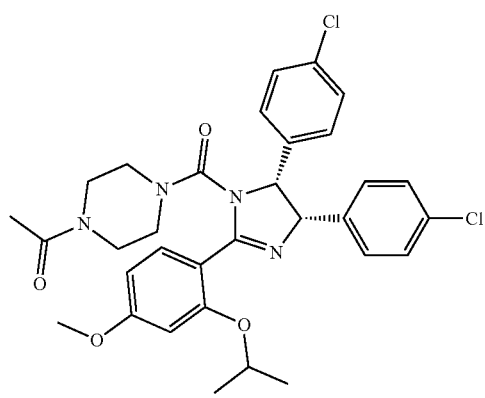 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker is attached, for example, via the methoxy group or as a hydroxyl group); and 2. Trans-4-Iodo-4'-Boranyl-Chalcone

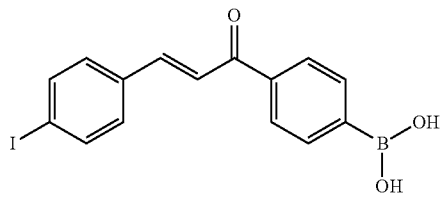 [SMILES: O=C(/C=C/c1ccc(I)cc1)c1ccc(B(O)O)cc1]

(derivatized where a linker is attached, for example, via a hydroxy group).

IV. HDAC Inhibitors:

HDAC Inhibitors (derivatized) include, but are not limited to:

1. Finnin, M. S. et al. Structures of Histone Deacetylase Homologue Bound to the TSA and SAHA Inhibitors. (1999, *Nature*, 40:188-193).

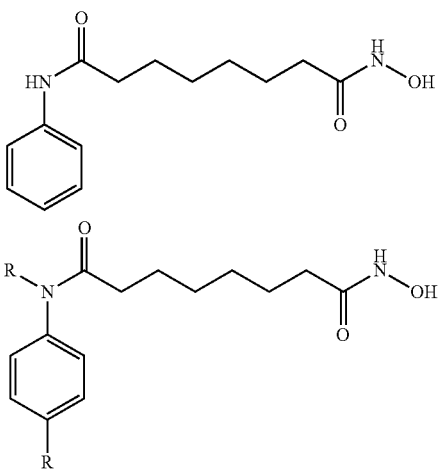

(Derivatized where "R" designates a site for attachment, for example, of a linker; and 2. Compounds as defined by formula (I) of PCT WO0222577 ("DEACETYLASE INHIBITORS") (Derivatized where a linker is attached, for example, via the hydroxyl group);

V. Heat Shock Protein 90 (HSP90) Inhibitors:

HSP90 inhibitors useful according to the invention include but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C] Pyridines as Potent Inhibitors of the HSP90 Molecular Chaperone (2011,]. *Med. Chem.*, 54:7206), including YKB (N-[4-(3H-imidazo[4,5-C] Pyridin-2-yl)-9H-Fluoren-9-yl]-succinamide):

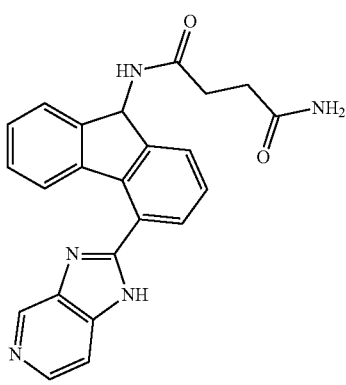 [SMILES: NC(=O)CCC(=O)NC1c2ccccc2-c2c(-c3nc4cnccc4[nH]3)cccc21]

derivatized where a linker is attached, for example, via the terminal amide group;

2. The HSP90 inhibitor p54 (modified) (8-[(2,4-dimethylphenyl)sulfanyl]-3]pent-4-yn-1-yl-3H-purin-6-amine):

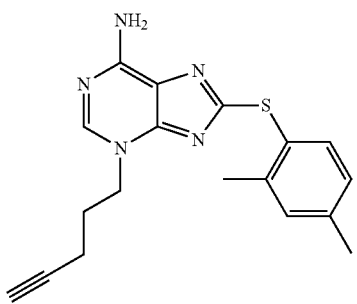 [SMILES: C#CCCCn1cnc(N)c2nc(Sc3ccc(C)cc3C)nc1-2]

where a linker is attached, for example, via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", (2008,]. *Med. Chem.*,51: 196), including the compound 2GJ (5-[2,4-dihydroxy-5-(1-methylethyl)phenyl]-n-ethyl-4-[4-(morpholin-4-ylmethyl)phenyl] isoxazole-3-carboxamide) having the structure:

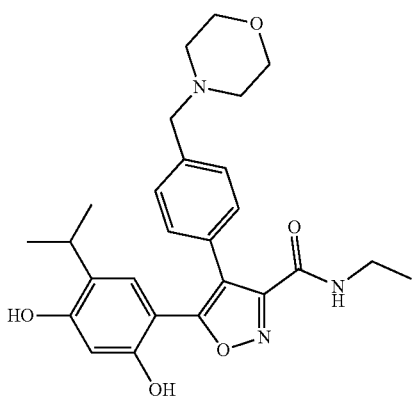 [SMILES: CCNC(=O)c1noc(-c2cc(C(C)C)c(O)cc2O)c1-c1ccc(CN2CCOCC2)cc1]

derivatized, where a linker is attached, for example, via the amide group (at the amine or at the alkyl group on the amine);

4. The HSP90 inhibitors (modified) identified in Wright, et al., Structure-Activity Relationships in Purine-Based Inhibitor Binding to HSP90 Isoforms, (2004 June, *Chem Biol.* 11(6): 775-85), including the HSP90 inhibitor PU3 having the structure:

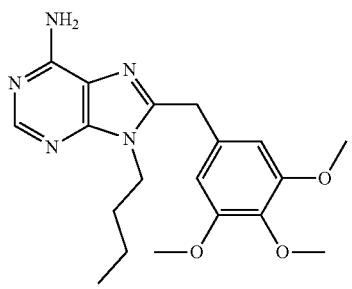 [SMILES: CCCCn1c(Cc2cc(OC)c(OC)c(OC)c2)nc2c(N)ncnc21]

where a linker group is attached, for example, via the butyl group; and

5. The HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a is attached, for example, via the amide group).

VI. Human Lysine Methyltransferase Inhibitors:

Human Lysine Methyltransferase inhibitors include, but are not limited to:

1. Chang et al. Structural Basis for G9a-Like protein Lysine Methyltransferase Inhibition by BIX-1294 (2009, *Nat. Struct. Biol.*,16(3):312).

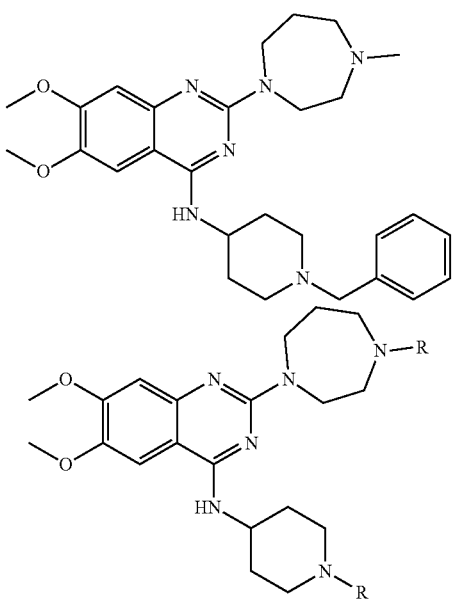

(Derivatized where "R" designates a site for attachment, for example, of a linker;

2. Liu, F. et al Discovery of a 2,4-Diamino-7-aminoalkoxyquinazoline as a Potent and Selective Inhibitor of Histone Methyltransferase G9a. (2009, *J. Med. Chem.*,52(24):7950).

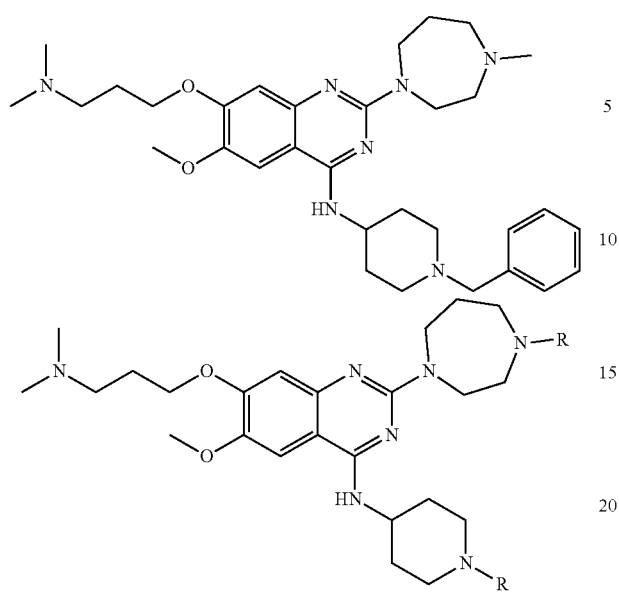

(Derivatized where "R" designates a potential site for attachment of a linker);

3. Azacitidine (derivatized) (4-amino-1--D-ribofuranosyl-1,3,5-triazin-2(1H)-one) (Derivatized where a linker is attached, for example, via the hydroxy or amino groups); and 4. Decitabine (derivatized) (4-amino-1-(2-deoxy-b-D-erythro-pentofuranosyl)-1, 3, 5-triazin-2(1H)-one) (Derivatized where a linker is attached, for example, via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, (2003 December, *Mol. Cell Proteomics,* 2 (12): 1350-1358);

2. Estradiol (derivatized), which may be bound to a linker as is generally described in Rodriguez-Gonzalez, et al., Targeting steroid hormone receptors for ubiquitination and degradation in breast and prostate cancer, (2008, *Oncogene* 27:7201-7211);

3. Estradiol, testosterone (derivatized) and related derivatives, including but not limited to DHT and derivatives and analogs thereof, having the structure(s) and binding to a linker as generally described in Sakamoto, et al., Development of Protacs to target cancer-promoting proteins for ubiquitination and degradation, (2003 December, *Mol. Cell Proteomics,* 2(12):1350-1358); and 4. Ovalicin, fumagillin (derivatized), and derivatives and analogs thereof, having the structure(s) and binding to a linker as is generally described in Sakamoto, et al., Protacs: chimeric molecules that target proteins to the Skp1-Cullin-F box complex for ubiquitination and degradation (2001 July, *Proc. Natl. Acad. Sci. USA,* 98(15): 8554-8559) and U.S. Pat. No. 7,208,157.

VIII. Immunosuppressive Compounds:

Immunosuppressive compounds include, but are not limited to:

1. AP21998 (derivatized), having the structure(s) and binding to a linker as is generally described in Schneekloth, et al., Chemical Genetic Control of Protein Levels: Selective in Vivo Targeted Degradation (2004, *J. Am. Chem. Soc.,* 126:3748-3754);

2. Glucocorticoids (e.g., hydrocortisone, prednisone, prednisolone, and methylprednisolone) (Derivatized where a linker is bound, e.g. to any of the hydroxyls) and beclometasone dipropionate (Derivatized where a linker is bound, e.g. to a proprionate);

3. Methotrexate (Derivatized where a linker can be bound, e.g. to either of the terminal hydroxyls);

4. Ciclosporin (Derivatized where a linker can be bound, e.g. at a of the butyl groups);

5. Tacrolimus (FK-506) and rapamycin (Derivatized where a linker group can be bound, e.g. at one of the methoxy groups); and 6. Actinomycins (Derivatized where a linker can be bound, e.g. at one of the isopropyl groups).

IX. Compounds Targeting the Aryl Hydrocarbon Receptor (AHR):

Compounds targeting the aryl hydrocarbon receptor (AHR) include, but are not limited to:

1. Apigenin (Derivatized in a way which binds to a linker as is generally illustrated in Lee, et al., Targeted Degradation of the Aryl Hydrocarbon Receptor by the PROTAC Approach: A Useful Chemical Genetic Tool, ChemBioChem Volume 8, Issue 17, pages 2058-2062, Nov. 23, 2007); and 2. SR1 and LGC006 (derivatized such that a linker is bound), as described in Boitano, et al., Aryl Hydrocarbon Receptor Antagonists Promote the Expansion of Human Hematopoietic Stem Cells (2010 September, *Science,* 329(5997):1345-1348).

X. Compounds Targeting RAF Receptor (Kinase):

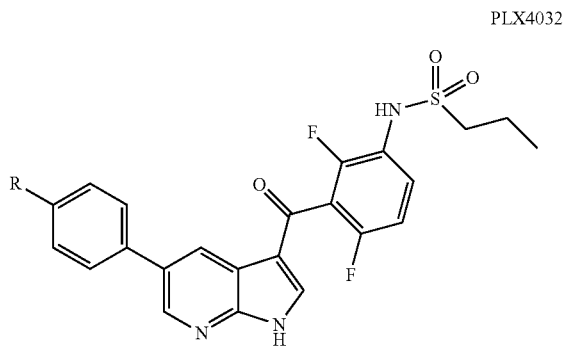

PLX4032

(Derivatized where "R" designates a site for linker attachment).

XI. Compounds Targeting FKBP:

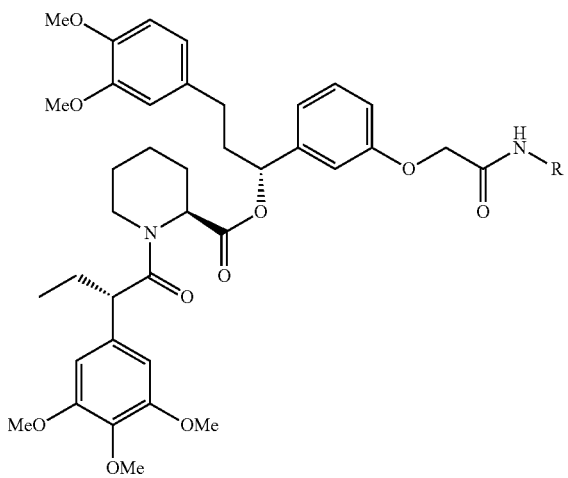

(Derivatized where "R" designates a site for linker attachment).

XII. Compounds Targeting Androgen Receptor (AR)

1. RU59063 Ligand (derivatized) at Androgen Receptor

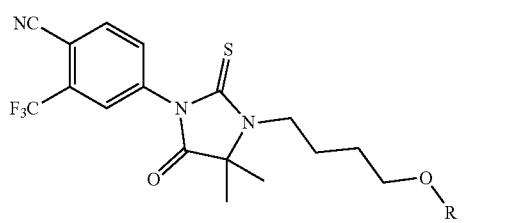

(Derivatized where "R" designates a site for linker attachment).

2. SARM Ligand (derivatized) of Androgen Receptor

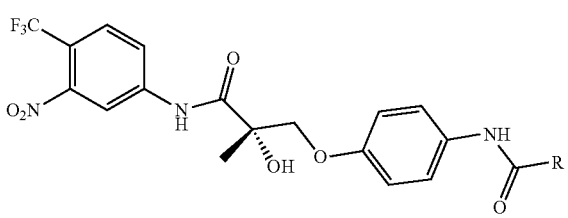

(Derivatized where "R" designates a site for linker attachment).

3. Androgen Receptor Ligand DHT (derivatized)

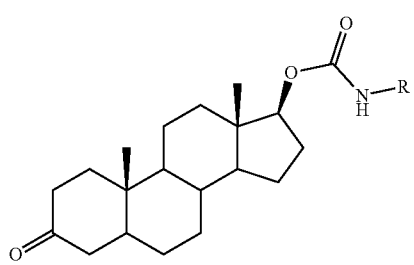

(Derivatized where "R" designates a site for linker attachment).

4. MDV3100 Ligand (derivatized)

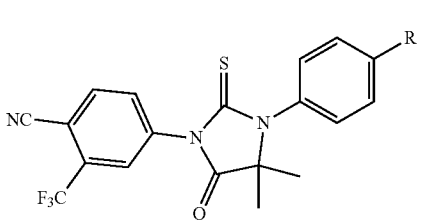

5. ARN-509 Ligand (derivatized)

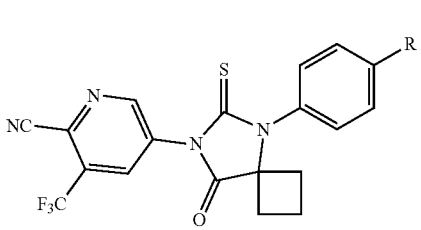

6. Hexahydrobenzisoxazoles

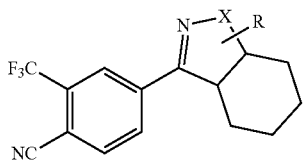

7. Tetramethylcyclobutanes

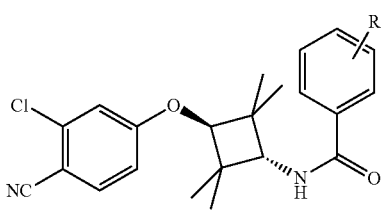

XIII. Compounds Targeting Estrogen Receptor (ER) ICI-182780

1. Estrogen Receptor Ligand

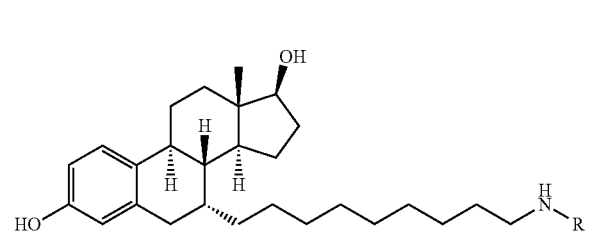

(Derivatized where "R" designates a site for linker attachment).

XIV. Compounds Targeting Thyroid Hormone Receptor (TR)

1. Thyroid Hormone Receptor Ligand (derivatized)

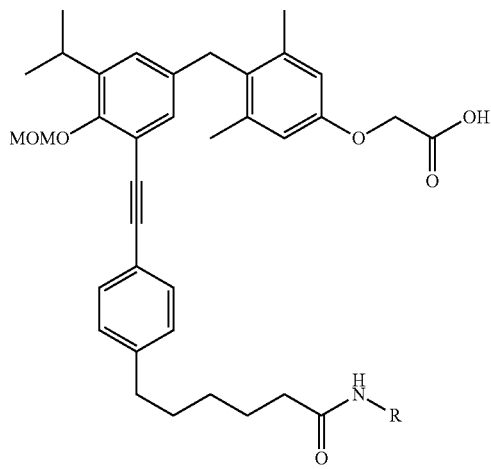

(Derivatized where "R" designates a site for linker attachment and MOMO indicates a methoxymethoxy group).

XV. Compounds targeting HIV Protease

1. Inhibitor of HIV Protease (derivatized)

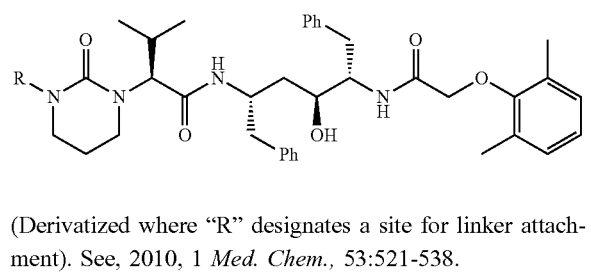

(Derivatized where "R" designates a site for linker attachment). See, 2010, 1 *Med. Chem.*, 53:521-538.

2. Inhibitor of HIV Protease

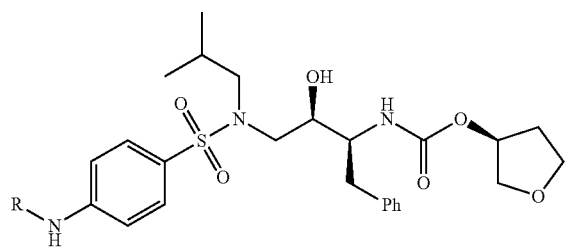

(Derivatized where "R" designates a potential site for linker attachment). See, 2010, 1 *Med. Chem.*, 53:521-538.

XVI. Compounds targeting HIV Integrase

1. Inhibitor of HW Integrase (derivatized)

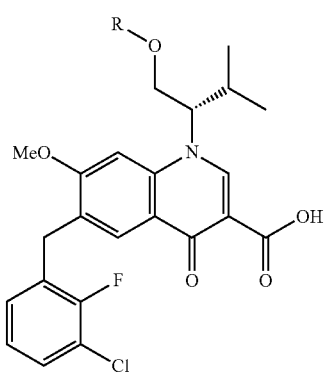

(Derivatized where "R" designates a site for linker attachment). See, 2010, *J. Med. Chem.*, 53:6466.

2. Inhibitor of HIV Integrase (derivatized)

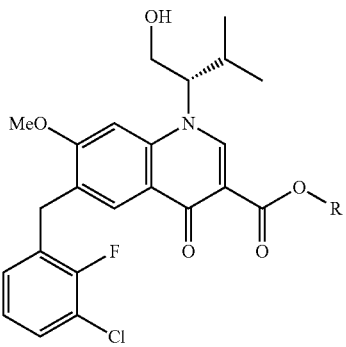

3. Inhibitor of HW integrase Isetntress (derivatized)

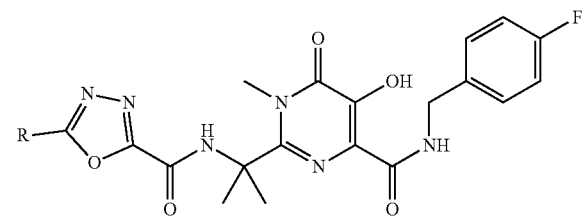

(Derivatized where "R" designates a site for linker attachment). See, 2010, *J. Med. Chem.*, 53:6466.

XVII. Compounds targeting HCV Protease
  1. Inhibitors of HCV Protease (derivatized)

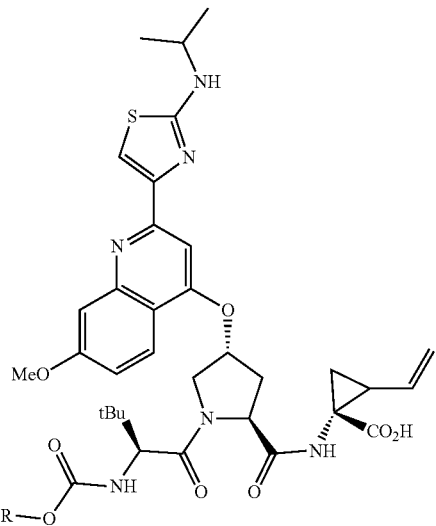

(Derivatized where "R" designates a site for linker attachment).

XVIII. Compounds Targeting Acyl-Protein Thioesterase-1 and -2 (APT1 and APT2)
  1. Inhibitor of APT1 and APT2 (derivatized)

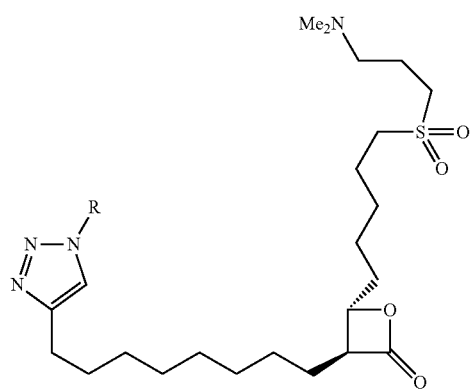

(Derivatized where "R" designates a site for linker attachment). See 2011, *Angew. Chem. Int. Ed.*, 50:9838-9842.

Target Proteins

A "target protein" useful according to the invention includes a protein or polypeptide that is selected by one of skill in the art for increased proteolysis in a cell.

Target proteins useful according to the invention include a protein or peptide, including fragments thereof, analogues thereof, and/or homologues thereof. Target proteins include proteins and peptides having a biological function or activity including structural, regulatory, hormonal, enzymatic, genetic, immunological, contractile, storage, transportation, and signal transduction. In certain embodiments, the target protein includes structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes, including microbes, viruses, fungi and parasites, including humans, other animals, including domesticated animals microbes, viruses, fungi and parasites, among numerous others, targets for drug therapy.

A target protein also includes targets for human therapeutic drugs. These include proteins which may be used to restore function in numerous polygenic diseases, including for example B7.1 and B7, TNFR1, TNFR2, NADPH oxidase, Bc1I/Bax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAK STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras/Raf/MEK/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Target binding partners of the invention can also be haloalkane dehalogenase enzymes. Compounds according to the present invention which contain chloroalkane peptide binding moieties (C1-C12 often about C2-C10 alkyl halo groups) may be used to inhibit and/or degrade haloalkane dehalogenase enzymes which are used in fusion proteins or related diagnostic proteins as described in PCT/US2012/063401 filed Dec. 6, 2011 and published as WO 2012/078559 on Jun. 14, 2012, the contents of which is incorporated by reference herein.

A Bifunctional Molecule According to the Invention Includes a Target Protein Binding Partner and a Binding Partner of Rpn11.

Providing Rpn11:

Rpn11 can be provided as follows. Rpn11 is expressed as a dimer with PSMD7 (Rpn8) in the same fashion as the yeast orthologs (See Worden et al, NSMB 2014; DOI: 2771). Plasmids containing GST- and hexahistidine-tagged, full-length PSMD14 (DU22812 and DU22813, respectively) are purchased from the Division of Signal Transduction and Therapeutics (DSTT) at the University of Dundee. The gene for PSMD7 (Rpn8, AKA) is purchased from Addgene (Plasmid #22558). The domains of PSMD7 and PSMD14 which are PCR amplified and cloned include the MPN (Mpr 1, Pad1 N-terminal) or JAMM (JAB1/MPN/Mov34 metalloenzyme) domain, and a C-terminal domain. Portions of these domains also may be amplified and cloned. For example, residues 2-243 of PSDM14 and 1-180 of PSMD7 are amplified by PCR and cloned into a pCDFDuet™-1 (or equivalent) vector containing a TEV-cleavable hexahistidine tag.

Rpn11 can be expressed and purified according to methods well known in the art. A method for expressing and purifying Rpn11 includes the following protocol:

Constructs expressing Rpn11 are transformed into *E. coli* BL21(DE3) cells and grown at 37° C. until an OD600 of around 0.8 is achieved. The temperature is then lowered, and protein expression is induced by the addition of IPTG. Cells are harvested 16 h post-induction and resuspended in a binding buffer containing protease inhibitors. Cells are lysed with a French press and then clarified by centrifugation.

GST-tagged proteins are purified according to a modified method of Lee et al, *Sci Rep* 2015; DOI: 10.1038/srep10757. Affinity chromatography using glutathione sepharose 4B resin is performed. On-column cleavage of the GST-tag is performed using the PreScission protease. The resulting protein is transferred to low-salt buffer using a desalting column. Anion exchange chromatography is performed using a Resource Q (or equivalent) column, followed by size exclusion chromatography using a Superdex75 16-600 (or equivalent) column.

His-tagged proteins are purified via a method modified from Worden et al, NSMB 2014; DOI: 10.1038/nsmb.2771. Affinity chromatography using Ni-NTA resin is performed. The resulting material is cleaved overnight with TEV protease. A second affinity column is used to remove cleaved His tags. The resulting material is transferred to low-salt buffer using a desalting column. Anion exchange chromatography using Resource Q (or equivalent) column is performed, followed by size exclusion chromatography using Superdex75 16-600 (or equivalent) column The Rpn11 binding partner to be used for conjugation can also be synthesized as follows:

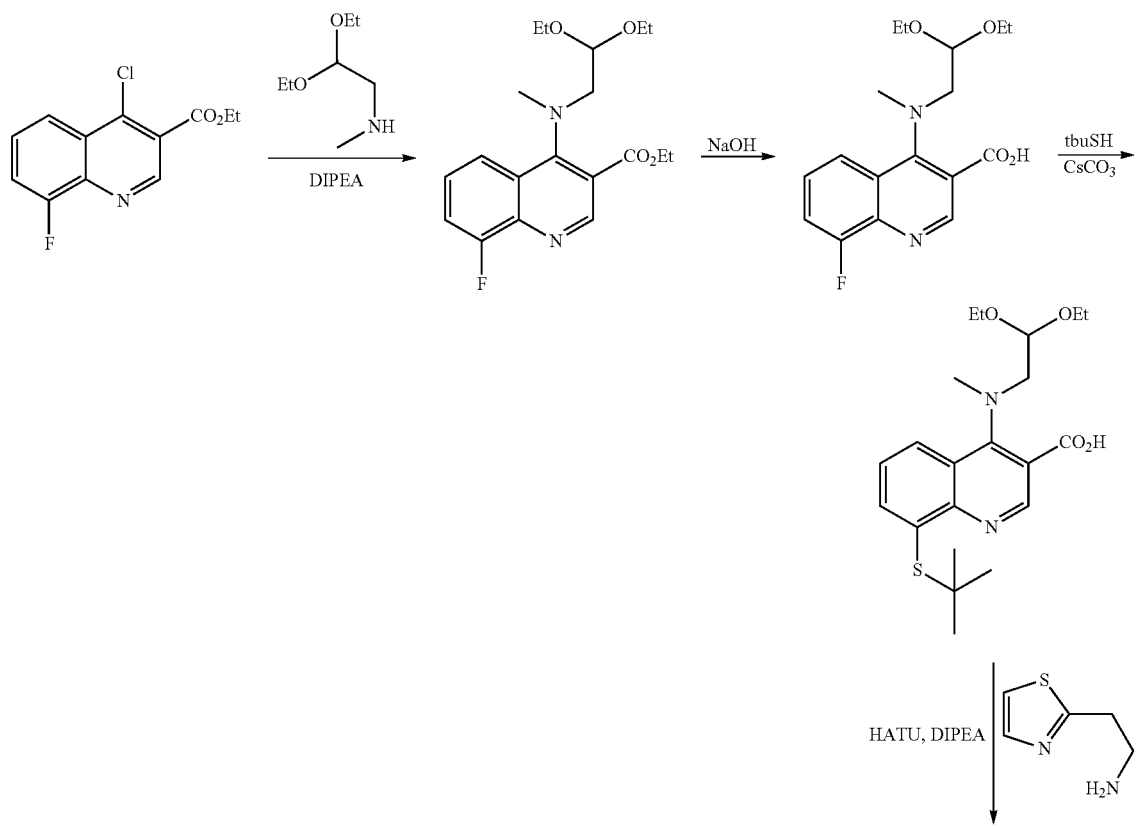

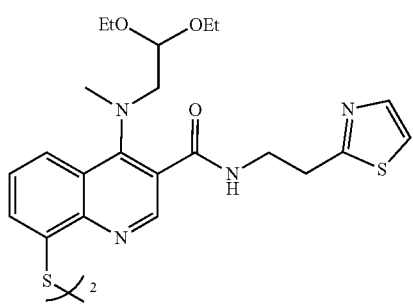
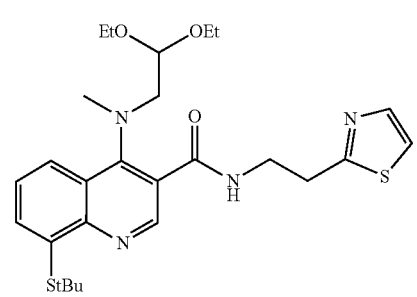

Linkers Useful According to the Invention

A linker useful according to the invention connects an Rpn11 binding partner and a target protein binding pal filer such that the resulting molecule can induce degradation of a target to which the target protein binding pal leer binds. In one embodiment, the linker has first and second ends and is covalently bound to the Rpn11 binding partner at one end and to the target binding partner at the other end.

The first and second ends of the linker can be identical or different to provide a linker that is symmetrical or asymmetrical. The end of a linker can have a functional group selected from: amide, oxime, keto group, carbon, ether, ester, carbamate amongst others. A linker can comprise a PEG linker having one or more ethylene glycol subunits, an alkyl linker comprising one or more $CH_2$ groups, a sulfoxide, a ring, for example a phenyl ring or a pyrimidine ring, a triazole, an ether, a PEG variant and a combination thereof. In certain embodiments, the linker includes alternating (—$CH_2$— ethylene glycol-units).

In one embodiment a "linker" has amine and/or oxime functional groups, and, in particular, the invention provides for a linker having both amine and oxime positioned at opposite ends of the linker, so as to provide an asymmetric linkage. In an embodiment of the invention, the linker is a non-cleavable, straight-chain polymer. In another embodiment, the linker is a chemically-cleavable, straight-chain polymer. In a further embodiment, the linker is a non-cleavable, optionally substituted hydrocarbon polymer. In another embodiment, the linker is a photolabile optionally substituted hydrocarbon polymer.

In certain embodiments the linker is a substituted or unsubstituted polyethylene glycol linker having from 1-12 ethylene glycol subunits, for example, 1-10 ethylene glycol subunits, 1-8 ethylene glycol subunits, 2-12 ethylene glycol submits, 2-8 ethylene glycol subunits, 3-8 ethylene glycol subunits, 3-6 ethylene glycol subunits and 1 ethylene glycol subunit, 2 ethylene glycol subunits, 3 ethylene glycol subunits, 4 ethylene glycol subunits, 5 ethylene glycol subunits, 6 ethylene glycol subunits, 7 ethylene glycol subunits, 8 ethylene glycol subunits, 9 ethylene glycol subunits, 10 ethylene glycol subunits, 11 ethylene glycol subunits or 12 ethylene glycol subunits.

In certain embodiments the linker is a substituted or unsubstituted alkyl linker having from 1-12 —$CH_2$— subunits, for example, 1-10 —$CH_2$— subunits, 1-8 —$CH_2$— subunits, 2-12 —$CH_2$— submits, 2-8 —$CH_2$— subunits, 3-8 —$CH_2$— subunits, 3-6 —$CH_2$— subunits and 1 —$CH_2$— subunit, 2 —$CH_2$— subunits, 3 —$CH_2$— subunits, 4 —$CH_2$— subunits, 5 —$CH_2$— subunits, 6 —$CH_2$—, 7 —$CH_2$— subunits, 8 —$CH_2$— subunits, 9 —$CH_2$— subunits, 10 —$CH_2$— subunits, 11 —$CH_2$— subunits or 12—$CH_2$— subunits.

The linker can comprise a substituted PEG linker or a substituted alkyl linker that includes at any point along the linker an O, P, S, N or Si atom. The linker can also be substituted at any point along the linker with a combination of an aryl, alkylene, alkyl, benzyl, heterocyle, triazole, sulfoxide or phenyl group.

In some embodiments, the linker comprises a combination of PEG subunits and alkyl-ether chains, for example, (—$(CH_2CH_2)_{1-11}$—O—$(CH_2CH_2)_{1-11}$—O—) or (—$(CH_2CH_2)_{1-11}$—O—) etc. . . . . . In some embodiments, the linker comprises a combination of $CH_2$ subunits and oxygen, for example, alkyl-ether, (—$(CH_2)_{1-11}$—O—$(CH_2)_{1-11}$—O—) or (—$(CH_2)_{1-11}$—O—), etc. . . . . In some embodiments the linker comprises a combination of a PEG subunits and a ring structure. In other embodiments, the linker comprises a combination of a $CH_2$ subunit and a ring structure.

A linker is of a length such that the Rpn11 binding partner and the target protein binding partner are separated by a distance from 18-95 Å, for example, 18-25 Å for a linker comprising 2-4 ethylene glycol subunits, 25-33 Å for a linker comprising 4-6 ethylene glycol subunits, 33-39 Å for a linker comprising 6-8 ethylene glycol subunits, 39-53 Å for a linker comprising 8-12 ethylene glycol subunits and, 53 to 95 Å for a linker comprising 12-24 ethylene glycol subunits. In one embodiment, Rpn11 binding partner and a target protein binding partner of a bifunctional molecule of the invention connected via a linker may be separated by a distance of 2 atoms, 3 atoms, 4 atoms, 5 atoms, 6 atoms, 7 atoms, 8 atoms, 9 atoms, 10 atoms, 11 atoms, 12 atoms, 13 atoms, 14 atoms, 15 atoms, 16 atoms, 17 atoms, 18 atoms, 19 atoms, 20 atoms, 21 atoms, 22 atoms, 23 atoms, 24 atoms, 25 atoms, 26 atoms, 27 atoms, 28 atoms, 29 atoms, 30 atoms, 40 atoms, 50 atoms, 60 atoms, 70 atoms, 80 atoms and 90 or more atoms.

The length, stability and flexibility of a linker useful according to the invention permits a given spacing or distance between the two binding partners of a bifunctional molecule according to the invention; in turn, the spacing between two binding partners of a given molecule permits a target protein bound by the bifunctional molecule to assume a configuration that facilitates degradation of the target protein.

A linker according to the invention is considered stable if it does not undergo degradation or cleavage when stored as a pure material or in solution. A linker according to the invention is considered biologically stable if it is not metabolized.

In certain embodiments, binding partners are connected via one or more linkers. In some embodiments, binding partners are connected directly by a covalent bond; such a direct connection is within the term "linker".

Linkers useful according to the invention include but are not limited to

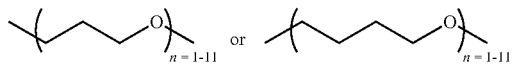

and combinations thereof, for example,

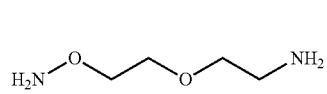

A linker according to the invention can include a ring structure, for example,

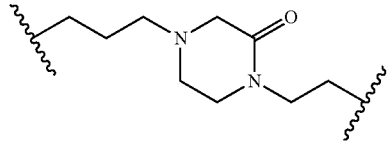 [SMILES: *CCCN1CCN(CC*)C(=O)C1]

Linkers useful according to the invention can comprises a PEG linker having at one end an oxime and at the other end an amine, for example, PEG2
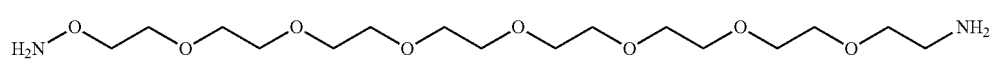

PEG4
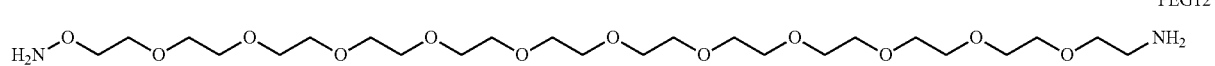

PEG8
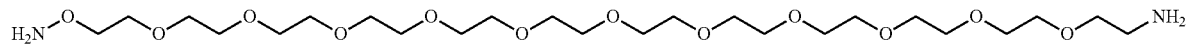

PEG12

A linker according to the invention can include a linker selected from:

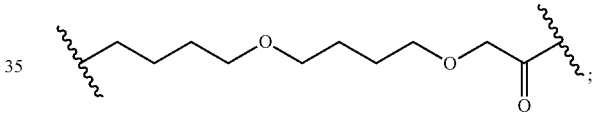

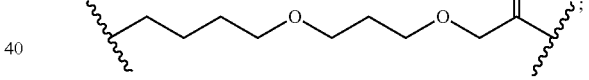

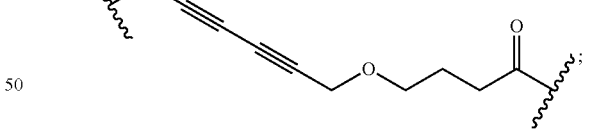

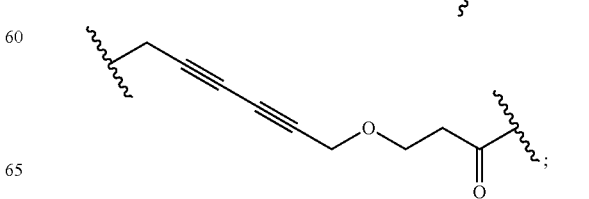

293
-continued
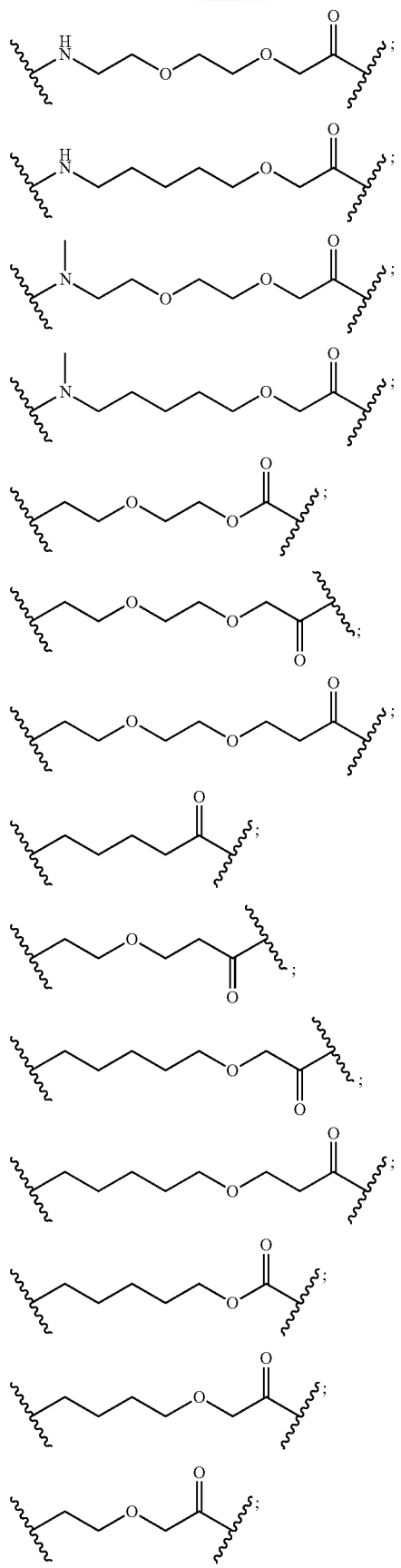
294
-continued
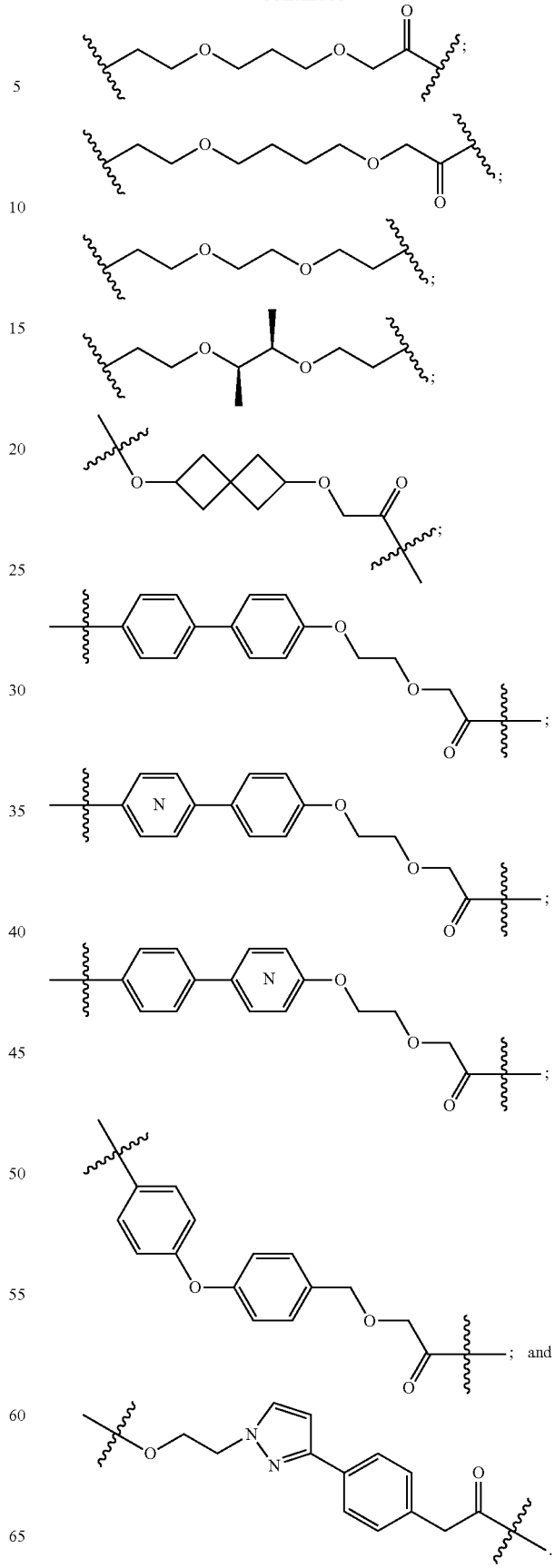

295

-continued

296

-continued

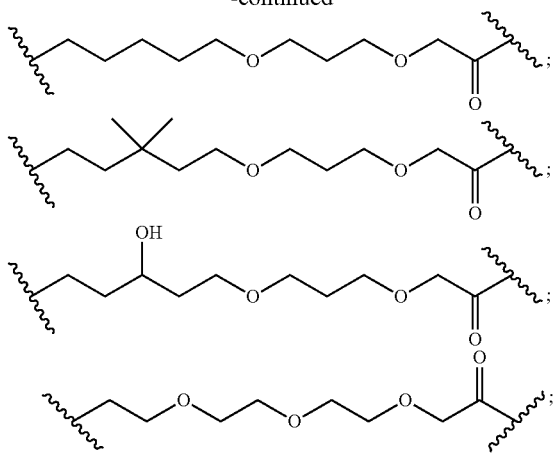

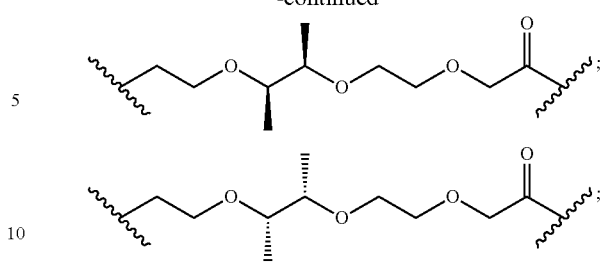

A linker according to the invention can be prepared by mono-tosylating PEG and then reacting the mono-tosylated PEG with potassium phthalimide in DMF or ACN at 90° C. The product of that reaction is tosylated or mesylated and reacted with N-hydroxy phthalimide in the presence of TEA as a base. Final deprotection can be achieved by treatment with excess of hydrazine hydrate in refluxing ethanol.

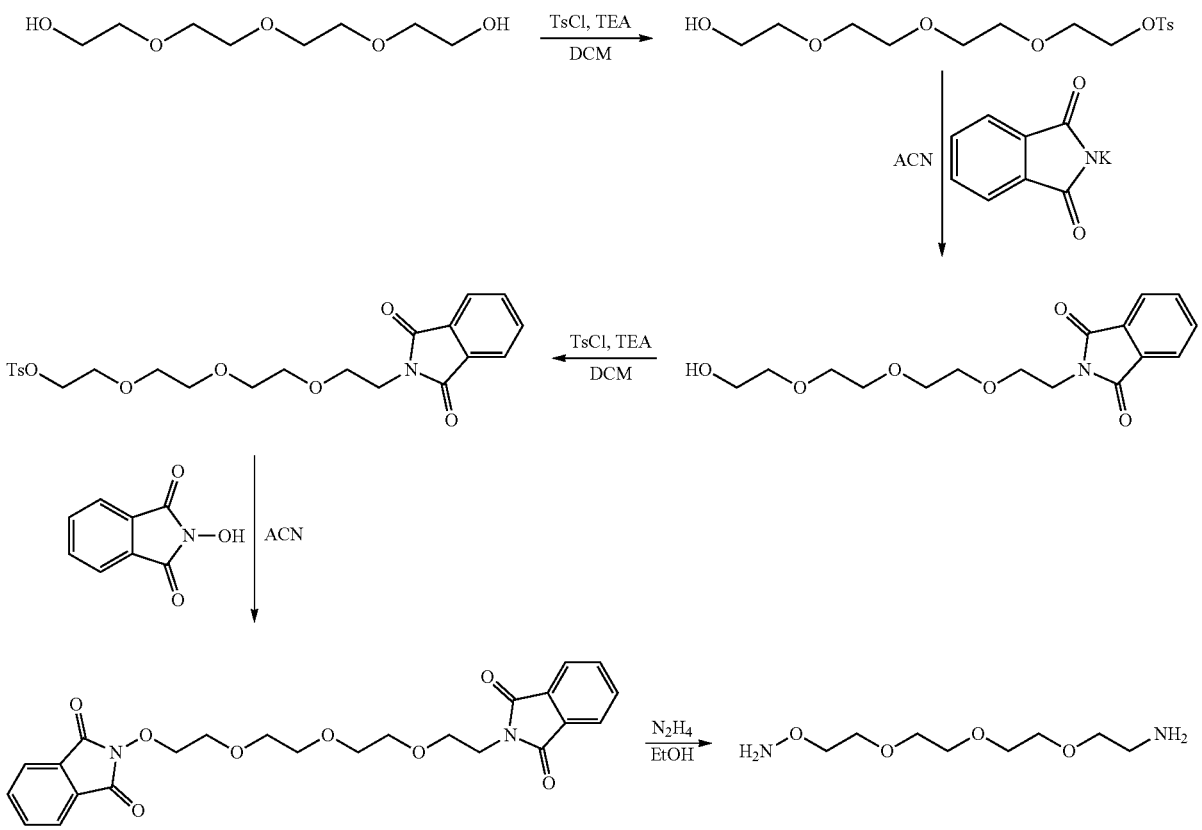

A linker according to the invention can also be prepared by reacting mono-BOC protected PEG amines with Boc-aminoxyacetic acid and an amide coupling reagent. The product is deprotected acid, for example in the presence of HCl.

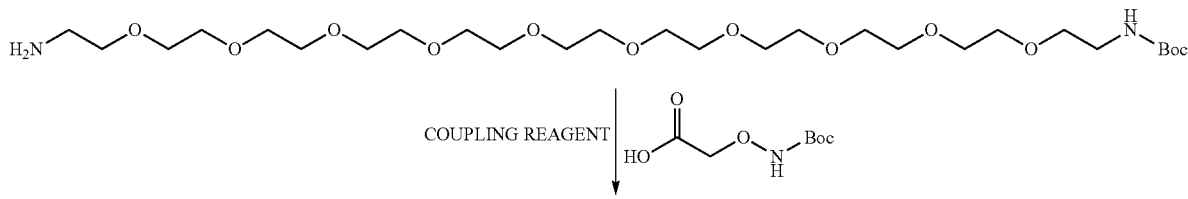

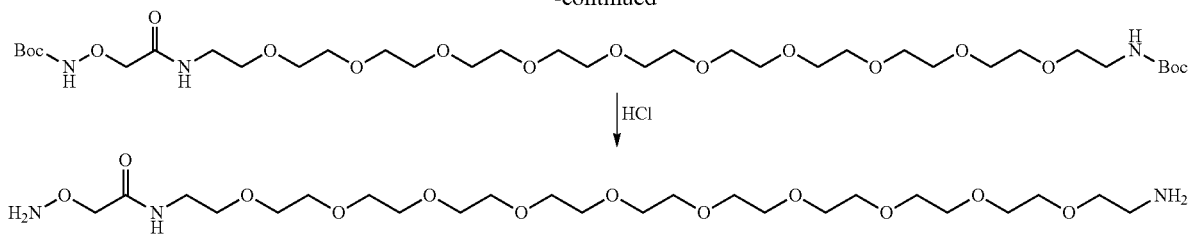

↓ HCl

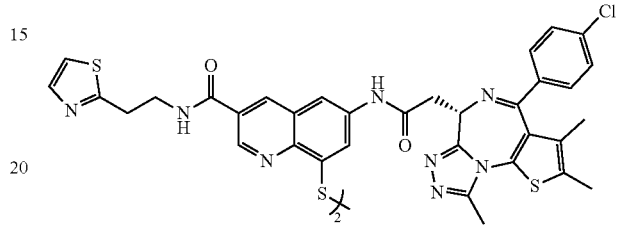

The invention provides for a bifunctional molecule wherein the binding partners are connected directly and are synthesized for example as follows:

Synthesis of an Rpn11-BET Targeting Conjugate

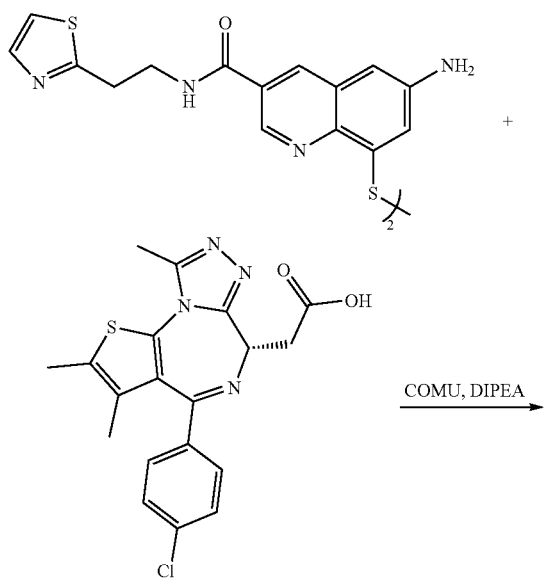

-continued

Exemplary Molecules

The invention provides for a molecule having an Rpn11 binding partner and a target protein binding partner, for example, as disclosed herein.

Kinase-Targeting Molecules Comprising an Rpn11 Binding Partner

The invention provides for molecules comprising an Rpn11 binding partner and a kinase-targeting partner. Exemplary structures are shown below.

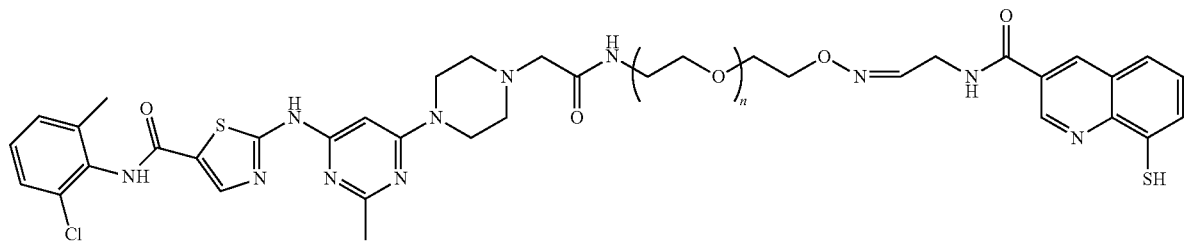

n = 1-11

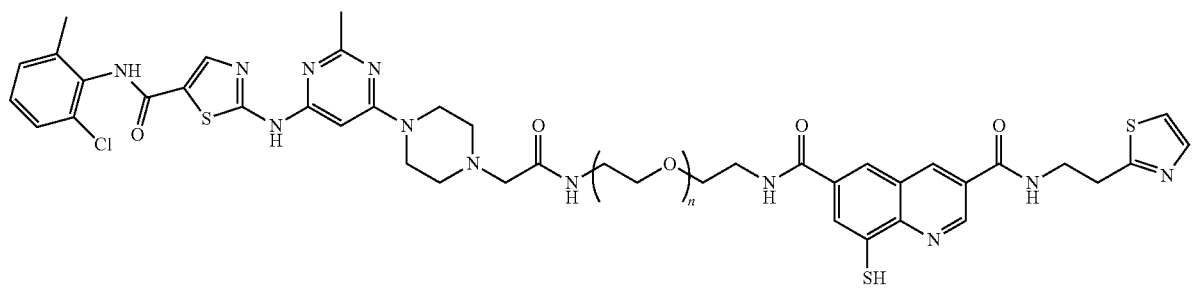

n = 1-11

-continued
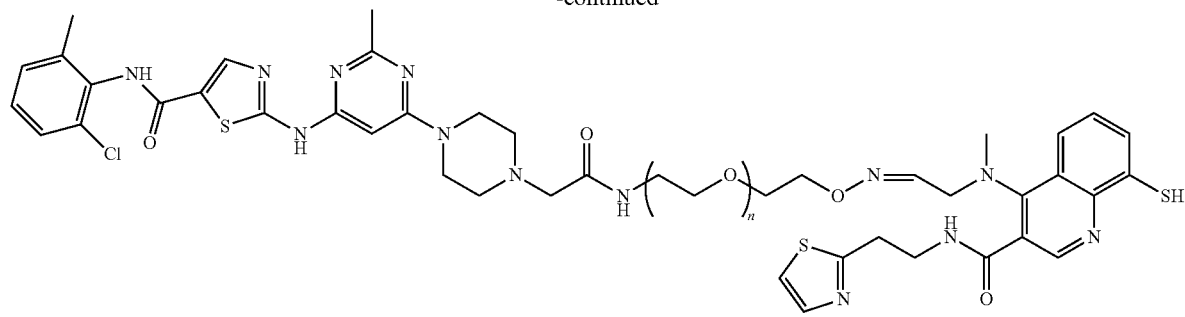
n = 1-11
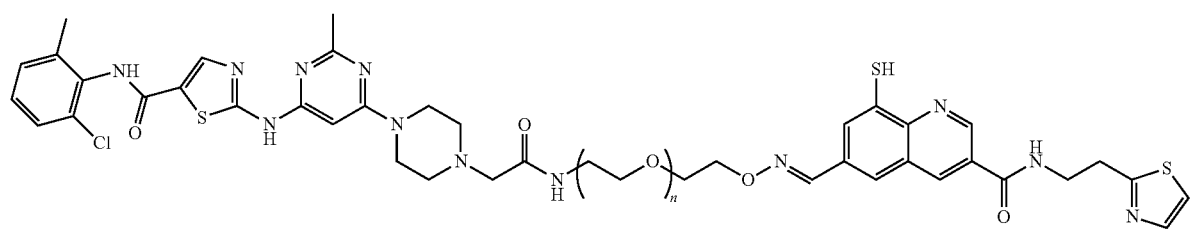
n = 1-11
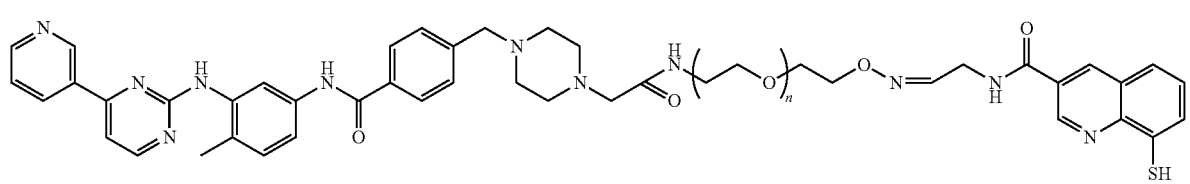
n = 1-11
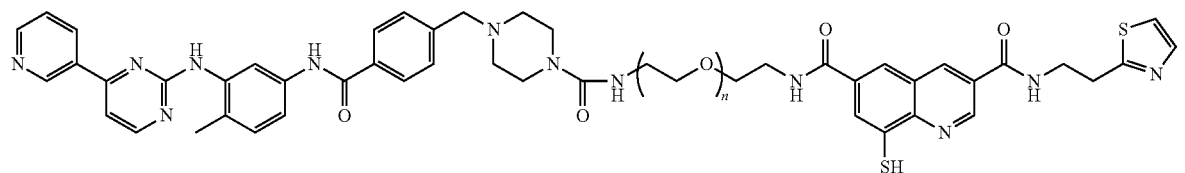
n = 1-11
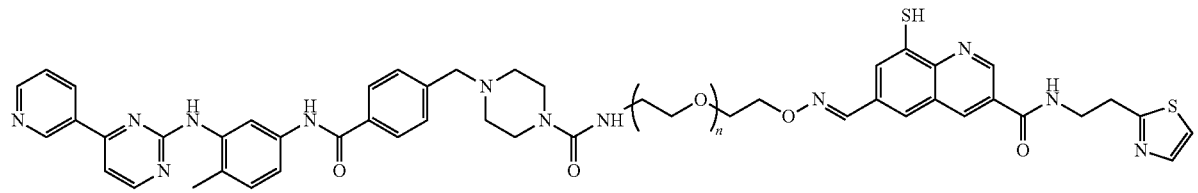
n = 1-11
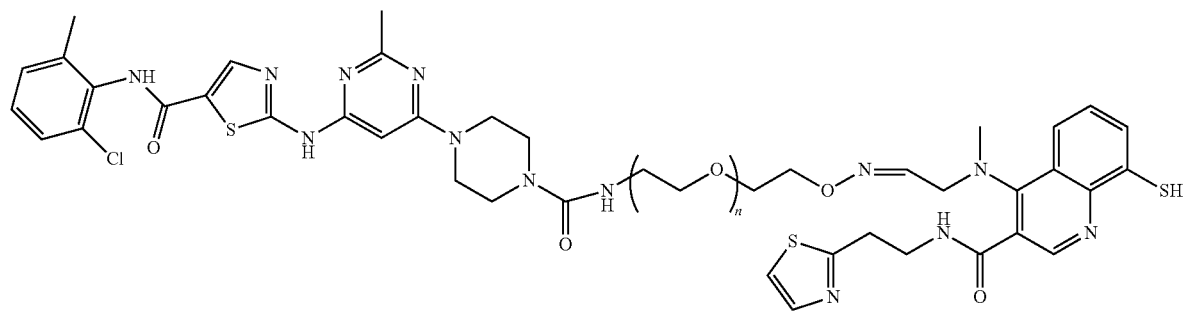
n = 1-11

BET-Targeting Molecules Comprising an Rpn11 Binding Partner
The invention provides for molecules comprising an Rpn11 binding partner and a BET-targeting partner. Exemplary structures are shown below.
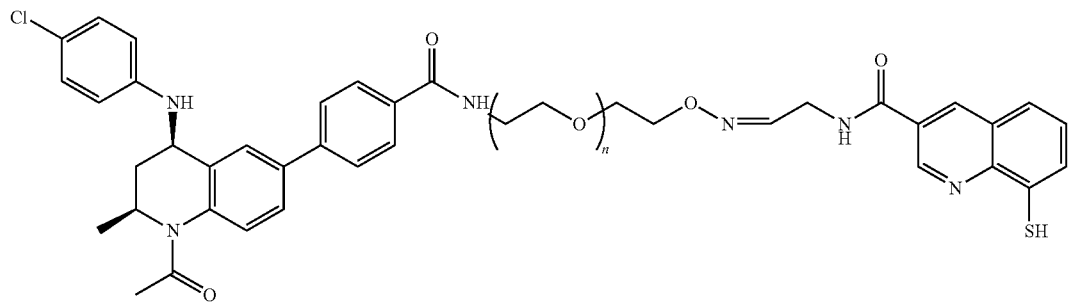
n = 1-11
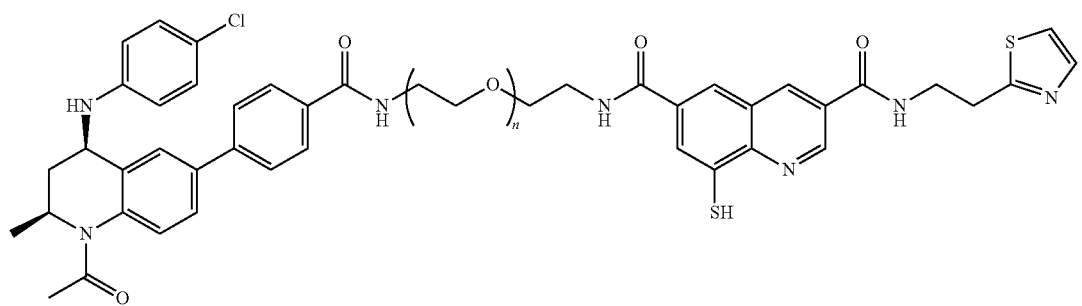
n = 1-11
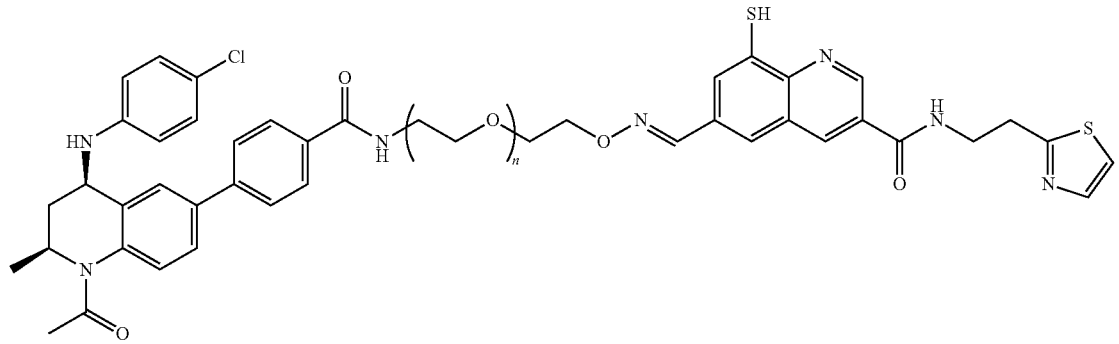
n = 1-11
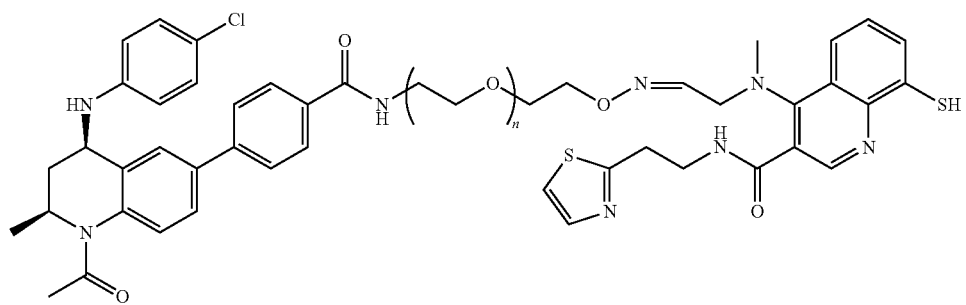
n = 1-11

303
-continued
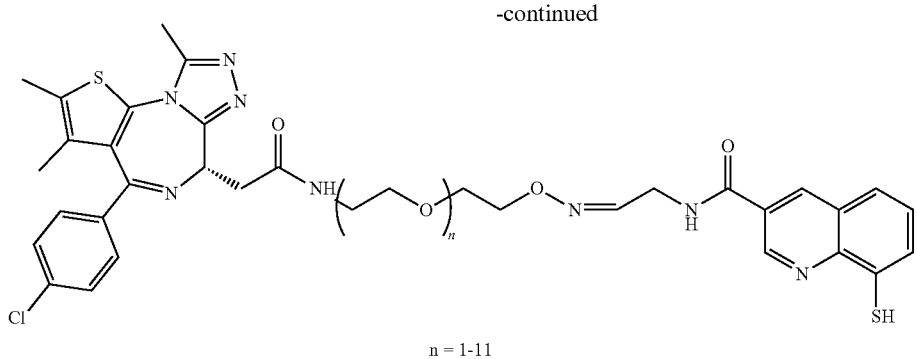
n = 1-11
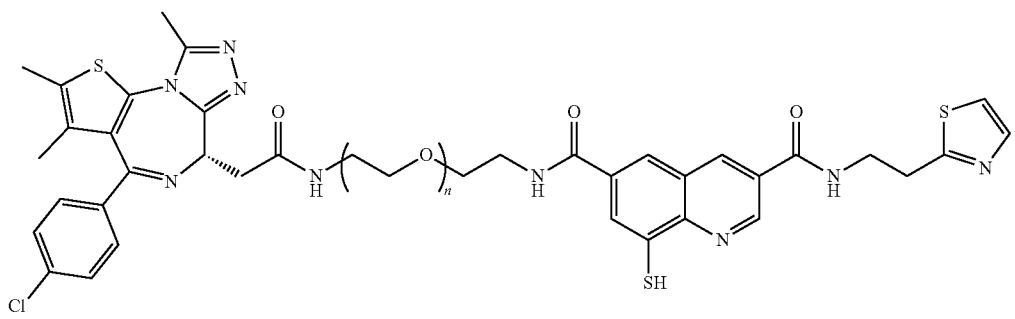
n = 1-11
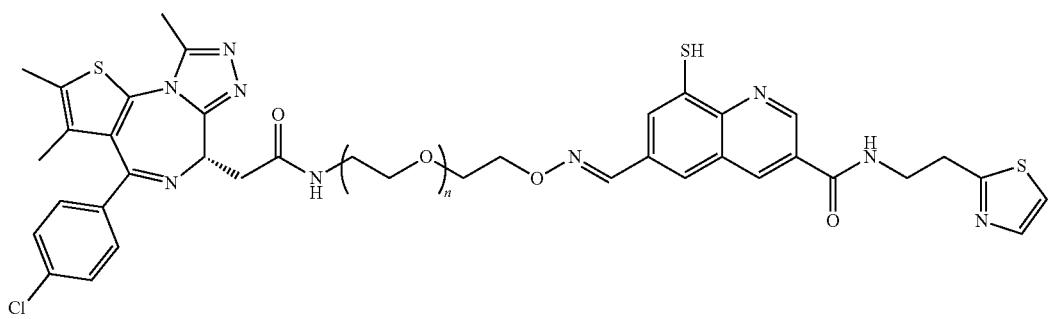
n = 1-11
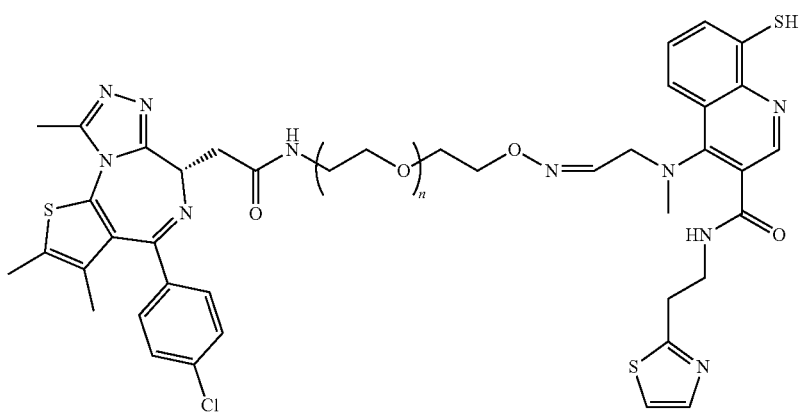
n = 1-11

Methods of Synthesis

Methods of synthesis well known in the art are used to synthesize the molecules of the invention. The molecules of the invention can be synthesized, for example, by oxime, amide coupling or by reductive amination.

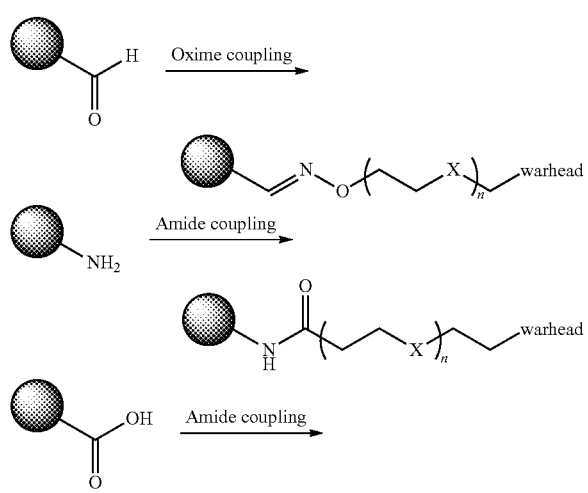

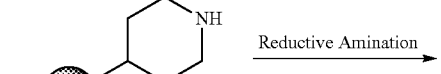

A bifunctional molecule of the invention comprising an Rpn11 binding partner linked to a target protein binding partner can be synthesized according to any one of the methods shown below. However, alternative methods of synthesis also may be employed.

Synthesis of a BCR/Abl Kinase Targeting Bifunctional Molecule Comprising an Rpn11 Binding Partner which is Another Capzimin Derivative Connected to Dasatinib Via a PEG Linker Having an Amine at Both Termini.

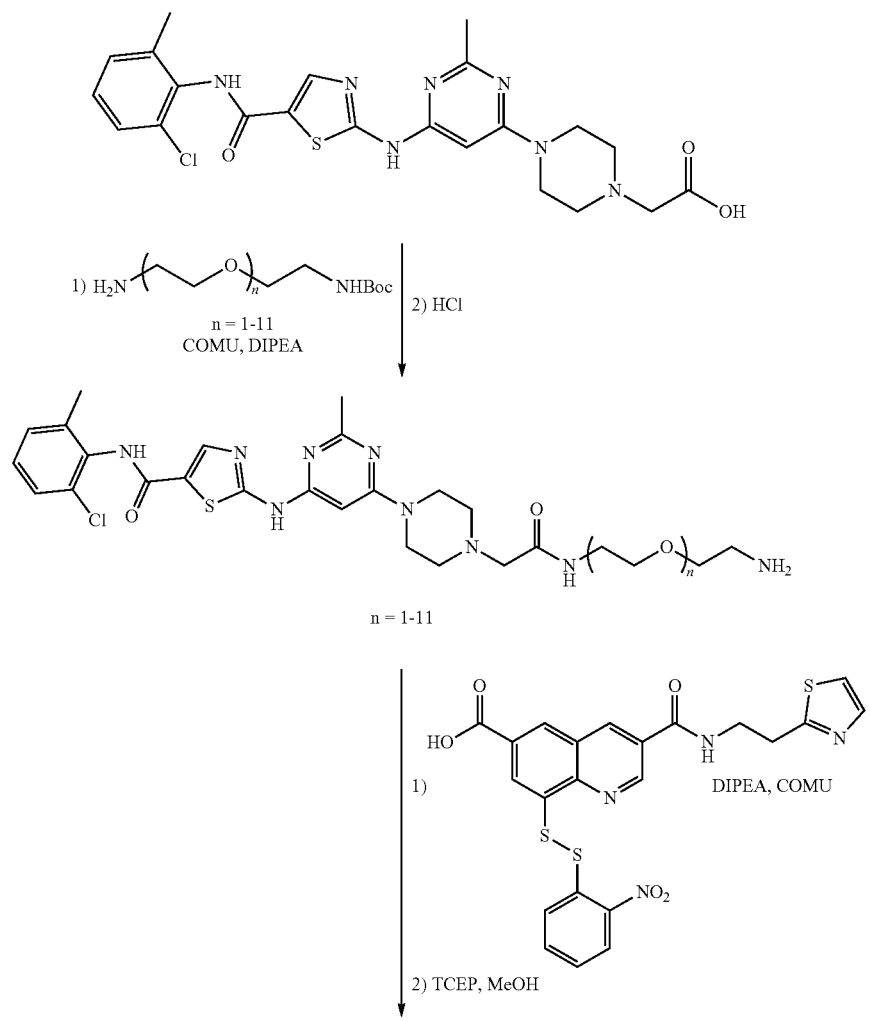

-continued

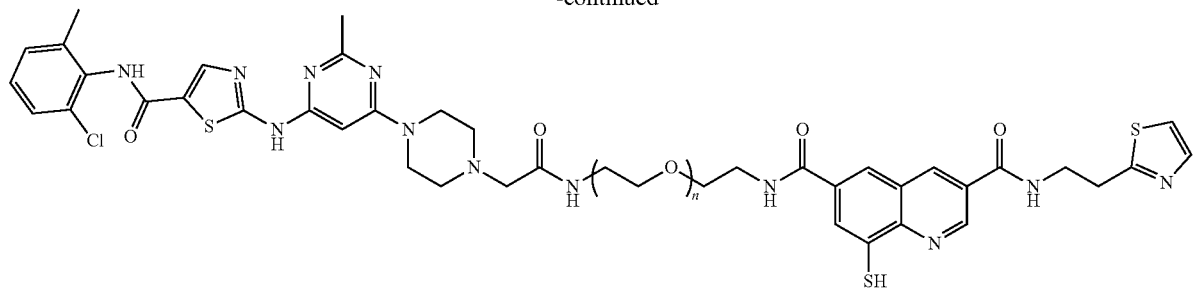

These bifunctional molecules can be prepared, for example, by using an amide coupling reagent e.g., HATU, COMU, HBTU, HCTU, PyBOP, EDC, DCC, DIC; a base i.e. TEA, DIPEA, NMM and a suitable solvent i.e. DCM, DMF, NMP, THF. Subsequently, first Boc deprotection is achieved by using acid e.g. HCl or TFA in a suitable solvent, i.e., DCM, MeOH, Dioxane, Ethanol, Diethyl ether. Following a second coupling reaction, final deprotection is achieved by using a reducing agent e.g. TCEP, or DTT, or another disulphide reducing agent.

Use of a Bifunctional Molecule Comprising an Rpn11 Binding Partner Linked to a Target Protein Binding Partner for Degradation The invention provides for methods of degrading a target protein of interest using an bifunctional molecule comprising an Rpn11 binding partner linked to a target protein binding partner. The methods can be used in vitro and in vivo. The methods involve contacting a target protein of interest, for example, an isolated target protein of interest or a cell comprising the target protein of interest, with a bifunctional molecule of the invention, under conditions and for a length of time, that allow for degradation of the target protein.

Determining Degradation of a Target Protein

Degradation is determined by measuring and comparing the amount of a target protein in the presence and absence of a bifunctional molecule of the invention. Degradation can be determined, for example, by performing immunoblotting assays, Western blot analysis and ELISA with cells that have been treated or untreated with a bifunctional molecule. Success of protein degradation is provided as an amount of protein degraded at a particular time point. Degradation has occurred if a decrease in the amount of target protein is observed, at a particular time point, in the presence a bifunctional molecule of the invention.

More particularly, degradation has occurred if at least a 10% decrease in the amount of a protein is observed, for example, 20%, 30%, 40%, 50%, 60%, 70%, 80%, 90% or 100%, within 24 hours or more, for example, 24 hours, 30 hours, 36 hours, 42 hours, 48 hours, 54 hours, 60 hours, 66 hours and 72 hours, in the presence of 1 nM to 10 µM of a bifunctional molecule of the invention, for example, 1 nM, 10 nM, 100 nM 1 µM, and 10 µM.

Pharmaceutical Compositions

In certain embodiments, the present invention provides for a pharmaceutical composition comprising the molecules of the present invention. The molecule can be suitably formulated and introduced into the environment of the cell by a means that allows for a sufficient portion of the molecule to enter the cell to induce degradation of the target protein which binds to the target protein binding partner of the molecule, and increases or decreases a cellular function.

The molecule of the instant invention can be formulated in buffer solutions such as phosphate buffered saline solutions. Such compositions typically include the molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™. (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 1006-10 (viral-mediated delivery); or Putnam (1996), Am. J. Health Syst. Pharm. 53(2), 151-160, erratum at Am. J. Health Syst. Pharm. 53(3), 325 (1996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage faun employed and the route of administration utilized. For a compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a molecule of the invention (i.e., an effective dosage) depends on the molecule selected. For instance, single dose amounts in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a molecule of the invention can include a single treatment or, preferably, can include a series of treatments.

In certain embodiments, the dosage of an bifunctional molecule according to the invention is in the range of 5 mg/kg/week to 500 mg/kg/week, for example 5 mg/kg/week, 10 mg/kg/week, 15 mg/kg/week, 20 mg/kg/week, 25 mg/kg/week, 30 mg/kg/week, 35 mg/kg/week, 40 mg/kg/ week, 45 mg/kg/week, 50 mg/kg/week, 55 mg/kg/week, 60 mg/kg/week, 65 mg/kg/week, 70 mg/kg/week, 75 mg/kg/week, 80 mg/kg/week, 85 mg/kg/week, 90 mg/kg/week, 95 mg/kg/week, 100 mg/kg/week, 150 mg/kg/week, 200 mg/kg/week, 250 mg/kg/week, 300 mg/kg/week, 350 mg/kg/week, 400 mg/kg/week, 450 mg/kg/week and 500 mg/kg/week. In certain embodiments, the dosage of an bifunctional molecule according to the invention is in the range of 10 mg/kg/week to 200 mg/kg/week, 20 mg/kg/week to 150 mg/kg/week or 25 mg/kg/week to 100 mg/kg/week. In certain embodiments the bifunctional molecule is administered 1×per week for a duration of 2 weeks to 6 months, for example, 2 weeks, 3 weeks, 4, weeks, 5 weeks, 6 weeks, 7 weeks, 8 weeks, 9 weeks, 10 weeks, 11 weeks, 12 weeks, 13 weeks, 26 weeks, 6 months, 8 months, 10 months or 1 year or more. In certain embodiments, the molecule is administered 2× per week. In other embodiments, the bifunctional molecule is administered every other week. In certain embodiments, the bifunctional molecule is administered intravenously.

The molecule of the invention can be formulated as a pharmaceutical composition which comprises a pharmacologically effective amount of a molecule and pharmaceutically acceptable carrier. A pharmacologically or therapeutically effective amount refers to that amount of an bifunctional molecule agent effective to produce the intended pharmacological, therapeutic or preventive result. The phrases "pharmacologically effective amount" and "therapeutically effective amount" or simply "effective amount" refer to that amount of an bifunctional molecule effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general, a suitable dosage unit of a molecule will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the molecule can be administered once daily. However, the therapeutic agent may also be dosed in dosage units containing two, three, four, five, six or more sub-doses administered at appropriate intervals throughout the day. In that case, the molecule contained in each sub-dose must be correspondingly smaller in order to achieve the total daily dosage unit. The dosage unit can also be compounded for a single dose over several days, e.g., using a conventional sustained release formulation which provides sustained and consistent release of the molecule over a several day period. Sustained release formulations are well known in the art. In this embodiment, the dosage unit contains a corresponding multiple of the daily dose. Regardless of the formulation, the pharmaceutical composition must contain the molecule in a quantity sufficient to be active, for example, to induce degradation of the target protein which is bound to the target protein binding partner of the molecule and, in certain embodiments, cause a change in cellular function. The composition can be compounded in such a way that the sum of the multiple units of the molecule together contains a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of the molecule in plasma may be measured by standard methods, for example, by high performance liquid chromatography.

The pharmaceutical compositions can be included in a kit, container, pack, or dispenser together with instructions for administration.

Methods of Treatment

The present invention provides for both prophylactic and therapeutic methods of treating a subject at risk of (or susceptible to) a disease or disorder caused, in whole or in part, by overexpression of a target protein.

"Treatment", or "treating" as used herein, is defined as the application or administration of a therapeutic agent (e.g., a molecule of the invention) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., a molecule of the invention). Subjects at risk for the disease can be identified by, for example, any one or a combination of diagnostic or prognostic assays as described herein. Administration of a prophylactic agent can occur prior to the detection of, e.g., viral particles in a subject, or the manifestation of symptoms characteristic of the disease or disorder, such that the disease or disorder is prevented or, alternatively, delayed in its progression.

Another aspect of the invention pertains to methods of treating subjects therapeutically, i.e., alter onset of symptoms of the disease or disorder. These methods can be performed in vitro or, alternatively, in vivo (e.g., by administering the molecule of the invention to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype"). Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, molecule as described herein can be used in an animal model to determine the efficacy, toxicity, or side effects of treatment with the agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

The bifunctional molecules of the invention are useful for increasing proteolysis of a selected target protein. A protein is selected for targeted proteolysis in order to reduce the amount of that protein in a cell. A reduction in the amount of a given target protein in a cell may be advantageous in order to treat, prevent, or reduce the deleterious effects of a given disease. In some cases, a given disease involves the presence of an increased amount of a given target protein in a cell. A subject is said to be treated for a disease if following administration of the bifunctional molecule to cells or a subject of the invention, one or more symptoms of the disease are reduced or eliminated.

Animal Models

In order to test a bifunctional molecule for activity in facilitating proteolysis of a selected target protein, the molecule may be administered to an animal, and the effect on the animal assessed Animal models useful according to the invention include but are not limited to the following:

| Animal Model | Therapeutic Area |
| --- | --- |
| B6C3F1 Mouse | Cardiovascular |
| CB6F1 Mouse | Cardiovascular |
| CD2F1 (CDF1) Mouse | Cardiovascular |
| Dahl/Salt Sensitive Rat | Cardiovascular |
| DBA/2 Mouse | Cardiovascular |
| FHH Rat | Cardiovascular |
| Hartley Guinea Pig | Cardiovascular |
| IAF Hairless Guinea Pig | Cardiovascular |
| LVG Golden Syrian Hamster | Cardiovascular |
| Mongolian Gerbil | Cardiovascular |
| New Zealand White Rabbit | Cardiovascular |
| Obese Prone CD Rat | Cardiovascular |
| Obese Resistant CD Rat | Cardiovascular |
| Spontaneously Hypertensive (SHR) Rat | Cardiovascular |
| Spontaneously Hypertensive Heart Failure (SHHF) Rat | Cardiovascular |
| Spontaneously Hypertensive Obese (SHROB) Rat | Cardiovascular |
| Spontaneously Hypertensive Stroke Prone (SHRSP) Rat | Cardiovascular |
| SS-13BN Rat | Cardiovascular |
| Wistar Furth Rat | Cardiovascular |
| Wistar IGS Rat | Cardiovascular |
| Wistar Kyoto (WKY) Rat | Cardiovascular |
| Zucker Rat | Cardiovascular |
| B10.A/Cr Mouse | Inflammation |
| Lewis Rat | Inflammation |
| Ly5.1 Mouse | Inflammation |
| NCG Mouse | Inflammation |
| OT I Mouse | Inflammation |
| OT II Mouse | Inflammation |
| SJL-Elite Mouse | Inflammation |
| Wistar IGS Rat | Inflammation |
| C57BL/6-Germ-Free Mouse | Metabolic Disease |
| ZDF Rat | Metabolic Disease |
| C57BL/6-Germ-Free Mouse | Neuroscience |
| AKR Mouse | Oncology |
| Athymic Nude Mouse | Oncology |
| BALB/c Nude Mouse | Oncology |
| BDIX Rat | Oncology |
| Buffalo Rat | Oncology |
| C57BL/6-Germ-Free Mouse | Oncology |
| CD-1 Nude Mouse | Oncology |
| Copenhagen Rat | Oncology |
| Fox Chase CB17 Mouse | Oncology |
| Fox Chase SCID Beige Mouse | Oncology |
| Fox Chase SCID Mouse | Oncology |
| Immortomouse | Oncology |
| NCG Mouse | Oncology |
| NCI SCID/NCr Mouse | Oncology |
| NIH-III Nude Mouse | Oncology |
| NMRI Nude Mouse | Oncology |
| Noble Rat | Oncology |
| NOD SCID Mouse | Oncology |
| NU/NU Nude Mouse | Oncology |
| OFA Rat | Oncology |
| RNU Rat | Oncology |
| SCID Hairless Congenic (SHC) Mouse | Oncology |
| SCID Hairless Outbred (SHO) Mouse | Oncology |
| Swiss Nude Mice | Oncology |
| Wistar Furth Rat | Oncology |

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

315

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

The materials, methods, and examples are illustrative only and not intended to be limiting to the various embodiments of the invention described herein.

EXAMPLES

Example 1—Synthesis of a Kinase Targeting Molecule Comprising an Rpn11 Binding Partner A molecule of the invention comprising a target protein binding partner that targets a kinase connected via a linker to an Rpn11 binding partner is produced, in one embodiment, by the following method. To synthesize a bifunctional molecule of the invention comprising a target protein binding partner that targets a kinase partner connected via a linker to an Rpn11 binding partner, the Rpn11 binding partner is functionalized with an aldehyde group that can be reacted with an aminoxy-containing linker and subsequently with a kinase inhibitor-carboxylic acid derivative under amide coupling conditions to yield the desired bifunctional molecule.

The starting components for synthesis of a kinase targeting molecule comprising an Rpn11, binding partner are prepared, for example, according to the following synthetic scheme:

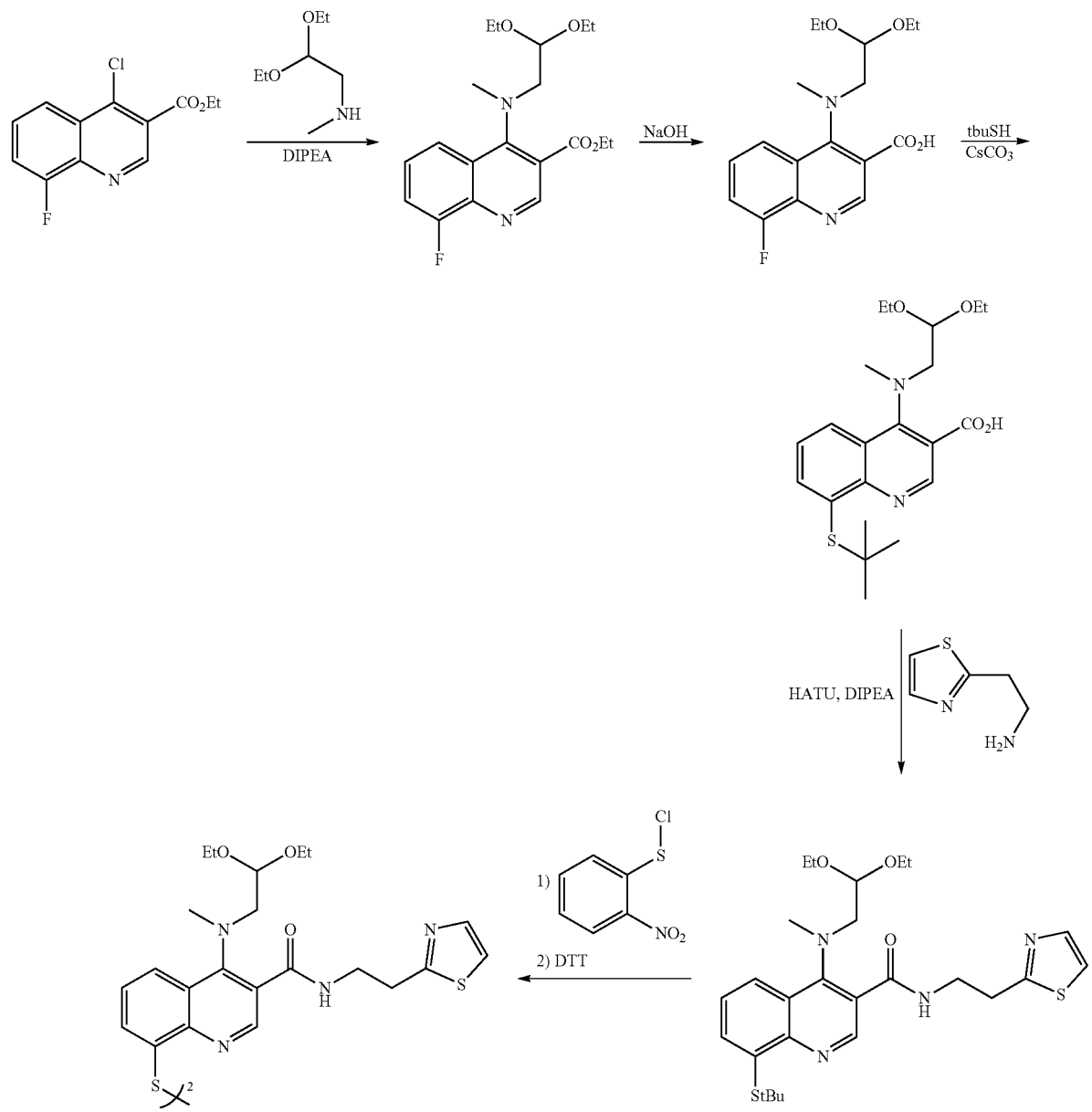

The following synthetic scheme is used to synthesize a kinase targeting molecule comprising an Rpn11, binding partner.

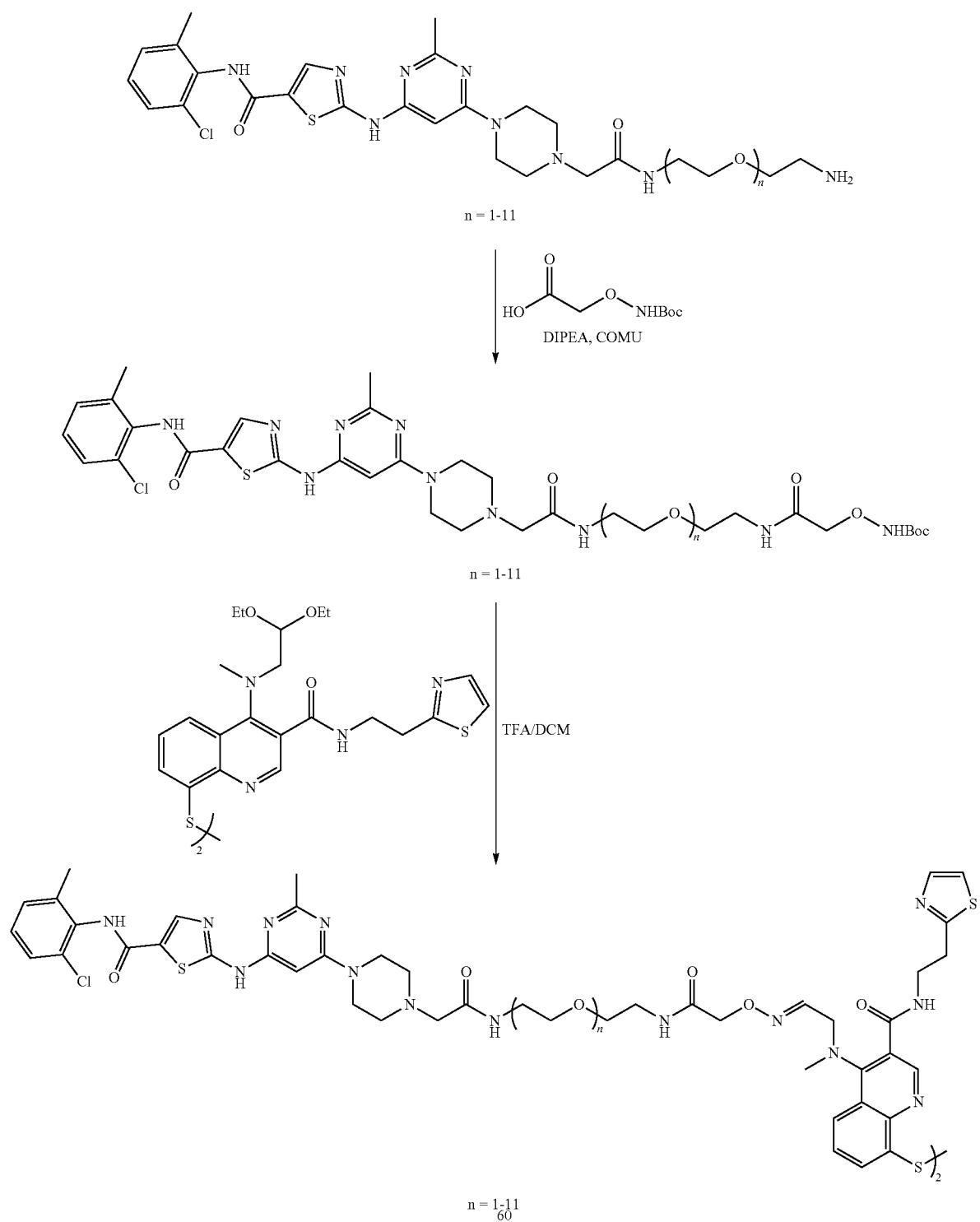

Example 2—Synthesis of a BET-Targeting Molecule Comprising an Rpn11 Binding Partner A molecule of the invention comprising a target protein binding partner that targets a BET connected via a linker to an Rpn11 binding partner is produced by the following method. To synthesize a BET-targeting molecule comprising an Rpn11 binding partner, the Rpn11 binding partner is functionalized with an aldehyde group, reacted with an aminoxy-containing linker and subsequently with a kinase inhibitor-carboxylic acid derivative under amide coupling conditions to yield the desired bifunctional molecule.

The starting components for synthesis of a kinase targeting molecule comprising an Rpn11, binding partner are prepared, for example, according to the following synthetic scheme:
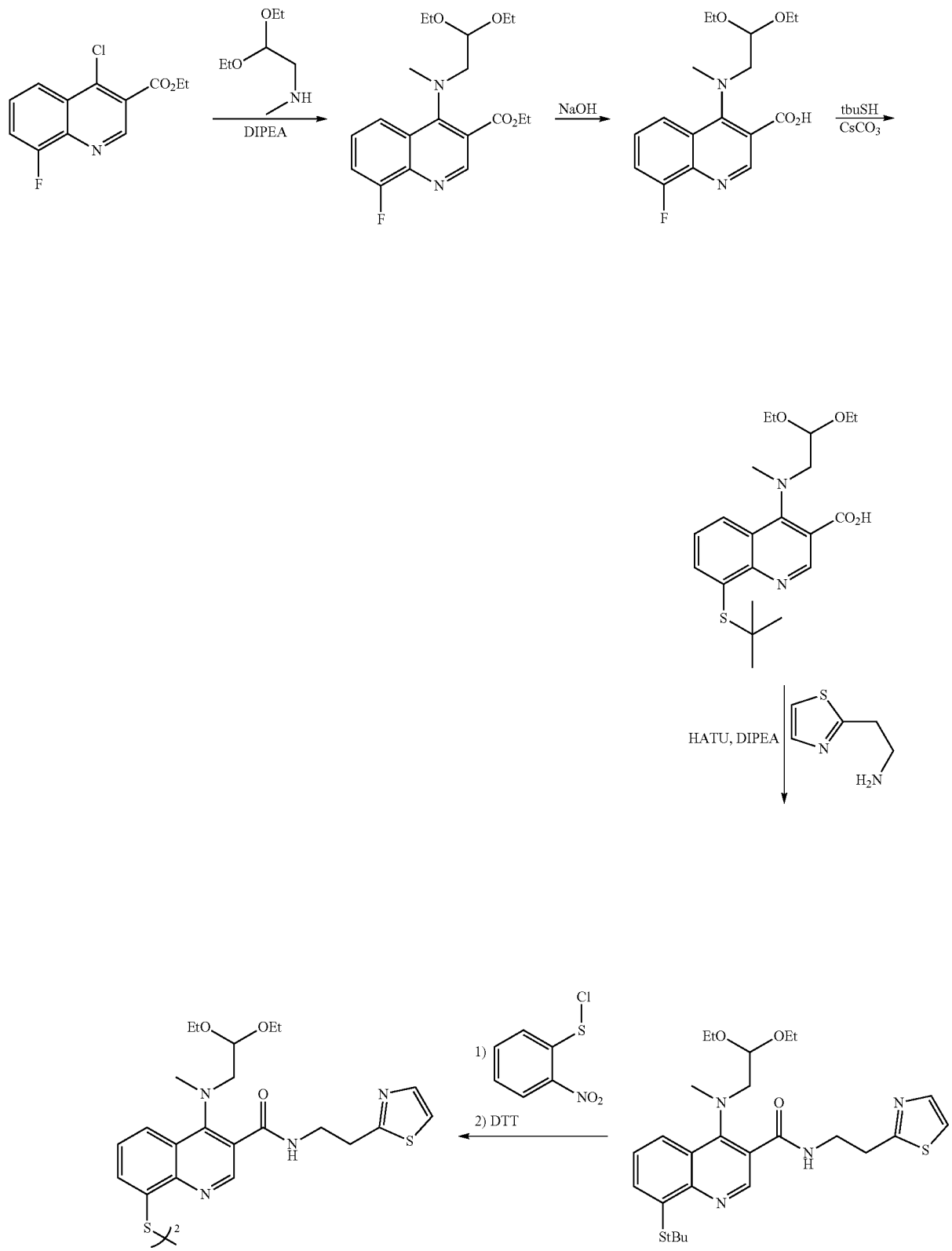

A BET-targeting molecule comprising an Rpn11 binding partner is synthesized as follows:
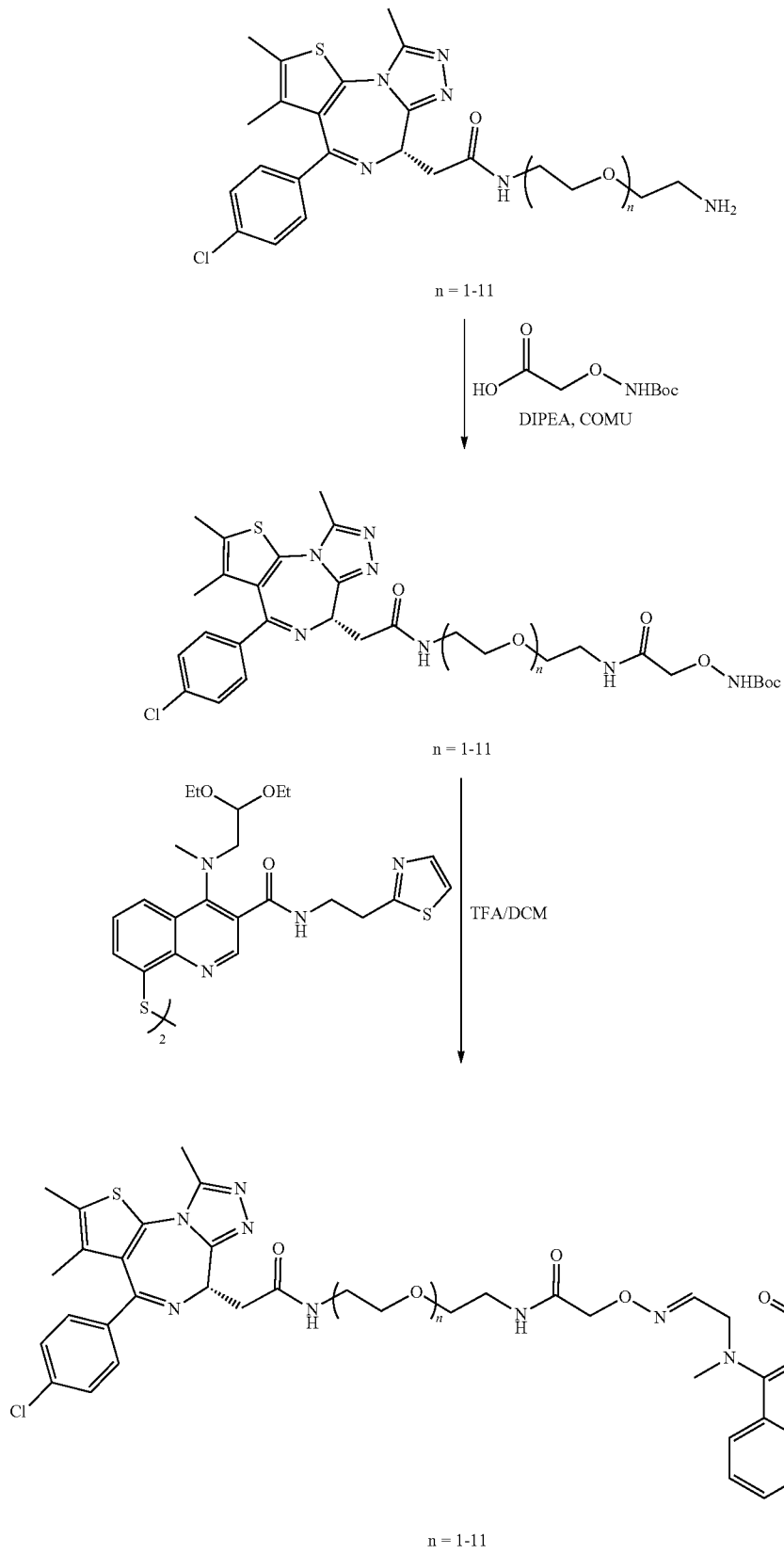

Example 3—Binding of a Bifunctional Molecule to Rpn11 and Target Protein

Binding of a bifunctional molecule of the invention to Rpn11 and a target protein of interest is determined by, for example, using the NanoBRET™ protein-protein interaction system according to the manufacturer's protocol (Promega), or a cellular thermal shift assay (CETSA), followed by Western blot or mass spectrometry analysis.

For analysis of binding of an Rpn11 binding partner to Rpn11, isothermal calorimetry (ITC) and surface plasmon resonance (SPR) may be used to directly assess the binding of the binding partner to a dimer of PSMD14 and PSMD7 (Rpn11 and Rpn8, respectively). A fluorescence polarization (FP) assay can also be employed to facilitate higher-throughput testing of molecules, similar to established methods involving the displacement of an Oregon Green-labeled tetra-ubiquitin substrate (Li et al. (Nat. Chem. Biol. 2017; DOI: 10.1038/nchembio.2326) or Ub-LysGly$^{TAMRA}$ (DOI: 10.1016/j.molcel.2014.12.039).

Isothermal calorimetry (ITC) and/or surface plasmon resonance (SPR) can also be used to directly assess the binding of molecules to the target proteins.

Example 4—Target Protein Degradation

Target protein degradation may be determined by measuring the amount of target protein in the presence and absence of a bifunctional molecule of the invention. Degradation is determined, for example, by performing immunoblotting assays, Western blot analysis and ELISA with cells that have been treated or untreated with a bifunctional molecule. Success of protein degradation is provided as an amount of protein degraded at a particular time point. Degradation has occurred if a decrease in the amount of a protein is observed, at a particular time point, in the presence a bifunctional molecule of the invention.

Example 5—Preparation of Inhibitor-Linker Conjugates

Commercially available chemicals were purchased from Apollo Scientific, Sigma-Aldrich, Fluorochem, or Manchester Organics and used without any further purification.

All reactions were carried out using anhydrous solvents. Preparative HPLC was performed on a Gilson preparative HPLC with a Waters X-Bridge C18 column (100 mm×19 mm; 5 µm particle size, flow rate 25 mL/min) using a gradient from 5% to 95% v/v acetonitrile in water with 0.01% v/v of formic acid over 15 min (METHOD 1) or using a gradient from 5% to 95% v/v acetonitrile in water with 0.01% v/v of aqueous ammonium hydroxide over 15 min (METHOD 2).

Liquid chromatography-mass spectrometry (LC-MS) analyses were performed with either an Agilent HPLC 1100 series connected to a Bruker Daltonics MicroTOF or an Agilent Technologies 1200 series HPLC connected to an Agilent Technologies 6130 quadrupole spectrometer. For LC-MS the analytical column used was a Waters X-bridge C18 column (50 mm×2.1 mm×3.5 mm particle size); flow rate, 0.5 mL/min with a mobile phase of water/MeCN+ 0.01% HCOOH (METHOD 1A); 95/5 water/MeCN was initially held for 0.5 min followed by a linear gradient from 95/5 to 5/95 water/MeCN over 3.5 min which was then held for 2 min. The purity of all the compounds was evaluated using the analytical LC-MS system described before, and purity was >95%.

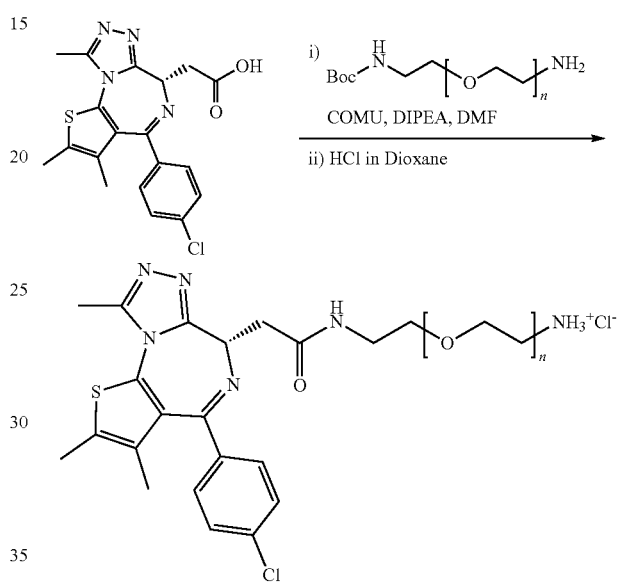

To a solution of mono-Boc protected diamine linker (0.1 mmol, 1 eq) and JQ1-COOH (40 mg, 0.1 mmol, 1 eq) in DMF (1 mL), COMU (43 mg, 1 mmol, 1 eq) and DIPEA (48 microL) were added. The reaction mixture was stirred at room temperature for 1 hour, then quenched with ice cold water. Volatiles were removed in vacuum and the crude mixture was purified by preparative HPLC (METHOD 2). Fractions containing the desired product were evaporated under reduced pressure and the residue was dissolved in DCM (1 mL) and treated with a solution of anhydrous HCl in dioxane (4M, 1 mL). After 1 hour, volatiles were removed under reduced pressure and the residue was freeze dried in order to remove any excess of acid. Analytical data (HRMS) are provided in Table II shown below.

| Example | Structure | m/z [M + H]$^+$ |
|---|---|---|
| S1 | (structure shown) | 487.1605 |

-continued
| Example | Structure | m/z [M + H]⁺ |
|---|---|---|
| S2 | 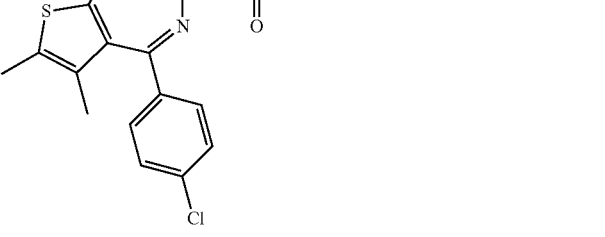 | 531.1867 |
| S3 | 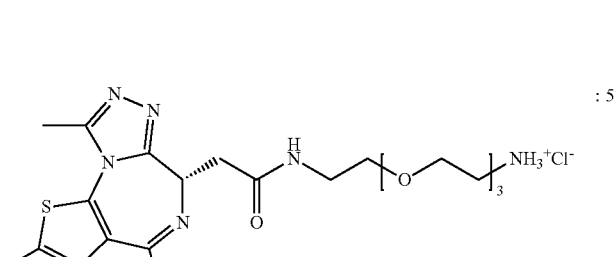 | : 575.2129 |
| S4 | 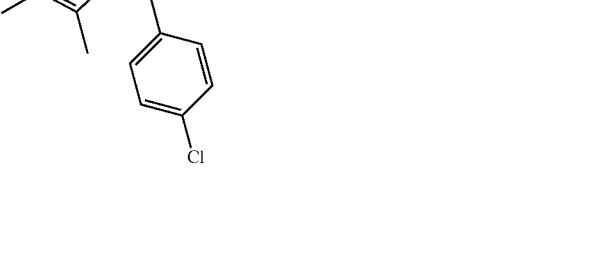 | 663.2653 |
| S5 | 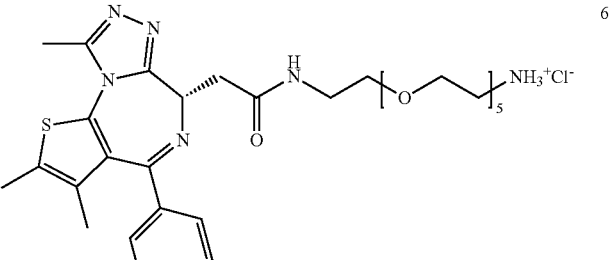 | 751.3178 |

| Example | Structure | m/z [M + H]+ |
|---|---|---|
| S6 | 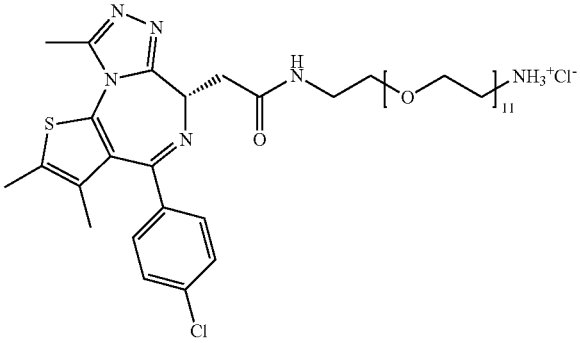 | 927.4226 |
| S7 | 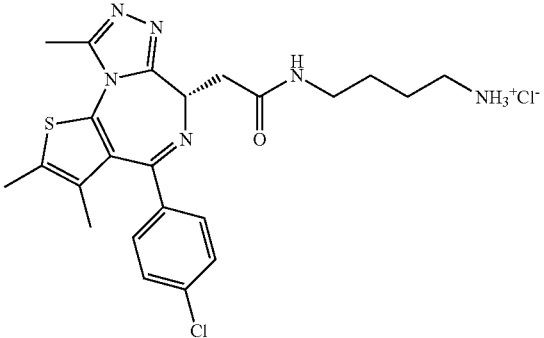 | 471.1656 |
| S8 | 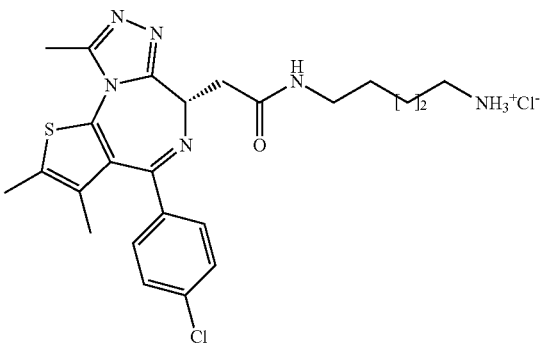 | 485.1812 |
| S9 | 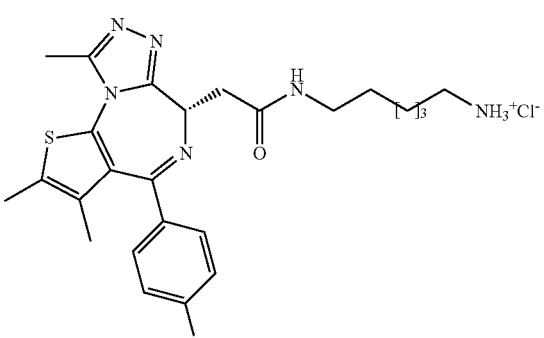 | 499.1969 |

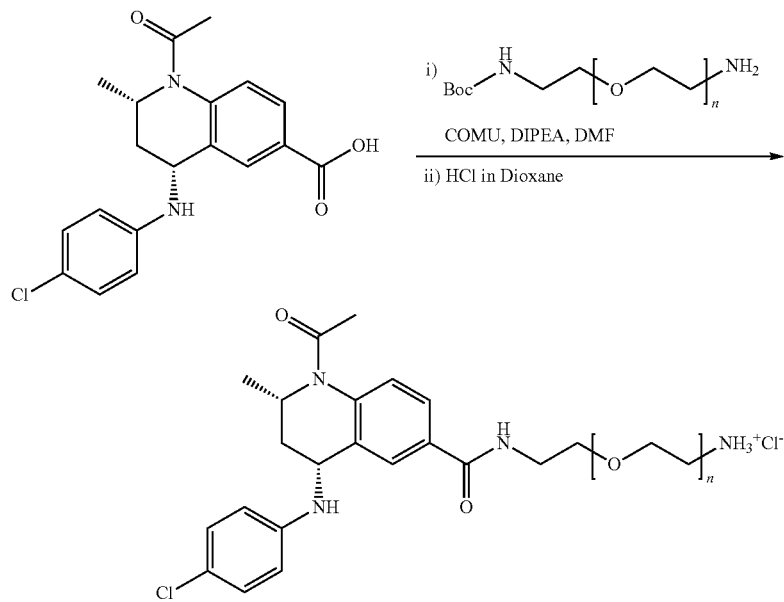

To a solution of mono-Boc protected diamine linker (0.1 mmol, 1 eq) and iBET726 (36 mg, 0.1 mmol, 1 eq) in DMF (1 mL), COMU (43 mg, 1 mmol, 1 eq) and DIPEA (48 microL) were added. The reaction mixture was stirred at room temperature for 1 hour, then quenched with ice cold water. Volatiles were removed in vacuum and the crude mixture was purified by preparative HPLC (METHOD 2). Fractions containing the desired product were evaporated under reduced pressure and the residue was dissolved in DCM (1 mL) and treated with a solution of anhydrous HCl in dioxane (4M, 1 mL). After 1 hour, volatiles were removed under reduced pressure and the residue was freeze dried in order to remove any excess of acid. Analytical data (HRMS) are provided in table III shown below.

| Example | Structure | m/z [M + H]+ |
|---|---|---|
| S10 | 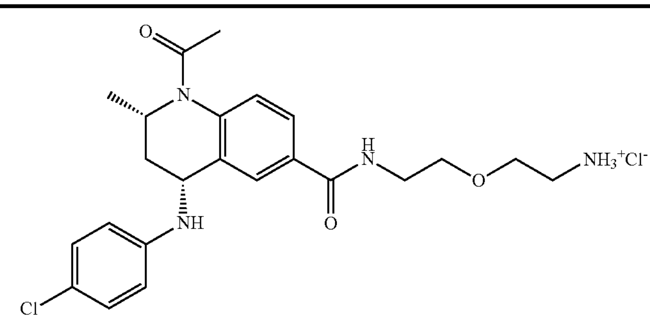 | 445.1928 |
| S11 | 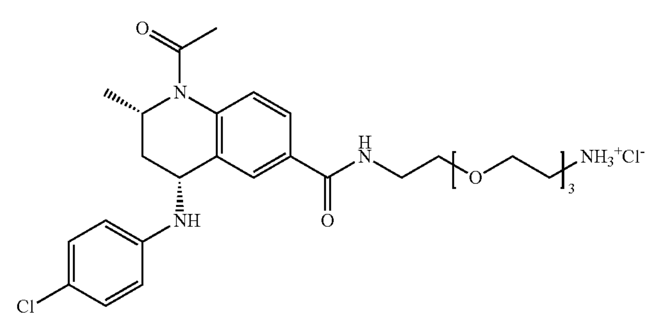 | 533.2452 |

-continued
| Example | Structure | m/z [M + H]+ |
|---|---|---|
| S12 | 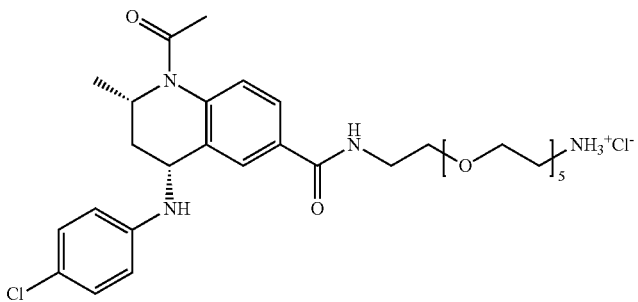 | 621.2977 |
| S13 | 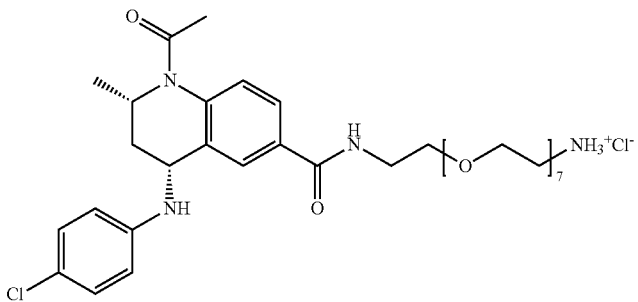 | 709.3501 |
| S14 | 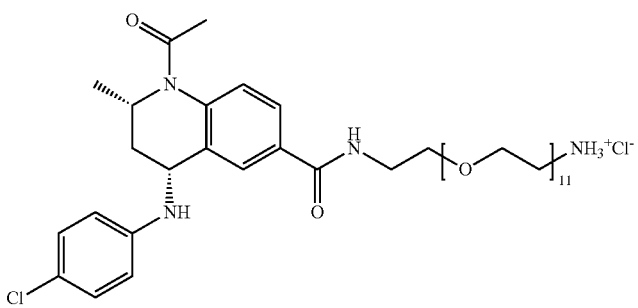 | 885.4550 |
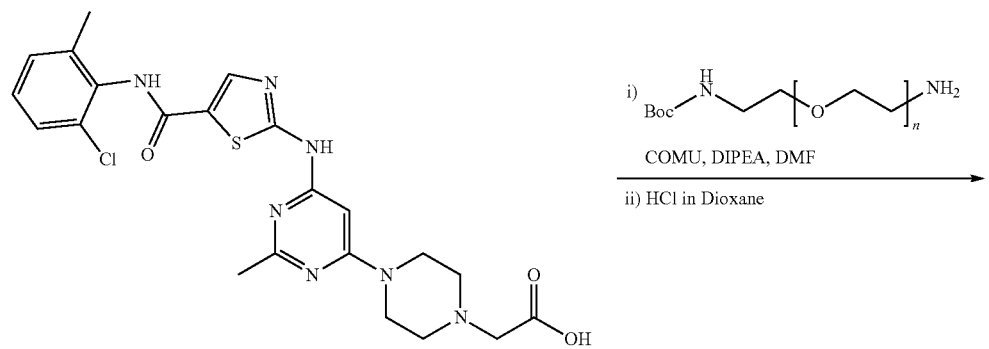

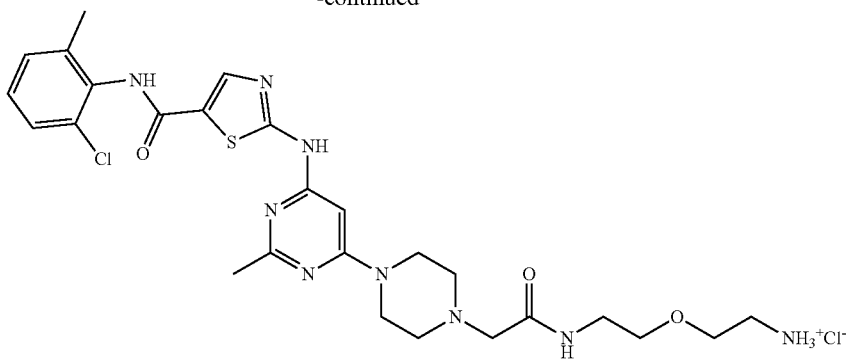

To a solution of mono-Boc protected diamine linker (0.1 mmol, 1 eq) and Dasatinib-COOH (50 mg, 0.1 mmol, 1 eq) in DMF (1 mL), COMU (43 mg, 1 mmol, 1 eq) and DIPEA (48 μL) were added. The reaction mixture was stirred at room temperature for 1 hour, then quenched with ice cold water. Volatiles were removed in vacuum and the crude mixture was purified by preparative HPLC (METHOD 2).

Fractions containing the desired product were evaporated under reduced pressure and the residue was dissolved in DCM (1 mL) and treated with a solution of anhydrous HCl in dioxane (4M, 1 mL). After 1 hour, volatiles were removed under reduced pressure and the residue was freeze dried in order to remove any excess of acid. Analytical data (HRMS) are provided in table IV shown below.

| Example | Structure | m/z [M + H]$^+$ |
|---|---|---|
| S15 | 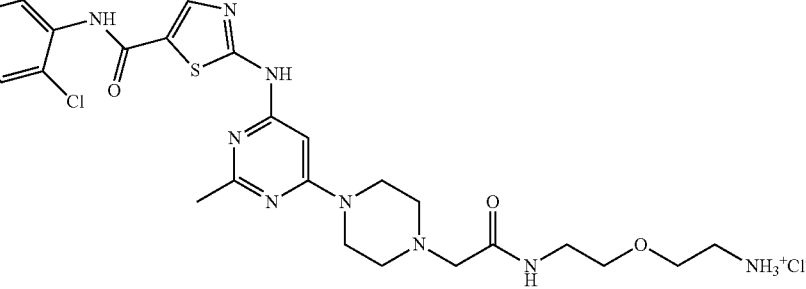 | 588.2194 |
| S16 | 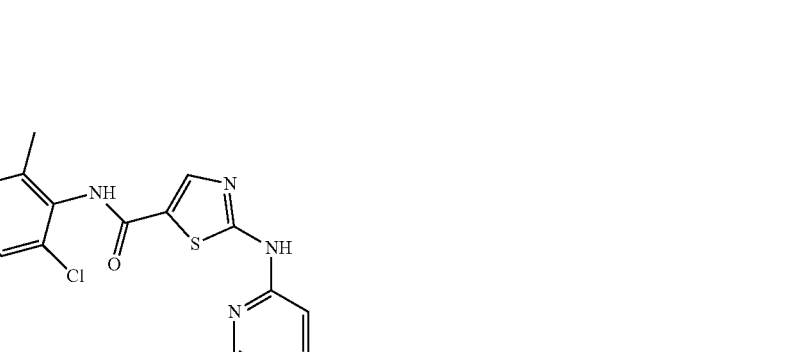 | 676.2718 |

-continued
| Example | Structure | m/z [M + H]+ |
|---|---|---|
| S17 | 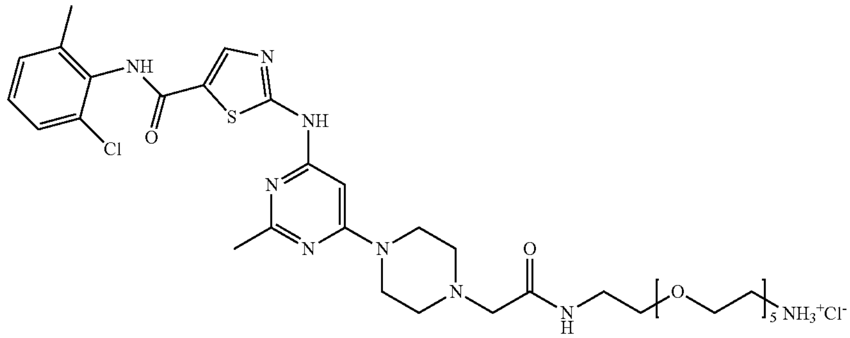 | 764.3242 |
| S18 | 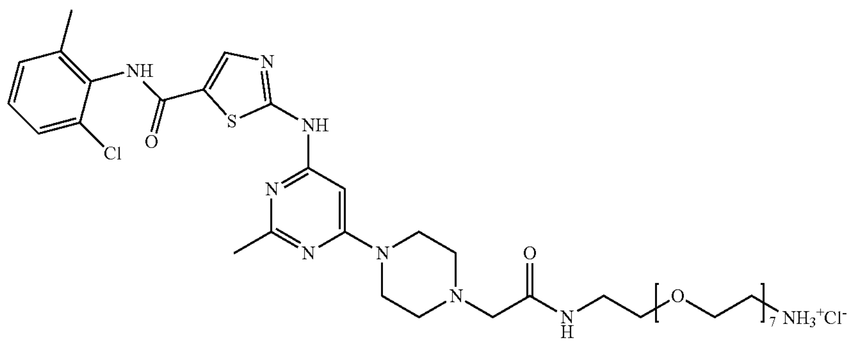 | 852.3767 |
| S19 | 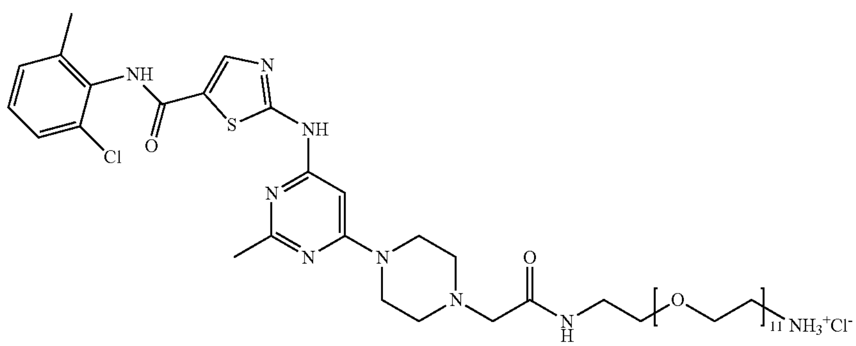 | 1028.4815 |
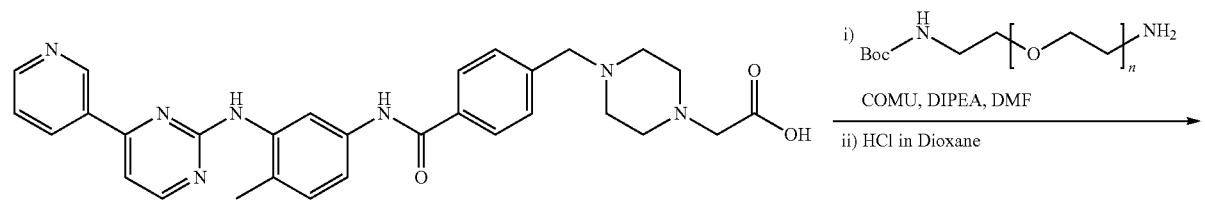
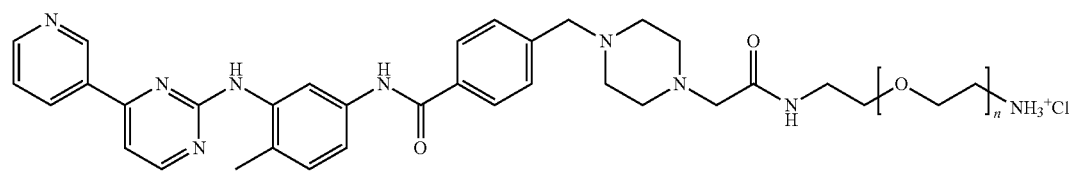

To a solution of mono-Boc protected diamine linker (0.1 mmol, 1 eq) and Imatinib-COOH (54 mg, 0.1 mmol, 1 eq) in DMF (1 mL), COMU (43 mg, 1 mmol, 1 eq) and DIPEA (48 µL) were added. The reaction mixture was stirred at room temperature for 1 hour, then quenched with ice cold water. Volatiles were removed in vacuum and the crude mixture was purified by preparative HPLC (METHOD 2).

Fractions containing the desired product were evaporated under reduced pressure and the residue was dissolved in DCM (1 mL) and treated with a solution of anhydrous HCl in dioxane (4M, 1 mL). After 1 hour, volatiles were removed under reduced pressure and the residue was freeze dried in order to remove any excess of acid. Analytical data (HRMS) are provided in table V shown below.

| Example | Structure | m/z [M + H]+ |
|---|---|---|
| S20 | 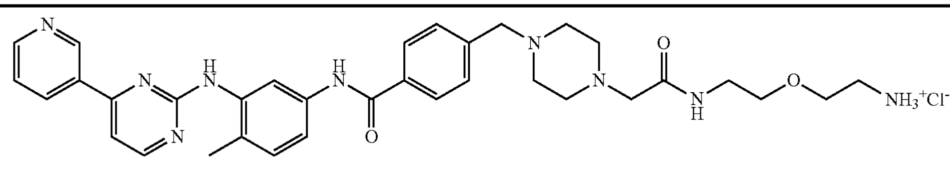 | 624.3332 |
| S21 | 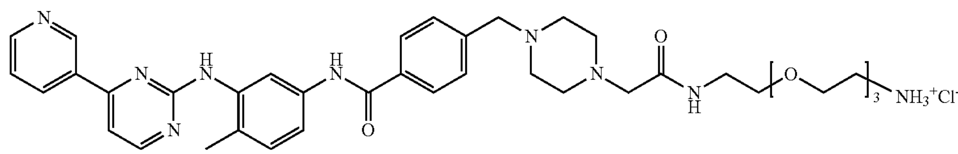 | 712.3857 |
| S22 | 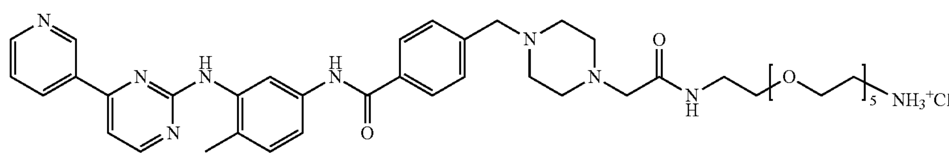 | 800.4381 |
| S23 | 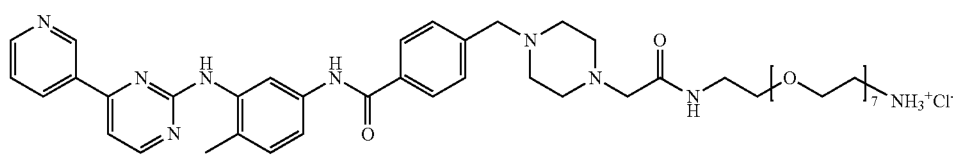 | 888.4905 |
| S24 | 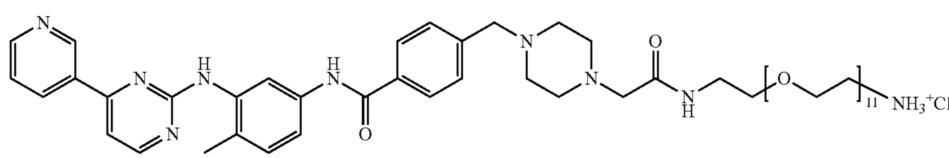 | 1064.5954 |

Example 6—Preparation of 8-(Cert-butylthio)-6-cyanoquinoline-3-carboxylic acid

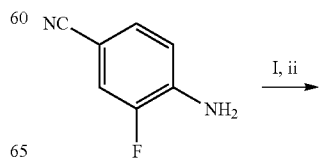

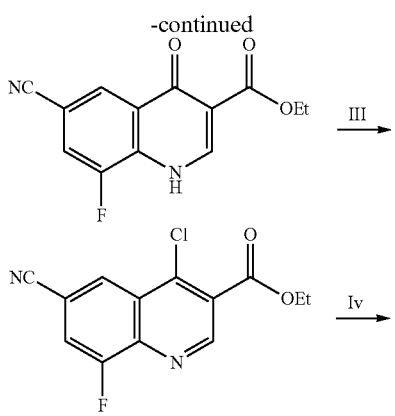

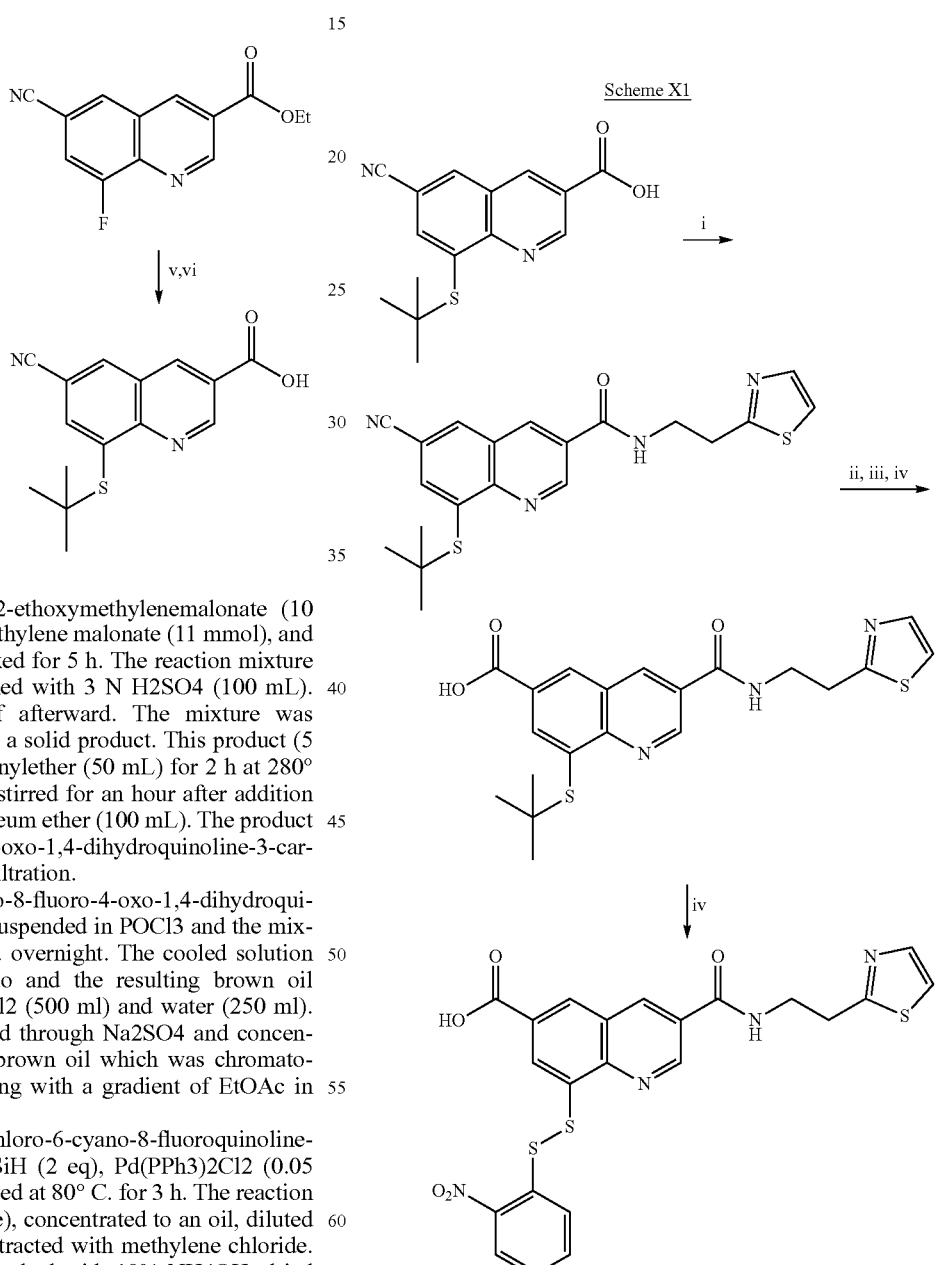

A mixture of diethyl 2-ethoxymethylenemalonate (10 mmol), diethyl 2 ethoxymethylene malonate (11 mmol), and toluene (30 mL) was refluxed for 5 h. The reaction mixture was then cooled and washed with 3 N H2SO4 (100 mL). Toluene was distilled off afterward. The mixture was scratched vigorously to get a solid product. This product (5 g) was refluxed with diphenylether (50 mL) for 2 h at 280° C. It was then cooled and stirred for an hour after addition of a small amount of petroleum ether (100 mL). The product ethyl 6-cyano-8-fluoro-4-oxo-1,4-dihydroquinoline-3-carboxylate was isolated by filtration.

The crude ethyl 6-cyano-8-fluoro-4-oxo-1,4-dihydroquinoline-3-carboxylate was suspended in POCl3 and the mixture was heated at 100° C. overnight. The cooled solution was concentrated in vacuo and the resulting brown oil partitioned between CH2Cl2 (500 ml) and water (250 ml). Organic extracts were dried through Na2SO4 and concentrated in vacuo to give a brown oil which was chromatographed on silica gel eluting with a gradient of EtOAc in Heptane.

A mixture of ethyl 4-chloro-6-cyano-8-fluoroquinoline-3-carboxylate (1 eq), Et3SiH (2 eq), Pd(PPh3)2Cl2 (0.05 eq), in acetonitrile was heated at 80° C. for 3 h. The reaction mixture was filtered (Celite), concentrated to an oil, diluted with 10% NH4OH, and extracted with methylene chloride. The organic extract was washed with 10% NH4OH, dried (MgSO4), and concentrated to give ethyl 6-cyano-8-fluoroquinoline-3-carboxylate as a yellow solid (40 g, 0.18 mol, 95%).

To a solution of ethyl 6-cyano-8-fluoroquinoline-3-carboxylate (1 eq) in DMF, tBuSH and Cs2CO3 (3 eq), were added. The mixture was stirred at 130° C. for 18 h. The solution was evaporated to dryness and the crude material was taken up in water and acidified with 6M HCl until a precipitate was formed (pH 2). The precipitate was filtered and dried under vacuum. The crude (1 eq) was dissolved in ethanol and treated with LiOH (1M, 2 eq), at room temperature until consumption of the starting material. The reaction mixture was carefully acidified to pH=4, volatile were removed and the product 8-(tert-butylthio)-6-cyanoquinoline-3-carboxylic acid was isolated by crystallization.

Example 7—Preparation of 8-((2-nitrophenyl)disulfaneyl)-3-((2-(thiazol-2-yl)ethyl)carbamoyl)quinoline-6-carboxylic acid Scheme X1 i) 2-(thiazol-2-yl)ethan-1-amine, COMU, DIPEA, DMF; ii) NaOME in MeOH, then aq. HCl, then LiOH; iv) 2-nitrophenyl hypochlorothioite in acetic acid.

To a solution of 8-(tert-butylthio)-6-cyanoquinoline-3-carboxylic acid (1 eq) and 2-(thiazol-2-yl)ethan-1-amine (1 eq) in DMF (50 mL per mmol), COMU (1 eq) and DIPEA (3 eq) were added. The reaction mixture was stirred at room temperature until consumption of the starting materials. The crude mixture was then poured in iced water and the product 8-(tert-butylthio)-6-cyano-N-(2-(thiazol-2-yl)ethyl)quinoline-3-carboxamide was isolated by filtration.

To a mixture of 8-(tert-butylthio)-6-cyano-N-(2-(thiazol-2-yl)ethyl)quinoline-3-carboxamide in anhydrous methanol, a solution of sodium methoxide (1,1 eq, 1 M in methanol) was added dropwise at 0° C. The reaction was slowly let to warm up to room temperature overnight. HPLC analysis (METHOD 1A) of the reaction mixture showed complete conversion to the imino ether. 2M HCl was added until pH=2 and the reaction was stirred for 2 hours at room temperature. HPLC analysis (METHOD 1A) showed conversion of the imino ether to the corresponding methyl ester. At this point, a solution of 1M NaOH was added dropwise until pH=11. The mixture was stirred until HPLC analysis (METHOD 1A) showed formation of the desired acid. Water was added and careful acidification (pH=4) of the reaction mixture with 1 M HCl produced the formation of a precipitate which was extracted with a mixture of isopropanol (10%) in chloroform. The organic extract was dried over MgSO4 and purified by FCC (gradient of MeOH in DCM) to produced analytically pure 8-(tert-butylthio)-3-((2-(thiazol-2-yl)ethyl)carbamoyl)quinoline-6-carboxylic acid.

A mixture of 8-(tert-butylthio)-3-((2-(thiazol-2-yl)ethyl)carbamoyl)quinoline-6-carboxylic acid (1 eq) in acetic acid (100 mL per mmol) was treated with 2-nitrophenyl hypochlorothioite for 2 hours. HPLC analysis (METHOD 1 Å) showed complete conversion to the desired product, which was isolated by treating the reaction mixture with an excess of iced water. The product was isolated by filtration and dried under vacuum.

Example 8—3-((4-fluorobenzyl)carbamoyl)-8-((2-nitrophenyl)disulfaneyl)quinoline-6-carboxylic acid This derivative was prepared from 8-(tert-butylthio)-6-cyanoquinoline-3-carboxylic acid and 4-fluorobenzyl amine using the same procedure described for the preparation of 84(2-nitrophenyl)disulfaneyl)-3-((2-(thiazol-2-yl)ethyl)carbamoyl)quinoline-6-carboxylic acid.

Example 9 —Preparation of Capzimin Conjugates

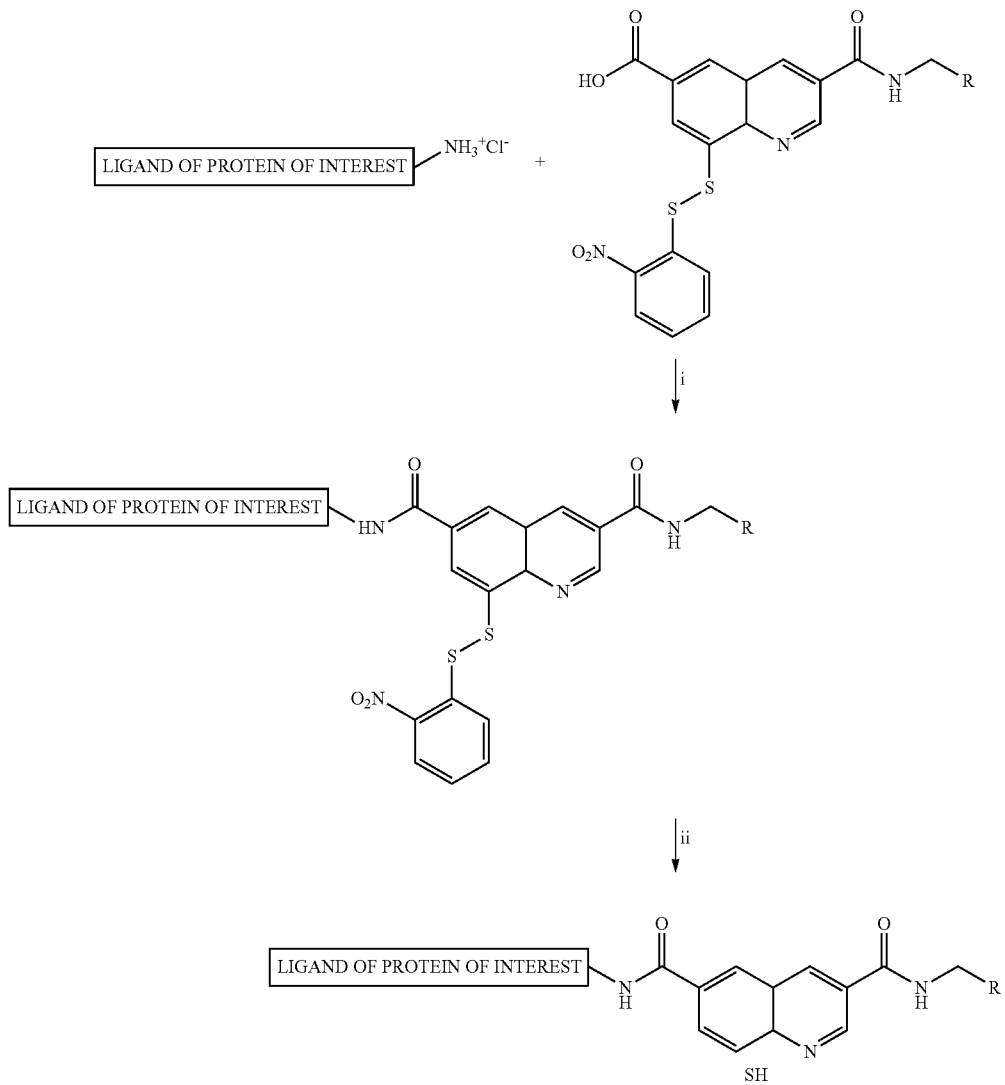

Scheme X2

-continued

R = 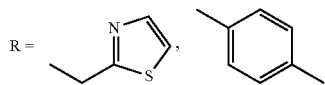

i) COMU, DIPEA, DMF; ii) TCEP, MeOH. To a solution of warhead-linker amine (0.01 mmol) in DMF (0.05 M), 8-((2-nitrophenyl)disulfaneyl)-3-((2-(thiazol-2-yl)ethyl)carbamoyl)quinoline-6-carboxylic acid (or 3-((4-fluorobenzyl)carbamoyl)-8-((2-nitrophenyl)disulfaneyl)quinoline-6-carboxylic acid) (0.01 mmol), COMU (0.01 mmol) and DIPEA (0.05 mmol) were added. The reaction mixture was left to react for 1 hour at room temperature, then water was added and solvents were removed under vacuum. The crude material was purified by reverse phase HPLC (METHOD 1). Solvents were removed under reduced pressure and the purified conjugated was dissolved in methanol (1mL). TCEP (0.05 mmol) were added and the mixture was left to react for 2 hours at room temperature, before being directly injected in preparative HPLC (METHOD 1) to obtain the final compounds.

Analytical data (HRMS) are provided in tables VI-IX shown below.

| Example | Structure | m/z [M + H]$^+$ |
|---|---|---|
| 11JQ1 | 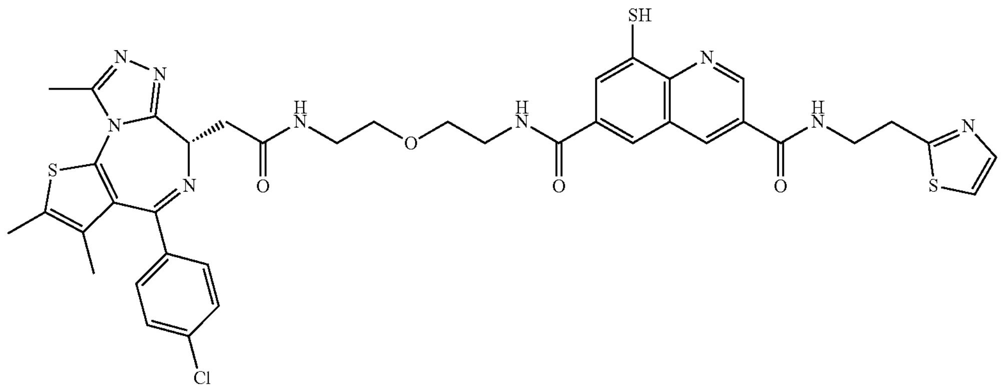 [SMILES: Cc1sc2c(c1C)C(c1ccc(Cl)cc1)=N[C@@H](CC(=O)NCCOCCNC(=O)c1cc(S)c3ncc(C(=O)NCCc4nccs4)cc3c1)c1nnc(C)n1-2] | 828.1897 |
| 11JQ2 | 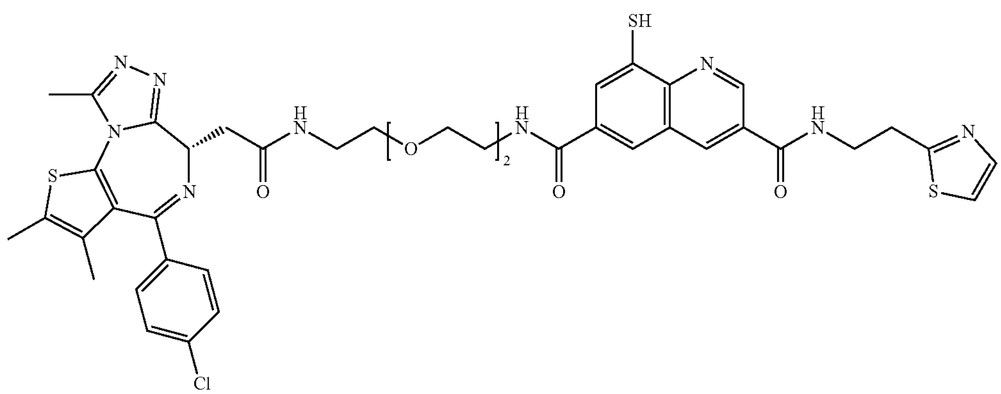 | 872.2160 |
| 11JQ3 | 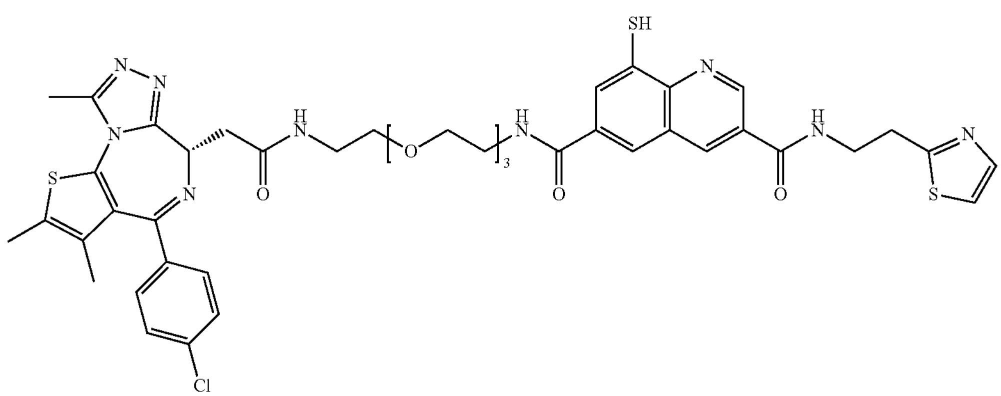 | 916.2422 |

-continued

| Example | Structure | m/z [M + H]+ |
|---------|-----------|--------------|
| 11JQ4 | 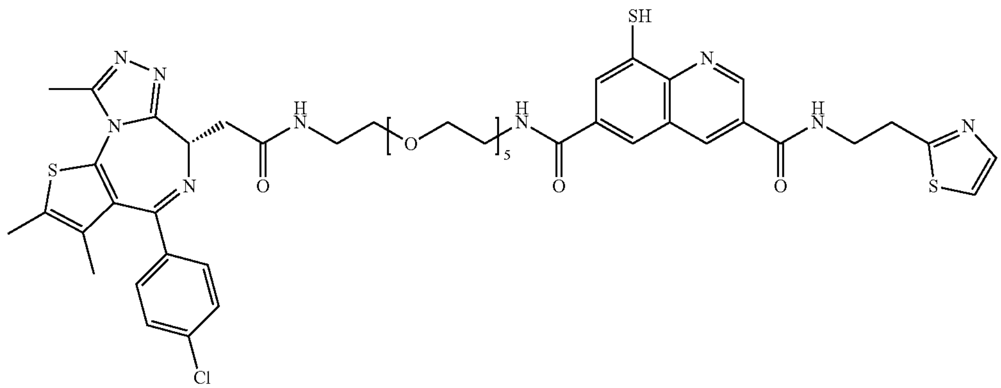 | 1004.2946 |
| 11JQ5 | 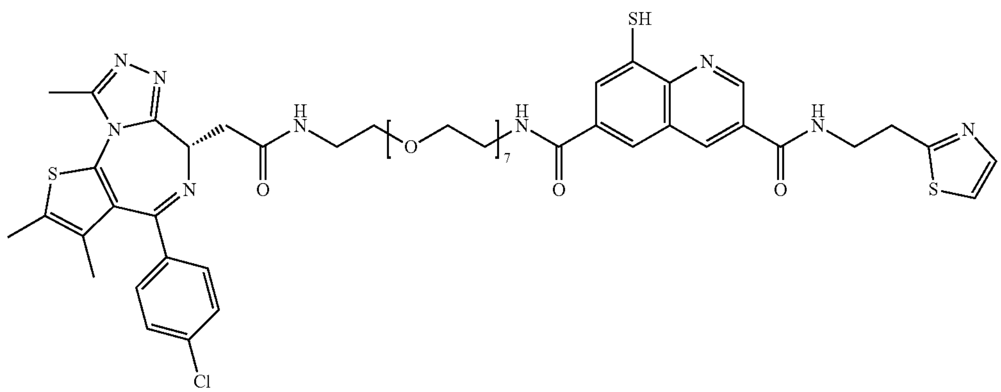 | 1092.3470 |
| 11JQ6 | 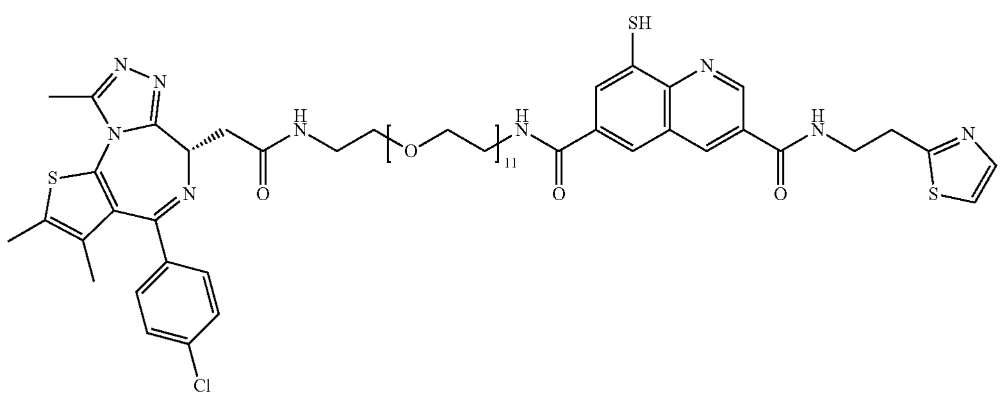 | 1268.4519 |
| 11JQ7 | 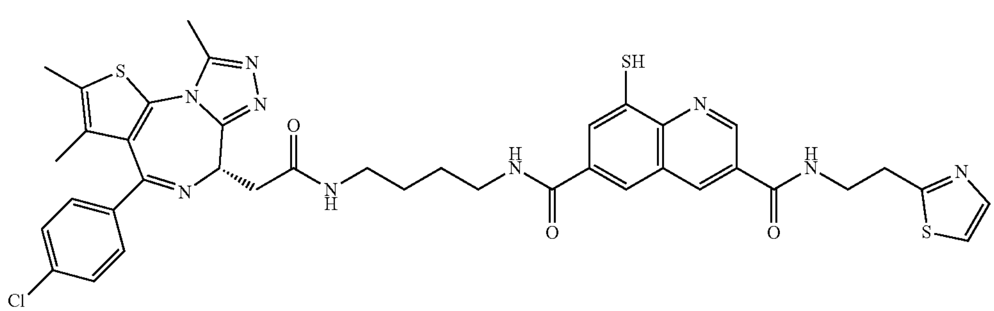 [SMILES: Cc1sc2c(c1C)C(c1ccc(Cl)cc1)=N[C@@H](CC(=O)NCCCCNC(=O)c1cc(S)c3ncc(C(=O)NCCc4nccs4)cc3c1)c1nnc(C)n1-2] | 812.1948 |

-continued
| Example | Structure | m/z [M + H]+ |
|---|---|---|
| 11JQ8 | 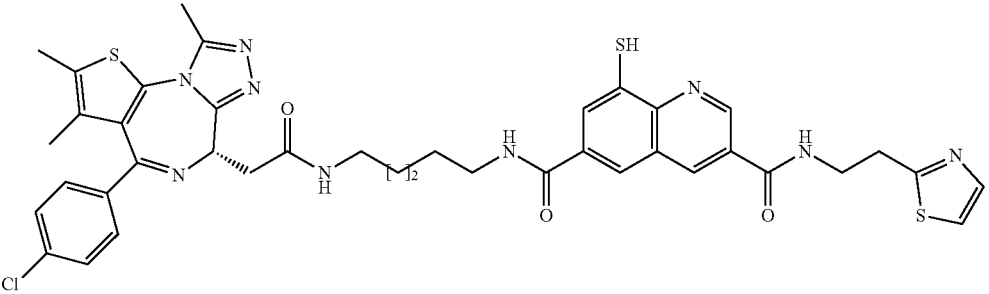 | 826.2105 |
| 11JQ9 | 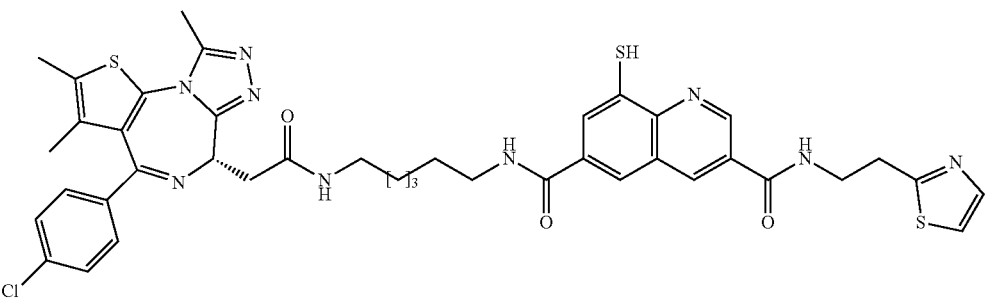 | 840.2261 |
| 11JQ10 | 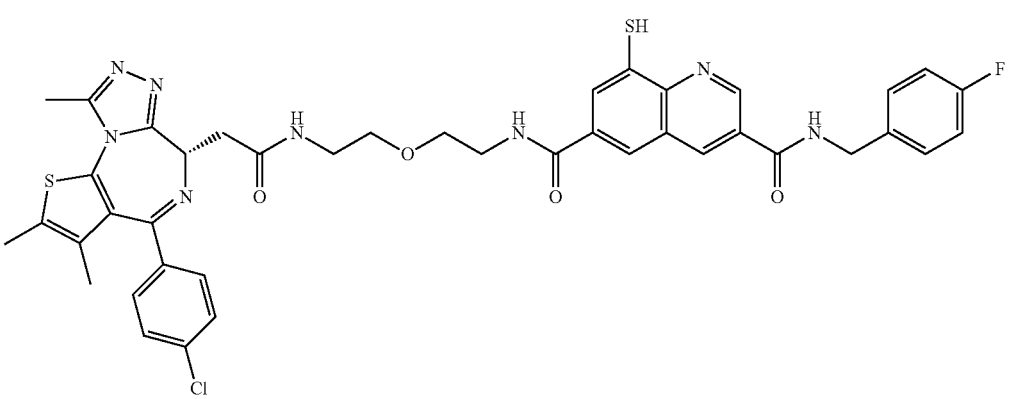 [SMILES: Cc1sc2c(c1C)C(c1ccc(Cl)cc1)=N[C@@H](CC(=O)NCCOCCNC(=O)c1cc(S)c3ncc(C(=O)NCc4ccc(F)cc4)cc3c1)c1nnc(C)n1-2] | 825.2130 |
| 11JQ11 | 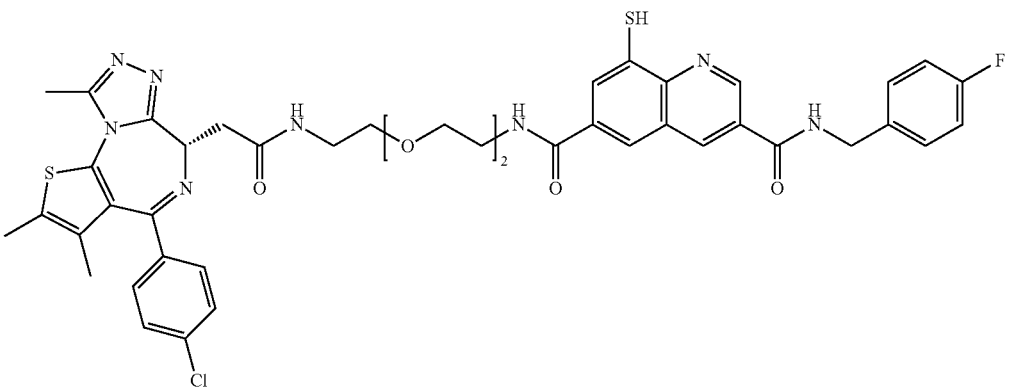 | 869.2392 |

| Example | Structure | m/z [M + H]⁺ |
|---|---|---|
| 11JQ12 | 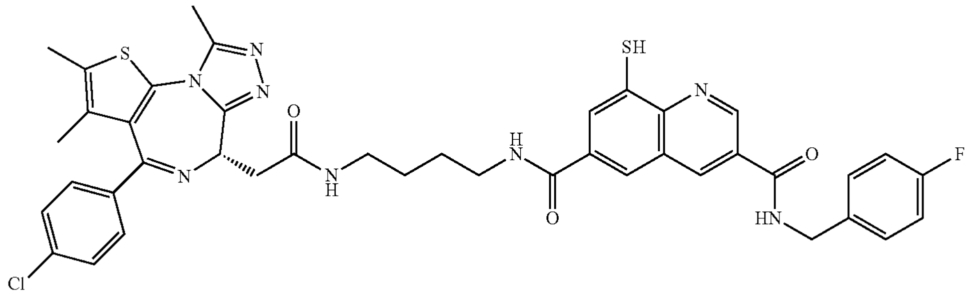 [SMILES: Cc1sc2c(c1C)C(c1ccc(Cl)cc1)=N[C@@H](CC(=O)NCCCCNC(=O)c1cc(S)c3ncc(C(=O)NCc4ccc(F)cc4)cc3c1)c1nnc(C)n1-2] | 809.2181 |
| 11JQ13 | 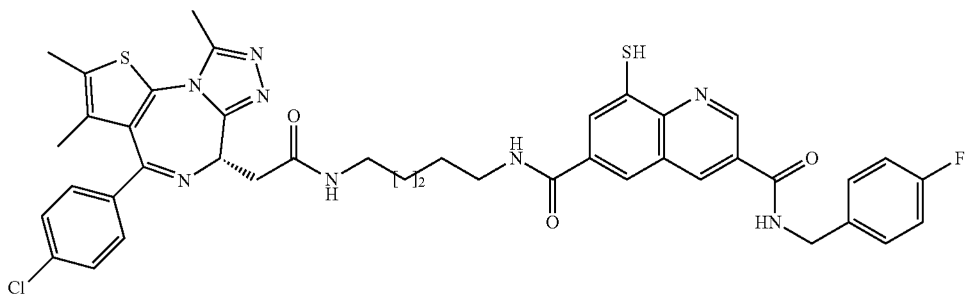 | 823.2337 |
| 11JQ14 | 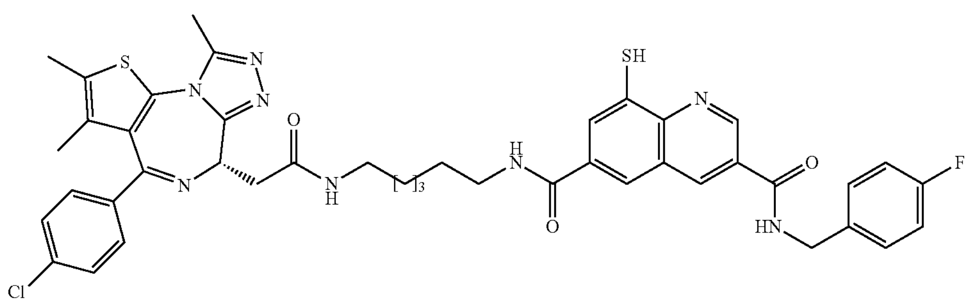 | 837.2494 |

TABLE VII

| Example | Structure | m/z [M + H]⁺ |
|---|---|---|
| 11IB1 | 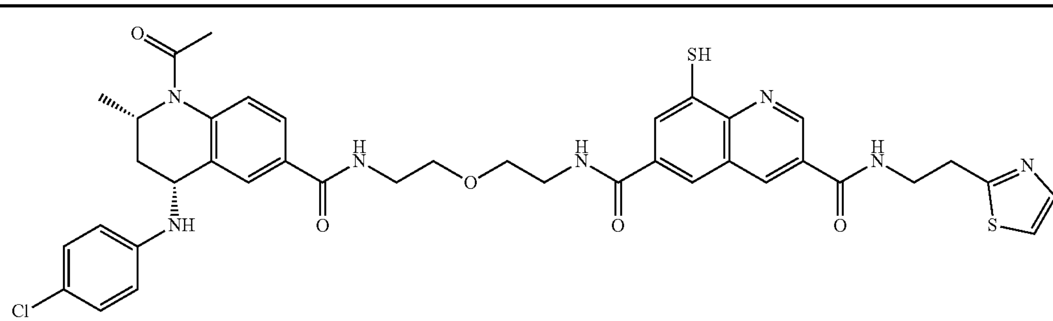 | 786.2221 |

TABLE VII-continued

| Example | Structure | m/z [M + H]+ |
|---|---|---|
| 11IB2 | 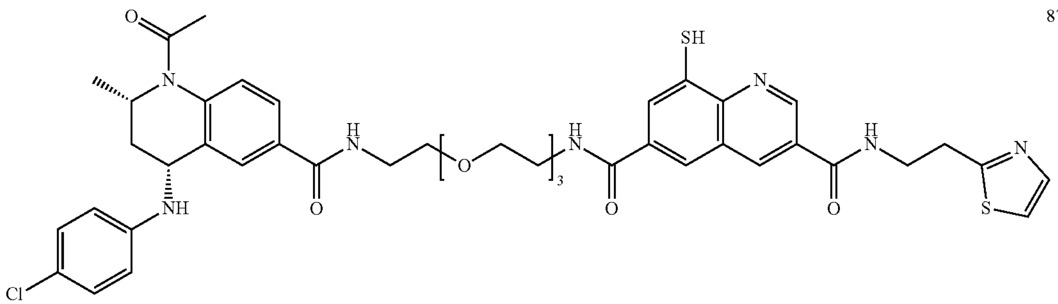 | 874.2745 |
| 11IB3 | 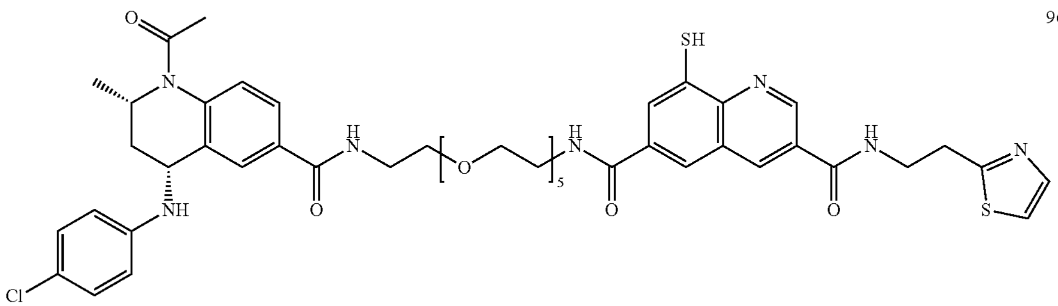 | 962.3269 |
| 11IB4 | 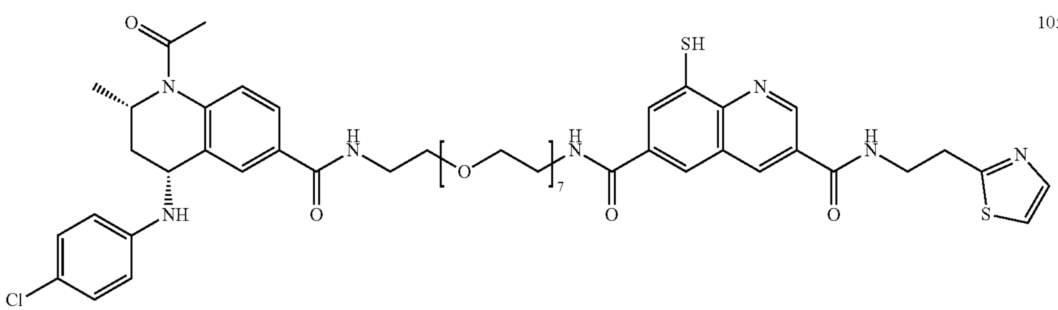 | 1050.3794 |
| 11IB5 | 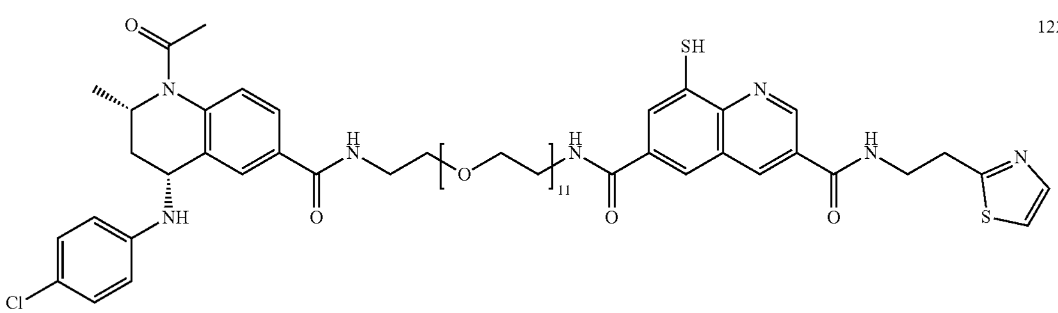 | 1226.4842 |

TABLE VIII

| Example | Structure | m/z [M + H]+ |
|---|---|---|
| 11DA1 | 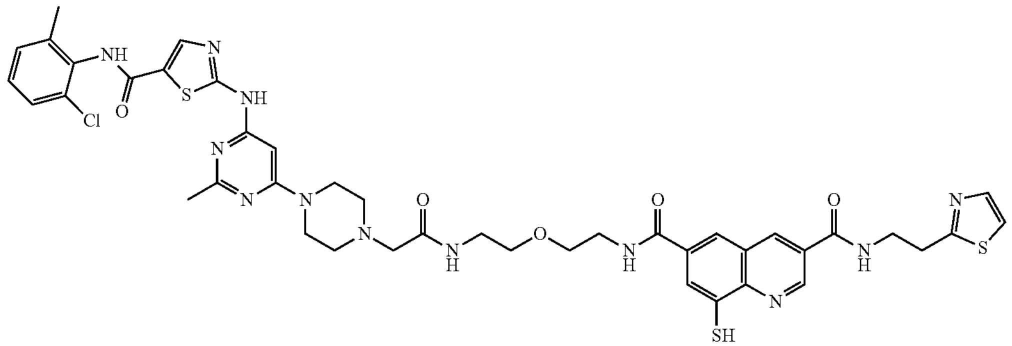 [SMILES: Cc1nc(Nc2ncc(C(=O)Nc3c(C)cccc3Cl)s2)cc(N2CCN(CC(=O)NCCOCCNC(=O)c3cc(S)c4ncc(C(=O)NCCc5nccs5)cc4c3)CC2)n1] | 929.2487 |
| 11DA2 | 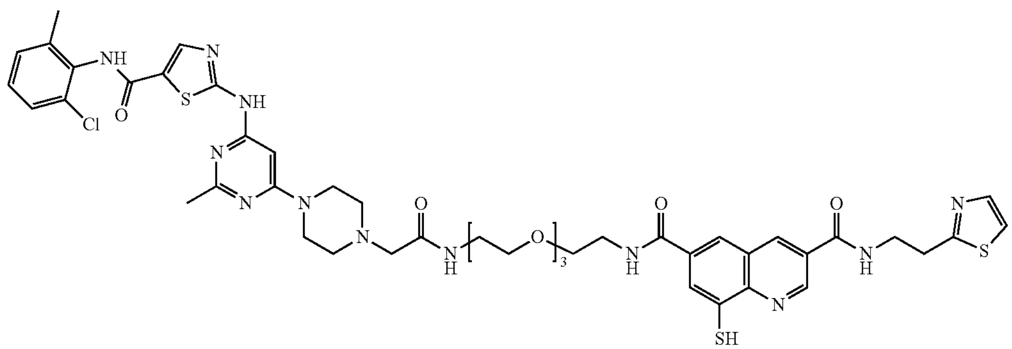 | 1017.3011 |
| 11DA3 | 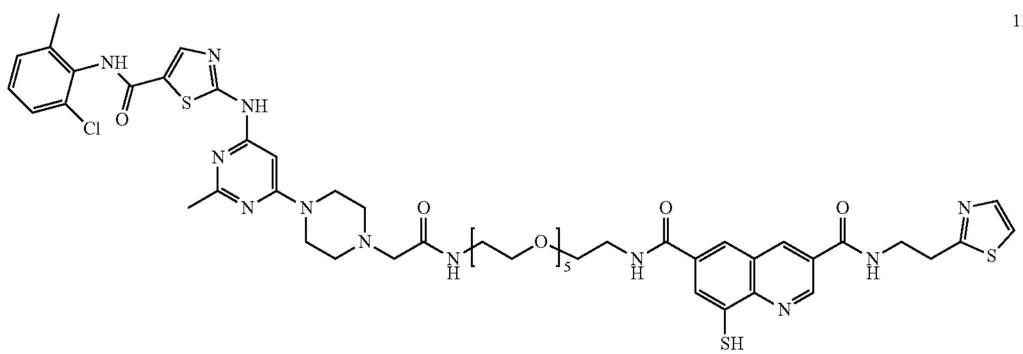 | 1105.3535 |
| 11DA4 | 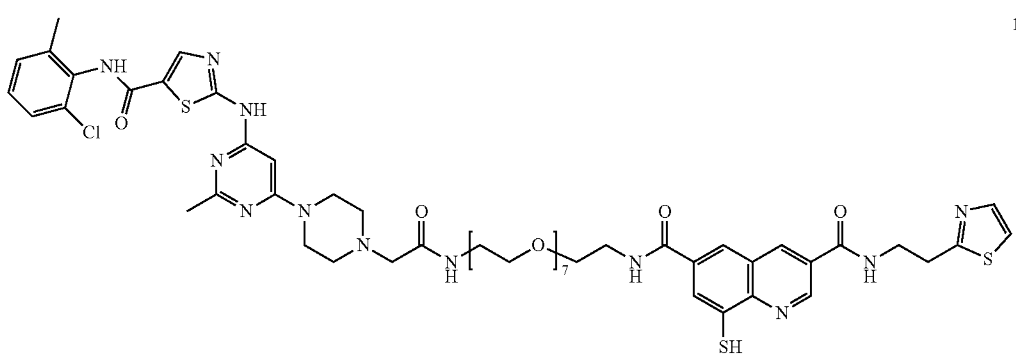 | 1193.4059 |

TABLE VIII-continued

| Example | Structure | m/z [M + H]+ |
|---|---|---|
| 11DA5 | 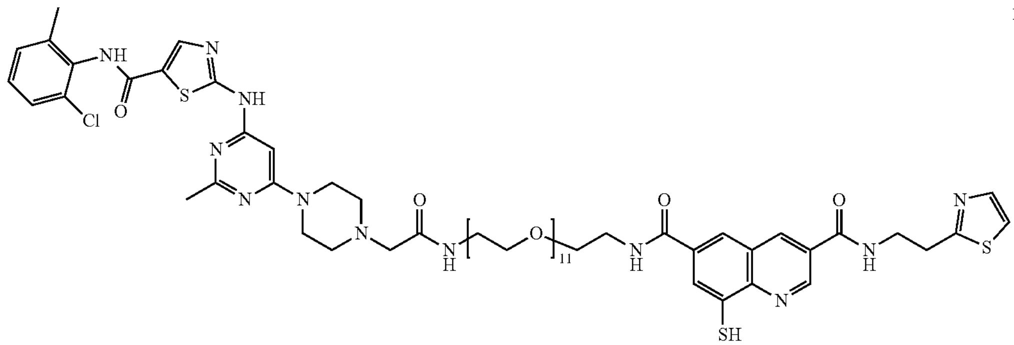 | 1369.5108 |

TABLE IX

| Example | Structure | m/z [M + H]+ |
|---|---|---|
| 11IM1 | 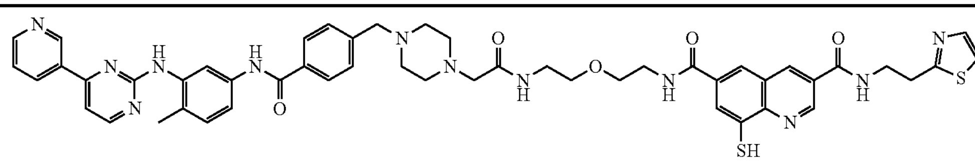 | 965.3625 |
| 11IM2 | | 1053.4149 |
| 11IM2 | | 1141.4674 |
| 11IM3 | 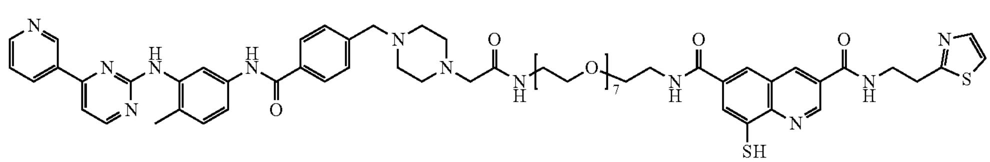 | 1229.5198 |
| 11IM4 | 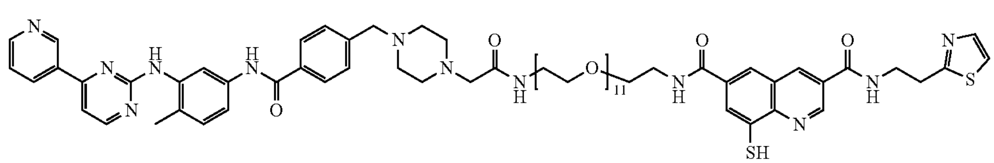 | 1405.6247 |

Example 10 — Preparation of Capzimin Conjugates-Benzoyl Ester Prodrugs

Method 1.

To a solution of warhead-linker amine (0.01 mmol) in DMF (0.05 M), 8-((2-nitrophenyl)disulfaneyl)-3-((2-(thiazol-2-yl)ethyl)carbamoyl)quinoline-6-carboxylic acid (0.01 mmol), COMU (0.01 mmol) and DIPEA (0.05 mmol) were added. The reaction mixture was left to react for 1 hour at room temperature, then water was added and solvents were removed under vacuum. The crude material was purified by reverse phase HPLC (METHOD 1). Solvents were removed under reduced pressure and the purified conjugated was dissolved in methanol (1 mL). TCEP (0.05 mmol) were added and the mixture was left to react for 2 hours at room temperature. Methanol was removed under vacuum and the crude mixture was suspended in anhydrous DCM (3 mL). TEA was added until pH=10 before beznoyl chloride (0.07 mmol) was added dropwise. After 1 hour at room temperature, HPLC analysis showed formation of the thioester. The solvent was removed under reduced pressure, the crude was dissolved in methanol and then injected in preparative HPLC (METHOD 1) to obtain the final compounds.

Method 2.

To a mixture 8-((2-nitrophenyl)disulfaneyl)-34(2-(thiazol-2-yl)ethyl)carbamoyl)quinoline-6-carboxylic acid (1 eq) in acetonitrile/water 8:2 (100 mL per mmol), TCEP (hydrochloride salt, 3 eq) was added. After 30 minutes, HPLC analysis (METHOD 1A) showed formation of the free thiol. Benzoyl chloride (1.5 eq) was added and the mixture was left to react at room temperature for 1 hour. The crude was concentrated under reduced pressure, dissolved in methanol and then injected in preparative HPLC (METHOD 1) to obtain pure 8-(benzoylthio)-3-((2-(thiazol-2-yl)ethyl)carbamoyl)quinoline-6-carboxylic acid. To a solution of warhead-linker amine (0.01 mmol) in DMF (0.05 M), 8-(benzoylthio)-3-((2-(thiazol-2-yl)ethyl)carbamoyl)quinoline-6-carboxylic acid (0.01 mmol), COMU (0.01 mmol) and DIPEA (0.05 mmol) were added. The reaction mixture was left to react for 1 hour at room temperature, solvents were removed under vacuum. The crude material was purified by reverse phase HPLC (METHOD 1). Analytical data (FIRMS) are provided in table X shown below

| Example | Structure | m/z [M + H]+ |
|---|---|---|
| 11JQ15 | 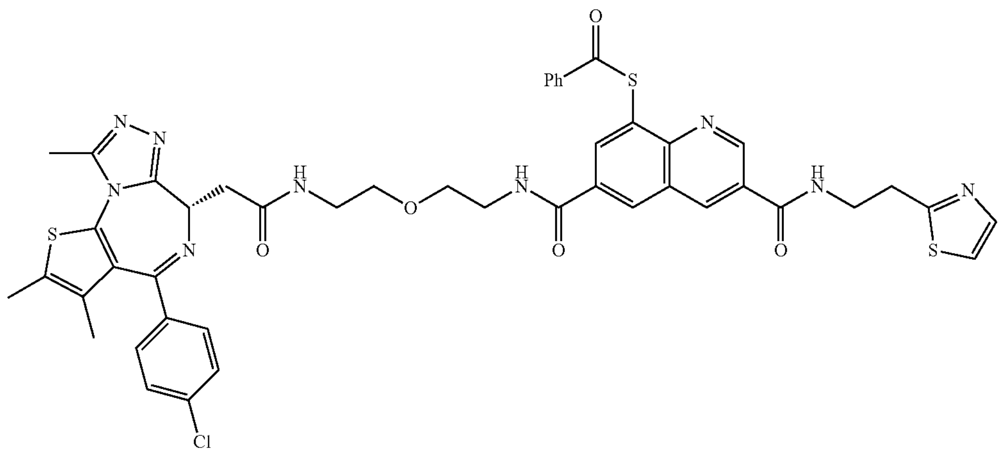 [SMILES: Cc1sc2c(c1C)C(c1ccc(Cl)cc1)=N[C@@H](CC(=O)NCCOCCNC(=O)c1cc(SC(=O)c3ccccc3)c3ncc(C(=O)NCCc4nccs4)cc3c1)c1nnc(C)n1-2] | 932.2160 |
| 11JQ16 | 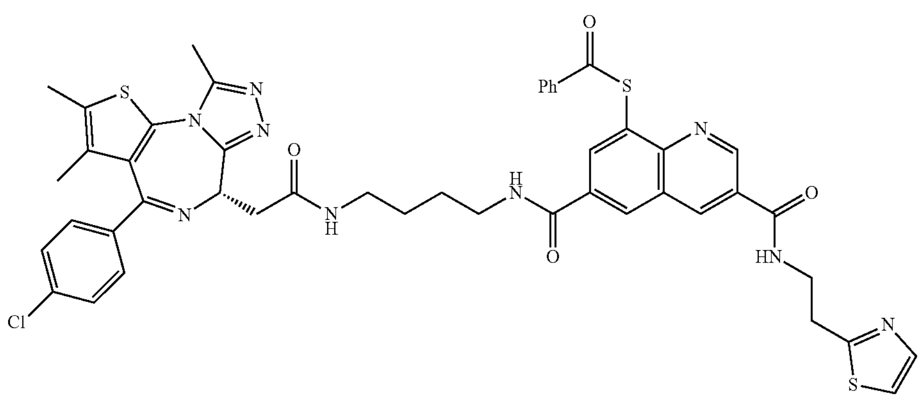 [SMILES: Cc1sc2c(c1C)C(c1ccc(Cl)cc1)=N[C@@H](CC(=O)NCCCCNC(=O)c1cc(SC(=O)c3ccccc3)c3ncc(C(=O)NCCc4nccs4)cc3c1)c1nnc(C)n1-2] | 916.2210 |

Example 11—Preparation of Negative Controls and 8-thioquinoline Conjugates

To a solution of warhead-linker amine (0.01 mmol) in DMF (0.05 M), 8-(tert-butylthio)-6-cyanoquinoline-3-carboxylic acid (0.01 mmol), COMU (0.01 mmol) and DIPEA (0.05 mmol) were added. The reaction mixture was left to react for 1 hour at room temperature, then water was added and solvents were removed under vacuum. The crude material was purified by reverse phase HPLC (METHOD 1) to obtain the final compounds.

| Example | Structure | m/z [M + H]⁺ |
|---|---|---|
| 11JQ17 | 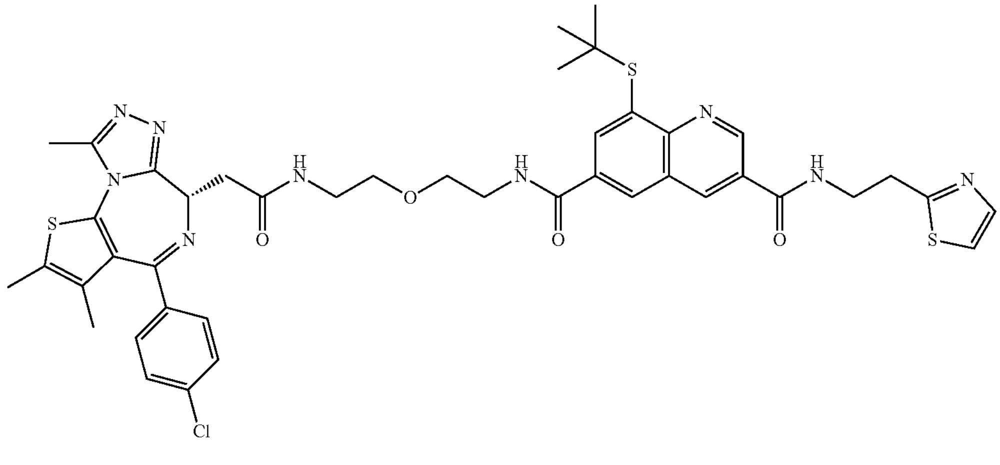 [SMILES: Cc1sc2c(c1C)C(c1ccc(Cl)cc1)=N[C@@H](CC(=O)NCCOCCNC(=O)c1cc(SC(C)(C)C)c3ncc(C(=O)NCCc4nccs4)cc3c1)c1nnc(C)n1-2] | 884.2523 |
| 11JQ18 | 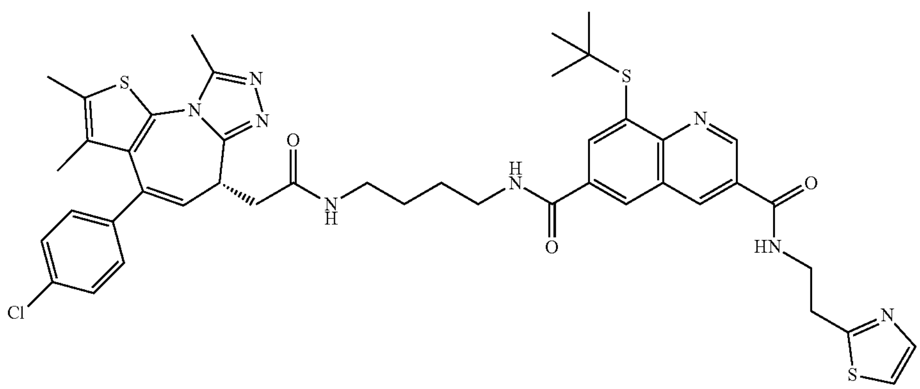 [SMILES: Cc1sc2c(c1C)C(c1ccc(Cl)cc1)=C[C@@H](CC(=O)NCCCCNC(=O)c1cc(SC(C)(C)C)c3ncc(C(=O)NCCc4nccs4)cc3c1)c1nnc(C)n1-2] | 868.2574 |

Preparation of 8-thioquinoline Conjugates:

To a solution of warhead-linker amine (0.01 mmol) in DMF (0.05 M), 8,8'-disulfanediylbis(quinoline-3-carboxylic acid) (0.005 mmol), COMU (0.01 mmol) and DIPEA (0.05 mmol) were added. The reaction mixture was left to react for 1 hour at room temperature, then water was added and solvents were removed under vacuum. The crude material was purified by reverse phase HPLC (METHOD 1). Solvents were removed under reduced pressure to obtain the desired products. Analytical data (HRMS) are provided in table XIa to XId shown below.

TABLE XIa

| Example | Structure | m/z [M + 2H]⁺⁺ |
|---|---|---|
| 11JQ19 | 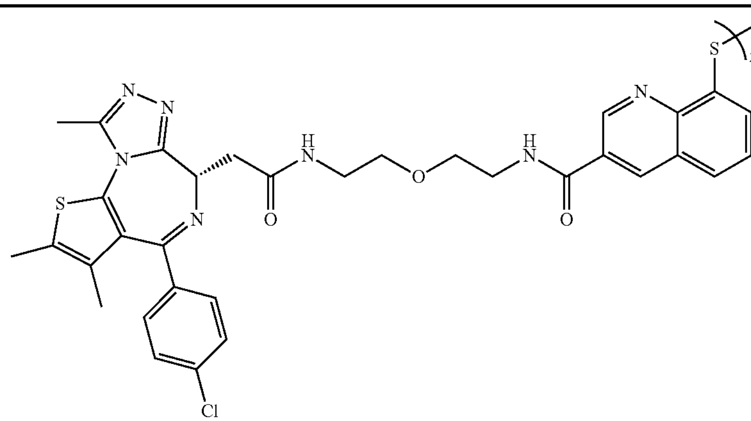 | 673.1697 |

TABLE XIa-continued
| Example | Structure | m/z [M + 2H]++ |
|---|---|---|
| 11JQ20 | 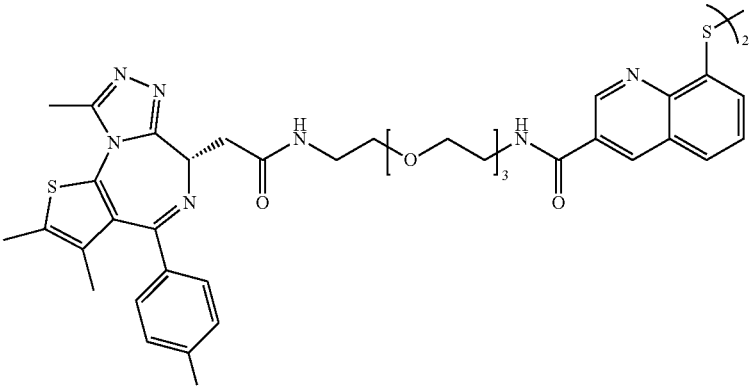 | 761.2221 |
| 11JQ21 | 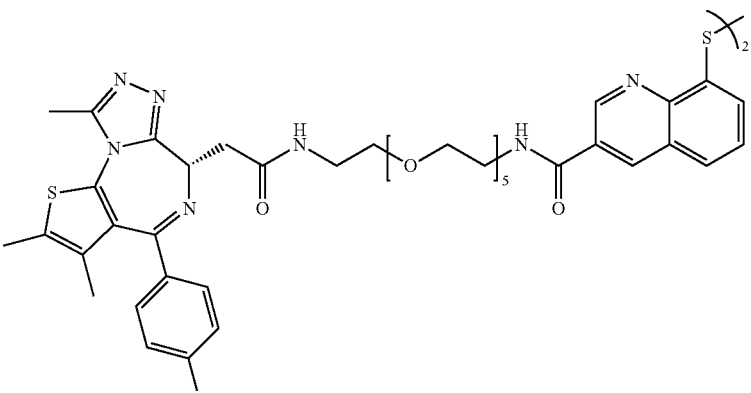 | 849.2745 |
| 11JQ22 | 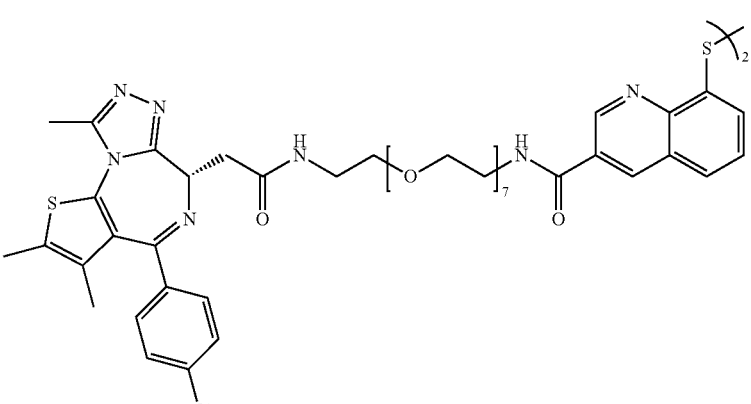 | 937.3269 |

TABLE XIa-continued
| Example | Structure | m/z [M + 2H]++ |
|---|---|---|
| 11JQ23 | 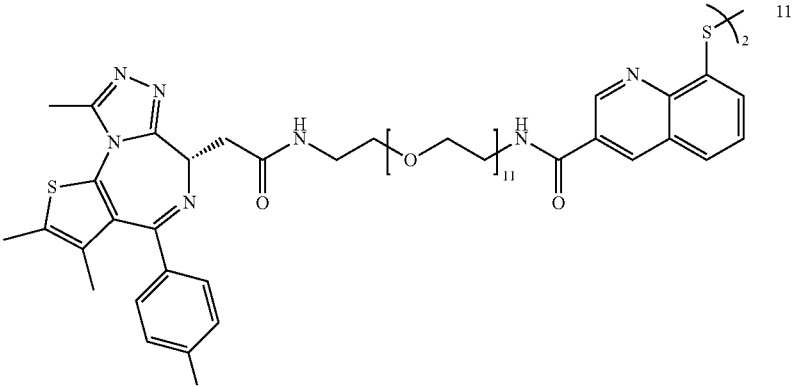 | 1113.4318 |
TABLE XIb
| Example | Structure | [M + 2H]++ |
|---|---|---|
| 11IB6 | 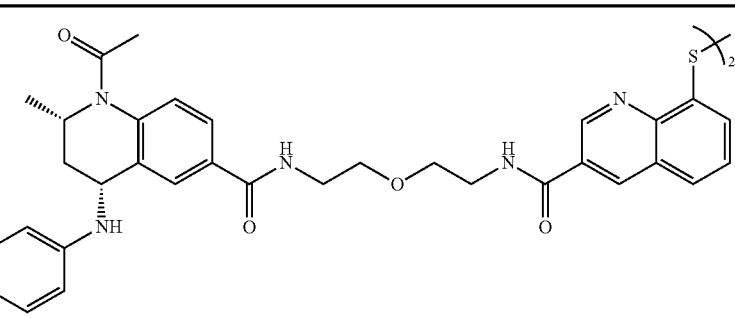 | 631.2020 |
| 11IB7 | 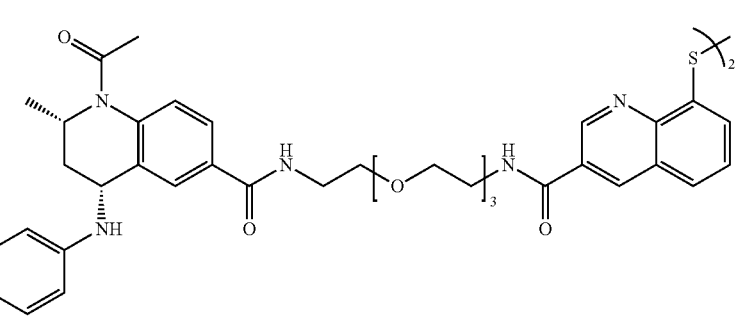 | 719.2544 |
| 11IB8 | 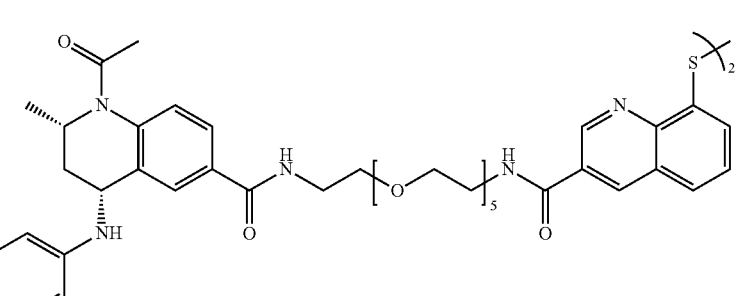 | 807.3069 |

TABLE XIb-continued
| Example | Structure | [M + 2H]++ |
|---|---|---|
| 11IB9 | 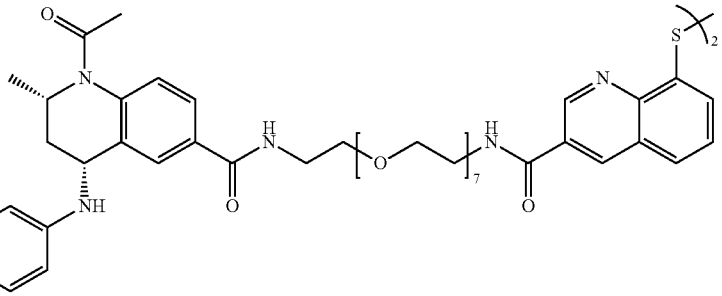 | 895.3593 |
| 11IB10 | 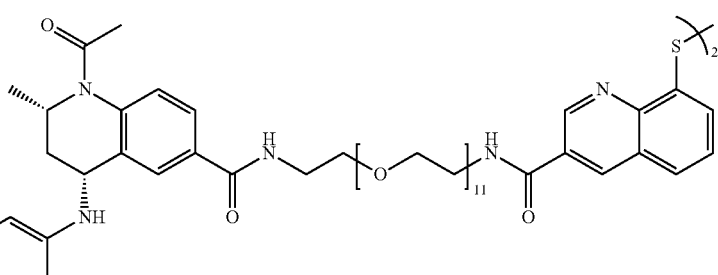 | 1071.4642 |
TABLE XIc
| Example | Structure | m/z [M + 2H]++ |
|---|---|---|
| 11DA6 | 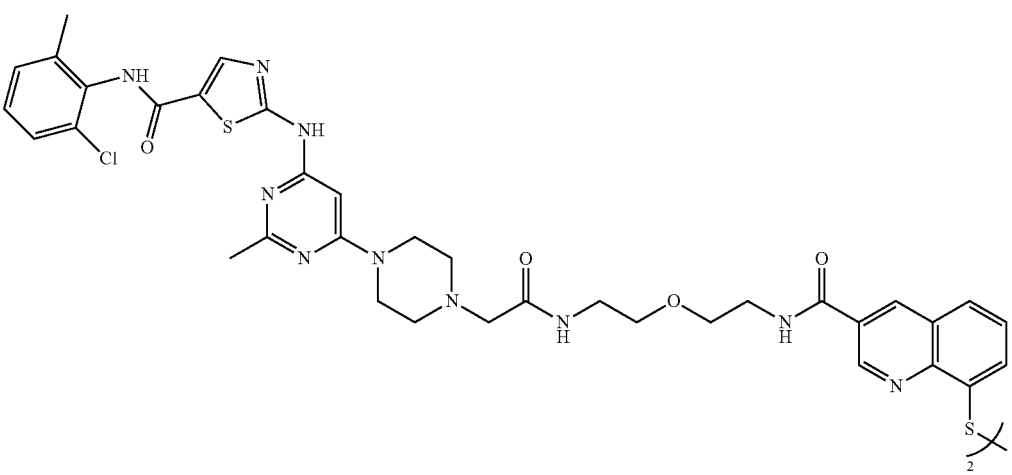 [SMILES: CSc1cccc2cc(C(=O)NCCOCCNC(=O)CN3CCN(c4cc(Nc5ncc(C(=O)Nc6c(C)cccc6Cl)s5)nc(C)n4)CC3)cnc12] | 774.2286 |

TABLE XIc-continued

| Example | Structure | m/z [M + 2H]++ |
|---|---|---|
| 11DA7 | 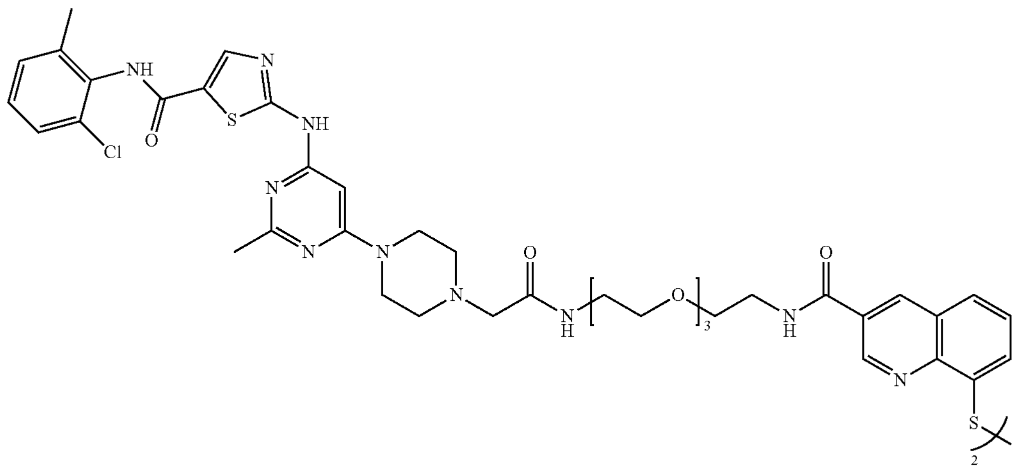 | 862.2810 |
| 11DA8 | 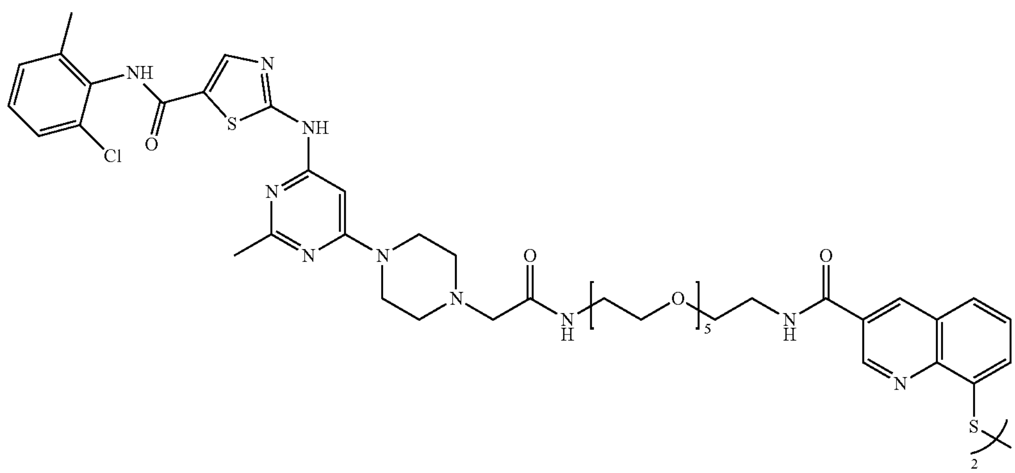 | 950.3334 |
| 11DA9 | 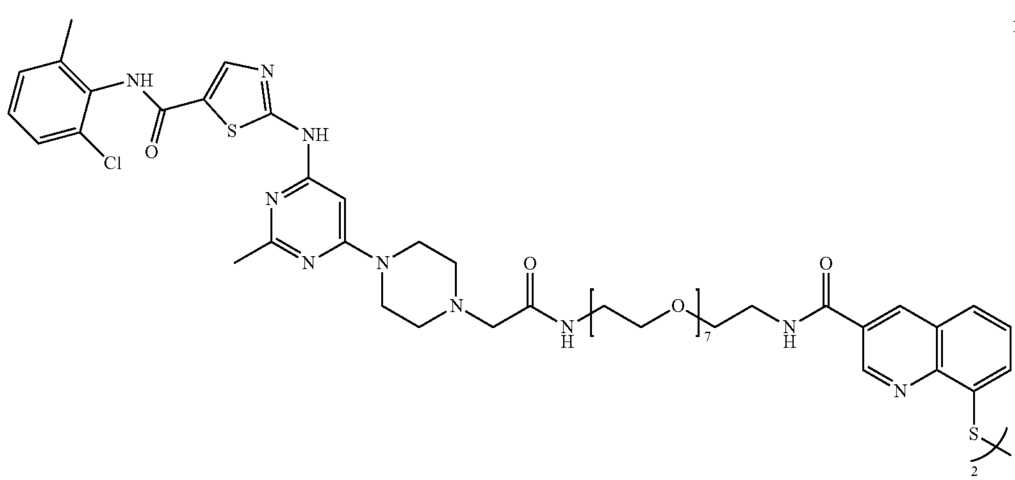 | 1038.3859 |

TABLE XIc-continued

| Example | Structure | m/z [M + 2H]++ |
|---|---|---|
| 11DA10 | 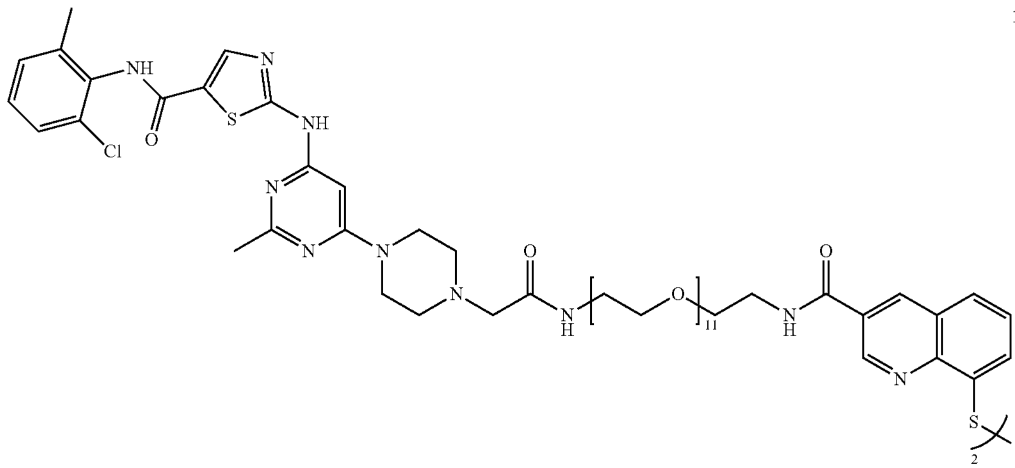 | 1214.4907 |

TABLE XId

| Example | Structure | m/z [M + 2H]++ |
|---|---|---|
| 11IM6 | 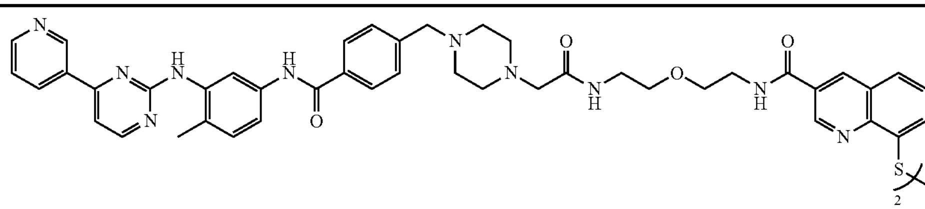 | 810.3424 |
| 11IM7 | 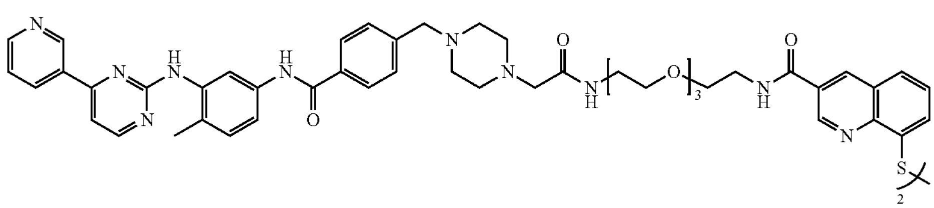 | 898.3949 |
| 11IM8 | 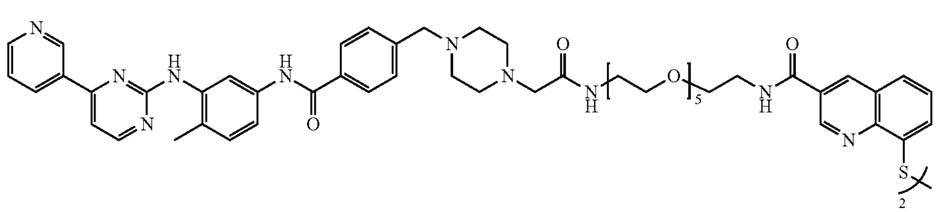 | 986.4473 |
| 11IM9 | 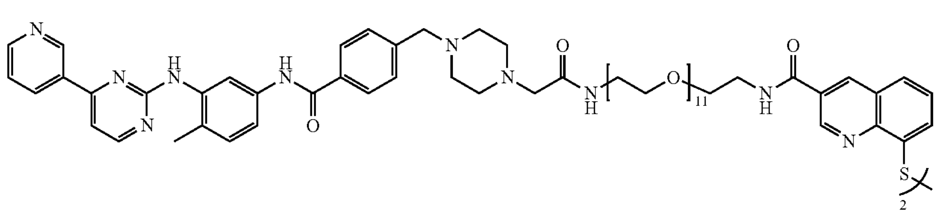 | 1074.4997 |

TABLE XId-continued

| Example | Structure | m/z [M + 2H]++ |
|---|---|---|
| 11IM10 | 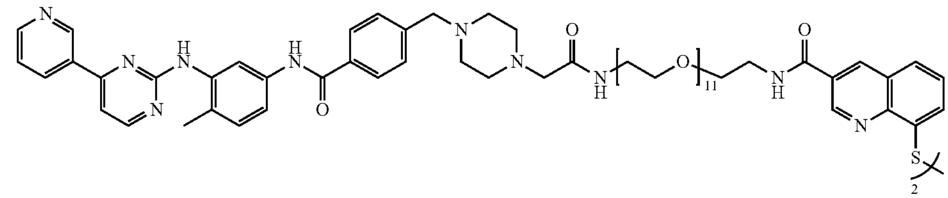 | 1250.6046 |

Example 12—Degradation of Bromo- and Extra-Terminal Domain Protein (BET) Proteins by Capzimin-Based Representative Compounds Cell culture. HeLa (CCL-2) and HEK293 (CRL-1573) cells were purchased from ATCC and cultured in DMEM medium (Gibco) supplemented with 10% FBS, 100 μg/mL penicillin/streptomycin and L-glutamine. Cells were grown at 37° C. and 5% $CO_2$ and were kept no longer than 30 passages. All cell lines were routinely tested for *mycoplasma* contamination using MycoAlert kit from Lonza.

HeLa ($5 \times 10^5$) and HEK293 ($1 \times 10^6$) cells were seeded in standard 6-well plates (2 mL medium) overnight before treatment with 1 μM compound with a final DMSO concentration of v/v. After 4 h incubation time, cells were washed with DPBS (Gibco) and lysed using 85 μL RIPA buffer (Sigma-Aldrich) supplemented with cOmplete Mini EDTA-free protease inhibitor cocktail (Roche) and benzonase. Lysates were clarified by centrifugation (20000 g, 10 min, 4° C.) and the total protein content of the supernatant was quantified using a Bradford colorimetric assay. Samples were prepared using equal amounts of total protein and LDS sample buffer (Invitrogen).

Immunoblotting. Proteins were separated by SDS-PAGE on NuPage 4-12% Bis-Tris gels, followed by transfer to Amersham Protran 0.45 NC nitrocellulose membrane (GE Healthcare) using wet transfer. Membranes were blocked using 5% w/v milk in Tris-buffered saline (TBS) with 0.1% Tween-20. Blots were probed (overnight at 4 □C) using anti-Brd2 (Abcam ab139690, 1:2,000 dilution), anti-Brd3 (Abcam ab50818, 1:500 dilution), and anti-Brd4 (Abcam ab128874, 1:1,000 dilution) primary antibodies, as appropriate. The next day, blots were washed with TBST and incubated (1 h at Room temperature) with anti-Tubulin hFAB-rhodamine (BioRad, 12004166) primary antibody, and either anti-rabbit IRDye 800CW (Licor 1:1,000 dilution) or anti-mouse IRDye 800CW (Licor 1:1,000 dilution) secondary antibody. Blots were developed using a Bio-Rad ChemiDoc MP Imaging System, and band quantification was performed using Image Studio software (LiCor). Band intensities were normalized to the tubulin loading control and reported as % of the average 0.1% DMSO vehicle intensity. Degradation data was plotted and analysed using Prism (Graphpad, version 8).

Figure 1:
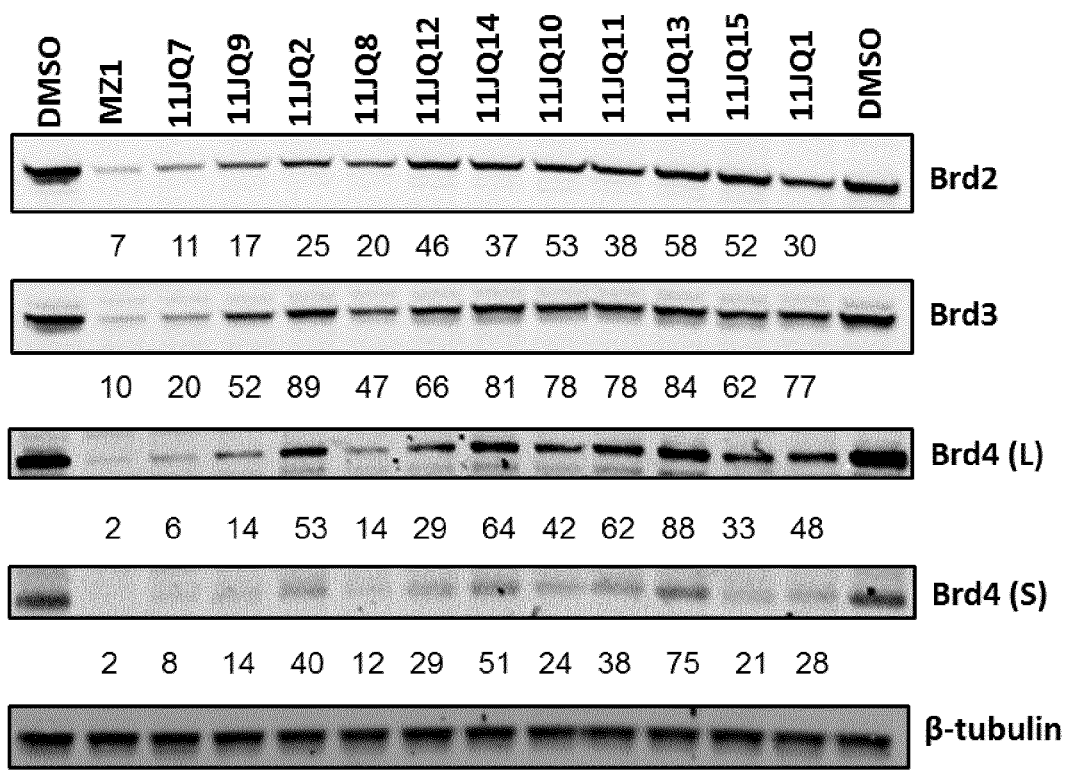
FIG. 1 shows immunoblot analysis of Brd2, Brd3 and Brd4 following 4 h treatment of HEK293 cells with 1 µM compound. MZ1 was used as a positive control. Values reported below each lane indicate BET abundance relative to the average 0.1% DMSO control.

Representative Western blots from HEK293 lysates in FIG. 1 show depletion of Brd2, Brd3 and Brd4 protein levels following 4 h treatment with 1 μM compounds. MZ1 was used as a positive control. Values reported below each lane indicate BET abundance relative to the average 0.1% DMSO control. All representative compounds show depletion of BRD2, BRD3 and BRD4, with a few compounds (11JQ7, for ex.) approaching the potency of PROTAC MZ1.

Example 13—Activity of Benzoyl Ester Prodrugs

Figure 2:
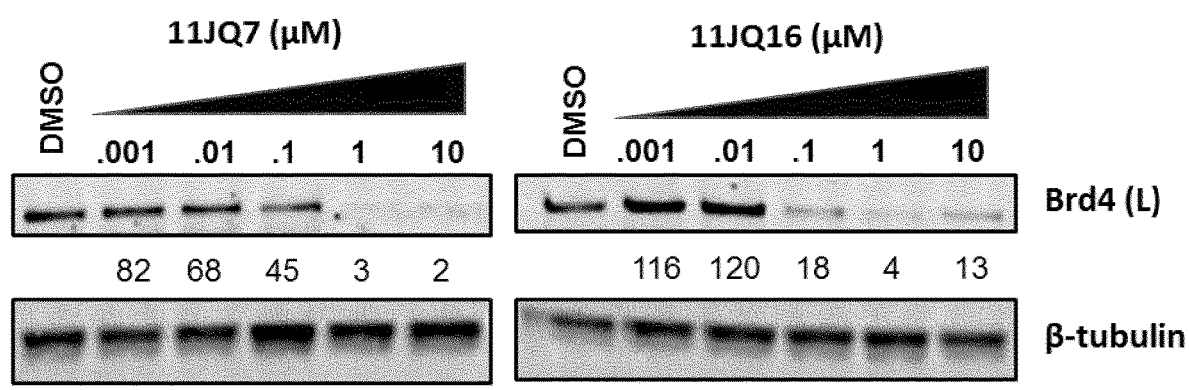
FIG. 2 shows immunoblot analysis of Brd4 following 4 h treatment of HEK293 cells with the indicated concentrations of 11JQ7 (parent compound) or 11JQ16 (prodrug). Values reported below each lane indicate BET abundance relative to the 0.1% DMSO control.

HEK293 ($1 \times 10^6$) cells incubated with DMSO, 11JQ7 or 11JQ16 compounds at the desired concentration (1 nM-10 μM), with a final DMSO concentration of 0.1% v/v. After 4 h treatment time, cells were lysed RIPA buffer and immunoblotted for Brd4 and β-tubulin. Values reported below each lane indicate BET abundance relative to the 0.1% DMSO control. Similar levels of BRD4 depletion are observed with both the benzoyl ester prodrug and the parent molecule. Results are shown in FIG. 2.

Example 14—Negative SAR of 11JQ15

Figure 3:
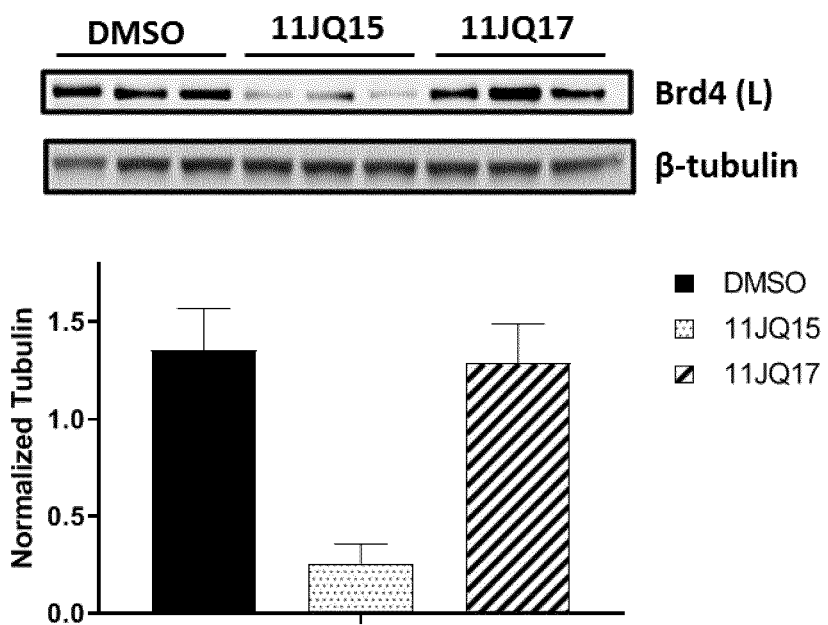
FIG. 3 shows representative immunoblot analysis of Brd4 following 4 h treatment of HEK293 cells with 1 µM 11JQ15 (active compound) or 11JQ17 (inactive ten-butyl). Band intensities were normalized to the tubulin loading control and reported as % of the 0.1% DMSO vehicle intensity. Degradation data was plotted and analysed using Prism (Graphpad, version 8), where bars are mean±SEM of three independent experiments.

HEK293 ($1 \times 10^6$) cells incubated with DMSO, 1 μM 11JQ15 or 1 μM 11JQ17 for 4 h with a final DMSO concentration of 0.1% v/v. Cells from three independent treatments (n=3) were lysed with RIPA buffer and immunoblotted for Brd4 and β-tubulin. Band intensities were normalized to the tubulin loading control and reported as % of the 0.1% DMSO vehicle intensity. Degradation data was plotted and analysed using Prism (Graphpad, version 8), where bars are mean±SEM of three independent experiments. Although significant depletion of Brd4 levels is observed with 11JQ15, there was minimal depletion following treatment with the test-butyl-capped equivalent, 11JQ17. Results are shown in FIG. 3.

Example 15—Concentration-Dependent BET Degradation by Capzimin-Based Representative Compounds HeLa ($5 \times 10^5$) and HEK293 ($1 \times 10^6$) cells were seeded in standard 6-well plates (2 mL medium) overnight before treatment with compounds at the desired concentration (1 nM-10 μM), with a final DMSO concentration of 0.1% v/v. After 4 h treatment time, cells were washed with DPBS (Gibco) and lysed using 85 μL RIPA buffer (Sigma-Aldrich) supplemented with cOmplete Mini EDTA-free protease inhibitor cocktail (Roche) and benzonase. Lysates were clarified by centrifugation (20000 g, 10 min, 4° C.) and the total protein content of the supernatant was quantified using a Bradford colorimetric assay. Samples were prepared using equal amounts of total protein and LDS sample buffer (Invitrogen). Band intensities were normalized to the tubulin loading control and reported as % of the average 0.1% DMSO vehicle intensity. Degradation data was plotted and analysed using Prism (Graphpad, version 8).

Figure 4:
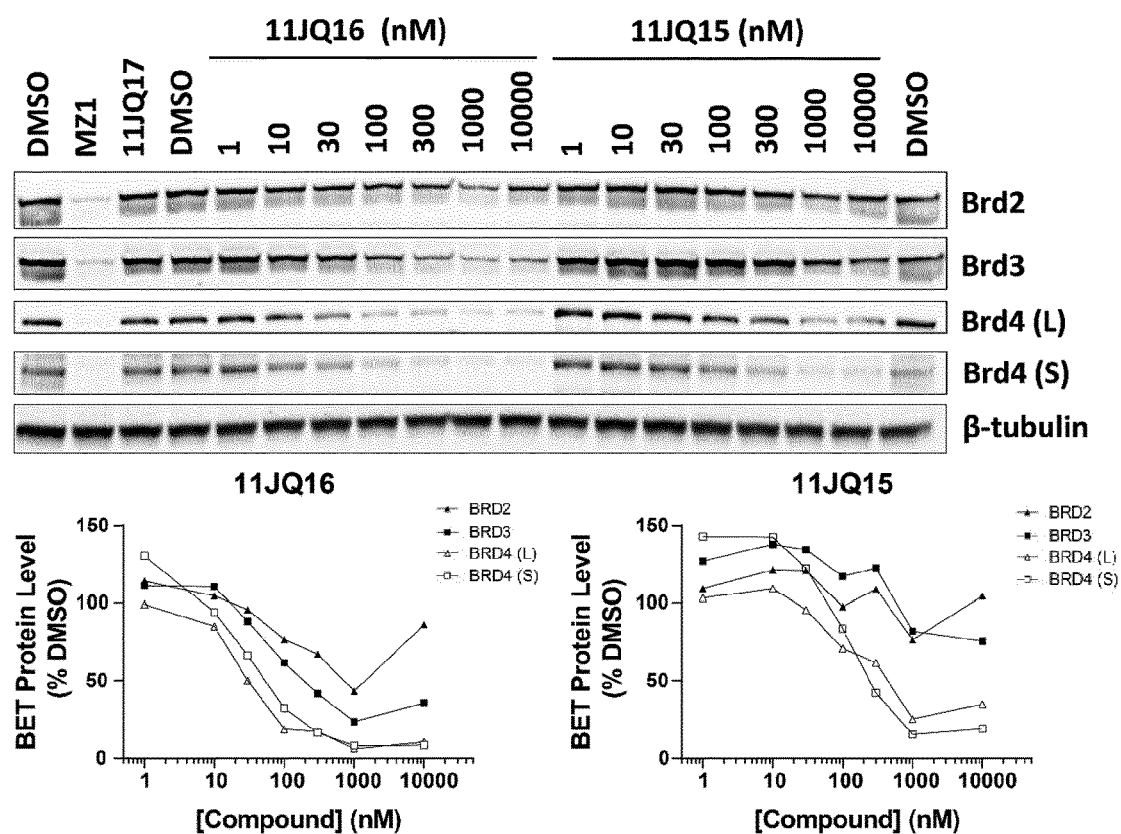
FIG. 4 shows immunoblot analysis of Brd2, Brd3 and Brd4 protein levels following 4 h treatment of HEK293 cells with increasing concentrations of 11JQ16 or 11JQ15. MZ1 and 11JQ17 were used at 1 µM for positive and negative controls, respectively.

Representative blots in FIG. 4 show depletion of Brd2, Brd3 and Brd4 protein levels following treatment with increasing concentrations of 11JQ16 or 11JQ15. MZ1 and 11JQ17 were used at 1 μM for positive and negative controls, respectively. Table XII shows DC50 parameters for representative compounds (11JQ17, 11JQ1, 11JQ15, 11JQ12, 11JQ7, and 11JQ16), where: Dmax is the maximum degradation observed and DC50 is the concentration required to reach 50% of the Dmax. For the table, $D_{max}$: +($D_{max}$≤25%); ++(26%≤$D_{max}$≤50%); +++ (51%≤$D_{max}$≤70%); ++++(71%≤$DC_{50}$: A ($DC_{50}$≤50 nM); B (51 nM≤$DC_{50}$≤500 nM); C (501 nM≤$DC_{50}$).

TABLE XII

Concentration-dependent Degradation by capzimin-based representative compounds

| | | HEK293 | | HeLa | |
|---|---|---|---|---|---|
| | Target | $D_{max}$ (%) | $DC_{50}$ | $D_{max}$ (%) | $DC_{50}$ |
| 11JQ17 | Brd2 | + | − | + | − |
| | Brd3 | + | − | + | − |
| | Brd4 (L) | + | − | + | − |
| | Brd4 (S) | + | − | + | − |
| 11JQ1 | Brd2 | ++++ | B | ++ | B |
| | Brd3 | +++ | C | +++ | C |
| | Brd4 (L) | ++++ | B | ++++ | B |
| | Brd4 (S) | ++++ | B | ++++ | B |
| 11JQ15 | Brd2 | ++ | B | ++ | B |
| | Brd3 | ++ | B | ++ | B |
| | Brd4 (L) | +++ | B | +++ | B |
| | Brd4 (S) | +++ | B | +++ | B |
| 11JQ12 | Brd2 | ++ | C | ++ | C |
| | Brd3 | ++ | C | + | C |
| | Brd4 (L) | ++++ | B | ++++ | C |
| | Brd4 (S) | ++++ | B | ++++ | C |
| 11JQ7 | Brd2 | ++++ | B | ++++ | C |
| | Brd3 | ++++ | C | ++++ | B |
| | Brd4 (L) | ++++ | B | ++++ | A |
| | Brd4 (S) | ++++ | B | ++++ | A |
| 11JQ16 | Brd2 | ++++ | B | +++ | B |
| | Brd3 | ++++ | A | +++ | C |
| | Brd4 (L) | ++++ | A | ++++ | B |
| | Brd4 (S) | ++++ | A | ++++ | B |

Example 16—Time-Dependent BET Degradation by Capzimin-Based Representative Compounds HEK293 (0.5×10⁶) cells were seeded in standard 6-well plates (2 mL medium) overnight before treatment with compounds at 1 μM concentration, with a final DMSO concentration of 0.1% v/v. After incubation for the desired time (0-24 hrs), cells were washed with DPBS (Gibco) and lysed using 85 μL RIPA buffer (Sigma-Aldrich) supplemented with complete Mini EDTA-free protease inhibitor cocktail (Roche) and benzonase. Lysates were clarified by centrifugation (20000 g, 10 min, 4° C.) and the total protein content of the supernatant was quantified using a Bradford colorimetric assay. Samples were prepared using equal amounts of total protein and LDS sample buffer (Invitrogen). Band intensities were normalized to the tubulin loading control and reported as % of the average 0.1% DMSO vehicle intensity. Degradation data was plotted and analysed using Prism (Graphpad, version 8).

Figure 5:
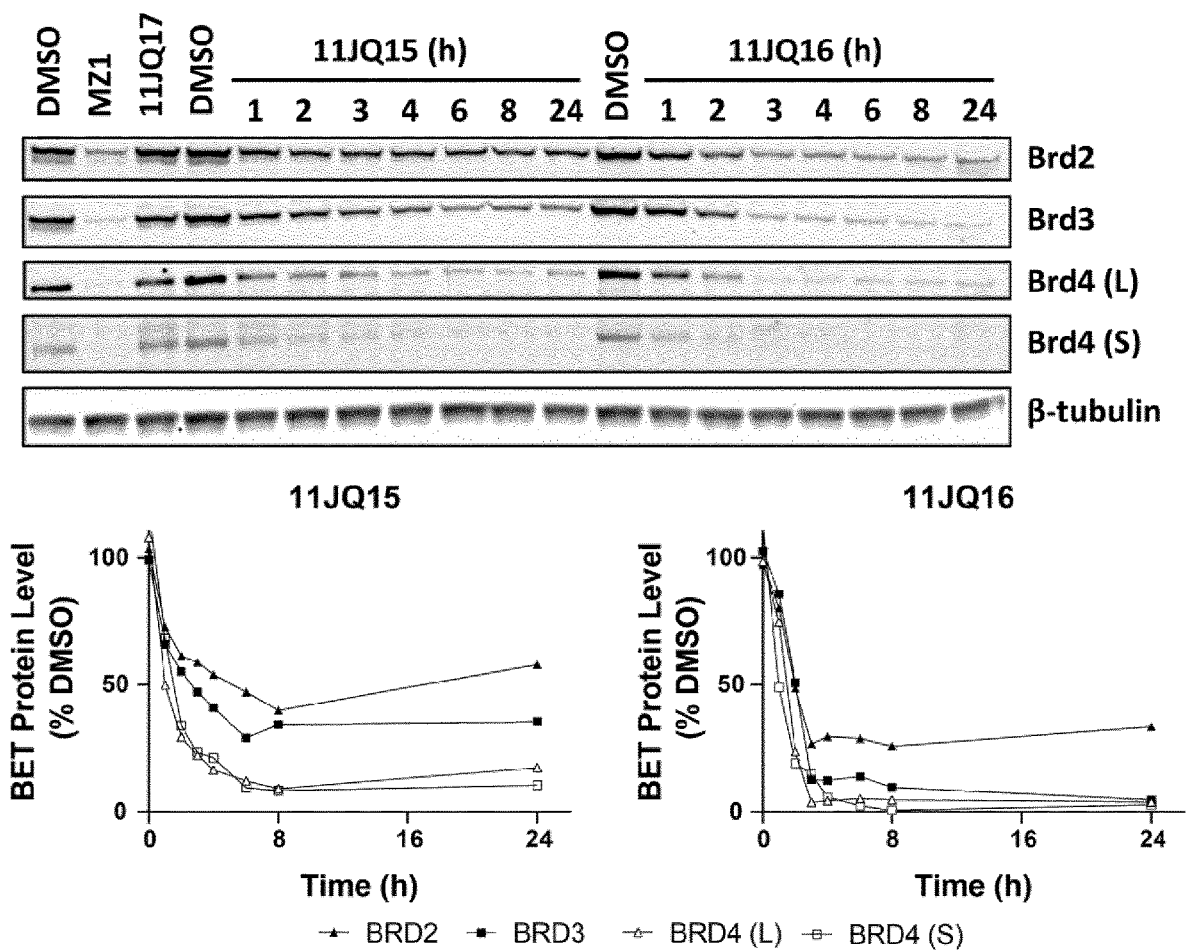
FIG. 5 shows immunoblot analysis of Brd2, Brd3 and Brd4 protein levels following 1 µM treatment of HEK293 cells for various time points with 11JQ16 or 11JQ15. MZ1 and 11JQ17 were used at 1 µM (4h) for positive and negative controls, respectively.

Representative blots in FIG. 5 show depletion of Brd2, Brd3 and Brd4 protein levels following 1 μM treatment at various time points with 11JQ16 or 11JQ15. MZ1 and 11JQ17 were used at 1 μM (4 h) for positive and negative controls, respectively. Table XIII shows timecourse parameters for representative compounds in HEK293 cells, where: $D_{max}$ is the maximum degradation observed, T1/2 (h) is the time required to reach 50% of the $D_{max}$, and Abs. T1/2 (h) is the time required to deplete 50% of the protein relative to DMSO.

TABLE XIII

Time-dependent Degradation by capzimin-based representative compounds

| | | HEK293 | | | HeLa | | |
|---|---|---|---|---|---|---|---|
| | Target | $D_{max}$ (%) | $T_{1/2}$ (h) | Abs. $T_{1/2}$ (h) | $D_{max}$ (%) | $T_{1/2}$ (h) | Abs. $T_{1/2}$ (h) |
| 11JQ1 | Brd2 | 60 | 1.0 | 3.5 | | ND | |
| | Brd3 | 90 | 2.7 | 3.5 | | ND | |
| | Brd4 (L) | 95 | 1.6 | 1.7 | | ND | |
| | Brd4 (S) | 95 | 2 | 1.9 | | ND | |
| 11JQ15 | Brd2 | 50 | 1.1 | 5.7 | | ND | |
| | Brd3 | 70 | 1.5 | 2.6 | | ND | |
| | Brd4 (L) | 90 | 0.8 | 1.1 | 90 | 3.5 | 4.3 |
| | Brd4 (S) | 90 | 0.9 | 1.2 | 90 | 2.8 | 3.3 |
| 11JQ7 | Brd2 | 80 | 1.8 | 3.2 | 50 | 4 | 4 |
| | Brd3 | 95 | 2.9 | 3.4 | | ND | |
| | Brd4 (L) | 98 | 1.2 | 1.2 | 100 | 2.3 | 2.4 |
| | Brd4 (S) | 99 | 1.9 | 1.9 | 100 | 3 | 3.1 |
| 11JQ16 | Brd2 | 75 | 1.7 | 2.7 | | ND | |
| | Brd3 | 95 | 1.6 | 1.9 | | ND | |
| | Brd4 (L) | 98 | 1.0 | 1.0 | | ND | |
| | Brd4 (S) | 95 | 0.6 | 0.6 | | ND | |

ND = not determined

Example 17: Mechanistic Evaluation of Capzimin-Based Representative Compounds

HeLa (5×10⁵) and HEK293 (1×10⁶) cells were seeded in standard 6-well plates (2 mL medium) overnight before pre-treatment with inhibitors (10 μM bortezomib, 10 μM capzimin, 10 μM JQ1). After a 0.5 h pre-incubation time, cells were subsequently treated with vehicle, 1 μM MZ1 or 1 μM 11JQ15, yielding a final overall DMSO concentration of 0.2% v/v. After 4 h incubation, cells were washed with DPBS (Gibco) and lysed using 85 μL RIPA buffer (Sigma-Aldrich) supplemented with cOmplete Mini EDTA-free protease inhibitor cocktail (Roche) and benzonase. Lysates were clarified by centrifugation (20000 g, 10 min, 4° C.) and the total protein content of the supernatant was quantified using a Bradford colorimetric assay. Samples were prepared using equal amounts of total protein and LDS sample buffer (Invitrogen).

Representative blot of HEK293 lysates in FIG. 6A shows depletion of Brd4 protein levels following 4 h treatment with 1 μM 11JQ15 or MZ1, in the presence and absence of 10 μM bortezomib, 10 μM capzimin, and 10 μM JQ1. Brd4 band intensities were normalized to tubulin loading control and reported in FIG. 6B as % of the average 0.1% DMSO vehicle intensity. Each bar is mean±SEM of three independent experiments performed in duplicate (n=3).

Degradation by 11JQ15 was completely blocked in the presence of bortezomib and JQ1, and was significantly blocked (p<0.01; paired t-test) in the presence of capzimin. Alternatively, MZ1 degradation was only blocked by bortezomib and JQ1. These data suggest that the degradation is proteasomal dependent.

Example 18: Unbiased Whole Proteome Analysis by TMT-Labelling MS

HEK293 (2.2×10 6) cells were seeded in 10 cm plates (10 mL medium) overnight before treatment with 1 μM compound for a final DMSO concentration of 0.1% v/v. After 4 h incubation time, cells were washed with 2× with DPBS (Gibco) and lysed using 500 μL lysis buffer (100 mM Tris, 4% (w/v) SDS, pH 8.0) supplemented with cOmplete Mini EDTA-free protease inhibitor cocktail (Roche) and benzonase. Lysates were briefly sonicated (2×10 s), clarified by centrifugation (20000 g, 10 min, 4° C.) and the total protein content of the supernatant was quantified using a BCA assay (Thermo Fisher Scientific).

Sample processing, digestion, desalting, labelling, and fractionation were performed at Fingerprint Proteomics (University of Dundee) as described previously [Gadd et al. 10.1038/nchembio.2329]. FIG. 7 depicts fold change of abundance of 7882 proteins comparing 11JQ15 to DMSO treatment (left) and comparing 1 µM 11JQ17 to DMSO treatment (right), as well as their respective p-values (t-test; n=3). It is clear that there is selective degradation of Brd2, Brd3 and Brd4 in the presence of the active compound 11JQ15. The tert-butyl equivalent (11JQ17) does not show any BET depletion, suggesting that a functional Capzimin based representative compound is required the degradation.

Example 19: Impact on Cell Viability by Capzimin-Based Representative Compounds The anti-proliferative effects of representative compounds and other compounds was measured using the CellTiter-Glo assay (Promega). MV4-11 cells were incubated in a sterile, white, clear-bottomed 384-well cell-culture microplate (Greiner Bio-one), at 2× concentration in RPMI media and a volume of 25 µl. The next day, test compounds were serially diluted in RPMI media to 2× concentration, then added to cells to make a final volume of 50 µl. After a 72 h incubation 25 µl of CellTiter-Glo reagent was added to each well. Following 15 minute incubation the luminescence signal was read on a Pherastar FS. The final concentration of assay components are as follows: $3 \times 10^5$ cells/ml, 0.05% DMSO, 5 µM and below compound. Data (FIG. 8) was processed and dose-response curves generated using Prism 8 (Graphpad).

The data shows a cytoxicity profile for 11JQ7 and 11JQ16 that is distinct from JQ1 and inactive 11JQ18, which is consistent with target degradation rather than target inhibition. Capzimin alone shows significantly less cytotoxicity.

Example 20: Effect of of Capzimin-Based Representative Compounds on c-MYC Levels and PARP Cleavage in MV4-11 Cells MV4-11 ($0.7 \times 10^6$ cells/mL) were seeded in 10 cm plates (10 mL DMEM supplemented with 10% FBS and L-glutamine) overnight before treatment with compounds at the desired concentration and with a final DMSO concentration of 0.1% v/v. After 6 h incubation time, cells were washed with 2× with DPBS (Gibco) and lysed using 85 µL RIPA buffer (Sigma-Aldrich) supplemented with cOmplete Mini EDTA-free protease inhibitor cocktail (Roche) and benzonase. Lysates were clarified by centrifugation (20000 g, 10 min, 4° C.) and the total protein content of the supernatant was quantified using a Bradford colorimetric assay. Samples were prepared using equal amounts of total protein and LDS sample buffer (Invitrogen). For immunoblot analysis, the following antibodies were used: anti-Brd4 (ab128874, 1:1,000 dilution), anti-cmyc (ab32072, 1:1000 dilution), anti-CPARP (CST-9541T, 1:1,000 dilution), and anti-Tubulin hFAB-rhodamine (BioRad, 12004166, 1:10000 dilution).

Representative immunoblots in FIG. 9 show depletion of Brd4 and c-MYC levels, and a corresponding increase in cleaved PARP, following treatment with increasing concentrations of 11JQ16. The increase in C-PARP is significantly greater than inhibitor (JQ1) alone and the negative control (11JQ18), which is consistent with a target degradation rather than inhibition.

Example 21. Capzimin-Based Representative Compounds Bind Human Rpn11

Isothermal titration calorimetry (ITC) was used to measure capzimin binding to purified human Rpn11 (residues 2-239) that was co-expressed with Rpn8 (residues 1-179). Titrations were performed in an ITC200 microcalorimeter (25° C., 750 rpm) with protein in the cell (40 µM) and ligand in the syringe (400 µM). Solutions were prepared with ITC buffer (20 mM Bis-Tris propane, 100 mM NaCl, 1 mM tris(2-carboxyethyl)phosphine (TCEP), pH 7.5) at a final DMSO concentration of 2%. The run consisted of 19 injections of 2 µL of protein solution at a rate of 0.5 µL/s with 120 s time intervals. An initial injection of 0.4 µL was made and discarded during data analysis. Data were fitted to a single binding-site model using the MicroCal PEAQ-ITC analysis software to obtain the dissociation constant $K_d$ (675 nM), the stoichiometry N (1.04) and the enthalpy of binding ΔH (−2.3 kcal/mol).

---

What is claimed:
1. A bifunctional molecule selected from the group consisting of:
(A)
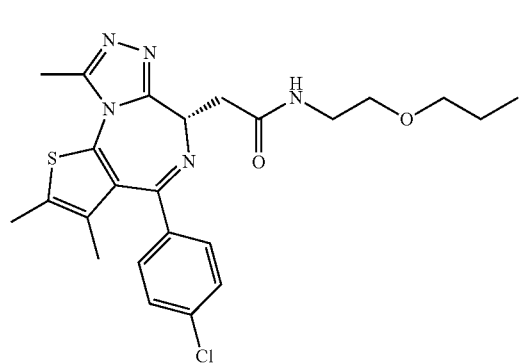
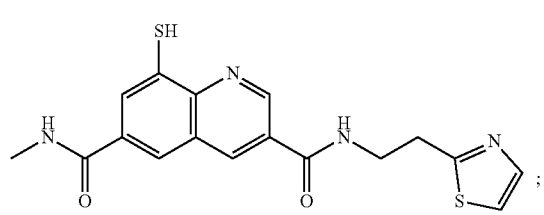
(B)
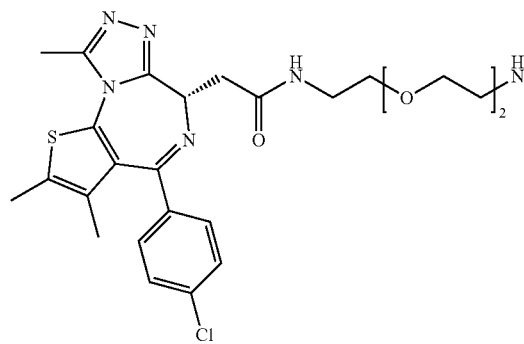
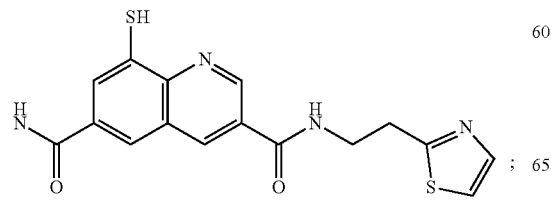
(C)
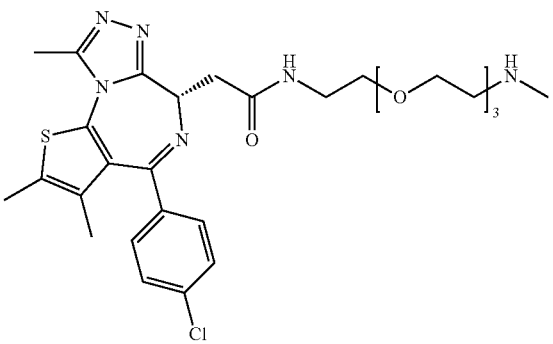
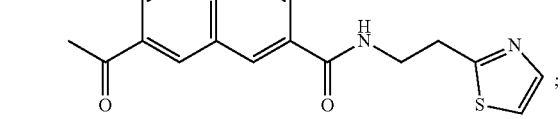
(D)
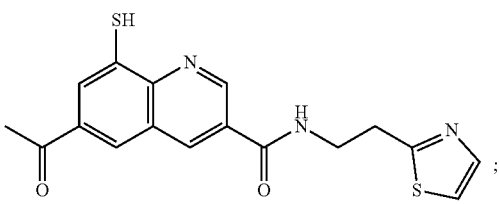

(E)
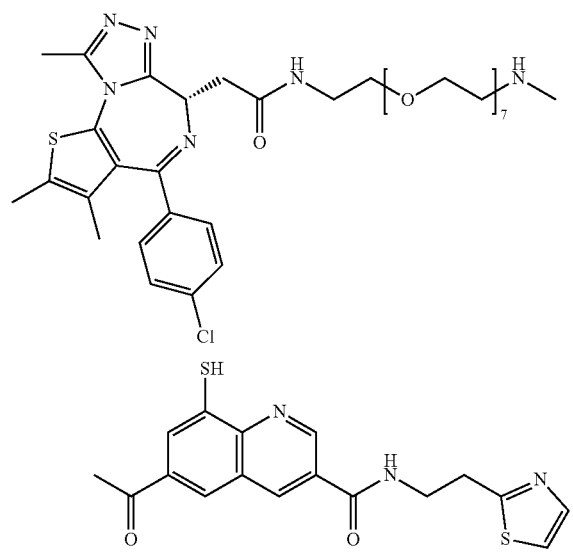
(F)
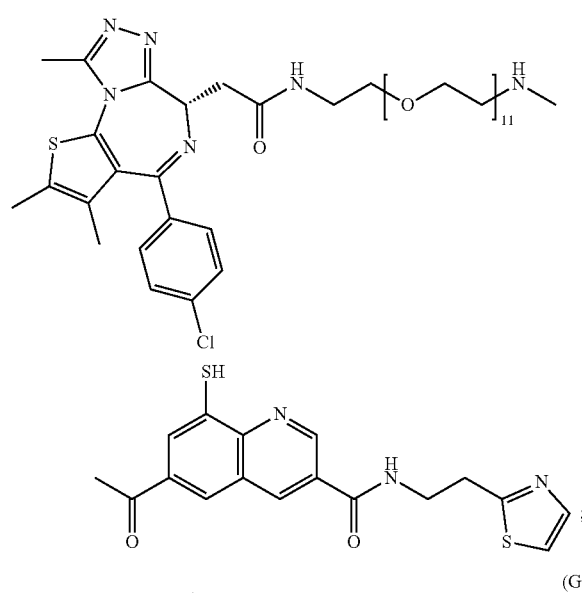
(G)
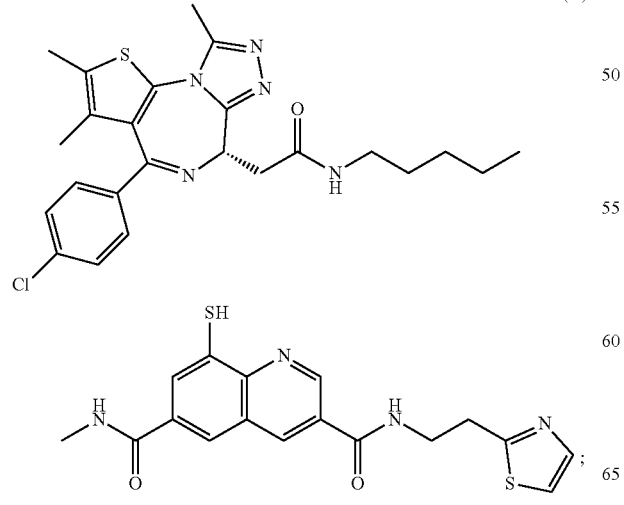
(H)
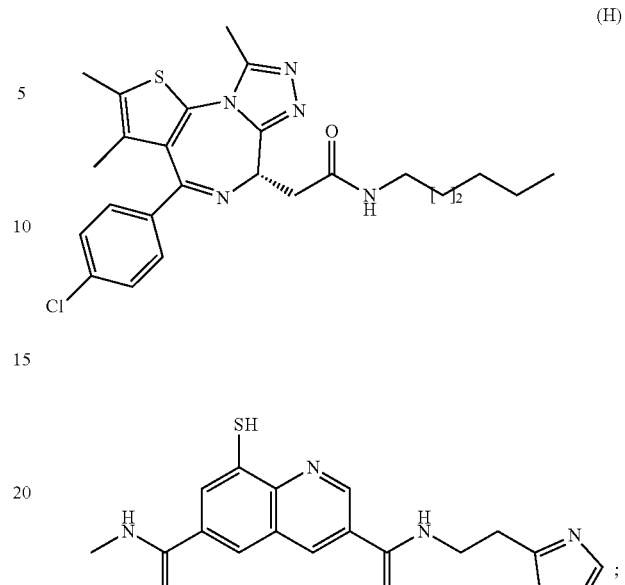
(I)
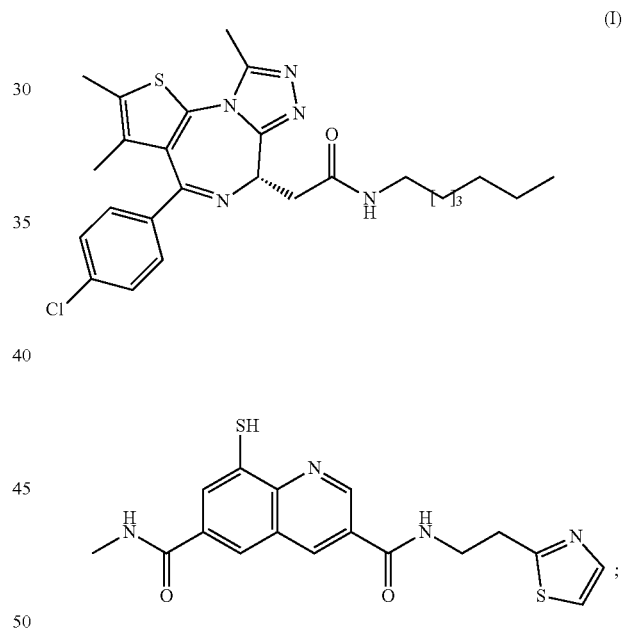
(J)
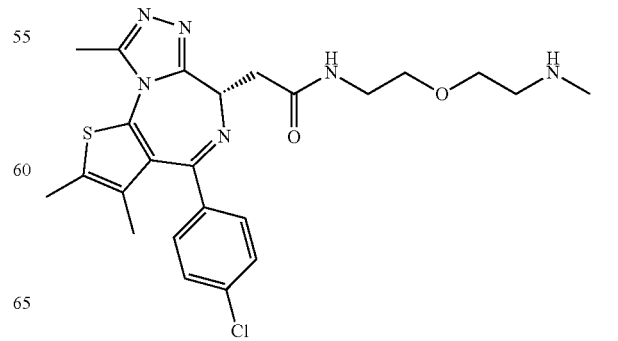

383
-continued
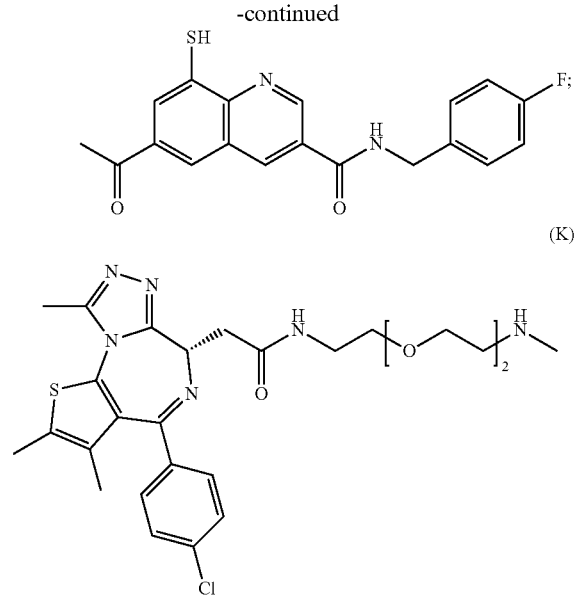
(K)
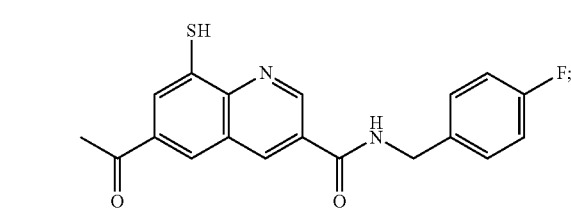
(L)
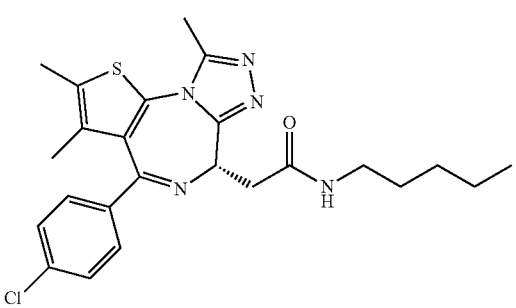
(M)
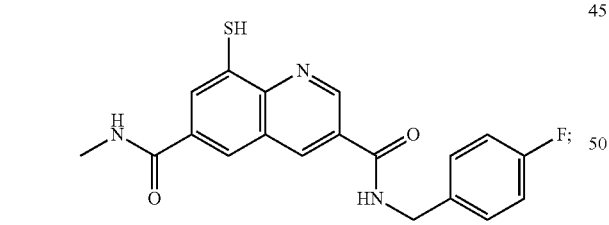
384
-continued
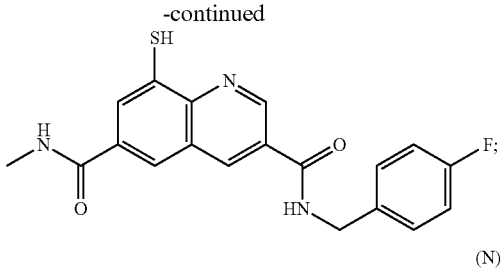
(N)
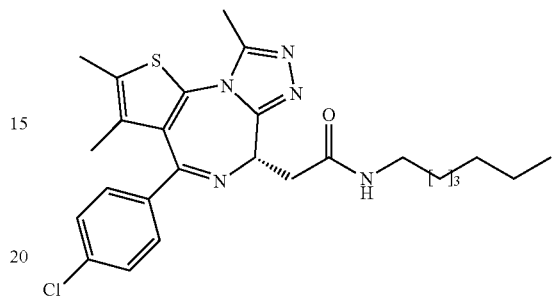
(O)
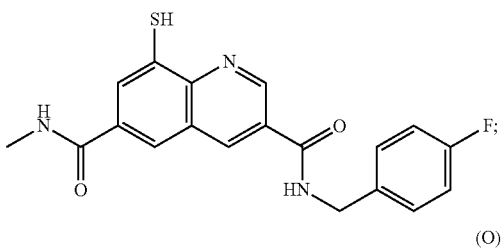
(P)
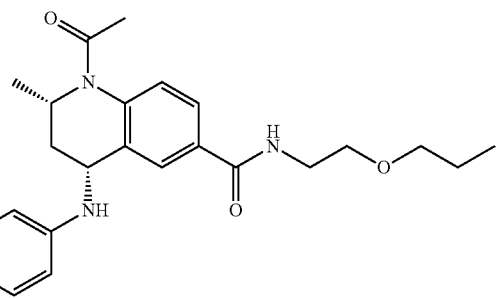
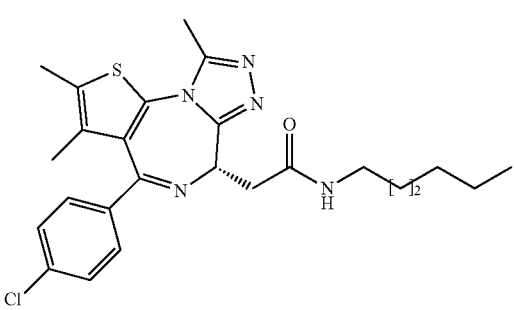
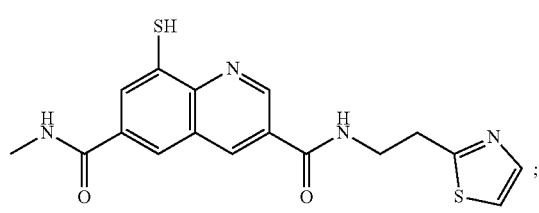
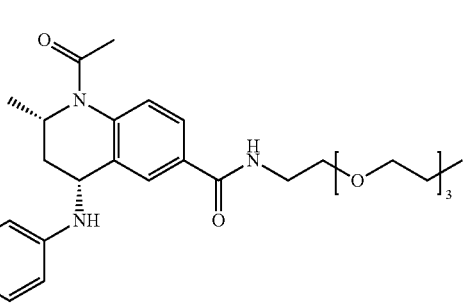

385
-continued
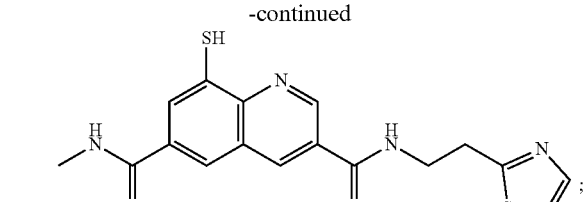
(Q)
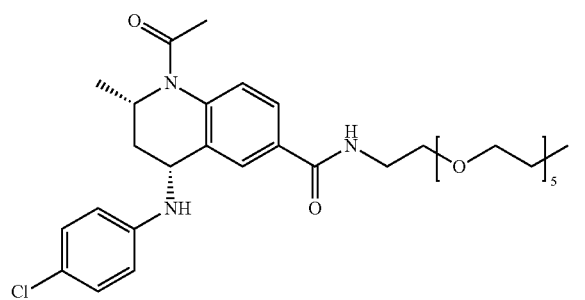
(R)
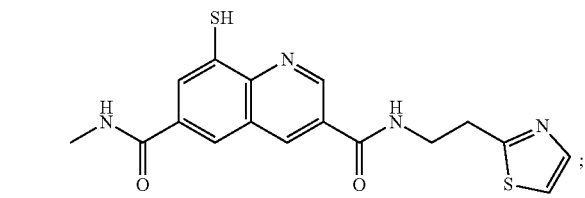
(S)
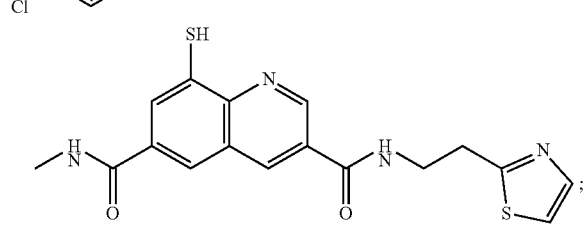
386
-continued
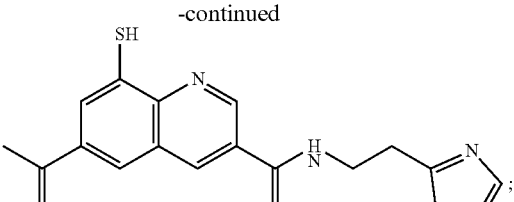
(T)
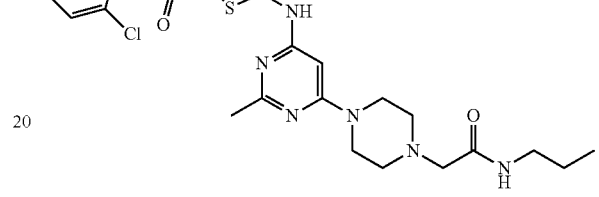
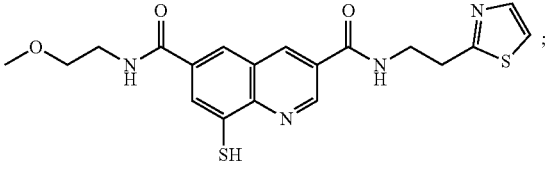
(U)
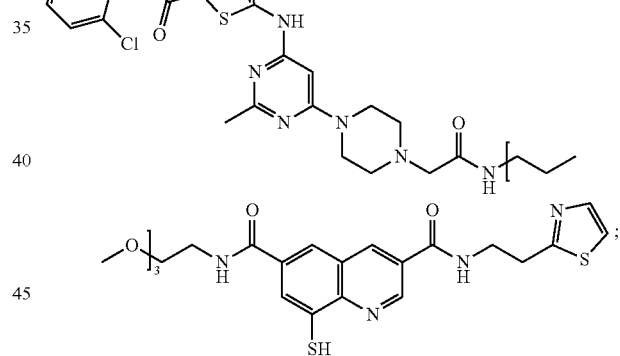
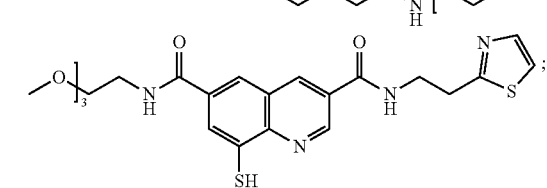
(V)
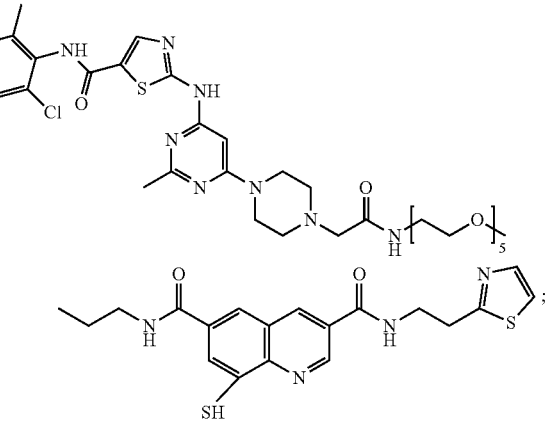

(W)
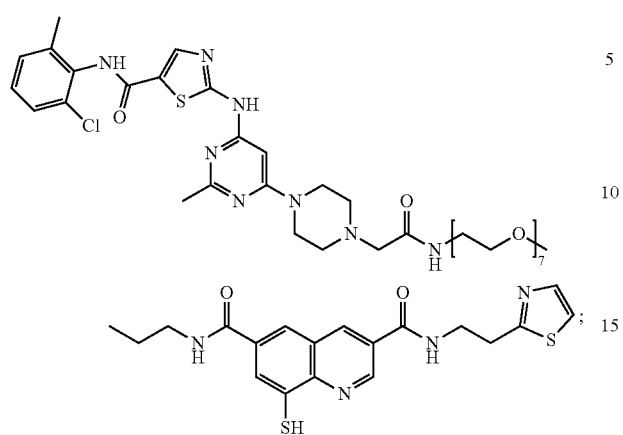
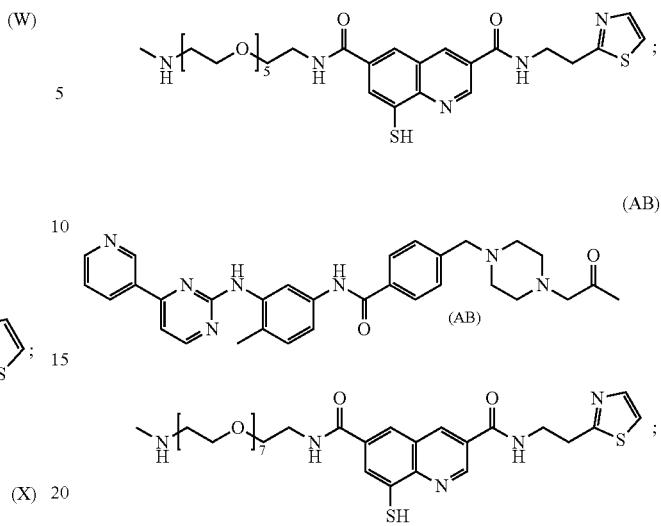
(X)
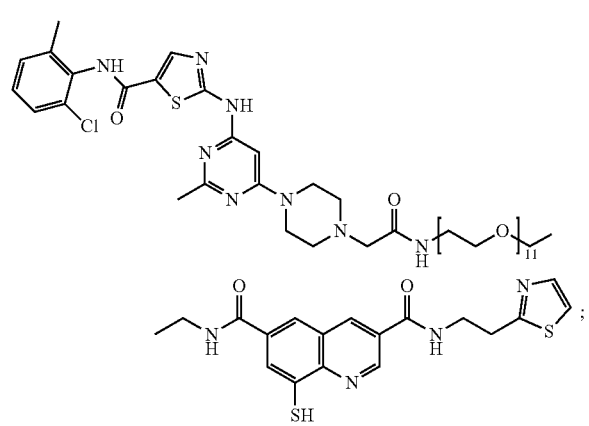
(Y)
(Z)
(AA)
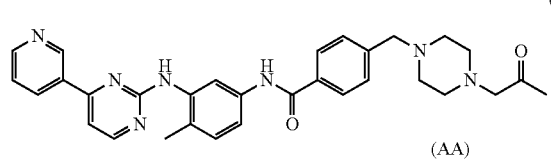
(AB)
(AC)
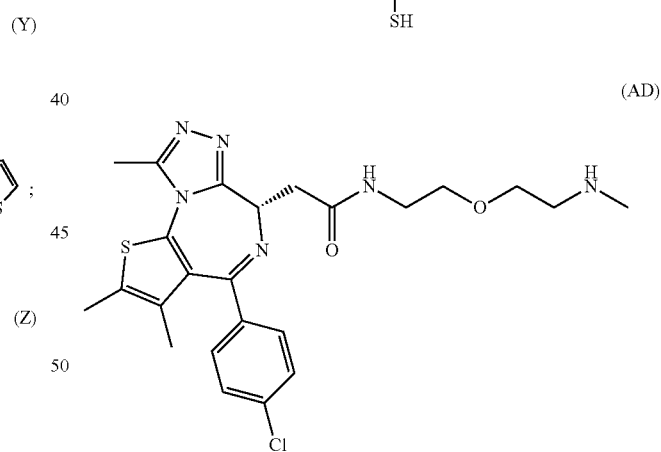
(AD)
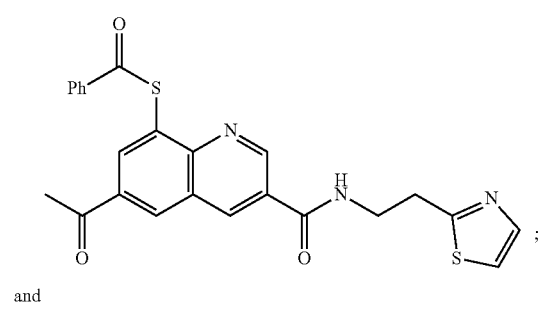
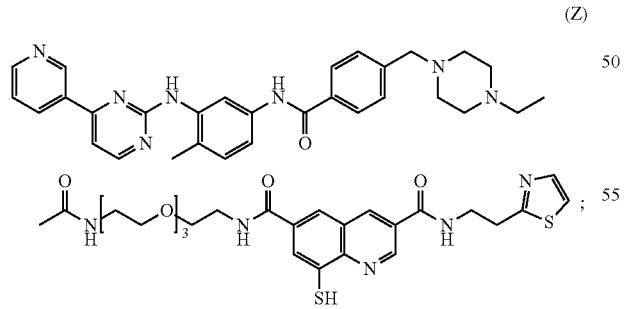
and

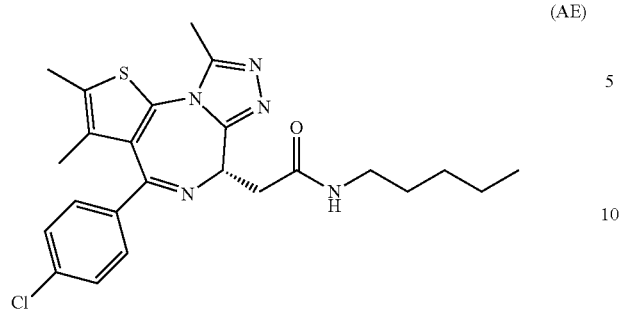
(AE)
2. A pharmaceutical composition comprising a bifunctional compound according to claim 1, and a pharmaceutically acceptable carrier.
* * * * *

SEQUENCE LISTING

```
<160> NUMBER OF SEQ ID NOS: 2

<210> SEQ ID NO 1
<211> LENGTH: 933
<212> TYPE: DNA
<213> ORGANISM: Homo sapiens

<400> SEQUENCE: 1
atggacagac ttcttagact tggaggaggt atgcctggac tgggccaggg gccacctaca      60
gatgctcctg cagtggacac agcagaacaa gtctatatct cttccctggc actgttaaaa     120
atgttaaaac atggccgtgc tggagttcca atggaagtta tgggtttgat gcttggagaa     180
tttgttgatg attataccgt cagagtgatt gatgtgtttg ctatgccaca gtcaggaaca     240
ggtgtcagtg tggaggcagt tgatccagtg ttccaagcta aaatgttgga tatgttgaag     300
cagacaggaa ggccggagat ggttgttggt tggtatcaca gtcaccctgg ctttggttgt     360
tggctttctg gtgtggatat caacactcag cagagctttg aagccttgtc ggagagagct     420
```

```
gtggcagtgg ttgtggatcc cattcagagt gtaaaaggaa aggttgttat tgatgccttc    480
agattgatca atgctaatat gatggtctta ggacatgaac caagacaaac aacttcgaat    540
ctgggtcact taaacaagcc atctatccag gcattaattc atggactaaa cagacattat    600
tactccatta ctattaacta tcggaaaaat gaactggaac agaagatgtt gctaaatttg    660
cataagaaga gttggatgga aggtttgaca cttcaggact acagtgaaca ttgtaaacac    720
aatgaatcag tggtaaaaga gatgttggaa ttagccaaga attacaataa ggctgtagaa    780
gaagaagata agatgacacc tgaacagctg gcaataaaga atgttggcaa gcaggacccc    840
aaacgtcatt tggaggaaca tgtggatgta cttatgacct caaatattgt ccagtgttta    900
gcagctatgt tggatactgt cgtatttaaa taa                                 933
```

<210> SEQ ID NO 2
<211> LENGTH: 310
<212> TYPE: PRT
<213> ORGANISM: Homo sapiens

<400> SEQUENCE: 2

```
Met Asp Arg Leu Leu Arg Leu Gly Gly Gly Met Pro Gly Leu Gly Gln
1               5                   10                  15

Gly Pro Pro Thr Asp Ala Pro Ala Val Asp Thr Ala Glu Gln Val Tyr
            20                  25                  30

Ile Ser Ser Leu Ala Leu Leu Lys Met Leu Lys His Gly Arg Ala Gly
        35                  40                  45

Val Pro Met Glu Val Met Gly Leu Met Leu Gly Glu Phe Val Asp Asp
    50                  55                  60

Tyr Thr Val Arg Val Ile Asp Val Phe Ala Met Pro Gln Ser Gly Thr
65                  70                  75                  80

Gly Val Ser Val Glu Ala Val Asp Pro Val Phe Gln Ala Lys Met Leu
                85                  90                  95

Asp Met Leu Lys Gln Thr Gly Arg Pro Glu Met Val Val Gly Trp Tyr
            100                 105                 110

His Ser His Pro Gly Phe Gly Cys Trp Leu Ser Gly Val Asp Ile Asn
        115                 120                 125

Thr Gln Gln Ser Phe Glu Ala Leu Ser Glu Arg Ala Val Ala Val Val
    130                 135                 140

Val Asp Pro Ile Gln Ser Val Lys Gly Lys Val Val Ile Asp Ala Phe
145                 150                 155                 160

Arg Leu Ile Asn Ala Asn Met Met Val Leu Gly His Glu Pro Arg Gln
                165                 170                 175

Thr Thr Ser Asn Leu Gly His Leu Asn Lys Pro Ser Ile Gln Ala Leu
            180                 185                 190

Ile His Gly Leu Asn Arg His Tyr Tyr Ser Ile Thr Ile Asn Tyr Arg
        195                 200                 205

Lys Asn Glu Leu Glu Gln Lys Met Leu Leu Asn Leu His Lys Lys Ser
    210                 215                 220

Trp Met Glu Gly Leu Thr Leu Gln Asp Tyr Ser Glu His Cys Lys His
225                 230                 235                 240

Asn Glu Ser Val Val Lys Glu Met Leu Glu Leu Ala Lys Asn Tyr Asn
                245                 250                 255

Lys Ala Val Glu Glu Glu Asp Lys Met Thr Pro Glu Gln Leu Ala Ile
            260                 265                 270

Lys Asn Val Gly Lys Gln Asp Pro Lys Arg His Leu Glu Glu His Val
        275                 280                 285
```

Asp Val Leu Met Thr Ser Asn Ile Val Gln Cys Leu Ala Ala Met Leu
    290                 295                 300
Asp Thr Val Val Phe Lys
305                 310